US008911981B2

(12) United States Patent
Li et al.

(10) Patent No.: US 8,911,981 B2
(45) Date of Patent: Dec. 16, 2014

(54) KETOL-ACID REDUCTOISOMERASE USING NADH

(71) Applicant: Butamax(TM) Advanced Biofuels LLC, Wilmington, DE (US)

(72) Inventors: Yougen Li, Lawrenceville, NJ (US); Der-Ing Liao, Wilmington, DE (US); Mark J. Nelson, Newark, DE (US); Daniel P. Okeefe, Ridley Park, PA (US)

(73) Assignee: Butamax Advanced Biofuels LLC, Wilmington, DE (US)

(*) Notice: Subject to any disclaimer, the term of this patent is extended or adjusted under 35 U.S.C. 154(b) by 0 days.

(21) Appl. No.: 13/838,899

(22) Filed: Mar. 15, 2013

(65) Prior Publication Data

US 2013/0344551 A1 Dec. 26, 2013

Related U.S. Application Data

(63) Continuation of application No. 12/637,905, filed on Dec. 15, 2009, which is a continuation-in-part of application No. 12/337,736, filed on Dec. 18, 2008, now Pat. No. 8,129,162.

(60) Provisional application No. 61/109,297, filed on Oct. 29, 2008, provisional application No. 61/015,346, filed on Dec. 20, 2007.

(51) Int. Cl.

| | |
|---|---|
| ***C12N 1/38*** | (2006.01) |
| ***C12N 9/02*** | (2006.01) |
| ***C12N 1/20*** | (2006.01) |
| ***C12N 1/14*** | (2006.01) |
| ***C12N 15/00*** | (2006.01) |
| ***C12P 7/06*** | (2006.01) |
| ***C12P 7/42*** | (2006.01) |
| ***C07H 21/04*** | (2006.01) |
| ***C12N 9/04*** | (2006.01) |
| ***C12N 15/70*** | (2006.01) |
| ***C12N 15/10*** | (2006.01) |
| ***C12P 7/16*** | (2006.01) |
| ***C12N 15/81*** | (2006.01) |

(52) U.S. Cl.

CPC . *C12N 15/81* (2013.01); *C12P 7/42* (2013.01); *C12N 9/0006* (2013.01); *C12N 15/70* (2013.01); *C12N 15/102* (2013.01); *C12Y 101/01086* (2013.01); *C12P 7/16* (2013.01); *Y02E 50/10* (2013.01)

USPC ... 435/243; 435/189; 435/252.3; 435/254.11; 435/254.21; 435/440; 435/320.1; 435/161; 435/146; 536/23.2

(58) Field of Classification Search

CPC ...... C12N 15/81; C12N 15/70; C12N 15/102; C12N 9/0006; C12P 7/16; C12P 7/42; C12Y 101/01086

USPC ................................ 435/243, 189, 161, 146

See application file for complete search history.

(56) References Cited

U.S. PATENT DOCUMENTS

| | | | |
|---|---|---|---|
| 4,683,202 | A | 7/1987 | Mullis et al. |
| 6,586,229 | B1 | 7/2003 | Ben-Bassat et al. |
| 7,851,188 | B2 | 12/2010 | Donaldson et al. |
| 7,993,889 | B1 | 8/2011 | Donaldson et al. |
| 8,129,162 | B2 | 3/2012 | Li et al. |
| 8,178,328 | B2 | 5/2012 | Donaldson et al. |
| 8,222,017 | B2 | 7/2012 | Li et al. |
| 8,273,558 | B2 | 9/2012 | Donaldson et al. |
| 2004/0248250 | A1 | 12/2004 | Nakai et al. |
| 2005/0112739 | A1 | 5/2005 | Golubkov et al. |
| 2007/0092957 | A1 | 4/2007 | Donaldson et al. |
| 2009/0163376 | A1 | 6/2009 | Li et al. |
| 2010/0197519 | A1 | 8/2010 | Li et al. |
| 2013/0344551 | A1 | 12/2013 | Li et al. |
| 2014/0057329 | A1 | 2/2014 | Li et al. |

FOREIGN PATENT DOCUMENTS

| | | |
|---|---|---|
| WO | 2005040392 | 5/2005 |

OTHER PUBLICATIONS

Abbad-Andaloussi, et al., Carbon and Electron Flow in *Clostridium butyricum* grown in Chemostat Culture on Glyceol and on Glucose, Microbiology 142:1149-1158, 1996.

Arthur, et al., Contribution of VanY D,D-Carboxypeptidase to Glycopeptide Resistance in *Enterococcus faecalis* by Hydrolysis of Peptidoglycan Precursors, Antimicrob. Agents Chemother. 38:1899-1903, 1994.

Aulabaugh, et al., Oxalyl Hydroxamates as Reaction-Intermediate Analogues for Ketol-Acid Reductoisomerase, Biochemistry 29:2824-2830 1990.

Biou, et al. The crystal structure of plant acetohydroxy acid isomeroreductase complexed with NADPH, two magnesium ions and a herbicidal transition state analog determined at 1.65 Å resolution, EMBO Journal 16:3405-3415, 1997.

van der Geize, et al., Targeted Disruption of the kstD Gene Encoding a 3-Ketosteroid delta1-Dehydrogenase Isoenzyme of *Rhodococcus erythropolis* Strain SQ1, Appl. Environ. Microbiol. 66:2029-2036, 2000.

Chunduru, et al., Mechanism of Ketol Acid Reductoisomerase—Steady State Analysis and Metal Ion Requirement, Biochemistry 28:486-493 1989.

de Cavalho, et al., Mycobacterium sp., *Rhodococcus erythropolis*, and *Pseudomonas putida* Behavior in the Presence of Organic Solvents, Microsc. Res. Tech. 64:215-22, 2004.

(Continued)

*Primary Examiner* — Yong Pak

(57) ABSTRACT

Methods for the evolution of NADPH specific ketol-add reductoisomerase enzymes to acquire NADH specificity are provided. Specific mutant ketol-acid reductoisomerase enzymes isolated from *Pseudomonas* that have undergone co-factor switching to utilize NADH are described.

16 Claims, 24 Drawing Sheets

(56) References Cited

Figure 1A:
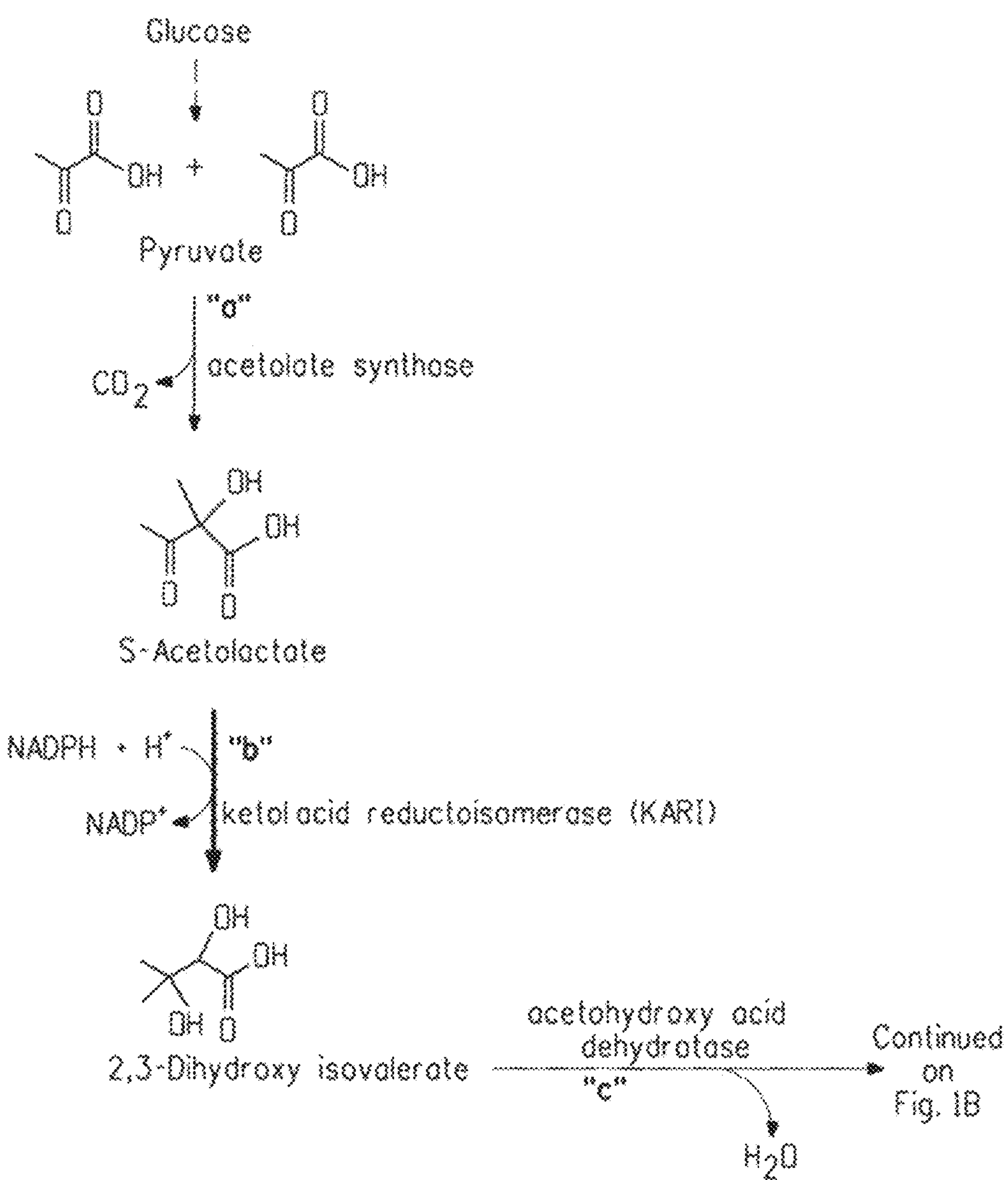

OTHER PUBLICATIONS de la Plaza, et al., Biochemical and molecular characterization of alpha-ketoisovalerate decarboxylase, an enzyme involved in the formation of aldehydes from amino acids by *Lactococcus lactis*, FEMS Microbiol. Lett. 238:367-374, 2004.
Deshpande, Ethanol Production from Cellulose by Coupled Saccharification/Fermentation using *Saccharomyces cerevisiae* and Cellulase Complex from *Sclerotium rolfsii* UV-8 Mutant, Appl. Biochem. Biotechnol. 36:227, 1992.
Dürre, et al., Solventogenic Enzymes of *Clostridium acetobutylicum*: Catalytic Properties, Genetic Organization, and Transcriptional Regulation, FEMS Microbiol. Rev. 17:251-262, 1995.
Dürre, New insights and novel developments in clostridial acetone/butanol/isopropanol fermentationAppl. Microbiol. Biotechnol. 49:639-648, 1998.
Eichenbaum, et al., Use of the Lactococcal nisA Promoter to Regulate Gene Expression in Gram-Positive Bacteria: Comparison of Induction Level and Promoter Strength, Appl. Environ. Microbiol. 64:2763-2769, 1998.
Fleming, et al., Extracellular Enzyme Synthesis in a Sporulation-Deficient Strain of *Bacillus licheniformis*, Appl. Environ. Microbiol. 61:3775-3780, 1995.
Flint, et al., The Role and Properties of the Iron-Sulfur Cluster in *Escherichia coli* Dihydroxy-acid Dehydratase, J. Biol. Chem. 268:14732-14742, 1993.
Ford, et al., Characterization of Ypr1p from *Saccharomyces cerevisiae* as a 2-methylbutyraldehyde reductase, Yeast 19:1087-1096, 2002.
Fujimoto, et al., pAM401-Based Shuttle Vectors That Enable Overexpression of Promoterless Genes and One-Step Purification of Tag Fusion Proteins Directly from *Enterococcus faecalis*, Appl. Environ. Microbiol. 67:1262-1267, 2001.
Gollop, et al., Physiological Implications of the Substrate Specificities of Acetohydroxy Acid Synthases from Varied Organisms, J. Bacteriol. 172:3444-3449, 1990.
Groot, et al., Technologies for Butanol Recovery Integrated with Fermentations, Process. Biochem. 27:61-75, 1992.
Guex, et al., Swiss-Model and the Swiss-PdbViewer: An Environment for Comparative Protein Modeling, Electrophoresis 18:2714-2723, 1997.
Hermann, et al., Isolation and Characterization of Butanol-Resistant Mutants of *Clostridium acetobutylicum*, Appl. Environ. Microbiol. 50:1238-1243, 1985.
Holtzclaw, et al., Degradative Acetolactate Synthase of *Bacillus subtilis*: Purification and Properties, J. Bacteriol. 121:917-922, 1975.
Jones, et al., Improved Methods for Building Protein Models in Electron Density Maps and the Location of Errors in these Models, Acta Crystallogr. A 47:110-119, 1991.
Kabelitz, et al., Effect of aliphatic alcohols on growth and degree of saturation of membrane lipids in *Acinetobacter calcoaceticus*, FEMS Microbiol. Lett. 220: 223-227, 2003.
Datsenko, et al., One-step inactivation of chromosomal genes in *Escherichia coli* K-12 using PCR products, Proc. Natl. Acad. Sci. USA 97:6640-6645, 2000.
Kleerebezem, et al., Controlled Gene Expression Systems for Lactic Acid Bacteria: Transferable Nisin-Inducible Expression Cassettes for *Lactococcus, Leuconostoc*, and *Lactobacillus* spp., Appl. Environ. Microbiol. 63:4581-4584, 1997.
Kostichka, et al., A small cryptic plasmid from *Rhodococcus erythropolis* : characterization and utility for gene expressionAppl. Microbiol. Biotechnol. 62:61-68, 2003.
Krogh, et al., Hidden Markov Models in Computational Biology, J. Mol. Biol. 235:1501-1531, 1994.
Larroy, et al., Characterization of the *Saccharomyces cerevisiae* YMR318C (ADH6) gene product as a broad specificity NADPH-dependent alcohol dehydrogenase: relevance in aldehyde reduction, Biochem. J. 361:163-172, 2002.
Maguin, et al., New Termosensitive Plasmid for Gram-Positive Bacteria, J. Bacteriol. 174:5633-5638, 1992.
Marinus, et al., Regulation of Isoleucine-Valine Biosynthesis in *Pseudomonas aeruginosa*, Genetics 63:547-56, 1969.
Nagarajan, et al., Modular Expression and Secretion Vectors for *Bacillus subtilis*, Gene 114:121-126, 1992.
Nakashima, et al., Isolation and Characterization of a Rolling-Circle-Type Plasmid from *Rhodococcus erythropolis* and Application of the Plasmid to Multiple-Recombinant-Protein Expression, Appl. Environ. Microbiol. 70:5557-5568, 2004.
Nallaapareddy, et al., Construction of Improved Temperature-Sensitive and Mobilizable Vectors and Their Use for Constructing Mutations in the Adhesin-Encoding acm Gene of Poorly Transformable Clinical *Enterococcus faecium* Strains, Appl. Environ. Microbiol. 72:334-345, 2006.
O'Sullivan, et al., High- and low-copy-number *Lactococcus* shuttle cloning vectors with features for clone screening, Gene 137:227-231, 1993.
Payne, et al., Use of Alkaline Phosphatase Fusions to Study Protein Secretion in *Bacillus subtilis*, J. Bacteriol. 173:2278-2282, 1991.
Renault, et al., Plasmid Vectors for Gram-positive Bacteria Swithching from High to Low Copy Number, Gene 183:175-182, 1996.
Scott, et al., Sequences of versatile broad-host-range vectors of the RK2 family, Plasmid 50:74-79, 2003.
Smit, et al., Identification, Cloning, and Characterization of a *Lactococcus lactis* Branched-Chain alpha-Keto Acid Decarboxylase Involved in Flavor Formation, Appl. Environ. Microbiol. 71:303-311, 2005.
Sulter, et al., Proliferation and metabolic significance of peroxisomes in *Candida boidinii* during drowth on D-alanine or oleic acid as the sole carbon source, Arch. Microbiol. 153:485 489, 1990.
Sulzenbacher, et al., Crystal Structure of *E. coli* Alcohol Dehydrogenase YqhD: Evidence of a Covalently Modified NADP Coenzyme, J. Mol. Biol. 342:489-502, 2004.
Tabor, et al., A bacteriophage T7 RNA polymerase/promoter system for controlled exclusive expression of specific genes, Proc. Acad. Sci. USA 82:1074, 1985.
Taghavi, et al., Electroporation of *Alcaligenes eutrophus* with (Mega) Plasmids and Genomic DNA Fragments, Appl. Environ. Microbiol. 60:3585-3591, 1994.
Tanimoto, et al., Analysis of the Conjugal Transfer System of the Pheromone-Independent Highly Transferable *Enterococcus* Plasmid pMG1: Identification of a tra Gene (traA) Up-Regulated during Conjugation, J. Bacteriol. 184:5800-5804, 2002.
Tao, et al., Construction of highly efficient *E. coli* expression systems containing low oxygen induced promoter and partition region, Appl. Microbiol. Biotechnol. 68:346-354, 2005.
Thompson, et al., Clustal W: improving the sensitivity of progressive multiple sequence alignment through sequence weighting, position-specific gap penalties and weight matrix choice, Nuc. Acid Res. 22:4673-4680, 1994.
Tomas, et al., Transcriptional Analysis of Butanol Stress and Tolerance in *Clostridium acetobutylicum*, J. Bacteriol. 186:2006-2018, 2004.
Tyagi, et al., The crystal structure of a bacterial Class II ketol-acid reductoisomerase: Domain conservation and evolution, Protein Sci. 14:3089-3100, 2005.
van Kranenburg, et al., Functional Analysis of Three Plasmids from *Lactobacillus plantarum*, Appl. Environ. Microbiol. 71:1223-1230, 2005.
Walker, et al., Isothermal in vitro amplification of DNA by a restriction enzyme/DNA polymerase systemProc. Natl. Acad. Sci. U.S.A. 89:392-396, 1992.
Wyckoff, et al., Characterization and Sequence Analysis of a Stable Cryptic Plasmid from *Enterococcus faecium* 226 and Development of a Stable Cloning Vector, Appl. Environ. Microbiol. 62:1481-1486, 1996.
Ausubel, F. M. et al., Current Protocols in Molecular Biology, published by Greene Publishing Assoc. and Wiley Interscience, 1987.
Bellion et al., Microb. Growth C1 Compd., [Int. Symp.], 7th (1993), 415 32. (eds): Murrell, J. Collin; Kelly, Don P. Publisher: Intercept, Andover, UK.
Thomas D. Brock in Biotechnology: A Textbook of Industrial Microbiology, Second Edition (1989) Sinauer Associates, Inc., Sunderland, MA.

(56) References Cited

OTHER PUBLICATIONS

Enzyme Structure and Mechanism, 2nd ed. Ferst; W.H. Freeman Press, NY, 1985; pp. 98-120.
Guide to Yeast Genetics and Molecular and Cell Biology, Part A, 2004, Christine Guthrie and Gerald R. Fink, eds., Elsevier Academic Press, San Diego, CA.
Manual of Methods for General Bacteriology, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, DC., 1994.
Sambrook, Fritsch and Maniatis, Molecular Cloning: A Laboratory Manual, Second Edition, Cold Spring Harbor Laboratory Press, Cold Spring Harbor, NY, 1989.
Silhavy et al. Experiments with Gene Fusions, Cold Spring Harbor Laboratory Press Cold Spring Harbor, NY, 1984.
Branden, et al., Introduction to Protein Structure, Garland Publishing Inc., New York, p. 247, 1991.
Kaneko, et al., Complete Genome Sequence of the Filamentous Nitrogen-fixing Cyanobacterium *Anabaena* sp. strain PCC 7120, DNA Res. 8:205-213, 227-253, 2001.
Dickinson, et al., An Investigation of the Metabolism to Isobutyl Alcohol in *Saccharomyces cerevisiae*, J. Biol. Chem. 273:25752-25756, 1998.
Oaxaca, et al., Formation of Ethanol and Higher Alcohols by Immobilized *Zymomonas mobilis* in Continuous Culture, ACTA Biotechnol. 11:523-532, 1991.
Eppink, et al., Switch of Coenzyme Specificity of p-Hydroxybenzoate Hydroxylase, J. Mol. Biol. 292:87-96, 1999.
Nakanishi, et al., Switch of Coenzyme Specificity of Mouse Lung Carbonyl Reductase by Substitution of Threonine 38 with Aspartic Acid, J. Biol. Chem. 272:2218-2222, 1997.
Kamerbeek, et al., Identifying Determinants of NADPH Specificity in Baeyer-Villiger Monooxygenases, Eur. J. Biochem. 271:2107-2116, 2004.
Nishiyama, et al., Alteration of Coenzyme Specificity of Malate Dehydrogenase from *Thermus flavus* by Site-directed Mutagenesis, J. Biol. Chem. 268:4656-4660, 1993.
Martinez-Julvez, et al., Towards a New Interaction Enzyme: Coenzyme, Biophys. Chem. 115:219-224, 2005.
Rane, et al., Reversal of the Nucleotide Specificity of Ketol Acid Reductoisomerase by Site-Directed Mutagenesis Identifies the NADPH Binding Site, Archiv. Biochem. Biophys. 338:83-89, 1997.
Ahn, et al., Crystal Structure of Class I Acetohydroxy Acid Isomeroreductase from *Pseudomonas aeruginosa*, J. Mol. Biol. 328:505-515, 2003.
Paulsen, et al., Complete genome sequence of the plant commensal *Pseudomonas fluorescens* Pf-5, Nature Biotechnol. 23:8730878, 2005.
Carugo, et al., NADP-Dependent Enzymes I: Conserved Stereochemistry of Cofactor Binding, Proteins: Structure, Function, and genetics 28:10-28, 1997.
Dumas, et al. Enzymology, Structure, and Dynamics of Acetohydroxy Acid Isomeroreductase, Acc. Chem. Res. 34:399-408, 2001.
Elmore, et al., Modification of the Nucleotide Cofactor-binding Site of Cytochrome P-450 Reductase to Enhance Turnover with NADH in vivo, J. Biol. Chem. 277:48960-48964, 2002.
Fisher, et al., The X-ray Structure of *Brassica napus* beta-keto acyl carrier protein reductase and its implication for substrate binding and catalysis, Structure 8:339-347, 2000.
Khoury, et al., Computational design of *Candida boidinii* xylose reductase for altered cofactor specificity, Protein Sci. 18:2125-2136, 2009.
Kuzuyama, et al., Characterizaton of 1-deoxy-D-xylulose 5-Phosphate Reductoisomerase, an Enzyme Involved in Isopentenyl Diphosphate Biosynthesis, and Identification of Its Catalytic Amino Acid Residues, J. Biol. Chem. 275:19928-19932, 2000.
Medina, et al., Probing the Determinants of Coenzyme Specificity in Ferredoxin-NADP+ Reductase by Site-directed Mutagenesis, J. Biol. Chem. 276:11902-11912, 2001.
Wierenga, et al., Prediction of the Occurence of the SDP-binding Beta-alpha-beta Fold in Proteins, Using an Amino Acid Sequence Fingerprint, J. Mol. Biol. 187:101-107, 1986.
Brinkmann-Chen, et al., General approach to reversing ketol-acid reductoisomerase cofactor dependence from NADPH to NADH, Proc. Natl. Acad. Sci. 110:10946-10951, 2013.
Rossmann, et al., Chemical and biological evolution of nucleotide-binding protein, Nature 250:194-199, 1974.
Curien, et al., Nucleotide sequence and characterization of a cDNA encoding the acetohydroxy acid isomeroreductase from *Arabidopsis thaliana*, Plant Molecular Biology 21:717-722, 1993.
Dumas, et al., Purification and characterization of acetohydroxyacid reductoisomerase from spinach chloroplasts, Biochem. J. 262:971-976, 1989.
Durner, et al., Ketol-Acid Reductoisomerase from Barley (*Hordeum vulgare*): Purification, Properties, and Specific Inhibition, Plant Physiol. 103:903-910, 1993.
Feeney, et al., A single amino acid substitution in lactate dehydrogenase improves the catalytic efficiency with an alternative coenzyme, Biochem. Biophys. Res. Commun. 166:667-672, 1990.
Inui, et al., Identification and sequence determination of the acetohydroxy acid isomeroreductase gene from *Brevibacterium flavum* MJ233, DNA Seq. 4:95-103, 1993.
Lauvergeat, et al., Site-directed mutagenesis of a serine residue in cinnamyl alcohol dehydrogenase, a plant NADPH-dependent dehydrogenase, affects the specificity for the coenzyme, Biochemistry 34:12426-12434, 1995.
Levskaya, et al., Synthetic biology: engineering *Escherichia coli* to see light, Nature 438:441-442, 2005.
Shiraishi, et al., Engineering of pyridine nucleotide specificity of nitrate reductase: mutagenesis of recombinant cytochrome b reductase fragment of *Neurospora crassa* NADPH:Nitrate reductase, Archives of Biochemistry and Biophysics 358:104-115, 1998.
Tyagi, et al., Probing the mechanism of the bifunctional enzyme ketol-acid reducoisomerase by site-directed mutagenesis of the active site, FEBS Journal 272:593-602, 2005.
Zhang, et al., Change of nucleotide specificity and enhancement of catalytic efficiency in single point mutants of *Vibrio harveyi* aldehyde dehydrogenase, Biochemistry 38:11440-11447, 1999.
International Search Report dated Jul. 6, 2009 for International Application No. PCT/US2008/087429.
U.S. Appl. No. 12/966,333, filed Dec. 13, 2010.
EBI Accession No. UniProt: Q8ZAC2, Entry Date Jun. 6, 2003.
EBI Accession No. UniProt: Q0AV19, Entry Date Jan. 15, 2008.
EBI Accession No. UniProt: Q02138, Entry Date Jul. 1, 1993.
EBI Accession No. UniProt: Q01292, Entry Date Apr. 1, 1993.
EBI Accession No. UniProt: P06168, Entry Date Jan. 1, 1988.
EBI Accession No. UniProt: P05793, Entry Date Nov. 1, 1988.
EBI Accession No. UniProt: B1ZV88, Entry Date Jun. 6, 2003.
She, et al., Q97YJ9—UNIPROTKB/Swiss-Prot. Database, Oct. 31, 2006.
Suerbaum, et al., UniProtKB Database, Accession Q7VGW6, 2003.
Kaneko, et al., Q8YUM—UniProt Database, Mar. 23, 2010.
GenBank No. NC_009135.1, Copeland, et al., Apr. 30, 2009; pp. 1-3.
GenBank No. NC_005791.1, Hendrickson, et al., Apr. 25, 2009, pp. 1-3.
GenBank No. NZ_AAWX01000002.1, Copeland, et al., Feb. 7, 2007; pp. 1-3.
GenBank No. NC_001144.4, Johnston, et al., Jun. 16, 2008; pp. 1-3.
GenBank No. NC_002754.1, She, et al., Apr. 26, 2009; pp. 1-3.
GenBank No. NC_003364.1, Fitz-Gibbon, et al., Apr. 24, 2009; pp. 1-3.
GenBank No. AAA25079, Peng, et al., Aug. 5, 1994; pp. 1-2.
GenBank No. AAA25161, Marugg, et al., Apr. 21, 1994; pp. 1-5.
GenBank No. AAA65614, Sokatch, Feb. 27, 2002; pp. 1-2.
GenBank No. AAA65615, Sokatch, Feb. 27, 2002; pp. 1-2.
GenBank No. AAA65617, Sokatch, Feb. 27, 2002; pp. 1-3.
GenBank No. AAA65618, Sokatch, Feb. 27, 2002; pp. 1-3.
GenBank No. AAS49166, Smit, et al., Dec. 27, 2004; pp. 1-5.
GenBank No. AJ746364, de la Plaza, et al., Apr. 15, 2005; pp. 1-4.
GenBank No. AY548760, Smit, et al., Dec. 27, 2004; pp. 1-2.
GenBank No. BX957219 obsolete and replaced by BX950229, Hendrickson, et al., May 8, 2008; pp. 1-369.

(56) References Cited

OTHER PUBLICATIONS

GenBank No. CAB14105, Kunst, et al., Oct. 1, 2009; pp. 1-10.
GenBank No. CAB14334, Kunst, et al., Oct. 1, 2009; pp. 1-4.
GenBank No. CAB14335, Kunst, et al., Oct. 1, 2009; pp. 1-4.
GenBank No. CAB14336, Kunst, et al., Oct. 1, 2009; pp. 1-4.
GenBank No. CAB14337, Kunst, et al., Oct. 1, 2009; pp. 1-4.
GenBank No. CAB15618, Kunst, et al., Oct. 1, 2009; pp. 1-9.
GenBank No. CAF29874, Hendrickson, et al., May 8, 2008; pp. 1-7.
GenBank No. CAG34226, de la Plaza, et al., Apr. 15, 2005; pp. 1-3.
GenBank No. L16975, Marugg, et al., Apr. 21, 1994; pp. 1-3.
GenBank No. M57613, Madhusudhan, et al., Feb. 27, 2002; pp. 1-7.
GenBank No. M73842, Peng, et al., Aug. 5, 1994; pp. 1-2.
GenBank No. NC__001142, Comman, et al., Jun. 9, 2009; pp. 1-2.
GenBank No. NC__003030, Nolling, et al., Oct. 22, 2009; pp. 1-653.
GenBank No. NC__001136, Jacq, et al., Dec. 9, 2009; pp. 1-216.
GenBank No. NC__001145, Bowman, et al., Dec. 9, 2009; pp. 1-351.
GenBank No. NC__001988, Nollings, et al., Apr. 26, 2009; pp. 1-147.
GenBank No. NC__003197, McClelland, et al., Mar. 30, 2010; pp. 1-186.
GenBank No. NP__012550, Goffeau, et al., Nov. 5, 2009, pp. 1-10.
GenBank No. NP__010656, Jacq, et al., downloaded Apr. 15, 2010, pp. 1-3.
GenBank No. NP__014051, Bowman, et al., Dec. 9, 2009, pp. 1-3.
GenBank No. NP__149189, Nolling, et al., Apr. 26, 2009; pp. 1-7.
GenBank No. NP__349892, Nolling, et al., Apr. 14, 2010; pp. 1-3.
GenBank No. NP__417484, Riley, et al., Apr. 9, 2010; pp. 1-5.
GenBank No. NP__461346, McClelland, et al, Apr. 30, 2009; pp. 1-8.
GenBank No. YP__026248, Riley, et al., Jul. 30, 2009; pp. 1-4.
GenBank No. Z99115 obsolete and replaced by AL009126, Kunst, et al., Nov. 15, 2007; pp. 1-114.
GenBank No. Z99116 obsolete and replaced by AL009126, Kunst, et al., Oct. 1, 2009; pp. 1-382.
GenBank No. Z99122 obsolete and replaced by AL009126, Kunst, et al., Apr. 18, 2005; pp. 1-112.
GenBank No. ZP__01224863.1, Mar. 24, 2006; pp. 1-2.
GenBank No. NC__003295.1, Salanoubat, et al., May 1, 2009; pp. 1-3.
GenBank No. NC__002516, Winsor, et al., Jun. 24, 2009; pp. 1-3.
GenBank No. NC__004129, Winsor, et al., Jun. 24, 2009; pp. 1-3.
GenBank No. O82043, Gu, et al., Jun. 16, 2009; pp. 1-3.
GenBank No. NP__977840.1, Rasko, et al., May 1, 2009; pp. 1-3.
GenBank No. NP__978252.1, Rasko, et al., May 1, 2009; pp. 1-3.
GenBank No. P05793, Daniels, et al., Jun. 16, 2009; pp. 1-9.
GenBank No. ZP__01313517.1, Copeland, et al., May 15, 2006; pp. 1-3.
Entrez GenBank Accession No. UNIPROT: Q4K608, Paulsen, et al., Apr. 2006.
Entrez GenBank Accession No. UNIPROT: Q6F821, Barbe, et al., Oct. 2004; pp. 1-2.

| Sequence ID | | |
|---|---|---|
| 17 | (44) | VGLRKGSATVAKA |
| 16 | (44) | VGLRSGSATVAKA |
| 18 | (162) | IGLRKGSNTFAEA |

FIG. 2A

| Sequence ID | | |
|---|---|---|
| 9 | (44) | VGLRKNGASWENAK |
| 10 | (44) | VGLRKNGASWNNAK |
| 11 | (44) | VGLRKNGASWENAK |
| 17 | (44) | VGLRKGSATVAKAE |
| 15 | (44) | VGLRKNGASWNKAV |
| 12 | (44) | IGVRKDGASWKAAI |
| 13 | (44) | VGLEREGKSWELAK |
| 14 | (44) | IGLRRGGKSWELAT |
| Consensus | | VGLRKNGASWE AK |

FIG. 2B

```
Sequence ID
                51                                                100
47      (18)  ~~~~KKVAIIGYDSQGHAHAQNLRD~~~~~~NGFDVVVGLRKG-KSWDKA
48      (17)  ~~~~KTVAVIGYGSQGHAQAQNLRD~~~~~~SGVEVVVGVRPG-KSFEVA
18      (51)  FKQIKQIGVIGWGSQAPAQAQNLKDSLTEAKSDVVVKIGLRKGSNSFAEA
16      (17)  ~~~~EKVAIIGYGSQGHAHACNLKD~~~~~~SGVDVIVGLRSGSATVAKA
17      (17)  ~~~~EKVAIIGYGSQGHAQACNLKD~~~~~~SGVDVIVGLRKGSATVAKA

                101                                               150
47      (57)  KEDGFE~~~~~VYTVAEAAKQADVVMILLPDELQPEVYEAEIAPNLQAGN
48      (56)  KTDGFE~~~~~VMSVSEAVKTAQVVQMLLPDEQQAHVYKAGVEENLAEGQ
18      (101)  KANGFSEENGTLGDMWETIKGSDLVLLLISDSAQADNYEKVFSHMK-PNS
16      (57)  EAHGLK~~~~~VADVKTAVAAADVVMILTPDEFQGRLYKEEIEPNLKKGA
17      (57)  EAHGLK~~~~~VTDVAAAVAGADLVMILTPDEFQSQLYKNEIEPNIKKGA

                151                                               200
47      (102)  SLVFAHGFNVHFDQVK~~~SPANVDVFLVAPKGPGHLVRRTFSEG~~~~~
48      (101)  MLLFSHGFNIHFGQIN~~~SPSYVDVAMVAPKSPGHLVRRVFQEG~~~~~
18      (150)  ILGLSHGFLLGHLQSLGQDFPKNISVIAVCPKGMGPSVRRLYVQGKEVNG
16      (102)  TLAFAHGFSIHYNQVV~~~ERADLDVIMIAPKAPGHTVRSEFVKG~~~~~
17      (102)  TLAFSHGFAIHYNQVV~~~ERADLDVIMIAPKAPGHTVRSEFVKG~~~~~

                201                                               250
47      (144)  GAVPALFAVYQDATGVATEKALSYAQGLGATRAGVLETTFKEETETDLFG
48      (143)  NGVPALVAVHQDATGTALRVALAYAKGVGCTRAGVIETTFQEETETDLFG
18      (200)  AGINSSFAVHQDVDGRATDVALGWSIALG~~SPFTFATTLEQEYKSDIFG
16      (144)  GGIPDLIAIYQDASGNAKNVALSYACGVGGGRTGIIETTFKDETETDLFG
17      (144)  GGIPDLIAIYQDASGNAKNVALSYAAGVGGGRTGIIETTFKDETETDLFG
```

FIG. 8

```
Sequence ID
                   10        20        30        40        50        60
           ....|....|....|....|....|....|....|....|....|....|....|....|
17         ------------------------------------------------------------
43         ------------------------------------------------------------
44         ------------------------------------------------------------
16         ------------------------------------------------------------
35         ------------------------------------------------------------
39         ------------------------------------------------------------
41         ------------------------------------------------------------
38         ------------------------------------------------------------
15         ------------------------------------------------------------
40         ------------------------------------------------------------
42         ------------------------------------------------------------
37         ------------------------------------------------------------
46         ------------------------------------------------------------
34         ------------------------------------------------------------
36         ------------------------------------------------------------
33         ------------------------------------------------------------
13         ------------------------------------------------------------
30         ------------------------------------------------------------
14         ------------------------------------------------------------
32         ------------------------------------------------------------
31         ------------------------------------------------------------
47         ------------------------------------------------------------
48         ------------------------------------------------------------
18         MAATAATTFSLSSSSSTSAAASKALKQSPKPSALNLGFLGSSSTIKACRSLKAARVLPSG
```

FIG. 9A

```
Sequence ID
                   70        80        90        100       110       120
         ....|....|....|....|....|....|....|....|....|....|....|....|
17       -----------M------------------KVFYDKDCDLS------IIQG---------
43       -----------M------------------KVFYDKDCDLS------IIQG---------
44       -----------M------------------KVFYDKDCDLS------IIQG---------
16       -----------M------------------KVFYDKDCDLS------IIQG---------
35       -----------M------------------QVYYDKDADLS------IIQG---------
39       -----------M------------------QVYYDKDCDLS------IIQG---------
41       -----------M------------------KVYYDKKCDLS------IIQG---------
38       -----------M------------------NVYYDKDCDLS------IVQG---------
19       -----------M------------------KVFYDKDADLS------LING---------
40       -----------M------------------KVYYDKDADLS------LIKQ---------
42       -----------M------------------KVFYDKDCDLS------IIQG---------
37       -----------M------------------QVYYDKKCDLS------IIQG---------
46       -----------M------------------KVFYDKDCDLS------IIQG---------
34       -----------M------------------KVYYDSDADLG------LIKS---------
36       -----------M--------------A--VSIYYDKDCDIN------LIKS---------
33       -----------M------------------RVYYDRDADVN------LIKS---------
13       -----------M--------------KCTSKIYTDNDANLD------LIKG---------
30       -----------M--------------TD-ATIVYDDDAEST------VLDG---------
14       -----------M--------------A---KIYTDAEASLE------PLKG---------
32       -----------M--------------A--IELLYDADADLS------LIQG---------
31       -----------M--------------V---KVYYNSDIKEN------VLAG---------
47       -----------M--------------A---KVYYEKDVTVN------VLKS---------
48       -----------M-------------------KTYYEKGNVS------LLNG---------
18       ANSGQSALSAQMVEAPSINTPSATTFDFDSSVFKKENVTLSGNDSYIVSSGPNLFPLLPD
```

FIG. 9B

```
Sequence ID
                 130       140       150       160       170       180
         ....|....|....|....|....|....|....|....|....|....|....|....|
17       -----KKVAIIGYGSQGHAQACNLKDS------GV-DVTVGLRKGSATVAKAEAHGLK--
43       -----KKVAIIGYGSQGHAQACNLKDS------GV-DVTVGLRKGSATVAKAEAHGLK--
44       -----KKVAIIGYGSQGHAQACNLKDS------GV-DVTVGLRKGSATVAKAEAHGLK--
16       -----KKVAIIGYGSQGHAHACNLKDS------GV-DVTVGLRSGSATVAKAEAHGLK--
35       -----KKVAVIGYGSQGHAHAMNLKES------GV-DVVVGLREGSSSAAKAQKAGLA--
39       -----KKVAIIGYGSQGHAHAMNLKDS------GV-DVCVGLRKGSGSWAKAENAGLA--
41       -----KKVAIIGYGSQGHAHACNLKDS------GV-DVTVGLRAGSASVAKAEAHGLT--
38       -----KKVAIIGYGSQGHAHAINLQDS------NV-DVTVGLRADSGSWKKAENAGLK--
15       -----KNVTIIGYGSQGHAHALNLNDS------GV-NVTVGLRENGASWNKAVNAGLQ--
40       -----KKVAIVGYGSQGHAHAMNLKDS------GV-DVTVALRPGSASAKKAENAGLT--
42       -----KKVAIIGYGSQGHAQACNLKDS------GV-DVTVGLRKGSATVAKAEAHGLK--
37       -----KKVAIIGYGSQGHAHACNLKDS------GV-DVVVGLRRGSSSIAKAEAYGLK--
46       -----KKVAIIGYGSQGHAQACNLKDS------GV-DVTIGLRKGSATVAKAEAHGLK--
34       -----KKIAIIGYGSQGHAHACNLRDS------GVAEVAIALRPGSASVKKAQDAGFK--
36       -----KKVAIIGYGSQGHAHAMNLRDS------GV-EVTIGLREGGQSWAKAQKAGFT--
33       -----KKVAVIGYGSQGHAHVINLRDS------GVKDVAVALRPGSASIEKAEAEGLK--
13       -----KHIAVIGYGSQGHAHACNLRDS------GL-NVVVGLREGKSWELAKSDGIT--
30       -----KTVAVIGYGSQGHAHAQNLRDS------GV-DVVVGLREDSSSRSKAEADGLD--
14       -----KTIAVIGYGSQGHAQALNLRDS------GL-EVTIGLRRGGKSWELATSEGFR--
32       -----KKVAIVGYGSQGHAHSQNLRDS------GV-EVVIGLREGSKSAEKAKEAGFE--
31       -----KTVAVIGYGSQGHAHALNLKES------GV-DVTVGVRQGK-SFTQAQEDGRK--
47       -----KKVAIIGYGSQGHAHACNLKDN------GF-DVVVGLRKGN-SWDKAKEDGFS--
48       -----KTVAVIGYGSQGHADAQNLRDS------GV-EVVVGVRPGK-SFEVAKTDGFE--
18       AFKGIKQIGVIGWGSQAPAQAQNLKDSLTEAKSDV-VVKIGLRKGSNSFAEARAAGFSEE
         *       *                         *  *  **        *
         GXGXX(G/A)
```

FIG. 9C

```
Sequence ID          190       200       210       220       230       240
                ....|....|....|....|....|....|....|....|....|....|....|....|
17           ---VTDVAAAVAGADLVMILIPDEFQSQLYKNEIEPNIKKGATLAFSHGFAIHYNQVVPR
43           ---VTDVASAVAAADLVMILTPDEFQSQLYKNEVEPNLKPGATLAFSHGFAIHYNQVVPR
44           ---VADVATAVAAADLVMILIPDEFQSALYKNEIEPNIKKGATLAFSHGFSIHYNQVVPR
16           ---VADVKTAVAAADVVMILTPDEFQGRLYKEDIEPNLKKGATLAFAHGFSIHYNQVVPR
35           ---VASIEDAAAQADVVMILAPDEHQAVIYHNQIAPNVKPGAAIAFAHGFNIHFGQIQPA
39           ---VKEVAEAVAGADVVMILIPDEFQAQLYKSEIEPNLKSGATLAFAHGFSIHYNQIVPR
41           ---VKSVKDAVAAADVVMILTPDEFQGRLYKDEIEPNLKKGATLAFAHGFSIHYNQVVPR
38           ---VAEVEEAVKAADIIMILIPDEFQKELYNDVIEPNIKQGATLAFAHGFAIHYNQVIPR
15           ---VKDVAEAVKDADVVMILLPDEQIADVYKNEVHGNIKQGAALAFAHGFNVHYGAVIPR
40           ---VKSVPEAVAGADLVMILIPDEFQSRLYRDEIEPNIKQGATLAFAHGFSIHYNQVVPR
42           ---VTDVASAVAAADLVMILIPDEFQSQLYKNEVEPNLKKGATLAFSHGFAIHYNQVVPR
37           ---TEDVASAVASADVVMVLTPDEFQAQLYKDEIEPNLKQGATLAFAHGFAIHYNQIVPR
46           ---VTDVATAVAAADLVMILIPDEFQGQLYKQEIEPNIKKGATLAFSHGFAIHYNQVVPR
34           ---VLTNAEAAKWADILMILAPDEHQAAIYADDLHDNLRPGDAIAFAHGLNIHFGLIEPR
36           ---VKSVKEATKEADLIMILAPDEIQSEIFNEEIKPELKAGKTLAFAHGFNIHYGQIVAP
33           ---VLTPADAAAWADVVMILTPDELQADLYKSELAANLKPGAALVFAHGLAIHFKLIEAR
13           ---FLHTKQAVKDADIIIILVPDNVQPTLWLESVQPYMKKGADLVFAHGFNIHYKLIDPP
30           ---VATPKGAAEQADLVSVLVPDEVQEAVYE-QIEDVLQPGDTLQFAHGFNIHYGQIEPS
14           ---VYRIGEAVRKADVILVLIPDMRQPKVWQDQIAPNLKEGVVVDFAHGFNVHFGLIKPP
32           ---VKTTAEAAAWADVIMILAPDTSQAEIFTNDIEPNLNAGDALLFGHGLNIHFDLIKPA
31           ---VFSVKEAAAQAEIIMILLPDEQQQKVYEAEIKDELTAGKSLVFAHGFNVHFHQIVPP
47           ---VITVAEAAKQADVVMILLPDELQPEVYEAEIAPNLQAGNSLVFAHGFNVHFDQVKPP
48           ---VMSVEEAVATAQVVQMLAPDTQQAHVYKAGVEESLREGQMLLFSHGFNIHFGQINPP
18           NGTLGDNWETIDGSDLVLLLISDSAQAQNYD-KVFSHMKPNSILGLSHGFLLGHLQSLGQ
```

FIG. 9D

```
Sequence ID
                  250       260       270       280       290       300
         ....|....|....|....|....|....|....|....|....|....|....|
17       A---DLQVVNMIAPKAKGHTVRSEFVKG------GGIPDLIAIYQDASGNAKDVALSYAAGV
43       A---DLQVINMIAPKAKGHTVRTEFVKG------GGIPDLIAVYQDASGNAQDVALSYASGV
44       A---DLQVVNMIAPKAKGHTVRSEFVKG------GGIPDLIAIYQDASGNAKDVALSYASGV
16       A---DLQVVNMIAPKAKGHTVRSEFVKG------GGIPDLIAIYQDASGNAKNVALSYAGGV
35       A---DLIVVNMVAPKGPGHLVRSTYVEG------GGVPSLIAIHQDATGNAKDIALSYASAR
39       A---DLQVVNMIAPKAKGHTVRSEFVKG------GGIPDLIAIYQDASGNAKDLALSYASGV
41       A---DLIVVNMIAPKAPGHTVRSEFVRG------GGIPDLIAVYQDASGNAKNLALSYAGGV
38       S---DLIVVNMVAPKAKGHTVRSEFAKG------GGIPDLIAIYQDASGQAKQLALSYAAGV
15       A---DLIVVNMVAPKAKGHTVRSTYAQG------GGVPHLIAVHQDXSGNAKDIALSYATAN
40       A---DLIVVNMIAPKAKGHTVRSEFVKG------GGIPDLIAIYQDASGNAKETALSYASAI
42       A---DLIVVNMIAPKAKGHTVRTEFVKG------GGIPDLIAVYQDASGNAKNVALSYASGV
37       K---DLIVVNMVAPKAKGHTVRTEFTKG------GGIPDLIAIYQDASGNAKNVALSYASGI
46       A---DLIVVNMIAPKAKGHTVRSEFVKG------GGIPDLIAIYQDASGNAKNVALSYASGV
34       K---DIIVVNMIAPKGKGHTVRSEYVRG------GGVPCLVAVYQDASGNAKDIALAYASGI
36       K---GIDVVNMIAPKAKGHTVRREFSIG------GGTPCLIAIHQDESKNAKNLALSYASAI
33       A---DLIVVTMVAPKSHGKTVRSEYLKG------GGVPCLVAVHQNPTGNALELALSYASAI
13       K---DSDVVNMIAPKGKGPTVRSTYKAG------GGVPALVAVHQDVSSTALHKALAIAKGI
30       E---DVNVVNMVAPKSHGHLVRRNYEND------EGTPGLIAVYQEPSGEAHQLALAYAKAI
14       K---NIDVVNMVAPKAKGKAVRSEYLAG------RGVPALVAVYQDYGGQALKYALALAKGI
32       D---GIIVVDMVAPKGKGHLVRPQFVDG------KGVPCLIAVHQDPTGEAQALILSYAAAI
31       A---DVIVVFLVAPKSPGHLVRRTYEQG------AGVPALIAIYQDVTGEAKDKALAYAKGI
47       A---NVINVFLVAPKSKGHLVRRTFSEG------GAVPALSAVYQDATGVAIEKALSYADGI
48       S---YVDVRMVAEISNSHLVERVEQEG------NGVPALVAVHQDATGTALHVALAYAKGV
18       DFPKNISVIAVCPKGMGPSVRRLYVQGKEVNGAGINSSFAVHQDVDGRATDVALGWSIAL
         *             *
```

FIG. 9E

```
Sequence ID
                310       320       330       340       350       360
       ....|....|....|....|....|....|....|....|....|....|....|....|
17     GGGRTGIIETTFKDEIETDLFGEQAVLCGGTVELVKAGFETLVEAGYAPEMAYFECLHEL
43     GGGRTGIIETTFKDEIETDLFGEQAVLCGGTVELVKAGFETLVEAGYAPEMAYFECLHEL
44     GGGRTGIIETTFKDEIETDLFGEQAVLCGGTVELVKAGFETLVEAGYAPEMAYFECLHEL
16     GGGRTGIIETTFKDEIETDLFGEQAVLCGGCVELVKAGFETLVEAGYAPEMAYFECLHEL
35     GGGRAGVIETSFREEIETDLFGEQAVLCGGITSLIQAGFETLVEAGYAPEMAYFECLHET
39     GGGRTGIIETTFKDEIETDLFGEQAVLCGGAVELVKAGFETLVEAGYAPEMAYFECLHEL
41     GGGRTGIIETTFKDEIETDLFGEQAVLCGGCVELVKAGFETLVEAGYAPEMAYFECLHEL
38     GGGRSGIIETTFKDEIETDLFGEQAVLCGGAVELVKMGFETLTEAGYAPEMAYFECLHEL
15     GGGRAGIIETNFREEIETDLFGEQAVLCGGTVELIKAGFETLVEAGYAPEMAYFECLHEL
40     GGGRTGIIETTFKDEIETDLFGEQAVLCGGAVELVKAGFDTLVEAGYAPEMAYFECLHEL
42     GGGRTGIIETTFKDEIETDLFGEQAVLCGGTVELVKAGFETLVEAGYAPEMAYFECLHEL
37     GGGRTGIIETTFKDEIETDLFGEQAVLCGGAVELVKAGFETLTEAGYAPEMAYFECLHEL
46     GGGRTGIIETTFKDEIETDLFGEQAVLCGGTVELVKAGFETLVEAGYAPEMAYFECLHEL
34     GGGRSGVIETTFREEVETDLFGEQAVLCGGLTALITAGFETLTEAGYAPEMAFFECMHEM
36     GGGRTGIIETTFKAEIETDLFGEQAVLCGGLSALIQAGFETLVEAGYEPEMAYFECLHEM
33     GGGRSGIIETTFREECETDLFGEQVVLCGGLSKLIQYGFETLVEAGYAPEMAYFECLHEV
13     GATRAGVIETTFKEEIETDLFGEQVILMGGIMELMRAAFETLVEEGYQPEVAYFETINEL
30     GCTRAGVVETTFREEIETDLFGEQAVLCGGVTSLVKTGYETLVDAGYSPEMAYFECLNEL
14     GATRAGVIETTFAEEIETDLIGEQIVLMGGLMELIKKGFEVLVEMGYQPEVAYFEVLNEA
32     GGARAGVIETTFEAEIVTDLFGEQAVLCGGTEELVKVGFEVLTEAGYEPEMAYFEVLHEL
31     GGARAGVLETTFKEEIETDLFGEQAVLCGGLSALVKAGFETLTEAGYQPELAYFECLHEL
47     GATRAGVLETTFKEEIETDLFGEQAVLCGGVTALVKAGFETLVDAGYQPELAYFECLHEL
48     GCTRAGVIETTFQEEIETDLFGEQTVLCGGVTALVKAGFETLTEGGYRPEIAYFECLHEL
18     GSPF--TFATTLEQEYKSDIFGERGILLGAVHGIVECLFRRYTESGMSEDLAYKNTVECI
```

FIG. 9F

| Sequence ID | 370 380 390 400 410 420 |
| --- | --- |
| 17 | K-LIVDLMYEGGLADMNYGISNNAEYGEYVTGPEVINAESRQAMPNALKPIQGGEYAKMF |
| 43 | K-LIVDLMYEGGLANMNYGISNNAEYGEYVTGPEVINAESRQAMANALKRIQGGEYAKMF |
| 44 | K-LIVDLMYEGGLANMNYGISNNAEYGEYVTGPEVINEESRKAMPNALKRIQGGEYAKMF |
| 16 | K-LIVDLMYEGGLANMNYGIGNNAEYGEYVTGPEVINAESRAAMPNALKRIQGGEYAKMF |
| 35 | K-LIVDLLYQGGLANMKYGISNTADYGDFTKGPKVINEEGREAMEEILAEIQGGEFAPEF |
| 39 | K-LIVDLMYEGGLANMNYGISNNAEYGEYVTGPEVINEQGRAAMPNALKRIQGGEYAKMF |
| 41 | K-LIVDLMFEGGLANMNYGISNDAEYGEYVTGPEVINEQSRQAMRDALKRIQGGEYAKMF |
| 38 | K-LIVDLMYEGGLADMNYGISNNAEYGEYVTGPEVIGEQGREAMPNALKRIQGGDYAKMF |
| 15 | K-LIVDLIYEGGIGNMNYGIGNNAEYGEYVTSPRVVTAETKQAMKQCLIDIQTGEYAKSF |
| 40 | K-LIVDLMYEGGLANMNYGISGNAEYGEYVTGVKVINEQGRAAMKECLAEIQKGAYAKKF |
| 42 | K-LIVDLMYEGGLANMNYGISNNAEYGEYVTGPEVINAESRQAMPNALKRIQGGEYAKMF |
| 37 | K-LIVDLMYEGGLANMNYGISNNAEYGEYVTGPEVINEQSREAMRNALKRIQGGEYAKMF |
| 46 | K-LIVDLMYEGGLANMNYGISNNAEYGEYVTGPEVIGEEGRKAMPNALKPIQGGEYAKMF |
| 34 | K-LIVDLIYEAGLANMRYGIGNTAEYGDIVSGPRVINEESKNAMKAILDDIQSGRFVGKF |
| 36 | K-LIVDLIYQGGLADMRYGVSNTAEYGDYITGPKIITKETKEAMKGVLKDIQNGEFAKDF |
| 33 | K-LIVDLIYEGGLANMRYGISNTAEYGDYVTGSRIITEATKASMKRVLADIQSGRFVRDW |
| 13 | K-MLVDLVYEMGISGMLMAVSDTAKYGGMTVGKFVIDESVRKPNKEALQRIKSGKFADEW |
| 30 | K-LIVDLMYEGGVGDMWRGVSDTAEYGGLTEGDEIVDDHAREKMEEVLEEVQNGTFAKDW |
| 14 | K-LIMDLIWQHGIYGMLAGVSDTAKYGGLTVGPAVIGDVRRKMKEAAMRVKSGEFAKEW |
| 32 | K-LIVDLMFEGGISNMNYGVSDTAEFGGYLSGPRVIDAQTKSRMEDILTDIQSGTFTKEL |
| 31 | K-LIVDLMYEGGLAGMRYGISDTAQWGDFVSGPRVVDAKVKESMKEVLKDIQNGTFAKEW |
| 47 | K-LIVDLMYEGGLAEMRYGVSDTAQWGDFVSGPRVVTEDTKKAMGTVLAEIQSGTFARGW |
| 48 | K-LIVDLMYEGGLTNMRKGIGDTAEFGDYVTSGPIVTDETKKEMKRVLTEIQKGEFAKEW |
| 18 | TGVISKTISTHGKLALYHSLSEEGKK-DFQAAYSASYYPSMGILYECIEDVADGGEIRSV |

FIG. 9G

```
Sequence ID
                        430       440       450       460       470       480
                ....|....|....|....|....|....|....|....|....|....|....|....|
17              ISEGATGYP~~SMTAKRRNDAAHGIE~IISEQLRSMMPWIGANKIVDKAKN~~~~~~~~~
43              ITEGATGYP~~SMTAKRRNNAEHSID~VIGEKLREMMPWIAANKIVDKDKD~~~~~~~~~
44              ISEGATNYP~~SMTAKRRNDAAHGIE~IISEQLRSMMPWISANKIVDKTKN~~~~~~~~~
16              ITEGAANYP~~SMTAYRRNNAAHPIE~QISEKLRAMMPWIAANKIVDKSKN~~~~~~~~~
35              VLENQASGP~~TLTARRELAASHEIE~VVGERLRQMMPWINANKLVDKDKN~~~~~~~~~
39              IAEGARNYP~~SMTAYRRNDAAHPIE~QVSERLRSMMPWIASNKIVDKGKN~~~~~~~~~
41              ITEGAANYP~~SMTAYRRNNAAHQIE~VVGEKLRTMMPWIAANKIVGKTKD~~~~~~~~~
38              ISEGATNYP~~SMTARRRNDAEHQIE~ITGAKLRQMMPWIGGNKIIDKDKN~~~~~~~~~
15              LLENKAGAP~~TLISARRLTADHQIE~QVGAKLRAMMPWIAKNKLVDQSKN~~~~~~~~~
40              ILEGQANYP~~EMTAWRENNAAHQIE~VVGAKLREMMPWIAANKLVDHSKN~~~~~~~~~
42              ISEGATGYP~~SMTAKRRNDAAHGIE~IISEKLRSMMPWIAANKIVDKDKN~~~~~~~~~
37              IDEGALNYP~~SNTARRRQNAAHEIE~TVGEKLRSMMPWISANKIVGKDKD~~~~~~~~~
46              ISEGATNYP~~SMTAKRRNDAAHGIE~IISEQLRSMMPWISANKIVDKTKN~~~~~~~~~
34              VLDNHAGQP~~ELKAARKENAAHPIE~QVSARLRQMMPWIASNKLVDKARN~~~~~~~~~
36              ILERRANFA~~RMHADRKLMNDSLIE~KTGREIRRMMPWISAKKLVDKGKN~~~~~~~~~
33              MLECKAGQP~~SFKATRRIQKEHVIE~VVGEKLRQMMPWISKNKLVDKARN~~~~~~~~~
13              VEEYGRGMP~~TVVNGLSNVQNSLEE~KIGTQLRDLVQK~~~~~~GKPKS~~~~~~~~~
30              ISENQAGRP~~SYKQLRAAEKNHDIE~AVGEDLRALFAW~~~~~~GDD~~~~~~~~~~~
14              VEEYNRGAP~~TLEKLMEEARTHPIE~KVGEEMRKLLF~~~GP~~~~~~~~~~~~~~~~
32              IANVENGNT~~ELEGLKASYNNHFIE~ETGAKLRDLMSWVKYDAHAETA~~~~~~~~~~~
31              IVENQVNRP~~RFNAIRAGENSHQID~VVGRKLREMMPFVKQGRKEEAVVSVAQN~~~~~
47              IAERKAGRP~~NFHATNEKSNEHEIE~VVGRKIAEMMPFV~QPAVKVGNR~~~~~~~~~
48              ILENQAGRP~~TYNANKKAEQNHQLE~KVGAELREMMSWIDAPKELVRK~~~~~~~~~~
18              VLAGRRFYEKEGLPAFPMGKIDQTRMWKVCEKVRSVRF~~AGD~~LGPLYPFTAGVYVAL
```

FIG. 9H

```
Sequence ID
                    490       500       510       520       530       540
            ....|....|....|....|....|....|....|....|....|....|....|....|
17          ------------------------------------------------------------
43          ------------------------------------------------------------
44          ------------------------------------------------------------
16          ------------------------------------------------------------
35          ------------------------------------------------------------
39          ------------------------------------------------------------
41          ------------------------------------------------------------
38          ------------------------------------------------------------
15          ------------------------------------------------------------
40          ------------------------------------------------------------
42          ------------------------------------------------------------
37          ------------------------------------------------------------
46          ------------------------------------------------------------
34          ------------------------------------------------------------
36          ------------------------------------------------------------
33          ------------------------------------------------------------
13          ------------------------------------------------------------
30          ------------------------------------------------------------
14          ------------------------------------------------------------
32          ------------------------------------------------------------
31          ------------------------------------------------------------
47          ------------------------------------------------------------
48          ------------------------------------------------------------
18          MMAQIEILRKKGHSYSEIINESVIEAVDSLNPFMHARGVSFMVDNCSTTARLGSRKWAPR
```

FIG. 9I

```
Sequence ID
                     550       560       570       580       590       600
            ....|....|....|....|....|....|....|....|....|....|....|....|
17          ------------------------------------------------------------
43          ------------------------------------------------------------
44          ------------------------------------------------------------
16          ------------------------------------------------------------
35          ------------------------------------------------------------
39          ------------------------------------------------------------
41          ------------------------------------------------------------
38          ------------------------------------------------------------
15          ------------------------------------------------------------
40          ------------------------------------------------------------
42          ------------------------------------------------------------
37          ------------------------------------------------------------
46          ------------------------------------------------------------
34          ------------------------------------------------------------
36          ------------------------------------------------------------
33          ------------------------------------------------------------
13          ------------------------------------------------------------
30          ------------------------------------------------------------
14          ------------------------------------------------------------
32          ------------------------------------------------------------
31          ------------------------------------------------------------
47          ------------------------------------------------------------
48          ------------------------------------------------------------
18          FDYILSQQALVAVDNGAPINQQLISNFLSDPVHEAIGVCAQLRFSVDISVTADADFVRPE
```

FIG. 9J

| | Sequence ID |
|---|---|
| .... | |
| ---- | 17 |
| ---- | 43 |
| ---- | 44 |
| ---- | 16 |
| ---- | 35 |
| ---- | 39 |
| ---- | 41 |
| ---- | 38 |
| ---- | 15 |
| ---- | 40 |
| ---- | 42 |
| ---- | 37 |
| ---- | 46 |
| ---- | 34 |
| ---- | 36 |
| ---- | 33 |
| ---- | 13 |
| ---- | 30 |
| ---- | 14 |
| ---- | 32 |
| ---- | 31 |
| ---- | 47 |
| ---- | 48 |
| LRQA | 18 |

FIG. 9K

```
                         *->gMfafskVYYDkDadlsGhdsylihGKkVAvIGYGSQGHAHAqNLrD
                              M    kV+YDkD+dls     +i+GKkVA+IGYGSQGHA+A+NL+D
Sequence ID 17       1     -M----KVFYDKDCDLS-----IIQGKKVAIIGYGSQGHAQACNLKD 37

                           SGVdVvVGlRkGsaSwakAeaaGfkVktvaEAvaqADvVmiLlPDefQse
                           SGVdV+VGlRkGsa++akAea+G+kV +va Ava+AD+VmiL+PDefQ++
Sequence ID 17      38     SGVDVTVGLRKGSATVAKAEAHGLKVTDVAAAVAGADLVMILTPDEFQSQ 87

                           vYeesIepnLkpGatLaFAHGFNIHfgqIvPrafPkDiDViMVAPKgPGH
                           +Y++eIepn+k+GatLaF+HGF+IH++q+vPra   D+DViM+APK+PGH
Sequence ID 17      88     LYKNEIKPNIKKGATLAFSHGFAIHYNQVVPRA---DLDVIMIAPKAPGH 134

                           tVRreYvkGgGVPaLiAVyQDasGnAkdlALsYAkgiGggRAGvIETTFk
                           tVR+e+vkGgG+P+LiA+yQDasGnAk++ALsYA+g+GggR+G+IETTFk
Sequence ID 17     135     TVRSEFVKGGGIPDLIAIYQDASGNAKNVALSYAKGVGGGRTGIIETTFK 184

                           eETETDLFGEQaVLCGGvteLVkaGFETLVEaGYaPEmAYFECLHElKLI
                           +ETETDLFGEQaVLCGG++eLVkaGFETLVEaGYaPEmAYFECLHElKLI
Sequence ID 17     185     DETETDLFGEQAVLCGGTVELVKAGFETLVEAGYAPEMAYFECLHELKLI 234
```

FIG. 10A

```
                          VDLmYEgGIanMrySiSdTAeYGdyvtGprVIdeeskeaMkevLkdIQsG
                          VDLmYEgGIanM+ySiS++AeYG+yvtGp+VI++es++aM+++Lk+IQ+G
Sequence ID 17       235 VDLMYEGGIANMNYSISNNAEYGEYVTGPEVINAESRQAMRNALKRIQDG 284

                          eFAkewilEnqaGyPketltalrrneaeHqIEWkVGekLRsmmpWIaanK
                          e+Ak++i+E+++GyP  ++ta rrn+a+H IE  +Ge+LRsmmpWI anK
Sequence ID 17       285 EYAKMFISEGATGYP--SMTAKRRNNAAHGIE-IIGEQLRSMMPWIGANK 331

                          lvdkdkn<-*
                          +vdk+kn
Sequence ID 17       332 IVDKAKN    338
```

FIG. 10B

| Mutant | 24 | 33 | 47 | 50 | 52 | 53 | 61 | 80 | 156 |
|---|---|---|---|---|---|---|---|---|---|
| 16445E4 | | L | P | V | D | G | F | I | V |
| 16468D7 | F | L | T | I | D | R | F | I | V |
| 16469F3 | | L | E | A | D | A | F | I | |
| JB1C6 | F | L | H | D | Y | Y | F | I | V |

the cofactor specificity domain the cofactor binding affinity domain

| Mutant | 24 | 33 | 47 | 50 | 52 | 53 | 61 | 80 | 156 | Km (μM) (NADH) |
|---|---|---|---|---|---|---|---|---|---|---|
| JEA7 | F | L | P | N | D | A | F | I | V | 10.6 |
| JED1 | | L | N | N | D | A | F | I | V | 11.0 |
| JEA1 | F | L | P | F | D | | F | I | V | 9.1 |
| JEG2 | F | L | F | A | D | A | F | I | V | 9.4 |
| JEG4 | F | L | N | N | D | A | F | I | V | 9.6 |

KETOL-ACID REDUCTOISOMERASE USING NADH

This application is a continuation of U.S. Ser. No. 12/637,905, filed Dec. 15, 2009, which is a continuation-in-part of U.S. Ser. No. 12/337,736, filed Dec. 18, 2008, now U.S. Pat. No. 8,129,162, and claims the benefit of the U.S. Provisional Applications, 61/015,346, filed Dec. 20, 2007, and 61/109,297, filed Oct. 29, 2008.

FIELD OF THE INVENTION

The invention relates to protein evolution. Specifically, ketol-acid reductoisomerase enzymes have been evolved to use the cofactor NADH instead of NADPH.

BACKGROUND OF THE INVENTION

Ketol-acid reductoisomerase enzymes are ubiquitous in nature and are involved in the production of valine and isoleucine, pathways that may affect the biological synthesis of isobutanol. Isobutanol is specifically produced from catabolism of L-valine as a by-product of yeast fermentation. It is a component of "fusel oil" that forms as a result of incomplete metabolism of amino acids by yeasts. After the amine group of L-valine is harvested as a nitrogen source, the resulting α-keto acid is decarboxylated and reduced to isobutanol by enzymes of the Ehrlich pathway (Dickinson, et al., J. Biol. Chem., 273: 25752-25756, 1998).

Addition of exogenous L-valine to the fermentation increases the yield of isobutanol, as described by Dickinson et al., supra, wherein it is reported that a yield of isobutanol of 3 g/l is obtained by providing L-valine at a concentration of 20 g/L in the fermentation. In addition, production of n-propanol, isobutanol and isoamylalcohol has been shown by calcium alginate immobilized cells of *Zymomonas mobilis* (Oaxaca, et al., Acta Biotechnol., 11: 523-532, 1991).

An increase in the yield of C3-C5 alcohols from carbohydrates was shown when amino acids leucine, isoleucine, and/or valine were added to the growth medium as the nitrogen source (WO 2005040392).

While methods described above indicate the potential of isobutanol production via biological means these methods are cost prohibitive for industrial scale isobutanol production. The biosynthesis of isobutanol directly from sugars would be economically viable and would represent an advance in the art. However, to date the only ketol-acid reductoisomerase (KARI) enzymes known are those that bind NADPH in its native form, reducing the energy efficiency of the pathway. A KARI that would bind NADH would be beneficial and enhance the productivity of the isobutanol biosynthetic pathway by capitalizing on the NADH produced by the existing glycolytic and other metabolic pathways in most commonly used microbial cells. The discovery of a KARI enzyme that can use NADH as a cofactor as opposed to NADPH would be an advance in the art.

The evolution of enzymes having specificity for the NADH cofactor as opposed to NADPH is known for some enzymes and is commonly referred to as "cofactor switching". See for example Eppink, et al. (J. Mol. Biol., 292: 87-96, 1999), describing the switching of the cofactor specificity of strictly NADPH-dependent p-Hydroxybenzoate hydroxylase (PHBH) from *Pseudomonas fluorescens* by site-directed mutagenesis; and Nakanishi, et al., (J. Biol. Chem., 272: 2218-2222, 1997), describing the use of site-directed mutagenesis on a mouse lung carbonyl reductase in which Thr-38 was replaced by Asp (T38D) resulting in an enzyme having a 200-fold increase in the $K_M$ values for NADP(H) and a corresponding decrease of more than 7-fold in those for NAD(H). Co-factor switching has been applied to a variety of enzymes including monooxygenases, (Kamerbeek, et al., Eur. J. Biochem., 271: 2107-2116, 2004); dehydrogenases; Nishiyama, et al., J. Biol. Chem., 268: 4656-4660, 1993; Ferredoxin-NADP reductase, Martinez-Julvez, et al., Biophys. Chem., 115: 219-224, 2005); and oxidoreductases (US2004/0248250).

Rane et al., (Arch. Biochem. Biophys., 338: 83-89, 1997) discuss cofactor switching of a ketol acid reductoisomerase isolated from *E. coli* by targeting four residues in the enzyme for mutagenesis, (R68, K69, K75, and R76,); however the effectiveness of this method is in doubt.

Although the above cited methods suggest that it is generally possible to switch the cofactor specificity between NADH and NADPH, the methods are enzyme specific and the outcomes unpredictable. The development of a ketol-acid reductoisomerase having a high specificity for NADH with decreased specificity for NADPH would greatly enhance this enzyme's effectiveness in the isobutanol biosynthetic pathway and hence increase isobutanol production. However, no such KARI enzyme has been reported.

SUMMARY OF THE INVENTION

Applicants have solved the stated problem by identifying a number of mutant ketol-acid reductoisomerase enzymes that either have a preference for specificity for NADH as opposed to NADPH or use NADH exclusively in their reaction. The method involves mutagenesis of certain specific residues in the KARI enzyme to produce the co-factor switching.

Accordingly the invention provides A mutant ketol-acid reductoisomerase enzyme comprising the amino acid sequence as set forth in SEQ ID NO: 29; a nucleic acid molecule encoding a mutant ketol-acid reductoisomerase enzyme having the amino acid sequence as set forth in SEQ ID NO:19; a mutant ketol-acid reductoisomerase enzyme as set for in SEQ ID NO:19; a mutant ketol-acid reductoisomerase enzyme having the amino acid sequence selected from the group consisting of SEQ ID NO: 24, 25, 26, 27, 28, 67, 68, 70, 75, 79, 80, 81 and 82; and a mutant ketol-acid reductoisomerase enzyme as set forth in SEQ ID NO:17 comprising at least one mutation at a residue selected from the group consisting of 24, 33, 47, 50, 52, 53, 61, 80, 115, 156, 165, and 170.

In another embodiment the invention provides a method for the evolution of an NADPH binding ketol-acid reductoisomerase enzyme to an NADH using form comprising:

a) providing a ketol-acid reductoisomerase enzyme which uses NADPH having a specific native amino acid sequence;
b) identifying the cofactor switching residues in the enzyme of (a) based on the amino acid sequence of the *Pseudomonas fluorescens* ketol-acid reductoisomerase enzyme as set for the in SEQ ID NO:17 wherein the cofactor switching residues are at positions selected from the group consisting of: 24, 33, 47, 50, 52, 53, 61, 80, 115, 156, 165, and 170; and
c) creating mutations in at least one of the cofactor switching residues of (b) to create a mutant enzyme wherein said mutant enzyme binds NADH.

In another embodiment the invention provides a method for the production of isobutanol comprising:

a) providing a recombinant microbial host cell comprising the following genetic constructs:

i) at least one genetic construct encoding an acetolactate synthase enzyme for the conversion of pyruvate to acetolactate;

ii) at least one genetic construct encoding a ketol-acid reductoisomerase enzyme of either of claim 1 or 6;

iii) at least one genetic construct encoding an acetohydroxy acid dehydratase for the conversion of 2,3-dihydroxyisovalerate to α-ketoisovalerate, (pathway step c);

iv) at least one genetic construct encoding a branched-chain keto acid decarboxylase, of the conversion of α-ketoisovalerate to isobutyraldehyde, (pathway step d);

v) at least one genetic construct encoding a branched-chain alcohol dehydrogenase for the conversion of isobutyraldehyde to isobutanol (pathway step e); and b) growing the host cell of (a) under conditions where iso-butanol is produced.

In another embodiment the invention provides a method for the evolution and identification of an NADPH binding ketol-acid reductoisomerase enzyme to an NADH using form comprising:

a) providing a ketol-acid reductoisomerase enzyme which uses NADPH having a specific native amino acid sequence;

b) identifying the amino acid residues in the native amino acid sequence whose side chains are in close proximity to the adenosyl 2'-phosphate of NADPH as mutagenesis targets;

c) creating a library of mutant ketol-acid reductoisomerase enzymes from the class I ketol-acid reductoisomerase enzyme of step (a), having at least one mutation in at least one of the mutagenesis target sites of step (b); and d) screening the library of mutant ketol-acid reductoisomerase enzymes of step (c) to identify NADH binding mutant of ketol-acid reductoisomerase enzyme.

Alternatively the invention provides a method for evolution of an NADPH specific ketol-acid reductoisomerase enzyme to an NADH using form comprising:

a) providing a mutant enzyme having an amino acid sequence selected from the group consisting of SEQ ID NOs: 28, 67, 68, 69, 70, and 84;

b) constructing a site-saturation library targeting amino acid positions 47, 50, 52 and 53 of the mutant enzyme of (a); and c) screening the site-saturation library of (b) to identify mutants which accept NADH instead of NADPH as cofactor.

Similarly the invention provides a method for evolution of an NADPH specific ketol-acid reductoisomerase enzyme to an NADH using form comprising:

a) providing a DNA fragment encoding a mutant enzyme having an amino acid sequence selected from the group consisting of SEQ ID NOs: 85, 86, 87, 88, 89, 90, 91, 92, 93, 94, 95, 96, 97, and 98 containing mutations in cofactor specificity domain;

b) producing a DNA fragment cofactor specificity domain of (a);

c) providing a DNA fragment encoding a mutant enzyme having mutations in cofactor binding affinity domain selected from the group consisting of SEQ ID NOs: 28, 67, 68, 69, 70, 84 and 86;

d) incorporating mutations of step (b) into mutants of step (c); and e) screening mutants of step (d) for mutant enzymes having a ratio of NADH/NADPH utilization is greater than one.

BRIEF DESCRIPTION OF THE FIGURES AND SEQUENCE DESCRIPTIONS

The invention can be more fully understood from the following detailed description, the Figures, and the accompanying sequence descriptions, which form part of this application.

Figure 1B:
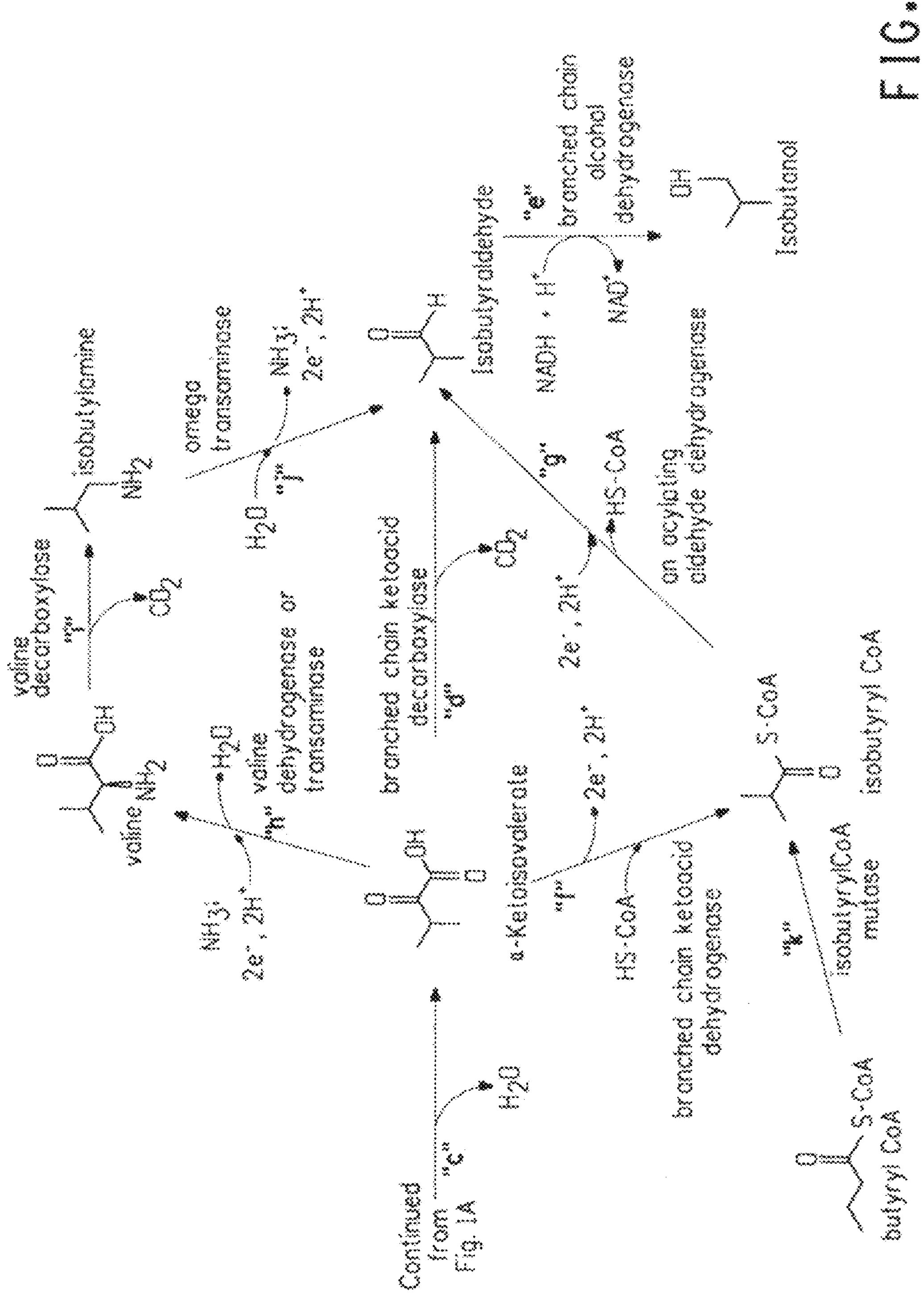

FIGS. 1A and 1B—Show four different isobutanol biosynthetic pathways. The steps labeled "a", "b", "c", "d", "f", "g", "h", "i", "j" and "k" represent the substrate to product conversions described below.

FIGS. 2A and 2B—Multiple sequence alignment (MSA) of KARI enzymes from different recourses; FIG. 2A—MSA among three NADPH-requiring KARI enzymes; FIG. 2B—MSA among PF5-KARI and other KARI enzymes, with promiscuous nucleotide specificity, where, MMC5—is from *Methanococcus maripaludis* C5; MMS2—is from *Methanococcus maripaiudis* S2; MNSB—is from *Methanococcus vanniellii* SB; ilv5—is from *Saccharomyces corevisiae* ilv5; KARI-D1—is from *Sulfolobus solfataricus* P2 ilvC; KARI-D2—is from *Pyrobaculum aerophilum* P2ilvC; and KARI S1—is from *Raistonia solanacearum* GMI1000 ivlC.

Figure 3:
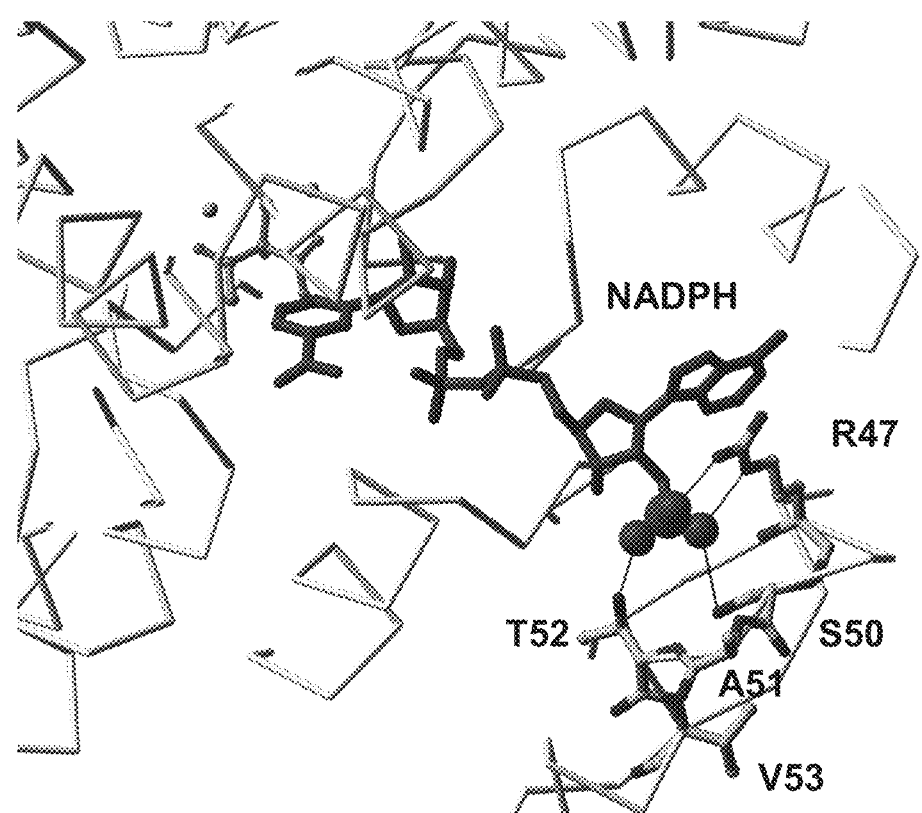

FIG. 3—Interaction of phosphate binding loop with NADPH based on homology modeling.

Figure 4:
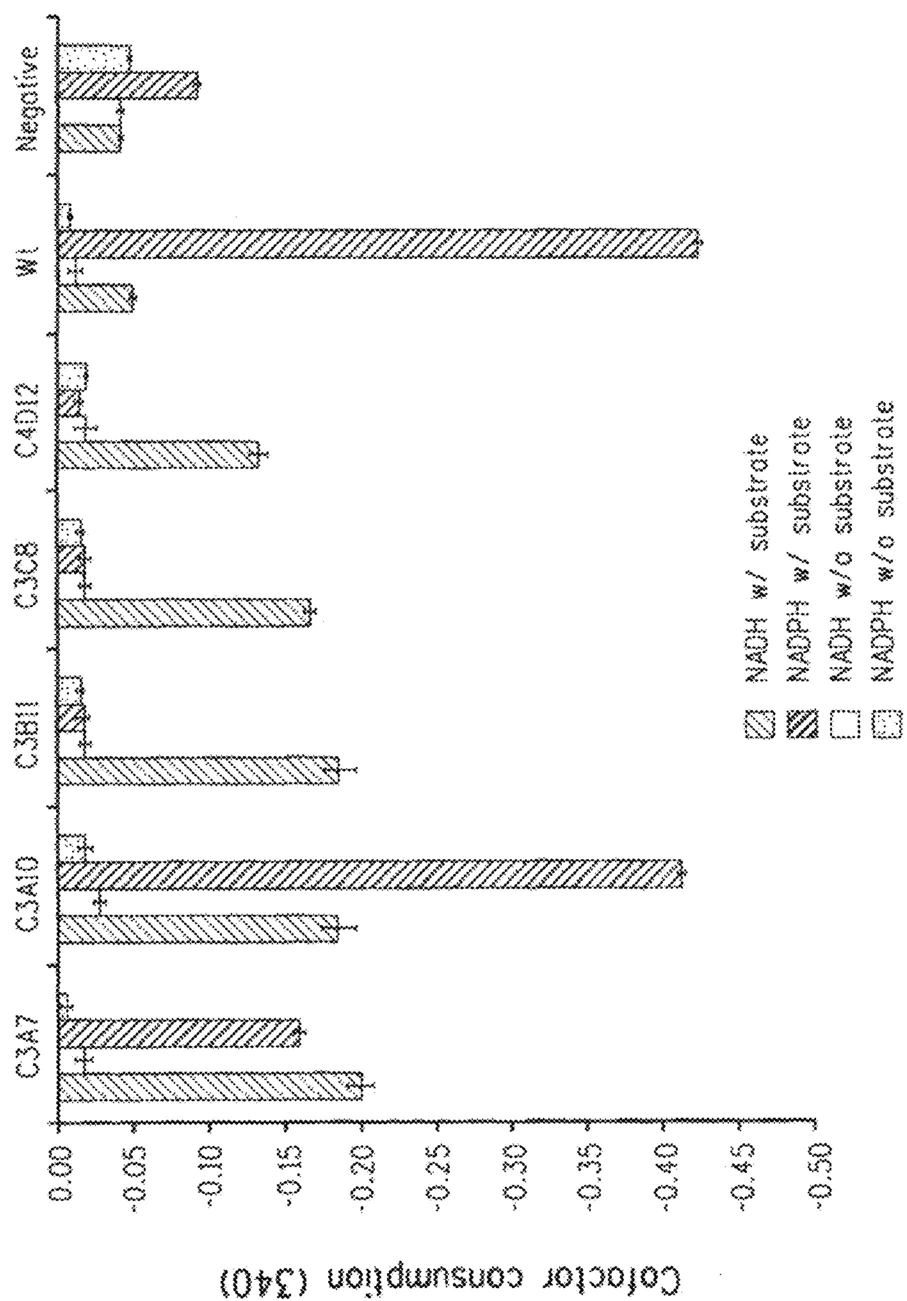
Figure 5A:
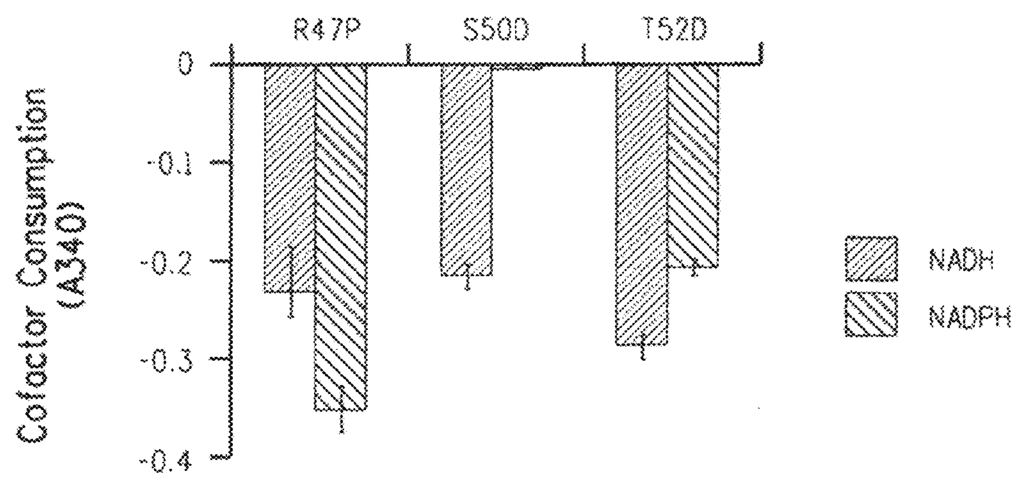
Figure 5B:
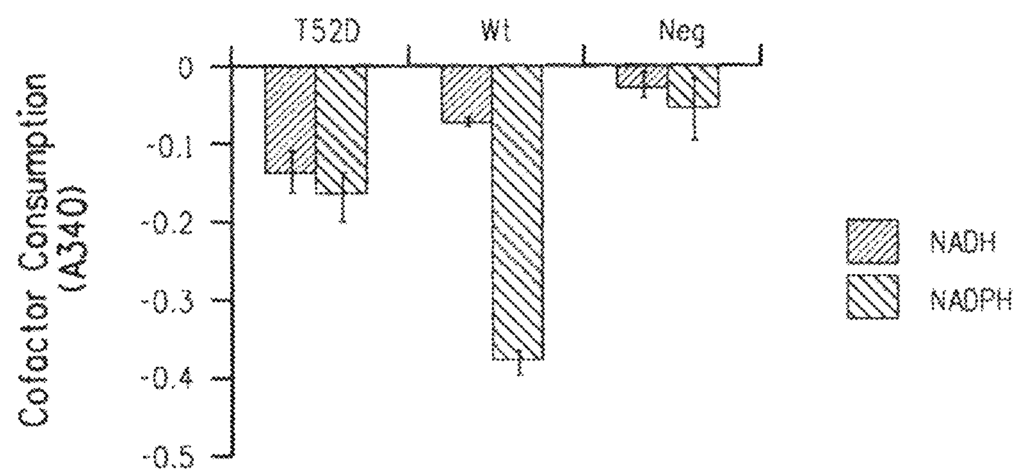

FIG. 4—KARI activities of top performers from library C using cofactor NADH versus NADPH. Activity and standard deviation were derived from triple experiments. The mutation information is as follows: C3A7=R47Y/S50A/T52D/V53W; C3A10=R47Y/S50A/T52G/V53W; C3B11=R47F/S50A/T52DA/53W; C3C8=R47G/S50M/T52D/V53W; and C4D12=R47C/S50MT52D/V53W FIGS. 5A and 5B—FIG. 5A-C*omparison* of KARI activities of top performers from libraries E, F and G using cofactors NADH and NADPH. FIG. 5B—KARI activities of positive control versus wild type Pf5-ilvC using cofactors NADH. Activity and standard deviation were derived from at least three parallel experiments. "Wt" represents the wild type of Pf5-ilvC and "Neg" means negative control. Experiments for NADH and NADPH reactions in FIG. 5A were 30 min; in FIG. 5B were 10 min.

Figure 6:
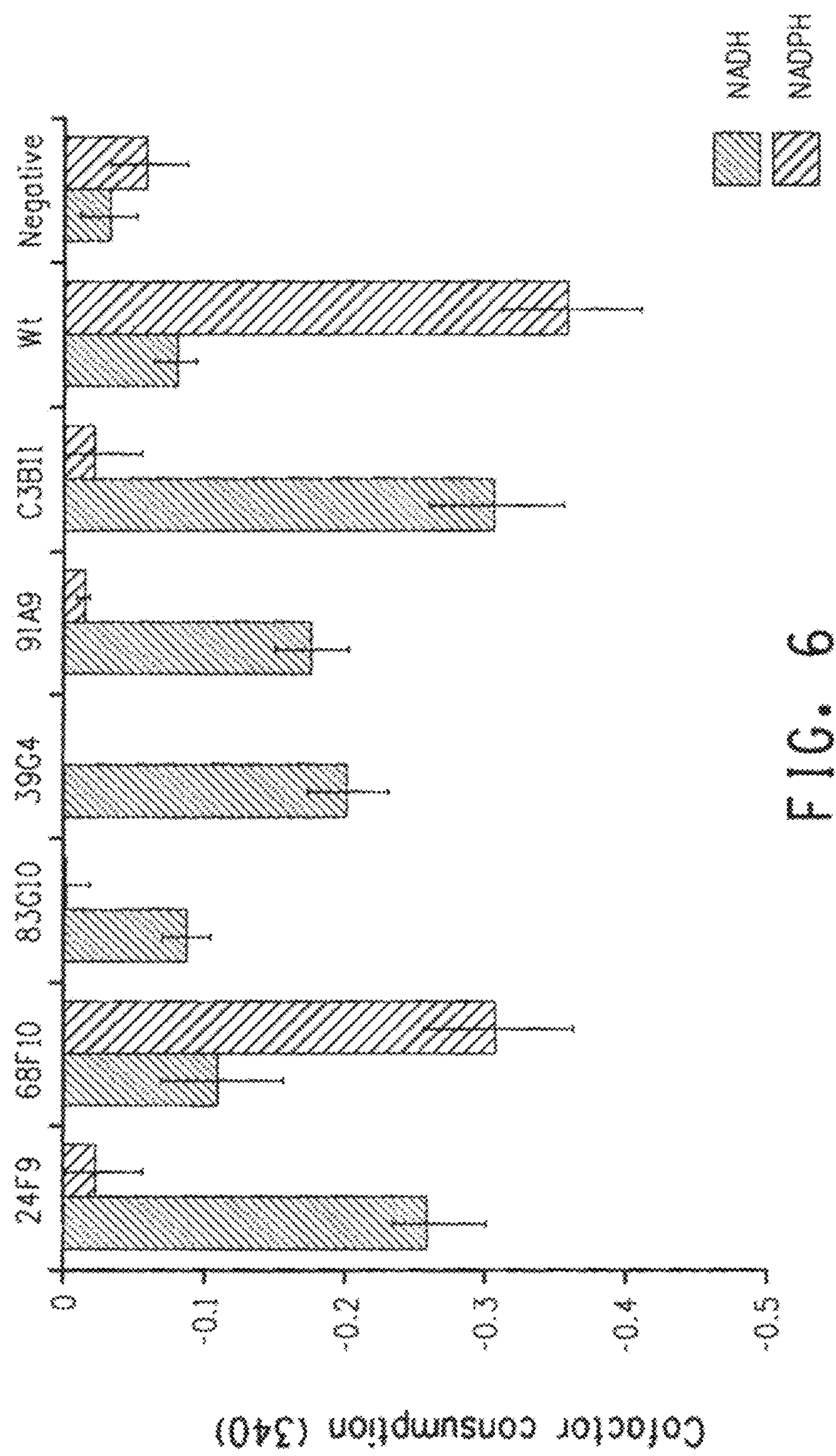

FIG. 6—Activities of top performers from library H using cofactors NADH versus NADPH. Activity and standard deviation were derived from triple experiments. Mutation information is as follows: 24F9=R47P/S50G/T52D; 68F10=R47P/T52S; 83G10=R47P/S50D/T52S; 39G4=R47P/S50C/T52D; 91A9=R47P/S50CT52D; and C3B11=R47F/S50A/T52D/V53W and Wt is wild type.

Figure 7:
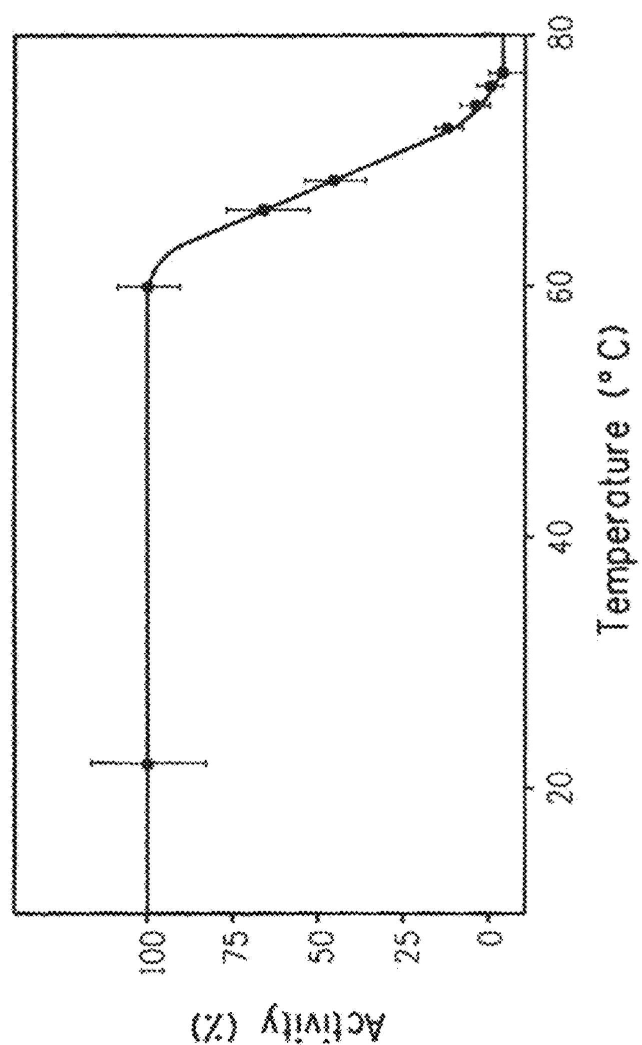

FIG. 7—Thermostability of wild type PF5-ilvC. The remaining activity of the enzyme after heating at certain temperatures for 10 min was the average number of triple experiments and normalized to the activity measured at room temperature.

FIG. 8—Multiple DNA sequence alignment among 5 naturally existing KARI molecules. The positions both bolded and boxed were identified by error prone PCR and the positions only boxed were targeted for mutagenesis.

FIGS. 9A through 9k—Alignment of the twenty-four functionally verified KARI sequences. The GxGXX(G/A) motif involved in the binding of NAD(P)H is indicated below the alignment.

FIGS. 10A and 10B—An example of the alignment of *Pseudomonas fluorescens* Pf-5 KARI to the profile HIM of KARI. The eleven positions that are responsible for co-factor switching are boxed.

Figures 11A, 11B:
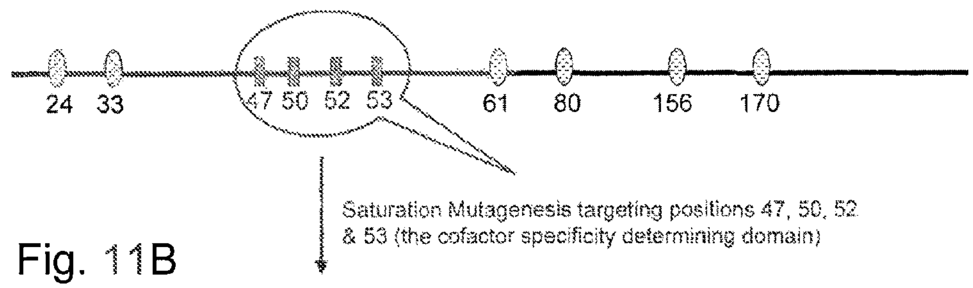

FIG. 11A is a linear depiction of the KARI amino acid sequence with specific amino acids numbered. The cofactor specificity domain residues are shown in shaded rectangles. The cofactor binding domain is shown in dotted ovals. FIG. 11B is a table that shows changed amino acids, using single letter code, at numbered positions in four KART mutants.

Figures 12A, 12B, 12C, 12D:
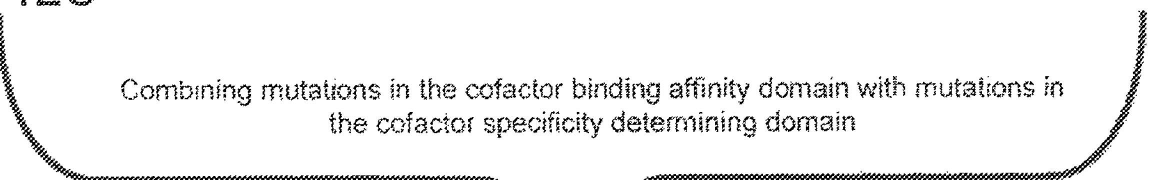

FIG. 12A is a linear depiction of the KARI amino acid sequence. The cofactor specificity domain residues are shown in shaded rectangles. FIG. 12B is a linear depiction of the KARI amino acid sequence with specific amino acids of the cofactor binding domain shown in dotted ovals. FIG. 12C depicts incorporation of the domain swapping library into the mutants containing $K_M$ improving mutations. FIG. 12D is a table summarizing the $K_M$ values for NADH for mutations resulting from combining mutations in the cofactor binding affinity domain with mutations in the cofactor specificity determining domain.

Table 9—is a table of the Profile HMI of the KARI enzymes described in Example 3. The eleven positions in the profile HMM representing the columns in the alignment which correspond to the eleven cofactor switching positions in *Pseudomonas fluorescens* Pf-5 KARI are identified as positions 24, 33, 47, 50, 52, 53, 61, 80, 115, 156, and 170. The lines corresponding to these positions in the model file are highlighted in yellow. Table 9 is submitted herewith electronically and is incorporated herein by reference.

The following sequences conform with 37 C.F.R. 1.821-1.825 ("Requirements for Patent Applications Containing Nucleotide Sequences and/or Amino Acid Sequence Disclosures—the Sequence Rules") and are consistent with the World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37C.F.R. §1.822.

TABLE 1

Oligonucleotide Primers Used In This Invention

| SEQUENCE ID No. | SEQUENCE | Description |
|---|---|---|
| 1 | TGATGAACATCTTCGCGTATTCGCCGTCCT | Reverse Primer for pBAD vector |
| 2 | GCGTAGACGTGACTGTTGGCCTGNNTAAAGGCNN GGCTNNCTGGGCCAAGGCT GAAGCCCACGGCTTG | Forward primer library C |
| 3 | GCGTAGACGTGACTGTTGGCCTGNNTAAAGGCTCG GCTACCGTTGCCAAGGCTGAAGCCCACGGCTTG | Forward primer for library E |
| 4 | GCGTAGACGTGACTGTTGGCCTGCGTAAAGGCNNT GCTACCGTTGCCAAGGCTGAAGCCCACGGCTTG | Forward primer for library F |
| 5 | GCGTAGACGTGACTGTTGGCCTGCGTAAAGGCTCG GCTNNTGTTGCCAAGGCTGAAGCCCACGGCTTG | Forward primer for library G |
| 6 | GCGTAGACGTGACTGTTGGCCTGNNTAAAGGCNNT GCTNNTGTTGCCAAGGCTGAAGCCCACGGCTTG | Forward primer for library H |
| 7 | AAGATTAGCGGATCCTACCT | Sequencing primer (forward) |
| 8 | AACAGCCAAGCTTTTAGTTC | Sequencing primer (reverse) |
| 20 | CTCTCTACTGTTTCTCCATACCCG | pBAD_266-021308f |
| 21 | CAAGCCGTGGGCTTCAGCCTTGGCKNN | PF5_53Mt022908r |
| 22 | CGGTTTCAGTCTCGTCCTTGAAG | pBAD_866-021308 |
| 49 | GCTCAAGCANNKAACCTGAAGG | pBAD-405-C33_090808f |
| 50 | CCTTCAGGTTKNNTGCTTGAGC | pBAD-427-C33_090808r |
| 51 | GTAGACGTGNNKGTTGGCCTG | pBAD-435-T43_090808f |
| 52 | CAGGCCAACKNNCACGTCTAC | pBAD-456-T43_090808r |
| 53 | CTGAAGCCNNKGGCNNKAAAGTGAC | pBAD-484-H59L61_090808f |
| 54 | GTCACTTTKNNGCCKNNGGCTTCAG | pBAD-509-H59L61_090808r |
| 55 | GCAGCCGTTNNKGGTGCCGACT | pBAD-519-A71_090808f |

TABLE 1-continued

Oligonucleotide Primers Used In This Invention

| SEQUENCE ID No. | SEQUENCE | Description |
|---|---|---|
| 56 | AGTCGGCACCKNNAACGGCTGC | pBAD-541-A71_090808r |
| 57 | CATGATCCTGNNKCCGGACGAG | pBAD-545-T80_090808f |
| 58 | CTCGTCCGGKNNCAGGATCATG | pBAD-567-T80_090808r |
| 59 | CAAGAAGGGCNNKACTCTGGCCT | pBAD-608-A101_090808f |
| 60 | AGGCCAGAGTKNNGCCCTTCTTG | pBAD-631-A101_090808r |
| 61 | GTTGTGCCTNNKGCCGACCTCG | pBAD-663-R119_090808f |
| 62 | CGAGGTCGGCKNNAGGCACAAC | pBAD-685-R119_090808r |
| 71 | GTAGACGTGACTGTTGGCCTGNNKAAAGGCNNKGCTNNKNNKGCCAAGGCTGAAGCCCACGG | PF5_4Mt111008.f |
| 72 | CCGTGGGCTTCAGCCTTGGCKNNKNNAGCKNNGCCTTTKNNCAGGCCAACAGTCACGTCTAC | PF5_4Mt111008.r |
| 73 | AAGATTAGCGGATCCTACCT | pBAD_230.f |
| 74 | GAGTGGCGCCCTTCTTGATGTTCG | pBAD_601_021308r |

Additional sequences used in the application are listed below. The abbreviated gene names in bracket are used in this disclosure.

SEQ ID NO: 9—*Methanococcus maripaludis* C5-ilvC (MMC5)—GenBank Accession Number NC_009135.1 Region: 901034.902026

SEQ ID NO: 10 is the *Methanococcus maripaludis* S2-ilvC (MMS2)—GenBank Accession Number NC_005791.1 Region: 645729.646721

SEQ ID NO: 11 is the *Methanococcus vannielii* SB-ilv5 (MVSB)—GenBank Accession Number NZ_AAWX01000002.1 Region: 302214.303206

SEQ ID NO: 12 is the *Saccharomyces cerevisiae* 11v5 (ilv5)—GenBank Accession Number NC_001144.4 Region: 838065.839252

SEQ ID NO: 13 is the *Sulfolobus solfalaricus* P2 ilvC (KARI-D1)—GenBank Accession Number NC_002754.1 Region: 506253.507260

SEQ ID NO: 14 is the *Pyrobaculum aerophilum* str. IM2 ilvC (KARI-D2)—GenBank Accession Number NC_003364.1 Region: 1976281.1977267

SEQ ID NO: 15 is the *Raistonia solanacearum* GM11000 ilvC (KARI-S1)—GenBank Accession Number NC_003295.1 Region: 2248264.2249280

SEQ ID NO: 16 is the *Pseudomonas aeruginosa* PAO1 ilvC—GenBank Accession Number NC_002516 Region: 5272455.5273471

SEQ ID NO: 17 is the *Pseudomonas fluorescens* PF5 ilvC—GenBank Accession Number NC_004129 Region: 6017379.6018395

SEQ ID NO: 18 is the *Spinacia oleracea* ilvC (Spinach-KARI)—GenBank Accession Number NC_002516 Region: 1.2050.

SEQ ID NO: 19 is the amino acid sequence of the mutant (Y24F/R47Y/S50A/T52D/V53A/L61F/G170A) of the ilvC native protein of *Pseudomonas fluorescens*.

SEQ ID NO: 23 is the DNA SEQ of the mutant (Y24F/R47Y/S50A/T52D/V53A/L61F/G170A) of the ilvC native protein of *Pseudomonas fluorescens*.

SEQ ID NO: 24 is the amino acid SEQ of the mutant ZB1 (Y24F/R47Y/S50A/T52D/V53A/L61F/A156V)

SEQ ID NO: 25 is the amino acid SEQ of the mutant ZF3 (Y24F/C33L/R47Y/S50A/T52D/V53A/L61F)

SEQ ID NO: 26 is the amino acid SEQ of the mutant ZF2 (Y24F/C33L/R47Y/S50A/T52D/V53A/L61F/A156V)

SEQ ID NO: 27 is the amino acid SEQ of the mutant ZB3 (Y24F/C33L/R47Y/S50A/T52D/V53A/L61F/G170A)

SEQ ID NO: 28 is the amino acid SEQ of the mutant Z4B8 (C33L/R47Y/S50A/T52D/V53A/L61F/T80I/A156V/G170A)

SEQ ID NO: 29 is a consensus amino acid sequence comprising all experimentally verified KARI point mutations as based on SEQ ID NO:17.

SEQ ID NO: 30 is the amino acid sequence for KARI from *Natronomonas pharaonis* DSM 2160

SEQ ID NO: 31 is the amino acid sequence for KARI from *Bacillus subtilis* subsp. *subtilis* str. 168

SEQ ID NO: 32 is the amino acid sequence for KARI from *Corynebacterium glutamicurn* ATCC13032

SEQ ID NO: 33 is the amino acid sequence for KARI from *Phaeospirilum molischianum*

SEQ ID NO: 34 is the amino acid sequence for KARI from *Zymomonas mobilis* subsp. *mobilis* ZM4

SEQ ID NO: 35 is the amino acid sequence for KARI *Alkalilimnicola ehrlichei* MLHE-1

SEQ ID NO: 36 is the amino acid sequence for KARI from *Campylobacter lari* RM2100

SEQ ID NO: 37 is the amino acid sequence for KARI from *Marinobacter aquaeolei* VT8

SEQ ID NO: 38 is the amino acid sequence for KARI *Psychrobacter arcticus* 273-4

SEQ ID NO: 39 is the amino acid sequence for KARI from *Hahella chejuensis* KCTC2396

SEQ ID NO: 40 is the amino acid sequence for KARI from *Thiobacillus denitrificans* ATCC25259

SEQ ID NO: 41 is the amino acid sequence for KARI from *Azotobacter vinelandii* AvOP SEQ ID NO: 42 is the amino acid sequence for KARI from *Pseudomonas syringae* pv, syringae B728a SEQ ID NO: 43 is the amino acid sequence for KARI from *Pseudomonas syringae* pv. tomato str. DC3000

SEQ ID NO: 44 is the amino acid sequence for KARI from *Pseudomonas putida* KT2440

SEQ ID NO: 45 is the amino acid sequence for KARI from *Pseudomonas entomophila* L48

SEQ ID NO: 46 is the amino acid sequence for KARI from *Pseudomonas mendocina* ymp SEQ ID NO: 47 is the amino acid sequence for KARI from *Bacillus cereus* ATCC 10987 NP__977840.1

SEQ ID NO: 48 is the amino acid sequence for KARI from *Bacillus cereus* ATCC10987 NP__978252.1

SEQ ID NO: 63 is the amino acid sequence for KARI from *Escherichia coli*—GenBank Accession Number P05793

SEQ ID NO: 64 is the amino acid sequence for KARI from *Marine Gamma Proteobacterium* HTCC2207 —GenBank Accession Number ZP__01224863.1

SEQ ID NO: 65 is the amino acid sequence for KARI from *Desulfuromonas acetoxidans*—GenBank Accession Number ZP__01313517i SEQ ID NO: 66 is the amino acid sequence for KARI from *Pisum sativum* (Pea)—GenBank Accession Number O82043

SEQ ID NO: 67 is the amino acid sequence for mutant 3361G8 (C33L/R47Y/S50A/T52D/V53A/L61F/T80I)

SEQ ID NO: 68 is the amino acid sequence for mutant 2H10 (Y24F/C33L/R47Y/S50A/T52D/V531I/L61F/T80I/A156V)

SEQ ID NO: 69 is the amino acid sequence for mutant 1D2 (Y24F/R47Y/S50A/T52D/V53A/L61F/T80I/A156V.

SEQ ID NO: 70 is the amino acid sequence for mutant 3F12 (Y24F/C33L/R47Y/S50A/T52D/V53A/L61F/T80I/A156V).

SEQ ID NO: 75 is the amino acid sequence for mutant JB1C6 (Y24F/C33L/R47H/S50D/T52Y/V53Y/L61F/T80I/A156V)

SEQ ID NO: 76 is the amino acid sequence for mutant 16445E4 (C33L/R47P/S50V/T52D/V53G/L61F/T80I/A156V)

SEQ ID NO: 77 is the amino acid sequence for mutant 16468D7 (Y24F/C33L/R47T/S50I/T52D/V53R/L61F/T80I/A156V)

SEQ ID NO: 78 is the amino acid sequence for mutant 16469F3 (C33L/R47E/S50A/T52D/V53A/L61F/T80I)

SEQ ID NO: 79 is the amino acid sequence for mutant JEA1 (Y24F/C33L/R47R/S50F/T52D/L61F/T80I/A156V)

SEQ ID NO: 80 is the amino acid sequence for mutant JEG2 (Y24F/C33L/R47F/S50A/T52D/V53A/L61F/T80I/A156V)

SEQ ID NO: 81 is the amino acid sequence for mutant JEG4 (Y24F/C33L/R47N/S50N/T52D/V53A/L61F/T80I/A56V)

SEQ ID NO: 82 is the amino acid sequence for mutant JEA7 (Y24 F/C33L/R47P/S50N/T52D/V53A/L61F/T80I/A156V)

SEQ ID NO: 83 is the amino acid sequence for mutant JED1 (C33L/R47N/S50N/T52D/V53A/L61F/T80I/A156V)

SEQ ID NO: 84 is the amino acid sequence for mutant 3361E1

SEQ ID NO: 85 is the amino acid sequence for mutant C2F6

SEQ ID NO: 86 is the amino acid sequence for mutant C3B11

SEQ ID NO: 87 is the amino acid sequence for mutant C4D12

SEQ ID NO: 88 is the amino acid sequence for mutant SE1

SEQ ID NO: 89 is the amino acid sequence for mutant SE2

SEQ ID NO: 90 is the amino acid sequence for mutant SB3

SEQ ID NO: 91 is the amino acid sequence for mutant SD3

SEQ ID NO: 92 is the amino acid sequence for mutant 9650E5

SEQ ID NO: 93 is the amino acid sequence for mutant 9667A11

SEQ ID NO: 94 is the amino acid sequence for mutant 9862B9

SEQ ID NO: 95 is the amino acid sequence for mutant 9875B9

SEQ ID NO: 96 is the amino acid sequence for mutant 11461D8

SEQ ID NO: 97 is the amino acid sequence for mutant 11463

SEQ ID NO: 98 is the amino acid sequence for mutant 11518B4

DETAILED DESCRIPTION OF THE INVENTION

The present invention relates to the generation of mutated KARI enzymes to use NADH as opposed to NADPH. Such co-factor switched enzymes function more effectively in microbial systems designed to produce Isobutanol. Isobutanol is an important industrial commodity chemical with a variety of applications, where its potential as a fuel or fuel additive is particularly significant. Although only a four-carbon alcohol, butanol has the energy content similar to that of gasoline and can be blended with any fossil fuel. Isobutanol is favored as a fuel or fuel additive as it yields only $CO_2$ and little or no $SO_x$ or $NO_x$ when burned in the standard internal combustion engine. Additionally butanol is less corrosive than ethanol, the most preferred fuel additive to date.

The following definitions and abbreviations are to be use for the interpretation of the claims and the specification.

The term "invention" or "present invention" as used herein is meant to apply generally to all embodiments of the invention as described in the claims as presented or as later amended and supplemented, or in the specification.

The term "isobutanol biosynthetic pathway" refers to the enzymatic pathway to produce isobutanol. Preferred isobutanol biosynthetic pathways are illustrated in FIG. 1 and described herein.

The term "NADPH consumption assay" refers to an enzyme assay for the determination of the specific activity of the KARI enzyme, involving measuring the disappearance of the KARI cofactor, NADPH, from the enzyme reaction.

"KARI" is the abbreviation for the enzyme ketol-acid reductoisomerase.

The term "close proximity" when referring to the position of various amino acid residues of a KARI enzyme with respect to the adenosyl 2'-phosphate of NADPH means amino acids in the three-dimensional model for the structure of the enzyme that are within about 4.5 Å of the phosphorus atom of the adenosyl 2'-phosphate of NADPH bound to the enzyme.

The term "ketol-acid reductoisomerase" (abbreviated "KARI"), and "acetohydroxy acid isomeroreductase" will be used interchangeably and refer to the enzyme having the EC number, EC 1.1.1.86 (Enzyme Nomenclature 1992, Academic Press, San Diego). Ketol-acid reductoisomerase catalyzes the reaction of (S)-acetolactate to 2,3-dihydroxyisovalerate, as more fully described below. These enzymes are available from a number of sources, including, but not limited to *E. coli* GenBank Accession Number NC-000913

REGION: 3955993.3957468, *Vibrio cholerae* GenBank Accession Number NC-002505 REGION: 157441.158925, *Pseudomonas aeruginosa*, GenBank Accession Number NC-002516. (SEQ ID NO: 16) REGION: 5272455.5273471, and *Pseudomonas fluorescens* GenBank Accession Number NC-004129 (SEQ ID NO: 17) REGION: 6017379.6018395. As used herein the term "Class I ketol-acid reductoisomerase enzyme" means the short form that typically has between 330 and 340 amino acid residues, and is distinct from the long form, called class II, that typically has approximately 490 residues.

The term "acetolactate synthase" refers to an enzyme that catalyzes the conversion of pyruvate to acetolactate and $CO_2$.

Acetolactate has two stereoisomers ((R) and (S)); the enzyme prefers the (S)-isomer, which is made by biological systems. Preferred acetolactate synthases are known by the EC number 2.2.1.6 9 (*Enzyme Nomenclature* 1992, Academic Press, San Diego). These enzymes are available from a number of sources, including, but not limited to, *Bacillus subtilis* (GenBank Nos: CAB15618, Z99122, NCBI (National Center for Biotechnology Information) amino acid sequence, NCBI nucleotide sequence, respectively), *klebsiella pneumoniae* (Gen Bank Nos: AAA25079, M73842 and *Lactococcus lactic* (GenBank Nos: AAA25161, L16975).

The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248, NC_000913, *S. cerevisiae* (GenBank Nos: NP_012550, NC_001142), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactic* (GenBank Nos: AAS49166, AY548760; CAG34226, AJ746364, *Salmonella typhimurium* (GenBank Nos: NP-461346, NC-003197), and *Clostridium acetobutylicum* (GenBank Nos: NP-149189, NC-001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP-010656, NC-001136; NP-014051, NC-001145), *E. coli* (GenBank Nos: NP-417484, and *C. acetobutylicum* (GenBank Nos: NP-349892, NC_003030).

The term "branched-chain keto acid dehydrogenase" refers to an enzyme that catalyzes the conversion of α-ketoisovalerate to isobutyryl-CoA (isobutyryl-cofactor A), using $NAD^+$ (nicotinamide adenine dinucleotide) as electron acceptor. Preferred branched-chain keto acid dehydrogenases are known by the EC number 1.2.4.4. These branched-chain keto acid dehydrogenases comprise four subunits, and sequences from all subunits are available from a vast array of microorganisms, including, but not limited to, *B. subtilis* (GenBank Nos: CAB14336, Z99116; CAB14335, Z99116; CAB14334, Z99116; and CAB14337, Z99116) and *Pseudomonas putida* (GenBank Nos: AAA65614, M57613; AAA65615, M57613; AAA65617, M57613; and AAA65618, M57613).

The terms "$k_{cat}$" and "$K_M$" are known to those skilled in the art and are described in Enzyme Structure and Mechanism, $2^{nd}$ ed. (Ferst; W. H. Freeman Press, NY, 1985; pp 98-120). The term "$k_{cat}$", often called the "turnover number", is defined as the maximum number of substrate molecules converted to products per active site per unit time, or the number of times the enzyme turns over per unit time. $K_{cat}=V_{max}/[E]$, where [E] is the enzyme concentration (Ferst, supra). The terms "total turnover" and "total turnover number" are used herein to refer to the amount of product formed by the reaction of a KARI enzyme with substrate.

The term "catalytic efficiency" is defined as the $K_{cat}/K_m$ of an enzyme. Catalytic efficiency is used to quantify the specificity of an enzyme for a substrate.

The term "isolated nucleic acid molecule", "isolated nucleic acid fragment" and "genetic construct" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of a microorganism. A "foreign" gene refers to a gene not normally found in the host microorganism, but that is introduced into the host microorganism by gene transfer. Foreign genes can comprise native genes inserted into a nonnative microorganism, or chimeric genes. A "transgene" is a gene that has been introduced into the genome by a transformation procedure.

As used herein the term "coding sequence" refers to a DNA sequence that encodes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions, Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into the genome of a host microorganism, resulting in genetically stable inheritance. Host microorganisms containing the transformed nucleic acid fragments are referred to as "transgenic" or "recombinant" or "transformed" microorganisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host, The term "site-saturation library" refers to a library which contains random substitutions at a specific amino acid position with all 20 possible amino acids at once.

The term "error-prone PCR" refers to adding random copying errors by imposing imperfect or 'sloppy' PCR reaction conditions which generate randomized libraries of mutations in a specific nucleotide sequence.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host microorganism without altering the polypeptide encoded by the DNA.

Molecular Techniques

Standard recombinant DNA and molecular cloning techniques used here are well known in the art and are described by Sambrook et al. (Sambrook, Fritsch and Maniatis, *Molecular Cloning: A Laboratory Manual*, Second Edition, Cold Spring Harbor Laboratory Press, Cold Spring Harbor, N.Y., 1989) (hereinafter "Maniatis"); and by Silhavy et al. (*Experiments with Gene Fusions*, Cold Spring Harbor Laboratory Press Cold Spring Harbor, N.Y., 1984); and by Ausubel, F. M. et al., (*Current Protocols in Molecular Biology*, published by Greene Publishing Assoc. and Wiley-Interscience, 1987).

The present invention addresses a need that arises in the microbial production of isobutanol where the ketol-acid reductoisomerase enzyme performs a vital role. Wild type ketol-acid reductoisomerase enzymes typically use NADPH as their cofactor. However, in the formation of isobutanol an excess of NADH is produced by ancillary metabolic pathways. The invention provides mutant Class I KARI enzymes that have been evolved to utilize NADH as a cofactor, overcoming the cofactor problem and increasing the efficiency of the isobutanol biosynthetic pathway.

Production of isobutanol utilizes the glycolysis pathway present in the host microorganism. During the production of two molecules of pyruvate from glucose during glycolysis, there is net production of two molecules of NADH from $NAD^+$ by the glyceraldehyde-3-phosphate dehydrogenase reaction. During the further production of one molecule of isobutanol from two molecules of pyruvate, there is net consumption of one molecule of NADPH, by the KARI reaction, and one molecule of NADH by the isobutanol dehydrogenase reaction. The overall reaction of glucose to isobutanol thus leads to net production of one molecule of NADH and net consumption of one molecule of NADPH. The interconversion of NADH with NADPH is generally slow and inefficient; thus, the NADPH consumed is generated by metabolism (for example, by the pentose phosphate pathway) consuming substrate in the process. Meanwhile, the cell strives to maintain homeostasis in the $NAD^+$/NADH ratio, leading to the excess NADH produced in isobutanol production being consumed in wasteful reduction of other metabolic intermediates; e.g., by the production of lactate from pyruvate. Thus, the imbalance between NADH produced and NADPH consumed by the isobutanol pathway leads to a reduction in the molar yield of isobutanol produced from glucose in two ways: 1) unnecessary operation of metabolism to produce NADPH, and 2) wasteful reaction of metabolic intermediates to maintain NAD"/NADH homeostasis. The solution to this problem is to invent a KARI that is specific for NADH as its cofactor, so that both molecules of NADH produced in glycolysis are consumed in the synthesis of isobutanol from pyruvate.

Keto Acid Reductoisomerase (KARI) Enzymes

Acetohydroxy acid isomeroreductase or ketol-acid reductoisomerase (KARI; EC 1.1.1.86) catalyzes two steps in the biosynthesis of branched-chain amino adds and is a key enzyme in their biosynthesis. KARI is found in a variety of microorganisms and amino acid sequence comparisons across species have revealed that there are 2 types of this enzyme: a short form (class I) found in fungi and most bacteria, and a long form (class II) typical of plants.

Class I KARIs typically have between 330-340 amino acid residues. The long form KARI enzymes have about 490 amino acid residues. However, some bacteria such as *Escherichia coli* possess a long form, where the amino acid sequence differs appreciably from that found in plants. KARI is encoded by the ilvC gene and is an essential enzyme for growth of *E. coli* and other bacteria in a minimal medium. Typically KARI uses NADPH as cofactor and requires a divalent cation such as $Mg^{++}$ for its activity. In addition to utilizing acetolactate in the valine pathway, KARI also converts acetohydroxybutanoate to dihydroxymethylpentanoate in the isoleucine production pathway.

Class II KARIs generally consist of a 225-residue N-terminal domain and a 287-residue C-terminal domain. The N-terminal domain, which contains the NADPH-binding site, has an $\alpha/\beta$ structure and resembles domains found in other pyridine nucleotide-dependent oxidoreductases. The C-terminal domain consists almost entirely of $\alpha$ helices and is of a previously unknown topology.

The crystal structure of the *E. coli* KARI enzyme at 2.6 Å resolution has been solved (Tyagi, et al., *Protein Sci.,* 14: 3089-3100, 2005). This enzyme consists of two domains, one with mixed $\alpha/\beta$ structure which is similar to that found in other pyridine nucleotide-dependent dehydrogenases. The second domain is mainly $\alpha$-helical and shows strong evidence of internal duplication. Comparison of the active sites of KARI of *E. coli. Pseudomonas aeruginosa*, and spinach showed that most residues in the active site of the enzyme occupy conserved positions. While the *E. coli* KARI was crystallized as a tetramer, which is probably the likely biologically active unit, the *P. aeruginosa* KARI (Ahn, et al., J. Mol. Biol., 328: 505-515, 2003) formed a dodecamer, and the enzyme from spinach formed a dimer. Known KARIs are slow enzymes with a reported turnover number ($k_{cat}$) of 2 $s^{-1}$ (Aulabaugh et al.; Biochemistry, 29: 2824-2830, 1990) or 0.12 $s^{-1}$ (Rene et al., Arch. Biochem. Biophys. 338: 83-89, 1997) for acetolactate. Studies have shown that genetic control of isoleucine-valine biosynthesis in *E. coli* is different than that in *Ps. aeruginosa* (Marinus, et al., Genetics, 63: 547-56, 1969).

Identification of Amino Acid Target Sites for Cofactor Switching

It was reported that phosphate p2" oxygen atoms of NADPH form hydrogen bonds with side chains of Arg162, Ser165 and Ser167 of spinach KARI (Bion V., et al. The EMBO Journal, 16: 3405-3415, 1997). Multiple sequence alignments were performed, using vector NTI (Invitrogen Corp. Carlsbad, Calif.), with KARI enzymes from spinach, *Pseudomonas aeruginosa* (PAO-KARI) and *Pseudomonas fluorescens* (PF5-KARI). The NADPH binding sites are shown in FIG. 2A. The amino acids, argenine, threonine and serine appear to play similar roles in forming hydrogen bonds with phosphate p2' oxygen atoms of NADPH in KARI enzymes. Studies by Ahn et al., (J. Mol. Biol., 328: 505-515, 2003) had identified three NADPH phosphate binding sites (Arg47, Ser50 and Thr52) for *Pseudomonas aeruginosa* (PAO-KARI) following comparing its structure with that of the spinach KARI. Hypothesizing that these three NADPH phosphate binding sites of the three KARI enzymes used in the disclosure were conserved, Arg47, Ser50 and Thr52 of PF5-KARI were targeted as the phosphate binding sites for this enzyme. This hypothesis was further confirmed through homology modeling.

Multiple sequence alignment among PF5-ilvC and several other KARI enzymes with promiscuous nucleotide specificity was also performed. As shown in FIG. 2B, the amino acids of glycine (G50) and tryptophan (W53), in other KARI enzymes in FIG. 2B, always appear together as a pair in the sequences of those enzymes. It was therefore assumed that the tryptophan 53 bulky residue was important in determining nucleotide specificity and by reducing the size of nucleotide binding pocket one could favor binding of the smaller nucleotide, NADH. Position 53 of PF5-ilvC was therefore chosen as a target for mutagenesis.

Several site-saturation gene libraries were prepared containing genes encoding KARI enzymes by commercially available kits for the generation of mutants. Clones from each library were screened for improved KARI activity using the NADH consumption assay described herein. Screening resulted in the identification of a number of genes having mutations that can be correlated to KARI activity. The location of the mutations were identified using the amino acid sequence of the *Pseudomonas fluorescens* PF5/NC protein (SEQ ID NO:17). Mutants with improved KARI activity had mutations at one or more positions at amino acids: 24, 33, 47, 50, 52, 53, 61, 80, 115, 156, 165, and 170. More specifically desirable mutations included the following substitutions:

a) the residue at position 47 has an amino acid substitution selected from the group consisting of A, C, D, F, G, I, L, N, P, and Y;

b) the residue at position 50 has an amino acid substitution selected from the group consisting of A, C, D, E, F, G, M, N, V, W;

c) the residue at position 52 has an amino acid substitution selected from the group consisting of A, C, D, G, H, N, W;

d) the residue at position 53 has an amino acid substitution selected from the group consisting of A, H, I, W;

In another embodiment, additional mutagenesis, using error prone PCR, performed on the mutants listed above identified suitable mutation positions as: 156, 165, 61, 170, 115 and 24. More specifically the desirable mutants with lower $K_M$ for NADH contained the following substitutions:

e) the residue at position 156 has an amino acid substitution of V;

f) the residue at position 165 has an amino acid substitution of M;

g) the residue at position 61 has an amino acid substitution of F;

h) the residue at position 170 has an amino acid substitution of A;

i) the residue at position 24 has an amino acid substitution of F; and j) the residue at position 115 has an amino acid substitution of L.

In another embodiment, multiple sequence alignment of *Pseudomonas fluorescens* PF5-ilvC and *Bacillus cereus* ilvC1 and livC2 and spinach KARI was performed which allowed identification of positions 24, 33, 47, 50, 52, 53, 61, 80, 156 and 170 for further mutagenesis. More specifically mutants with much lower $K_m$ for NADH were obtained. These mutations are also based on the *Pseudomonas fluorescens*, KARI enzyme (SEQ ID NO:17) as a reference sequence wherein the reference sequence comprises at least one amino acid substitution selected from the group consisting of:

k) the residue at position 24 has an amino acid substitution of phenylalanine;
l) the residue at position 50 has an amino acid substitution of alanine;
m) the residue at position 52 has an amino acid substitution of aspartic acid;
n) the residue at position 53 has an amino acid substitution of alanine;
o) the residue at position 61 has an amino acid substitution of phenylalanine;
p) the residue at position 156 has an amino acid substitution of valine;
q) the residue at position 33 has an amino acid substitution of leucine;
r) the residue at position 47 has an amino acid substitution of tyrosine;
s) the residue at position 80 has an amino acid substitution of isoleucine;
and
t) the residue at position 170 has an amino acid substitution of alanine.

The present invention includes a mutant polypeptide having KARI activity, said polypeptide having an amino acid sequence selected from the group consisting of SEQ ID NO: 24, 25, 26, 27 and 28.

A consensus sequence for the mutant ilvC was generated from the multiple sequence alignment and is provided as SEQ ID NO: 29 which represents all experimentally verified mutations of the KARI enzyme based on the amino acid sequence of the KARI enzyme isolated from *Pseudomonas fluorescens*, (SEQ ID NO:17)

Additionally the present invention describes mutation positions identified using a profile Hidden Markov Model (HMM) built based on sequences of 25 functionally verified Class I and Class II KARI enzymes. Profile HMM identified mutation positions 24, 33, 47, 50, 52, 53, 61, 80, 115, 156, and 170 (the numbering is based on the sequences of *Pseudomonas fluorescens* PF5 KARI). Thus, it will be appreciated by the skilled person that mutations at these positions, as well as those discussed above that have been experimentally verified will also give rise to KARI enzymes having the ability to bind NADH.

Furthermore, applicants have discovered that the ketol-acid reductoisomerase enzyme has two functionally related domains: one domain affecting nucleotide specificity and the other domain impacting the $K_M$ for the cofactor (FIGS. 11 and 12). To examine whether this characteristic could be exploited to engineer the desired KARI mutants (i.e., mutants with high NADH activity ($K_M$<20 μM) and substantially decreased NADPH activity ($K_M$>100 μM)), two libraries were created.

One library was a four-site saturation library targeting the NADH or NADPH binding positions, i.e., amino acids at positions 47, 50, 52 and 53 (FIG. 11). To build this library, mutants which possessed both NADH and NADPH activities and $K_M$~10-20 μM for NADH, were selected from a group consisting of SEQ ID NOs: 28, 67, 68, 69, 70 and 84, as templates. Further saturation mutagenesis generated new mutants (i.e., mutants with SEQ ID NOs: 75-78) that possessed mainly NADH activity with very low NADPH activity.

The desirable mutants with higher NADH activity, following site saturation mutagenesis, comprised the following substitutions:

u) the residue at position 24 has an amino acid substitution of phenylalanine;
v) the residue at position 50 has an amino acid substitution of aspartic acid or valine or isoleucine or phenylalanine;
w) the residue at position 52 has an amino acid substitution of tyrosine or aspartic acid;
x) the residue at position 53 has an amino acid substitution of tyrosine or glycine, or argenine, or alanine;
y) the residue at position 61 has an amino acid substitution of phenylalanine;
z) the residue at position 156 has an amino acid substitution of valine;
aa) the residue at position 33 has an amino acid substitution of leucine;
bb) the residue at position 47 has an amino acid substitution of histidine, or proline, or threonine, or glutamic acid; and
cc) the residue at position 80 has an amino acid substitution of isoleucine.

The $K_M$ for NADH in the above mutants was still slightly high (e.g., JB1C6, SEQ ID NO: 74, has $K_M$ of 22 μM for NADH). To further improve the NADH $K_M$ of the mutant KARIs, a "domain swapping library", which combined the nucleotide switching mutations and mutations with improved $K_M$ for NADH, was created (FIG. 12). More specifically, the beneficial mutations at positions 47, 50, 52 and 53 obtained in the site saturation experiment (see Tables 3 and 4), were transferred into mutants that possessed $K_M$~4-40 μM for NADH (SEQ ID NOs:24-28 and 67-70 and 84, see Tables 6 and 7). The resultant new mutants accepted NADH as cofactor with very low $K_M$~10 μM and greatly reduced NADPH activity. Examples of these mutants include: JEA1 (SEQ ID NO: 79), JEG2 (SEQ ID NO: 80), JEG4 (SEQ ID NO: 81), JEA7 (SEQ ID NO: 82) and JED1 (SEQ ID NO: 83).

Following domain swapping experiments, the mutants that possessed very low $K_M$ for NADH had the following substitutions:

dd) the residue at position 24 has an amino acid substitution of phenylalanine;
ee) the residue at position 50 has an amino acid substitution of alanine, asparagine, or phenylalanine;
ff) the residue at position 52 has an amino acid substitution of aspartic acid;
gg) the residue at position 53 has an amino acid substitution of alanine;
hh) the residue at position 61 has an amino acid substitution of phenylalanine;
ii) the residue at position 156 has an amino acid substitution of valine;
jj) the residue at position 33 has an amino acid substitution of leucine;
kk) the residue at position 47 has an amino acid substitution of asparagine, proline; and phenylalanine;
ll) the residue at position 80 has an amino acid substitution of isoleucine.

In one embodiment the present method includes a mutant polypeptide having KARI activity, said polypeptide having an amino acid sequence selected from the group consisting of SEQ ID NO: 24,-28, 67-70, and 75-98, In another embodiment the method provides an NADH KARI mutant with a $K_M$ for NADH <15 μM.

In a preferred embodiment, the mutant KARI JEA1 (SEQ ID NO: 79) has the following substitutions: Y24F/C33L/R47P/S50F/T52D/L61F/T80I/A156V In another preferred embodiment, the mutant KARI JEG2 (SEQ ID NO: 80) has the following substitutions: (Y24F/C33L/R47F/S50A/T52D/V53A/L61F/T80I/A156V)

In another preferred embodiment, the mutant KARI JEG4 (SEQ ID NO: 81), has the following substitutions: (Y24F/C33L/R47N/S50N/T52D/V53A/L61F/T80I/A156V)

In another preferred embodiment, the mutant KARI JEA7 (SEQ ID NO: 82), has the following substitutions: (Y24F/C33L/R47P/S50N/T52D/V53A/L61F/T80I/A156V)

In another preferred embodiment, the mutant KARI JED1 (SEQ ID NO: 83) has the following substitutions: (C33L/R47N/S50N/T52D/V53A/L61F/T80I/A156V)

In another embodiment the method provides an NADH accepting KARI mutant wherein the ratio of NADH/NADPH activity is greater than one. A consensus sequence for the mutant ilvC was generated from the multiple sequence alignment and is provided as SEQ ID NO: 29 which represents all experimentally verified mutations of the KARI enzyme based on the amino acid sequence of the KARI enzyme isolated from *Pseudomonas fluorescens* (SEQ ID NO:17).

The Host Strains for KARI Engineering

Two host strains, *E. coli* TOP10 from Invitrogen and *E. coli* Bw25113 (ΔilvC, an ilvC gene-knockout), were used for making constructs over-expressing the KARI enzyme in this disclosure. In the Bw25113 strain, the entire ilvC gene of the *E. coli* chromosome was replaced by a Kanamycin cassette using the Lambda red homology recombination technology described by Kirill et al., (Kirill A. Datsenko and Barry L. Wanner, Proc. Natl. Acad. Sci. USA, 97: 6640-6645, 2000).

Homology Modeling of PF5 KARI with Bound Substrates

The structure of PF5-KARI with bound NADPH, acetolactate and magnesium ions was built based on the crystal structure of *P. aeruginosa* PAO1-KARI (PDB ID 1NP3, Ahn H. J. et al., J. Mol. Biol., 328: 505-515, 2003) which has 92% amino acid sequence homology to PF5 KARI. PAO1-KARI structure is a homo-dodecamer and each dodecamer consists of six homo-dimers with extensive dimer interface. The active site of KARI is located in this dimer interface. The biological assembly is formed by six homo-dimers positioned on the edges of a tetrahedron resulting in a highly symmetrical dodecamer of 23 point group symmetry. For simplicity, only the dimeric unit (monomer A and monomer B) was built for the homology model of PF5-KARI in this study because the active site is in the homo-dimer interface.

The model of PF5-KARI dimer was built based on the coordinates of monomer A and monomer B of PAO1-KARI and sequence of PF5-KARI using DeepView/Swiss PDB viewer (Guex, N. and Peitsch, M. C., Electrophoresis, 18: 2714-2723, 1997). This model was then imported to program O (Jones, T. A. et al, Acta Crystallogr. A 47: 110-119, 1991) on a Silicon Graphics system for further modification.

The structure of PAO1-KARI has no NADPH, substrate or inhibitor or magnesium in the active site. Therefore, the spinach KARI structure (PDB ID 1yve, Biou V. et al., The EMBO Journal, 16: 3405-3415, 1997.), which has magnesium ions, NADPH and inhibitor (N-Hydroxy-N-isopropyloxamate) in the acetolacate binding site, was used to model these molecules in the active site. The plant KARI has very little sequence homology to either PF5— or PAO1 KARI (<20% amino acid identity), however the structures in the active site region of these two KARI enzymes are very similar. To overlay the active site of these two KARI structures, commands LSQ_ext, LSQ_improve, LSQ_mol in the program O were used to line up the active site of monomer A of spinach KARI to the monomer A of PF5 KARI model. The coordinates of NADPH, two magnesium ions and the inhibitor bound in the active site of spinach KARI were extracted and incorporated to molecule A of PF5 KARI. A set of the coordinates of these molecules were generated for monomer B of PF5 KARI by applying the transformation operator from monomer A to monomer B calculated by the program.

Because there is no NADPH in the active site of PAO1 KARI crystal structure, the structures of the phosphate binding loop region in the NADPH binding site (residues 44-45 in PAO1 KARI, 157-170 in spinach KARI) are very different between the two. To model the NADPH bound form, the model of the PF5-KARI phosphate binding loop (44-55) was replaced by that of 1yve (157-170). Any discrepancy of side chains between these two was converted to those in the PF5-KARI sequence using the mutate_replace command in program O, and the conformations of the replaced side-chains were manually adjusted. The entire NADPH/Mg/inhibitor bound dimeric PF5-KARI model went through one round of energy minimization using program CNX (ACCELRYS San Diego Calif., Bumger, A. T. and Warren, G. L., Acta Crystallogr., D 54: 905-921, 1998) after which the inhibitor was replaced by the substrate, acetolactate (AL), in the model. The conformation of AL was manually adjusted to favor hydride transfer of C4 of the nicotinamine of NADPH and the substrate. No further energy minimization was performed on this model (coordinates of the model created for this study are attached in a separate word file). The residues in the phosphate binding loop and their interactions with NADPH are illustrated in FIG. 3.

Application of a "Profile Hidden Markov Model" for Identification of Residue Positions Involved in Cofactor Switching in KARI Enzymes Applicants have developed a method for identifying KARI enzymes and the residue positions that are involved in cofactor switching from NADPH to NADH. To structurally characterize KARI enzymes, a Profile Hidden Markov Model (HMM) was prepared as described in Example 5 using amino acid sequences of 25 KARI proteins with experimentally verified function as outlined in Table 6. These KARIs were from [*Pseudomonas fluorescens* Pf-5 (SEQ ID NO: 17), *Sulfolobus solfataricus* P2 (SEQ ID NO: 13), *Pyrobaculum aerophilum* str. IM2 (SEQ ID NO: 14), *Natronomonas pharaonis* DSM 2160 (SEQ ID NO: 30), *Bacillus subtilis* subsp. *subtilis* str. 168 (SEQ ID NO: 31), *Corynebacterium glutamicum* ATCC 13032 (SEQ ID NO: 32), *Phaeospririlum molischianum* (SEQ ID NO: 33), *Ralstonia solanacearum* GMI1000 (SEQ ID NO: 15), *Zymomonas mobilis* subsp. *mobilis* ZM4 (SEQ ID NO: 34), *Alkalilimnicola ehrlichei* MLHE-1 (SEQ ID NO: 35), *Campylobacter* lani RM2100 (SEQ ID NO: 36), *Marinobacter aquaeolei* VT8 (SEQ ID NO: 37), *Psychrobacter arcticus* 273-4 (SEQ ID NO: 38), *Hahella chejuensis* KCTC 2396 (SEQ ID NO: 39), *Thiobacillus denitrificans* ATCC 25259 (SEQ ID NO: 40), *Azotobacter vinelandii* AvOP (SEQ ID NO: 41), *Pseudomonas syringae* pv. *syringae* B728a (SEQ ID NO: 42), *Pseudomonas syringae* pv. tomato str. DC3000 (SEQ ID NO: 43), *Pseudomonas putida* KT2440 (Protein SEQ ID NO: 44), *Pseudomonas entomophila* L48 (SEQ ID NO: 45), *Pseudomonas mendocina* ymp (SEQ ID NO: 46), *Pseudomonas aeruginosa* PAO1 (SEQ ID NO: 16), *Bacillus cereus* ATCC 10987 (SEQ ID NO: 47), *Bacillus cereus* ATCC 10987 (SEQ ID NO: 48), and *Spinacia oleracea* (SEQ ID NO: 18).

In addition using methods disclosed in this application, sequences of Class II KARI enzymes such as *E. coli* (SEQ ID NO: 63—GenBank Accession Number P05793), marine gamma *Proteobacterium* HTCC2207 (SEQ ID NO: 64—GenBank Accession Number ZP_01224863.1), *Desulfuromonas acetoxidans* (SEQ ID NO: 65—GenBank Accession Number ZP_01313517.1) and *Pisum sativum* (pea) (SEQ ID NO: 66—GenBank Accession Number O82043) could be mentioned.

This Profile HMM for KARIs may be used to identify any KARI related proteins. Any protein that matches the Profile HMM with an E value of <$10^{-3}$ using hmmsearch program in the HMMER package is expected to be a functional KARI, which can be either a Class I and Class II KARI. Sequences matching the Profile HMM given herein are then analyzed for the location of the 12 positions in *Pseudomonas fluorescens* Pf-5 that switches the cofactor from NADPH to NADH. The eleven nodes, as defined in the section of Profile HMM buiding, in the profile HMM representing the columns in the alignment which correspond to the eleven co-factor switching positions in *Pseudomonas fluorescens* Pf-5 KARI are identified as node 24, 33, 47, 50, 52, 53, 61, 80, 115, 156 and 170. The lines corresponding to these nodes in the model file are identified in Table 9. One skilled in the art will readily be able to identify these 12 positions in the amino acid sequence of a KARI protein from the alignment of the sequence to the profile HMM using hmm search program in HMMER package.

The KARI enzymes identified by this method, include both Class I and Class II KARI enzymes from either microbial or plant natural sources. Any KARI identified by this method may be used for heterologous expression in microbial cells.

For example each of the KARI encoding nucleic acid fragments described herein may be used to isolate genes encoding homologous proteins. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies [e.g., polymerase chain reaction (PCR) (Mullis et al., U.S. Pat. No. 4,683,202); ligase chain reaction (LCR) (Tabor, S. et al., Proc. Acad. Sci. USA 82:1074, 1985); or strand displacement amplification (SDA) (Walker, et al., Proc. Natl. Acad. Sci. U.S.A., 89: 392, 1992); and 3) methods of library construction and screening by complementation.

Although the sequence homology between Class I and Class II KARI enzymes is low, the three dimensional structure of both Classes of the enzymes, particularly around the active site and nucleotide binding domains is highly conserved (Tygai, R., et al., Protein Science, 34: 399-408, 2001). The key amino acid residues that make up the substrate binding pocket are highly conserved between these two Classes even though they may not align well in a simple sequence comparison. It can therefore be concluded that the residues affecting cofactor specificity identified in Class I KARI (e.g., positions 24, 33, 47, 50, 52, 53, 61, 80, 115, 156, and 170 of PF5 KARI) can be extended to Class II KARI enzymes.

Isobutanol Biosynthetic Pathways

Carbohydrate utilizing microorganisms employ the Embden-Meyerhof-Pamas (EMP) pathway, the Entner and Doudoroff pathway (EDP) and the pentose phosphate pathway (PPP) as the central, metabolic routes to provide energy and cellular precursors for growth and maintenance. These pathways have in common the intermediate glyceraldehyde-3-phosphate and, ultimately, pyruvate is formed directly or in combination with the EMP pathway. Subsequently, pyruvate is transformed to acetyl-cofactor A (acetyl-CoA) via a variety of means. Acetyl-CoA serves as a key intermediate, for example, in generating fatty acids, amino acids and secondary metabolites. The combined reactions of sugar conversion to pyruvate produce energy (e.g., adenosine-5'-triphosphate, ATP) and reducing equivalents (e.g., reduced nicotinamide adenine dinucleotide, NADH, and reduced nicotinamide adenine dinucleotide phosphate, NADPH). NADH and NADPH must be recycled to their oxidized forms ($NAD^+$ and $NADP^+$, respectively). In the presence of inorganic electron acceptors (e.g. $O_2$, $NO_3^-$ and $SO_4^{2-}$), the reducing equivalents may be used to augment the energy pool; alternatively, a reduced carbon byproduct may be formed.

There are four potential pathways for production of isobutanol from carbohydrate sources with recombinant microorganisms as shown in FIG. 1. All potential pathways for conversion of carbohydrates to isobutanol have been described in the commonly owned U.S. patent application Ser. No. 11/586,315, which is incorporated herein by reference.

The preferred pathway for conversion of pyruvate to isobutanol consists of enzymatic steps “a”, “b”, “c”, “d”, and “e” (FIGS. 1A and 1B) and includes the following substrate to product conversions:

a) pyruvate to acetolactate, as catalyzed for example by acetolactate synthase, b) (S)-acetolactate to 2,3-dihydroxyisovalerate, as catalyzed for example by acetohydroxy acid isomeroreductase, c) 2,3-dihydroxyisovalerate to α-ketoisovalerate, as catalyzed for example by acetohydroxy acid dehydratase, d) α-ketoisovalerate to isobutyraldehyde, as catalyzed for example by a branched-chain keto acid decarboxylase, and e) isobutyraldehyde to isobutanol, as catalyzed for example by, a branched-chain alcohol dehydrogenase.

This pathway combines enzymes involved in well-characterized pathways for valine biosynthesis (pyruvate to α-ketoisovalerate) and valine catabolism (α-ketoisovalerate to isobutanol). Since many valine biosynthetic enzymes also catalyze analogous reactions in the isoleucine biosynthetic pathway, substrate specificity is a major consideration in selecting the gene sources. For this reason, the primary genes of interest for the acetolactate synthase enzyme are those from *Bacillus* (alsS) and *Klebsiella* (budB). These particular acetolactate synthases are known to participate in butanediol fermentation in these microorganisms and show increased affinity for pyruvate over ketobutyrate (Gollop et al., J. Bacteriol., 172: 3444-3449, 1990); and (Holtzclaw et al., J. Bacteriol., 121: 917-922, 1975). The second and third pathway steps are catalyzed by acetohydroxy acid reductoisomerase and dehydratase, respectively. These enzymes have been characterized from a number of sources, such as for example, *E. coli* (Chunduru et al., Biochemistry, 28: 486-493, 1989); and (Flint et al., J. Biol. Chem., 268: 14732-14742, 1993). The final two steps of the preferred isobutanol pathway are known to occur in yeast, which can use valine as a nitrogen source and, in the process, secrete isobutanol. α-Ketoisovalerate can be converted to isobutyraldehyde by a number of keto acid decarboxylase enzymes, such as for example pyruvate decarboxylase. To prevent misdirection of pyruvate away from isobutanol production, a decarboxylase with decreased affinity for pyruvate is desired. So far, there are two such enzymes known in the art (Smit et al., Appl. Environ. Microbiol., 71: 303-311, 2005); and (de la Plaza et al., FEMS Microbiol. Lett., 238: 367-374, 2004). Both enzymes are from strains of *Lactococcus lactis* and have a 50-200-fold preference for ketoisovalerate over pyruvate. Finally, a number of aldehyde reductases have been identified in yeast, many with overlapping substrate specificity. Those known to prefer branched-chain substrates over acetaldehyde include, but are not limited to, alcohol dehydrogenase VI (ADH6) and Ypr1p (Larroy et al., Biochem. J., 361: 163-172, 2002); and (Ford et al., Yeast, 19: 1087-1096, 2002), both of which use NADPH as electron donor. An NADPH-dependent reductase, YqhD, active with branched-chain substrates has also been recently identified in *E. coli* (Sulzenbacher et al., J. Mol. Biol., 342: 489-502, 2004).

Two of the other potential pathways for isobutanol production also contain the initial three steps of “a”, “b” and “c” (FIG. 1A). One pathway consists of enzymatic steps “a”, “b”, “c”, “f”, “g”, “e” (FIGS. 1A and 1B). Step “f” containing a “branched-chain keto acid dehydrogenase (EC1.2.4.4). Step “g” containing an “acylating aldehyde dehydrogenase” (EC1.2.1.10) and 1.2.1.57 in addition to step “e” containing the “branched chain alcohol dehydrogenase”. The other potential pathway consists of steps “a”, “b”, “c”, “h”, “i”, “j”, “e” (FIGS. 1A and 1B). The term “transaminase” (step “h”) EC numbers 2.6.1.42 and 2.6.1.66. Step “h” consists of either a “valine dehydrogenase” (EC1.4.1.8 and EC1.4.1.9) or step “i”, a “valine decarboxylase” with an EC number 4.1.1.14. Finally step “j” will use an “omega transaminase” (EC2.6.1.18) to generate isobutyraldehyde which will be reduced by step “e” to produce isobutanol. All potential pathways for conversion of pyruvate to isobutanol are depicted in FIGS. 1A and 1B.

Additionally, a number of microorganisms are known to produce butyrate and/or butanol via a butyryl-CoA intermediate (Dürre, et al., FEMS Microbiol. Rev., 17: 251-262, 1995); and (Abbad-Andaloussi et al., Microbiology, 142: 1149-1158, 1996). Therefore isobutanol production in these microorganisms will take place using steps “k”, “g” and “e” shown in FIG. 1B. Step “k” will use an “isobutyryl-CoA mutase” (EC5.4.99.13). The nest step will involve using the “acylating aldehyde dehydrogenase” (EC 1.2.1.10 and EC1.2.1.57) to produce isobutyraldehyde followed by enzymatic step “e” to produce isobutanol. All these pathways are fully described in the commonly owned patent application Ser. No. 11/586,315, herein incorporated by reference.

Thus, in providing multiple recombinant pathways from pyruvate to isobutanol, there exist a number of choices to fulfill the individual conversion steps, and the person of skill in the art will be able to use publicly available sequences to construct the relevant pathways.

Microbial Hosts for Isobutanol Production

Microbial hosts for isobutanol production may be selected from bacteria, cyanobacteria, filamentous fungi and yeasts. The microbial host used for isobutanol production should be tolerant to isobutanol so that the yield is not limited by butanol toxicity. Microbes that are metabolically active at high titer levels of isobutanol are not well known in the art. Although butanol-tolerant mutants have been isolated from solventogenic Clostridia, little information is available concerning the butanol tolerance of other potentially useful bacterial strains. Most of the studies on the comparison of alcohol tolerance in bacteria suggest that butanol is more toxic than ethanol (de Cavalho, et al., Microsc. Res. Tech., 64: 215-22, 2004) and (Kabelitz, et al., FEMS Microbiol. Lett., 220: 223-227, 2003, Tomas, et al., J. Bacteriol., 186: 2006-2018, 2004) report that the yield of 1-butanol during fermentation in *Clostridium acetobutylicum* may be limited by 1-butanol toxicity. The primary effect of 1-butanol on *Clostridium acetobutylicum* is disruption of membrane functions (Hermann et al., Appl. Environ. Microbiol., 50: 1238-1243, 1985).

The microbial hosts selected for the production of isobutanol should be tolerant to isobutanol and should be able to convert carbohydrates to isobutanol. The criteria for selection of suitable microbial hosts include the following: intrinsic tolerance to isobutanol, high rate of glucose utilization, availability of genetic tools for gene manipulation, and the ability to generate stable chromosomal alterations.

Suitable host strains with a tolerance for isobutanol may be identified by screening based on the intrinsic tolerance of the strain. The intrinsic tolerance of microbes to isobutanol may be measured by determining the concentration of isobutanol that is responsible for 50% inhibition of the growth rate ($IC_{50}$) when grown in a minimal medium. The $IC_{50}$ values may be determined using methods known in the art. For example, the microbes of interest may be grown in the presence of various amounts of isobutanol and the growth rate monitored by measuring the optical density at 600 nanometers. The doubling time may be calculated from the logarithmic part of the growth curve and used as a measure of the growth rate. The concentration of isobutanol that produces 50% inhibition of growth may be determined from a graph of the percent inhibition of growth versus the isobutanol concentration. Preferably, the host strain should have an $IC_{50}$ for isobutanol of greater than about 0.5%.

The microbial host for isobutanol production should also utilize glucose at a high rate. Most microbes are capable of metabolizing carbohydrates. However, certain environmental microbes cannot metabolize carbohydrates to high efficiency, and therefore would not be suitable hosts.

The ability to genetically modify the host is essential for the production of any recombinant microorganism. The mode of gene transfer technology may be by electroporation, conjugation, transduction or natural transformation. A broad range of host conjugative plasmids and drug resistance markers are available. The cloning vectors are tailored to the host microorganisms based on the nature of antibiotic resistance markers that can function in that host.

The microbial host also has to be manipulated in order to inactivate competing pathways for carbon flow by deleting various genes. This requires the availability of either transposons to direct inactivation or chromosomal integration vectors. Additionally, the production host should be amenable to chemical mutagenesis so that mutations to improve intrinsic isobutanol tolerance may be obtained.

Based on the criteria described above, suitable microbial hosts for the production of isobutanol include, but are not limited to, members of the genera *Clostridium, Zymomonas, Escherichia, Salmonella, Rhodococcus, Pseudomonas, Bacillus, Vibrio, Lactobacillus, Enterococcus, Alcaligenes, Klebsiella, Paenibacillus, Arthrobacter, Corynebacterium, Brevibacterium, Pichia, Candida, Hansenula* and *Saccharomyces*. Preferred hosts include: *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis* and *Saccharomyces cerevisiae.*

Construction of Production Host

Recombinant microorganisms containing the necessary genes that will encode the enzymatic pathway for the conversion of a fermentable carbon substrate to isobutanol may be constructed using techniques well known in the art. In the present invention, genes encoding the enzymes of one of the isobutanol biosynthetic pathways of the invention, for example, acetolactate synthase, acetohydroxy acid isomeroreductase, acetohydroxy acid dehydratase, branched-chain α-keto acid decarboxylase, and branched-chain alcohol dehydrogenase, may be isolated from various sources, as described above.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer-directed amplification methods such as polymerase chain reaction (U.S. Pat. No. 4,683,202) to obtain amounts of DNA suitable for transformation using appropriate vectors. Tools for codon optimization for expression in a heterologous host are readily available. Some tools for codon optimization are available based on the GC content of the host microorganism.

Once the relevant pathway genes are identified and isolated they may be transformed into suitable expression hosts by means well known in the art. Vectors or cassettes useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, tip, $IP_L$, $IP_R$, T7, tac, and trc (useful for expression in *Escherichia coli, Alcaligenes*, and *Pseudomonas*) as well as the amy, apr, npr promoters and various phage promoters useful for expression in *Bacillus subtilis, Bacillus licheniformis*, and *Paenibacillus macerans*.

Termination control regions may also be derived from various genes native to the preferred hosts. Optionally, a termination site may be unnecessary, however, it is most preferred if included.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., Plasmid, 50: 74-79, 2003). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., J. Bacteriol., 174: 5633-5638, 1992). Additionally, in vitro transposomes are available to create random mutations in a variety of genomes from commercial sources such as EPICENTRE®.

The expression of an isobutanol biosynthetic pathway in various preferred microbial hosts is described in more detail below.

Expression of an Isobutanol Biosynthetic Pathway in *E. Coli*

Vectors or cassettes useful for the transformation of *E. coli* are common and commercially available from the companies listed above. For example, the genes of an isobutanol biosynthetic pathway may be isolated from various sources, cloned into a modified pUC19 vector and transformed into *E. coli* NM522.

Expression of an Isobutanol Biosynthetic Pathway in *Rhodococcus erythropolis*

A series of *E. coli-Rhodococcus* shuttle vectors are available for expression in *R. erythropolis*, including, but not limited to, pRhBR17 and pDA71 (Kostichka et al., Appl. Microbiol. Biotechnol., 62: 61-68, 2003). Additionally, a series of promoters are available for heterologous gene expression in *R. erythropolis* (Nakashima et al., Appl. Environ. Microbiol., 70: 5557-5568, 2004 and Tao et al., Appl. Microbiol. Biotechnol., 68: 346-354, 2005). Targeted gene disruption of chromosomal genes in *R. erythropolis* may be created using the method described by Tao et al., supra, and Brans et al. (Appl. Environ. Microbiol., 66: 2029-2036, 2000).

The heterologous genes required for the production of isobutanol, as described above, may be cloned initially in pDA71 or pRhBR71 and transformed into *E. coli*. The vectors may then be transformed into *R. erythropolis* by electroporation, as described by Kostichka et al., supra. The recombinants may be grown in synthetic medium containing glucose and the production of isobutanol can be followed using methods known in the art.

Expression of an Isobutanol Biosynthetic Dathway in *B. Subtilis*

Methods for gene expression and creation of mutations in *B. subtilis* are also well known in the art. For example, the genes of an isobutanol biosynthetic pathway may be isolated from various sources, cloned into a modified pUC19 vector and transformed into *Bacillus subtilis* BE1010. Additionally, the five genes of an isobutanol biosynthetic pathway can be split into two operons for expression. The three genes of the pathway (bubB, ilvD, and kivD) can be integrated into the chromosome of *Bacillus subtilis* BE1010 (Payne, et al., J. Bacteriol., 173, 2278-2282, 1991). The remaining two genes (ilvC and bdhB) can be cloned into an expression vector and transformed into the *Bacillus* strain carrying the integrated isobutanol genes Expression of an Isobutanol Biosynthetic Dathway in *B. Licheniformis*

Most of the plasmids and shuttle vectors that replicate in *B. subtilis* may be used to transform *B. licheniformis* by either protoplast transformation or electroporation. The genes required for the production of isobutanol may be cloned in plasmids pBE20 or pBE60 derivatives (Nagarajan et al., Gene, 114: 121-126, 1992). Methods to transform *B. licheniformis* are known in the art (Fleming et al. Appl. Environ. Microbiol., 61: 3775-3780, 1995). The plasmids constructed for expression in *B. subtilis* may be transformed into *B. licheniformis* to produce a recombinant microbial host that produces isobutanol.

Expression of an Isobutanol Biosynthetic Pathway in *Paenibacillus macerans*

Plasmids may be constructed as described above for expression in *B. subtilis* and used to transform *Paenibacillus*

*macerans* by protoplast transformation to produce a recombinant microbial host that produces isobutanol.

Expression of the Isobutanol Biosynthetic Pathway in *Alcalienes* (*Ralstonia*) *eutrophus*

Methods for gene expression and creation of mutations in *Alcaligenes eutrophus* are known in the art (Taghavi et al., Appl. Environ. Microbiol., 60: 3585-3591, 1994). The genes for an isobutanol biosynthetic pathway may be cloned in any of the broad host range vectors described above, and electroporated to generate recombinants that produce isobutanol. The poly(hydroxybutyrate) pathway in *Alcaligenes* has been described in detail, a variety of genetic techniques to modify the *Alcaligenes eutrophus* genome is known, and those tools can be applied for engineering an isobutanol biosynthetic pathway.

Expression of an Isobutanol Biosynthetic Pathway in *Pseudomonas putida*

Methods for gene expression in *Pseudomonas putida* are known in the art (see for example Ben-Bassat et al., U.S. Pat. No. 6,586,229, which is incorporated herein by reference). The butanol pathway genes may be inserted into pPCU18 and this ligated DNA may be electroporated into electrocompetent *Pseudomonas putida* DOT-T1 C5aAR1 cells to generate recombinants that produce isobutanol.

Expression of an Isobutanol Biosynthetic Pathway in *Saccharomyces cerevisiae*

Methods for gene expression in *Saccharomyces cerevisiae* are known in the art (e.g., *Methods in Enzymology*, Volume 194, *Guide to Yeast Genetics and Molecular and Cell Biology*, Part A, 2004, Christine Guthrie and Gerald R. Fink, eds., Elsevier Academic Press, San Diego, Calif.). Expression of genes in yeast typically requires a promoter, followed by the gene of interest, and a transcriptional terminator. A number of yeast promoters can be used in constructing expression cassettes for genes encoding an isobutanol biosynthetic pathway, including, but not limited to constitutive promoters FBA, GPD, ADH1, and GPM, and the inducible promoters GAL1, GAL10, and CUP1. Suitable transcriptional terminators include, but are not limited to FBAt, GPDt, GPMt, ERG10t, GAL1t, CYC1, and ADH1. For example, suitable promoters, transcriptional terminators, and the genes of an isobutanol biosynthetic pathway may be cloned into *E. coli-yeast* shuttle vectors.

Expression of an Isobutanol Biosynthetic Pathway in *Lactobacillus plantarum*

The *Lactobacillus* genus belongs to the Lactobacillales family and many plasmids and vectors used in the transformation of *Bacillus subtilis* and *Streptococcus* may be used for *lactobacillus*. Non-limiting examples of suitable vectors include pAMβ1 and derivatives thereof (Renault et al., Gene 183:175-182, 1996); and (O'Sullivan et al., Gene, 137: 227-231, 1993); pMBB1 and pHW800, a derivative of pMBB1 (Wyckoff et al., Appl. Environ. Microbiol., 62: 1481-1486, 1996); pMG1, a conjugative plasmid (Tanimoto et al., J. Bacteriol., 184: 5800-5804, 2002); pNZ9520 (Kleerebezem et al., Appl. Environ. Microbiol., 63: 4581-4584, 1997); pAM401 (Fujimoto et al., Appl. Environ. Microbiol., 67: 1262-1267, 2001); and pAT392 (Arthur et al., Antimicrob. Agents Chemother., 38: 1899-1903, 1994). Several plasmids from *Lactobacillus plantarum* have also been reported (van Kranenburg R, et al. Appl. Environ. Microbiol., 71: 1223-1230, 2005).

Expression of an Isobutanol Biosynthetic Pathway in Various *Enterococcus* species (*E. faecium, E. gallinarium*, and *E. faecalis*)

The *Enterococcus* genus belongs to the Lactobacillales family and many plasmids and vectors used in the transformation of *Lactobacilli, Bacilli* and *Streptococci* species may be used for *Enterococcus* species. Non-limiting examples of suitable vectors include pAMβ1 and derivatives thereof (Renault et al., Gene, 183: 175-182, 1996); and (O'Sullivan et al., Gene, 137: 227-231, 1993); pMBB1 and pHW800, a derivative of pMBB1 (Wyckoff et al. Appl. Environ. Microbiol., 62: 1481-1486, 1996); pMG1, a conjugative plasmid (Tanimoto et al., J. Bacteriol., 184: 5800-5804, 2002); pNZ9520 (Kleerebezem et al., Appl. Environ. Microbiol., 63: 4581-4584, 1997); pAM401 (Fujimoto et al., Appl. Environ. Microbiol., 67: 1262-1267, 2001); and pAT392 (Arthur et al., Antimicrob. Agents Chemother., 38: 1899-1903, 1994). Expression vectors for *E. faecalis* using the nisA gene from *Lactococcus* may also be used (Eichenbaum et al., Appl. Environ. Microbiol., 64: 2763-2769, 1998). Additionally, vectors for gene replacement in the *E. faecium* chromosome may be used (Nallaapareddy et al., Appl. Environ. Microbiol., 72: 334-345, 2006).

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, comsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic microorganisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32. (eds): Murrell, J. Collin; Kelly, Don P. Publisher: Intercept, Andover, UK). Similarly, various species of *Candida* will metabolize alanine or oleic acid (Sulter et al., Arch. Microbiol., 153: 485-489, 1990). Hence it is contemplated that the source of carbon utilized in the present invention may encompass a wide variety of carbon containing substrates and will only be limited by the choice of microorganism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for growth of the cultures and promotion of the enzymatic pathway necessary for isobutanol production.

Culture Conditions

Typically cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast Medium (YM) broth. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2',3'-monophosphate (cAMP), may also be incorporated into the fermentation medium.

Suitable pH ranges for the fermentation are between pH 5.0 to pH 9.0, where pH 6.0 to pH 8.0 is preferred for the initial condition.

Fermentations may be performed under aerobic or anaerobic conditions, where anaerobic or microaerobic conditions are preferred.

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired microorganism or microorganisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund (Appl. Biochem. Biotechnol., 36: 227, 1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth may be altered continuously while the cell concentration, measured by medium turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for isobutanol production.

Methods for Isobutanol Isolation from the Fermentation Medium

The biologically produced isobutanol may be isolated from the fermentation medium using methods known in the art for Acetone-butanol-ethanol (ABE) fermentations (see for example, Durre, Appl. Microbiol. Biotechnol. 49: 639-648, 1998), and (Groot et al., Process. Biochem. 27: 61-75, 1992 and references therein). For example, solids may be removed from the fermentation medium by centrifugation, filtration, decantation and isobutanol may be isolated from the fermentation medium using methods such as distillation, azeotropic distillation, liquid-liquid extraction, adsorption, gas stripping, membrane evaporation, or pervaporation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987. Materials and methods suitable for the maintenance and growth of bacterial cultures are also well known in the art. Techniques suitable for use in the following Examples may be found in *Manual of Methods for General Bacteriology*. Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

The meaning of abbreviations used is as follows: "Å" means Angstrom, "min" means minute(s), "h" means hour(s), "μl" means microliter(s), "ng/μl" means nano gram per microliter, "pmol/μl" means pico mole per microliter, "ml" means milliliter(s), "L" means liter(s), "g/L" mean gram per liter, "ng" means nano gram, "sec" means second(s), "ml/min" means milliliter per minute(s), "w/v" means weight per volume, "v/v" means volume per volume, "nm" means nanometer(s), "mm" means millimeter(s), "cm" means centimeter(s), "mM" means millimolar, "M" means molar, "mmol" means millimole(s), "μmole" means micromole(s), "g" means gram(s), "μg" means microgram(s), "mg" means milligram(s), "g" means the gravitation constant, "rpm" means revolutions per minute, "HPLC" means high performance liquid chromatography, "MS" means mass spectrometry, "HPLC/MS" means high performance liquid chromatography/mass spectrometry, "EDTA" means ethylendiamine-tetraacetic acid, "dNTP" means deoxynucleotide triphosphate, "° C." means degrees Celsius, and "V" means voltage.

The oligonucleotide primers used in the following Examples have been described herein (see Table 1).

High Throughput Screening Assay of Gene Libraries

High throughput screening of the gene libraries of mutant KARI enzymes was performed as described herein: 10× freezing medium containing 554.4 g/L glycerol, 68 mM of $(NH_4)_2SO_4$, 4 mM $MgSO_4$, 17 mM sodium citrate, 132 mM $KH_2PO_4$, 36 mM $K_2HPO_4$ was prepared with molecular pure water and filter-sterilized. Freezing medium was prepared by diluting the 10× freezing medium with the LB medium. An aliquot (200 μl) of the freezing medium was used for each well of the 96-well archive plates (cat #3370, Corning Inc. Corning, N.Y.).

Clones from the LB agar plates were selected and inoculated into the 96-well archive plates containing the freezing medium and grown overnight at 37° C. without shaking. The archive plates were then stored at −80° C. *E. coli* strain Bw25113 transformed with pBAD-H isB (Invitrogen) was always used as the negative control. For libraries C, E, F and G, mutant T52D of (PF5-ilvC) was used as the positive control. The mutant T52D was a mutant of PF5-ilvC in which the threonine at position 52 was changed to aspartic acid. For library H, mutant C3B11 (R47F/S50A/T52D/v53W of PF5-ilvC) was used as the positive control.

Clones from archive plates were inoculated into the 96-deep well plates. Each well contained 3.0 μl of cells from thawed archive plates, 300 μl of the LB medium containing 100 μg/ml ampicillin and 0.02% (w/v) arabinose as the inducer. Cells were the grown overnight at 37° C. with 80% humidity while shaking (900 rpm), harvested by centrifugation (4000 rpm, 5 min at 25° C.). (Eppendorf centrifuge, Brinkmann Instruments, Inc. Westbury, N.Y.) and the cell pellet was stored at −20° C. for later analysis.

The assay substrate, (R,S)-acetolactate, was synthesized as described by Aulabaugh and Schloss (Aulabaugh and Schloss, Biochemistry, 29: 2824-2830, 1990): 1.0 g of 2-acetoxy-2-methyl-3-oxobutyric acid ethyl ester (Aldrich, Milwaukee, Wis.) was mixed with 10 ml NaOH (1.0 M) and stirred at room temperature. When the solution's pH became neutral, additional NaOH was slowly added until pH ~8.0 was maintained. All other chemicals used in the assay were purchased from Sigma.

The enzymatic conversion of acetolactate to α,β-dihydroxyisovalerate by KARI was followed by measuring the disappearance of the cofactor, NADPH or NADH, from the reaction at 340 nm using a plate reader (Molecular Device, Sunnyvale, Calif.). The activity was calculated using the molar extinction coefficient of 6220 $M^{-1}$ $cm^{-1}$ for either NADPH or NADH. The stock solutions used were: $K_2HPO_4$ (0.2 M); $KH_2PO_4$ (0.2 M); EDTA (0.5 M); $MgCl_2$ (1.0 M); NADPH (2.0 mM); NADH (2.0 mM) and acetolactate (45 mM). The 100 ml reaction buffer mix stock containing: 4.8 ml $K_2HPO_4$, 0.2 ml $KH_2PO_4$, 4.0 ml $MgCl_2$, 0.1 ml EDTA and 90.9 ml water was prepared.

Frozen cell pellet in deep-well plates and BugBuster were warmed up at room temperature for 30 min at the same time. Each well of 96-well assay plates was filled with 120 μl of the reaction buffer and 20 μl of NADH (2.0 mM), 150 μof BugBuster was added to each well after 30 min warm-up and cells were suspended using Genmate (Tecan Systems Inc. San Jose, Calif.) by pipetting the cell suspension up and down (×5). The plates were incubated at room temperature for 20 min and then heated at 60° C. for 10 min. The cell debris and protein precipitates were removed by centrifugation at 4,000 rpm for 5 min at 25° C. An aliquot (50 μl) of the supernatant was transferred into each well of 96-well assay plates, the solution was mixed and the bubbles were removed by centrifugation at 4,000 rpm at 25° C. for 1 min. Absorbance at 340 nm was recorded as background, 20 μl of acetolactate (4.5 mM, diluted with the reaction buffer) was added to each well and mixed with shaking by the plate reader. Absorbance at 340 nm was recoded at 0, and 60 minutes after substrate addition. The difference in absorbance (before and after substrate addition) was used to determine the activity of the mutants. Mutants with higher KARI activity compared to the wild type were selected for re-screening.

About 5,000 clones were screened for library C and 360 top performers were selected for re-screen. About 92 clones were screened for library E and 16 top performers were selected for re-screening. About 92 clones were screened for library F and 8 top performers were selected for re-screening. About 92 clones were screened for library G and 20 top performers were selected for re-screening. About 8,000 clones were screened for library H and 62 top performers were selected for re-screening. The re-screening was described below as secondary assay.

Secondary Assay of Active Mutants

Cells containing pBad-ilvC and its mutants identified by high throughput screening were grown overnight, at 37° C., in 3.0 ml of the LB medium containing 100 μg/ml ampicillin and 0.02% (w/v) arabinose as the inducer while shaking at 250 rpm. The cells were then harvested by centrifugation at 18,000×g for 1 min at room temperature (Sigma micro-centrifuge model 1-15, Laurel, Md.). The cell pellets were re-suspended in 300 μof BugBuster Master Mix (EMD Chemicals). The reaction mixture was first incubated at room temperature for 20 min and then heated at 60° C. for 10 min. The cell debris and protein precipitate were removed by centrifugation at 18,000×g for 5 min at room temperature.

The reaction buffer (120 μl) prepared as described above was mixed with either NADH or NADPH (20 μl) stock and cell extract (20 μl) in each well of a 96-well assay plate. The absorbance at 340 nm at 25° C. was recorded as background. Then 20 μl of acetolactate (4.5 mM, diluted with reaction buffer) was added each well and mixed with shaking by the plate reader. The absorbance at 340 nm at 0 min, 2 min and 5 min after adding acetolactate was recorded. The absorbance difference before and after adding substrate was used to determine the activity of the mutants. The mutants with high activity were selected for sequencing.

Five top performers from "Library C" were identified and sequenced (FIG. 4). The best performer was mutant R47F/S50A/T52D/V53W, which completely reversed the nucleotide specificity. The best performers from "Libraries E, F and G" were R47P, S50D and T52D respectively (FIG. 5). For "Library H", 5 top performers were identified and sequenced (FIG. 6) and the best performer was R47P/S50G/T52D, which also completely reversed the nucleotide specificity. Enzymes containing activities higher than the background were considered positive.

KARI Enzyme Assay

KARI enzyme activity can be routinely measured by NADH or NADPH oxidation as described above, however to measure formation of the 2,3-dihydroxyisovalerate product directly, analysis of the reaction was performed using HPLC/MS.

Protein concentration of crude cell extract from Bugbuster lysed cells (as described above) was measured using the Bio-Rad protein assay reagent (BioRad Laboratories, Inc., Hercules, Calif. 94547). A total of 0.5 micrograms of crude extract protein was added to a reaction buffer consisting of 100 mM HEPES-KOH, pH 7.5, 10 mM $MgCl_2$, 1 mM glucose-6-phosphate (Sigma-Aldrich), 0.2 Units of *Leuconostoc mesenteroides* glucose-6-phosphate dehydrogenase (Sigma-Aldrich), and various concentrations of NADH or NADPH, to a volume of 96 μL. The reaction was initiated by the addition of 4 μL of acetolactate to a final concentration of 4 mM and a final volume of 100 μL. After timed incubations at 30° C., typically between 2 and 15 min, the reaction was quenched by the addition of 10 μL of 0.5 M EDTA, pH 8.0 (Life Technologies, Grand Island, N.Y. 14072). To measure the $K_M$ of NADH, the concentrations used were 0.03, 0.1, 0.3, 1, 3, and 10 mM.

To analyze for 2,3-dihydroxyisovalerate, the sample was diluted 10× with water, and 8.0 μl was injected into a Waters Acquity HPLC equipped with Waters SQD mass spectrometer (Waters Corporation, Milford, Mass.). The chromatography conditions were: flow rate (0.5 ml/min), on a Waters Acquity HSS T3 column (2.1 mm diameter, 100 mm length). Buffer A consisted of 0.1% (v/v) in water, Buffer B was 0.1% formic acid in acetonitrile. The sample was analyzed using 1% buffer B (in buffer A) for 1 min, followed by a linear gradient from 1% buffer B at 1 min to 75% buffer B at 1.5 min. The reaction product, 2,3-dihydroxyisovalerate, was detected by ionization at m/z=133, using the electrospray ionization devise at −30 V cone voltage. The amount of product 2,3-dihydroxyisovalerate was calculated by comparison to an authentic standard.

To calculate the $K_M$ for NADH, the rate data for DHIV formation was plotted in Kaleidagraph (Synergy Software, Reading, Pa.) and fitted to the single substrate Michaelis-Menton equation, assuming saturating acetolactate concentration.

Example 1

Construction of Site-Saturation Gene Libraries to Identify Mutants Accepting NADH as Cofactor Seven gene libraries were constructed (Table 2) using two steps: 1) synthesis of Megaprimers using commercially synthesized oligonucleotidies described in Table 1; and 2) construction of mutated genes using the Megaprimers obtained in step 1. These primers were prepared using high fidelity pfu-ultra polymerase (Stratagene, La Jolla, Calif.) for one pair of primer containing one forward and one reverse primer. The templates for libraries C, E, F, G and H were the wild type of PF5_ilvc. The DNA templates for library N were those mutants having detectable NADH activity from library C while those for library O were those mutants having detectable NADH activity from library H. A 50 μl reaction mixture contained: 5.0 μl of 10× reaction buffer supplied with the pfu-ultra polymerase (Stratagene), 1.0 μl of 50 ng/μl template, 1.0 μl each of 10 pmol/μl forward and reverse primers, 1.0 μl of 40 mM dNTP mix (Promega, Madison, Wis.), 1.0 μl pfu-ultra DNA polymerase (Stratagene) and 39 μl water. The mixture was placed in a thin well 200 μl tube for the PCR reaction in a Mastercycler gradient equipment (Brinkmann Instruments, Inc. Westbury, N.Y.). The following conditions were used for the PCR reaction: The starting temperature was 95° C. for 30 sec followed by 30 heating/cooling cycles. Each cycle consisted of 95° C. for 30 sec, 54° C. for 1 min, and 70° C. for 2 min. At the completion of the temperature cycling, the samples were kept at 70° C. for 4 min more, and then held awaiting sample recovery at 4° C. The PCR product was cleaned up using a DNA cleaning kit (Cat#D4003, Zymo Research, Orange, Calif.) as recommended by the manufacturer.

TABLE 2

Gene Libraries

| Library name | Templates | Targeted position(s) of Pf5__ilvC | Primers used |
|---|---|---|---|
| C | PF5__ilvc | 47, 50, 52 and 53 | SEQ ID No: 1 and 2 |
| E | PF5__ilvc | 47 | SEQ ID No: 1 and 3 |
| F | PF5__ilvc | 50 | SEQ ID No: 1 and 4 |
| G | PF5__ilvc | 52 | SEQ ID No: 1 and 5 |
| H | PF5__ilvc | 47, 50, and 52 | SEQ ID No: 1 and 6 |
| N | Good mutants from library C | 53 | SEQ ID NO: 20 and 21 |
| O | Good mutants from library H | 53 | SEQ ID NO: 20 and 21 |

The Megaprimers were then used to generate gene libraries using the QuickChange II XL site directed mutagenesis kit (Catalog #200524, Stratagene, La Jolla Calif.). A 50 μl reaction mixture contained: 5.0 μl of 10× reaction buffer, 1.0 μl of 50 ng/μl template, 42 μl Megaprimer, 1.0 μl of 40 mM dNTP mix, 1.0 μl pfu-ultra DNA polymerase. Except for the Megaprimer and the templates, all reagents used here were supplied with the kit indicated above. This reaction mixture was placed in a thin well 200 μl-capacity PCR tube and the following reactions were used for the PCR: The starting temperature was 95° C. for 30 sec followed by 25 heating/cooling cycles. Each cycle consisted of 95° C. for 30 sec, 55° C. for 1 min, and 68° C. for 6 min. At the completion of the temperature cycling, the samples were kept at 68° C. for 8 min more, and then held at 4° C. for later processing. Dpn I restriction enzyme (1.0 μl) (supplied with the kit above) was directly added to the finished reaction mixture, enzyme digestion was performed at 37° C. for 1 h and the PCR product was cleaned up using a DNA cleaning kit (Zymo Research). The cleaned PCR product (10 μl) contained mutated genes for a gene library.

The cleaned PCR product was transformed into an electro-competent strain of *E. coli* Bw25113 (ΔilvC) using a BioRad Gene Pulser II (Bio-Rad Laboratories Inc., Hercules, Calif.). The transformed clones were streaked on agar plates containing the LB medium and 100 μg/ml ampicillin (Cat#L1004, Teknova Inc. Hollister, Calif.) and incubated at 37° C. overnight. Dozens of clones were randomly chosen for DNA sequencing to confirm the quality of the library.

TABLE 3

List of some mutants having NADH activity identified from saturation libraries

| Mutant | Position 47 | Position 50 | Position 52 | Position 53 |
|---|---|---|---|---|
| SD2 | R47Y | S50A | T52H | V53W |
| SB1 | R47Y | S50A | T52G | V53W |
| SE1 | R47A | S50W | T52G | V53W |

TABLE 3-continued

List of some mutants having NADH activity identified from saturation libraries

| Mutant | Position 47 | Position 50 | Position 52 | Position 53 |
|---|---|---|---|---|
| SH2 | R47N | S50W | T52N | V53W |
| SB2 | R47I | | T52G | V53W |
| SG1 | R47Y | | T52G | V53W |
| SB3 | R47G | S50W | T52G | V53W |
| SE2 | R47P | S50E | T52A | V53W |
| SD3 | R47L | S50W | T52G | V53W |
| C2A6 | R47I | S50G | T52D | V53W |
| C3E11 | R47A | S50M | T52D | V53W |
| C3A7 | R47Y | S50A | T52D | V53W |
| C3B11 | R47F | S50A | T52D | V53W |
| C4A5 | R47Y | S50A | T52S | V53W |
| C3B12 | R47I | | T52D | V53W |
| C4H7 | R47I | | T52S | V53W |
| C1D3 | R47G | S50M | T52D | V53W |
| C4D12 | R47C | S50W | T52G | V53W |
| C1G7 | R47P | S50G | T52D | V53W |
| C2F6 | R47P | S50V | T52D | V53W |
| C1C4 | R47P | S50E | T52S | V53W |
| 6924F9 | R47P | S50G | T52D | |
| 6881E11 | R47P | S50N | T52C | |
| 6868F10 | R47P | | T52S | |
| 6883G10 | R47P | S50D | T52S | |
| 6939G4 | R47P | S50C | T52D | |
| 11463D8 | R47P | S50F | T52D | |
| 9667A11 | R47N | S50N | T52D | V53A |
| 9675C8 | R47Y | S50A | T52D | V53A |
| 9650E5 | R47N | S50W | T52G | V53H |
| 9875B9 | R47N | S50N | T52D | V53W |
| 9862B9 | R47D | S50W | T52G | V53W |
| 9728G11 | R47N | S50W | T52G | V53W |
| 11461D8 | R47F | S50A | T52D | V53A |
| 11461A2 | R47P | S50F | T52D | V53I |

Example 2

Construction of Error Prone PCR Librar

Mutants obtained in Example 1, with mutations in their cofactor binding sites which exhibited relatively good NADH activities, were used as the DNA template to prepare the error prone (ePCR) libraries using the GeneMorph II kit (Stratagene) as recommended by the manufacturer. All the epPCR libraries target the N-terminal (which contains the NADPH binding site) of PF5_KARI. The forward primer (SED ID No: 20) and the reverse primer (SED ID No: 22) were used for all ePCR libraries.

The DNA templates for the $n^{th}$ epPCR library were mutants having good NADH activity from the $(n-1)^{th}$ epPCR library. The templates of the first epPCR library were mutants having relatively good NADH activity from libraries N and O. The mutations rate of library made by this kit was controlled by the amount of template added in the reaction mixture and the number of amplification cycles. Typically, 1.0 ng of each DNA template was used in 100 μL of reaction mixture. The number of amplification cycles was 70. The following conditions were used for the PCR reaction: The starting temperature was 95° C. for 30 sec followed by 70 heating/cooling cycles. Each cycle consisted of 95° C. for 30 sec, 55° C. for 30 min, and 70° C. for 2 min. After the first 35 heating/cooling cycles finished, more dNTP and Mutazyme II DNA polymerase were added. The PCR product was cleaned up using a DNA cleaning kit (Cat#D4003, Zymo Research, Orange, Calif.) as recommended by the manufacturer. The cleaned PCR product was treated as Megaprimer and introduced into the vector using the Quickchange kit as described in Example 1. Table 4 below lists the KARI mutants obtained and the significant improvement observed in their NADH binding ability. The $K_M$ was reduced from 1100 μM for mutant C3B11 to 50 μM for mutant 12957G9.

TABLE 4

List of some mutants with their measured $K_M$ values

| Mutant | Mutation Locations | NADH $K_M$ (μM) |
|---|---|---|
| C3B11 | R47F/S50A/T52D/V53W | 1100 |
| SB3 | R47G/S50W/T52G/V53W | 500 |
| 11518B4 | R47N/S50N/T52D/V53A/A156V | 141 |
| 11281G2 | R47N/S50N/T52D/V53A/A156V/L165M | 130 |
| 12985F6 | R47Y/S50A/T52D/V53A/L61F/A156V | 100 |
| 13002D8 | R47Y/S50A/T52D/V53A/L61F/A156V/G170A | 68 |
| 12957G9 | Y24F/R47Y/S50A/T52D/V53A/L61F/G170A | 50 |
| 12978D9 | R47Y/S50A/T52D/V53A/L61F/Q115L/A156V | 114 |

Example 3

Identification of Amino Acids for Cofactor Specificity Switching Using Bioinformatic Tools To discover if naturally existing KARI sequences could provide clues for amino acid positions that should be targeted for mutagenesis, multiple sequence alignment (MSA) using PF5_KARI, its close homolog PAO1_KARI and three KARI sequences with measureable NADH activity, i.e., *B. Cereus* ilvC1 and ilvC2 and spinach KARI were performed (FIG. 8). Based on the multiple sequence alignment, positions 33, 43, 59, 61, 71, 80, 101, and 119 were chosen for saturation mutagenesis. Saturation mutagenesis on all of these positions was performed simultaneously using the QuickChange II XL site directed mutagenesis kit (Catalog #200524, Stratagene, La Jolla Calif.) with the manufacturer's suggested protocol. Starting material for this mutagenesis was a mixed template consisting of the mutants already identified in Example 2, Table 4. The primers used are listed in Table 5. The library of mutants thus obtained were named "library Z". Mutants with good NADH activity from this library were identified using high throughput screening and their KARI activity and the $K_M$ for NADH were measured as described above. These mutants (Table 6) possess much lower $K_M$ s for NADH compared to the parent templates (Table 4). A Megaprimer, using primers (SEQ ID Nos. 20 and 58), was created and mutations at positions 156 and 170 were eliminated. Further screening of this set of mutants identified mutant 3361G8 (SEQ ID NO: 67) (Table 7). The hits from library Z were further subjected to saturation mutagenesis at position 53 using primers (SEQ ID Nos. 20 and 21), and subsequent screening identified the remaining mutants in Table 7. As shown in Table 7 the new mutants possessed much lower $K_M$ for NADH (e.g., 4.0 to 5.5 μM) compared to mutants listed in Table 6 (e.g., 14-40 μM).

TABLE 5

| Primers for Example 5 | |
|---|---|
| Targeted position(s) of Pf5_ilvC | Primers |
| 33 | pBAD-405-C33_090808f: GCTCAAGCANNKAACCTGAAGG (SEQ ID NO: 49)<br>pBAD-427-C33_090808r: CCTTCAGGTTKNNTGCTTGAGC (SEQ ID NO: 50) |
| 43 | pBAD-435-T43_090808f: GTAGACGTGNNKGTTGGCCTG (SEQ ID NO: 51)<br>pBAD-456-T43_090808r: CAGGCCAACKNNCACGTCTAC (SEQ ID NO: 52) |
| 59 and 61 | pBAD-484-H59L61_090808f: CTGAAGCCNNKGGCNNKAAAGTGAC (SEQ ID NO: 53)<br>pBAD-509-H59L61_090808r: GTCACTTTKNNGCCKNNGGCTTCAG (SEQ ID NO: 54) |
| 71 | pBAD-519-A71_090808f: GCAGCCGTTNNKGGTGCCGACT (SEQ ID NO: 55)<br>pBAD-541-A71_090808r: AGTCGGCACCKNNAACGGCTGC (SEQ ID NO: 56) |
| 80 | pBAD-545-T80_090808f: CATGATCCTGNNKCCGGACGAG (SEQ ID NO: 57)<br>pBAD-567-T80_090808r: CTCGTCCGGKNNCAGGATCATG (SEQ ID NO: 58) |
| 101 | pBAD-608-A101_090808f: CAAGAAGGGCNNKACTCTGGCCT (SEQ ID NO: 59)<br>pBAD-631-A101_090808r: AGGCCAGAGTKNNGCCCTTCTTG (SEQ ID NO: 60) |
| 119 | pBAD-663-R119_090808f: GTTGTGCCTNNKGCCGACCTCG (SEQ ID NO: 61)<br>pBAD-685-R119_090808r: CGAGGTCGGCKNNAGGCACAAC (SEQ ID NO: 62) |

TABLE 6

List of some mutants with their measured $K_M$ values (positions to be mutated in this library were indentified by bioinformatic tools)

| Mutant | Mutation Locations | NADH $K_M$ (μM) |
|---|---|---|
| ZB1 | Y24F/R47Y/S50A/T52D/V53A/L61F/A156V (SEQ ID NO: 24) | 40 |
| ZF3 | Y24F/C33L/R47Y/S50A/T52D/V53A/L61F (SEQ ID NO: 25) | 21 |
| ZF2 | Y24F/C33L/R47Y/S50A/T52D/V53A/L61F/A156V (SEQ ID NO: 26) | 17 |
| ZB3 | Y24F/C33L/R47Y/S50A/T52D/V53A/L61F/G170A (SEQ ID NO: 27) | 17 |
| Z4B8 | C33L/R47Y/S50A/T52D/V53A/L61F/T80I/A156V (SEQ ID NO: 28) | 14 |

TABLE 7

Mutants further optimized for improved $K_M$ (for NADH)

| Mutant | Mutation Locations | NADH $K_m$ (μM) |
|---|---|---|
| 3361G8 | C33L/R47Y/S50A/T52D/V53A/L61F/T80I (SEQ ID NO: 67) | 5.5 |
| 2H10 | Y24F/C33L/R47Y/S50A/T52D/V53I/L61F/T80I/A156V (SEQ ID NO: 68) | 5.3 |
| 1D2 | Y24F/R47Y/S50A/T52D/V53A/L61F/T80I/A156V (SEQ ID NO: 69) | 4.1 |
| 3F12 | Y24F/C33L/R47Y/S50A/T52D/V53A/L61F/T80I/A156V (SEQ ID NO: 70) | 4.0 |
| 3361E1 | Y24F/R47Y/S50A/T52D/V53I/L61F (SEQ ID NO: 84) | 4.5 |

Further analyses using bioinformatic tools were therefore performed to expand the mutational sites to other KARI sequences as described below.

Sequence Analysis

Members of the protein family of ketol-acid reducoisomorase (KARI) were identified through BlastP searches of publicly available databases using amino acid sequence of *Pseudomonas fluorescens* PF5 KARI (SEQ ID NO:17) with the following search parameters: E value=10, word size=3, Matrix=Blosum62, and Gap opening=11 and gap extension=1, E value cutoff of $10^{-3}$. Identical sequences and sequences that were shorter than 260 amino acids were removed. In addition, sequences that lack the typical GxGXX (G/A) motif involved in the binding of NAD(P)H in the N-terminal domain were also removed. These analyses resulted in a set of 692 KARI sequences.

A profile HMM was generated from the set of the experimentally verified Class I and Class II KARI enzymes from various sources as described in Table 8. Details on building, calibrating, and searching with this profile HMM are provided below. Any sequence that can be retrieved by HMM search using the profile HMM for KARI at E-value above $1E^{-3}$ is considered a member of the KARI family. Positions in a KARI sequence aligned to the following in the profile HMM nodes (defined below in the section of profile HMM building) are claimed to be responsible for NADH utilization: 24, 33, 47, 50, 52, 53, 61, 80, 115, 156, and 170 (the numbering is based on the sequences of *Pseudomonas fluorescens* PF5 KARI).

Preparation of Profile HMM

A group of KARI sequences were expressed in *E. coli* and have been verified to have KARI activity These KARIs are listed in Table 6. The amino acid sequences of these experimentally verified functional KARIs were analyzed using the HMMER software package (The theory behind profile HMMs is described in R. Durbin, S. Eddy, A. Krogh, and G. Mitchison, Biological sequence analysis: probabilistic models of proteins and nucleic acids, Cambridge University Press, 1998; Krogh et al., J. Mol. Biol. 235:1501-1531, 1994), following the user guide which is available from HMMER (Janelia Farm Research Campus, Ashburn, Va.). The output of the HMMER software program is a profile Hidden Markov Model (profile HMM) that characterizes the input sequences. As stated in the user guide, profile HMMs are statistical descriptions of the consensus of a multiple sequence alignment. They use position-specific scores for amino acids (or nucleotides) and position specific scores for opening and extending an insertion or deletion. Compared to other profile based methods, HMMs have a formal probabilistic basis. Profile HMMs for a large number of protein families are publicly available in the PFAM database (Janelia Farm Research Campus, Ashbum, Va.).

The profile HMM was built as follows:

Step 1. Build a Sequence Alignment

The 25 sequences for the functionally verified KARIs listed above were aligned using Clustal W (Thompson, J. D., Higgins, D. G., and Gibson T. J., Nuc. Acid Res. 22: 4673 4680, 1994) with default parameters. The alignment is shown in FIG. 9.

TABLE 8

25 Experimentally verified KARI enzymes

| GI Number | Accession | SEQ ID NO: | Microorganism |
|---|---|---|---|
| 70732562 | YP_262325.1 | 17 | *Pseudomonas fluorescens* Pf-5 |
| 15897495 | NP_342100.1 | 13 | *Sulfolobus solfataricus* P2 |
| 18313972 | NP_560639.1 | 14 | *Pyrobaculum aerophilum* str. IM2 |
| 76801743 | YP_326751.1 | 30 | *Natronomonas pharaonis* DSM 2160 |
| 16079881 | NP_390707.1 | 31 | *Bacillus subtilis* subsp. *subtilis* str. 168 |
| 19552493 | NP_600495.1 | 32 | *Corynebacterium glutamicum* ATCC 13032 |
| 6225553 | O32414 | 33 | *Phaeospririlum molischianum* |
| 17546794 | NP_520196.1 | 15 | *Ralstonia solanacearum* GMI1000 |
| 56552037 | YP_162876.1 | 34 | *Zymomonas mobilis* subsp. *mobilis* ZM4 |
| 114319705 | YP_741388.1 | 35 | *Alkalilimnicola ehrlichei* MLHE-1 |
| 57240359 | ZP_00368308.1 | 36 | *Campylobacter lari* RM2100 |
| 120553816 | YP_958167.1 | 37 | *Marinobacter aquaeolei* VT8 |
| 71065099 | YP_263826.1 | 38 | *Psychrobacter arcticus* 273-4 |
| 83648555 | YP_436990.1 | 39 | *Hahella chejuensis* KCTC 2396 |
| 74318007 | YP_315747.1 | 40 | *Thiobacillus denitrificans* ATCC 25259 |
| 67159493 | ZP_00420011.1 | 41 | *Azotobacter vinelandii* AvOP |
| 66044103 | YP_233944.1 | 42 | *Pseudomonas syringae* pv. *syringae* B728a |
| 28868203 | NP_790822.1 | 43 | *Pseudomonas syringae* pv. tomato str. DC3000 |
| 26991362 | NP_746787.1 | 44 | *Pseudomonas putida* KT2440 |
| 104783656 | YP_610154.1 | 45 | *Pseudomonas entomophila* L48 |
| 146306044 | YP_001186509.1 | 46 | *Pseudomonas mendocina* ymp |
| 15599888 | NP_253382.1 | 16 | *Pseudomonas aeruginosa* PAO1 |
| 42780593 | NP_977840.1 | 47 | *Bacillus cereus* ATCC 10987 |
| 42781005 | NP_978252.1 | 48 | *Bacillus cereus* ATCC 10987 |
| 266346 | Q01292 | 18 | *Spinacia oleracea* |

Step 2. Build a Profile HMM

The hmmbuild program was run on the set of aligned sequences using default parameters. hmmbuild reads the multiple sequence alignment file, builds a new profile HMM, and saves the profile HMM to file. Using this program an uncalibrated profile was generated from the multiple sequence alignment for twenty-four experimentally verified KARIs as described above.

The following information based on the HMMER software user guide gives some description of the way that the hmmbuild program prepares a profile HMM. A profile HMM is a linear state machine consisting of a series of nodes, each of which corresponds roughly to a position (column) in the multiple sequence alignment from which it is built. If gaps are ignored, the correspondence is exact, i.e., the profile HMM has a node for each column in the alignment, and each node can exist in one state, a match state. The word “match” here implies that there is a position in the model for every position in the sequence to be aligned to the model. Gaps are modeled using insertion (I) states and deletion (D) states. All columns that contain more than a certain fraction x of gap characters will be assigned as an insert column. By default, x is set to 0.5. Each match state has an I and a D state associated with it. HMMER calls a group of three states (M/D/I) at the same consensus position in the alignment a “node”.

A profile HMM has several types of probabilities associated with it. One type is the transition probability—the probability of transitioning from one state to another. There are also emissions probabilities associated with each match state, based on the probability of a given residue existing at that position in the alignment. For example, for a fairly well-conserved column in an alignment, the emissions probability for the most common amino acid may be 0.81, while for each of the other 19 amino acids it may be 0.01.

A profile HMM is completely described in a HMMER2 profile save file, which contains all the probabilities that are used to parameterize the HMM. The emission probabilities of a match state or an insert state are stored as log-odds ratio relative to a null model: $\log_2$ (p_x)/(null_x). Where p_x is the probability of an amino acid residue, at a particular position in the alignment, according to the profile HMM and null_x is the probability according to the Null model. The Null model is a simple one state probabilistic model with pre-calculated set of emission probabilities for each of the 20 amino acids derived from the distribution of amino acids in the SWISSPROT release 24. State transition scores are also stored as log odds parameters and are proportional to $\log_2$(t_x). Where t_x is the transition probability of transiting from one state to another state.

Step 3. Calibrate the Profile HMM

The profile HMM was read using hmmcalibrate which scores a large number of synthesized random sequences with the profile (the default number of synthetic sequences used is 5,000), fits an extreme value distribution (EVD) to the histogram of those scores, and re-saves the HMM file now including the EVD parameters. These EVD parameters ($\mu$ and $\lambda$) are used to calculate the E-values of bit scores when the profile is searched against a protein sequence database. Hmmcalibrate writes two parameters into the HMM file on a line labeled “EVD”: these parameters are the $\mu$ (location) and $\lambda$(scale) parameters of an extreme value distribution (EVD) that best fits a histogram of scores calculated on randomly generated sequences of about the same length and residue composition as SWISS-PROT. This calibration was done once for the profile HMM.

The calibrated profile HMM for the set of KARI sequences is provided appended hereto as a profile HMM Excel chart (Table 9). In the main model section starting from the HMM flag line, the model has three lines per node, for M nodes (where M is the number of match states, as given by the LENG line). The first line reports the match emission log-odds scores: the log-odds ratio of emitting each amino acid from that state and from the Null model. The first number if the node number (1 . . . M). The next K numbers for match emission scores, one per amino acid. The highest scoring amino acid is indicated in the parenthesis after the node number. These log-odds scores can be converted back to HMM probabilities using the null model probability. The last number on the line represents the alignment column index for this match state. The second line reports the insert emission scores, and the third line reports on state transition scores: M→M, M→I, M→D; I—M, I—I; D→M, D→D; B→M; M→E.

Step 4. Test the Specificity and Sensitivity of the Built Profile HMMs

The Profile HMM was evaluated using hmmsearch, which reads a Profile HMM from hmmfile and searches a sequence file for significantly similar sequence matches. The sequence file searched contained 692 sequences (see above). During the search, the size of the database (Z parameter) was set to 1 billion. This size setting ensures that significant E-values against the current database will remain significant in the foreseeable future. The E-value cutoff was set at 10.

An hmmersearch, using hmmsearch, with the profile HMM generated from the alignment of the twenty-five KARIs with experimentally verified function, matched all 692 sequences with an E value<$10^{-3}$. This result indicates that members of the KARI family share significant sequence similarity. A hmmersearch with a cutoff of E value $10^{-3}$ was used to separate KARIs from other proteins.

Step 5. Identify Positions that are Relevant for NAD(P)H Utilization.

Eleven positions have been identified in KARI of *Pseudomonas fluorescens* Pf-5 that switches the cofactor from NADPH to NADH. Since the KARI sequences share significant sequence similarity (as described above), it can be reasoned that the homologous positions in the alignment of KARI sequences should contribute to the same functional specificity. The profile HMM for KARI enzymes has been generated from the multiple sequence alignment which contains the sequence of *Pseudomonas fluorescens* Pf-5 KARI. The eleven positions in the profile HMM representing the columns in the alignment which correspond to the eleven cofactor switching positions in *Pseudomonas fluorescens* Pf-5 KARI are identified as positions 24, 33, 47, 50, 52, 53, 61, 80, 115, 156, and 170. The lines corresponding to these positions in the model file are highlighted in yellow in Table 9.

For any query sequence, hmm search is used to search the profile HMM for KARI against the query sequence and the alignment of the query to the HMM is recorded in the output file. In the alignment section of the output, the top line is the HMM consensus. The amino acid shown for the consensus is the highest probability amino acid at that position according to the HMM (not necessarily the highest scoring amino acid). The center line shows letters for "exact" matches to the highest probability residue in the HMM, or a "+" when the match has a positive score. The third line shows the sequence itself. The positions in the query sequence that are deemed as relevant for cofactor switching are identified as those that are aligned to these eleven nodes in the profile HMM as described above. An example of the alignment of *Pseudomonas fluorescens* Pf-5 KARI to the profile HMM of KARI is shown in FIG. 10 and the eleven positions that are responsible for cofactor switching are shaded in grey.

Example 4

Construction of a Site-Saturation Gene Library for Complete Cofactor Switching to Nadh To construct the site-saturation gene library for KARI mutants, mutants 3361E1, 3361G8, 1D2, 2H10, 3F12, & Z4B8 (see Example 3, Tables 6 and 7) were used as templates. The library was constructed using QuickChange kit (Cat#200524, Stratagene, La Jolla, Calif.). The concentration of each mutant in the template mixture was 5.0 ng/μl. The two primers (2.5 nM) introducing saturation mutagenesis at positions 47, 50, 52 and 53, were PF5_4Mt111008.f (SEQ ID NO: 71) and PF5_4Mt111008.r (SEQ ID NO: 72).

The PCR Reaction Mixture Contained:

| | |
|---|---|
| 10 × reaction buffer | 5.0 μl |
| PF5_4Mt111008.f | 2.0 μl |
| PF5_4Mt111008.r | 2.0 μl |
| 50 × dNTP | 1.0 μl |
| DNA Template | 1.0 μl |
| PfuUltra | 1.0 μl |
| Water | 38 μl |

The PCR Reaction Program was:

| | |
|---|---|
| 1) 95° C. | 30 sec |
| 2) 95° C. | 30 sec |
| 3) 55° C. | 1.0 min |
| 4) 68° C. | 6.0 min |
| 5) Go to step (2) | Repeat 35 times |
| 6) 68° C. | 8.0 min |
| 7) 4° C. | press Enter |

The mixture was placed in a thin well 200 μl tube for the PCR reaction in a Mastercycler gradient equipment (Brinkmann Instruments, Inc. Westbury, N.Y.). After the PCR reaction, 1.0 μl Dpn I restriction enzyme (supplied with the kit above) was directly added into the PCR reaction mixture, which was then incubated at 37° C. for 1 h to remove the DNA templates. The Dpn I digested PCR product was cleaned up by the Zymo DNA clearance kit (Cat#D4003, Zymo Research, Orange, Calif.) as recommended by the manufacturer.

The cleaned PCR product was transformed into an electro-competent strain of *E. coli* Bw25113 (ΔilvC) using a BioRad Gene Pulser II (Bio-Rad Laboratories Inc., Hercules, Calif.). The transformed clones were streaked on agar plates containing the LB medium and 100 μg/ml ampicillin (Cat#L1004, Teknova Inc. Hollister, Calif.) and incubated at 37° C. overnight. Dozens of clones were randomly chosen for DNA sequencing to confirm the quality of the library. Several mutants identified in this library (Table 10 and FIG. 11) had very low NADPH activity while they had good NADH activity. Their cofactor consumption is listed in Table 11 (The data was based on three parallel measurements). "Negative" in the following Tables refers to an empty pBAD vector without the KARI gene.

TABLE 10

| List of some of the mutants identified in Example 1 | |
|---|---|
| Mutant | Mutation Locations |
| JB1C6 | Y24F/C33L/R47H/S50D/T52Y/V53Y/L61F/T80I/A156V |
| 16445E4 | C33L/R47P/S50V/T52D/V53G/L61F/T80I/A156V |
| 16468D7 | Y24F/C33L/R47T/S50I/T52D/V53R/L61F/T80I/A156V |
| 16469F3 | C33L/R47E/S50A/T52D/V53A/L61F/T80I |

TABLE 11

The cofactor consumption of some mutants following a 5 min reaction (decrease in $OD_{340}$ nm)

| | 0.2 mM NADH | | 0.2 mM NADPH | |
|---|---|---|---|---|
| Mutants | average | stdev | average | stdev |
| JB1C6 | −0.232 | 0.127 | −0.019 | 0.009 |
| 16445E4 | −0.152 | 0.057 | −0.013 | 0.001 |
| 16468D7 | −0.153 | 0.012 | −0.039 | 0.020 |
| 16469F3 | −0.054 | 0.069 | −0.025 | 0.016 |
| Z4B8 | −0.178 | 0.042 | −0.170 | 0.013 |
| PF5_WT | −0.078 | 0.014 | −0.320 | 0.024 |
| Negative | −0.061 | 0.029 | −0.015 | 0.014 |

Example 5

Construction of a Domain Swapping Library

In this Example the beneficial mutations outside the cofactor binding sites and the beneficial mutations within the cofactor binding sites were combined to create a domain swapping library.

Mutants, which had mutations in the cofactor binding site and exhibited only NADH activity (SE1, SB3, SE2, SD3, C2F6, C3B11, C4D12, 9650E5, 9667A11, 9862B9, 9875B9, 11461D8, 11463D8, 11518B4, SEQ ID NOs: 85-98), were used to obtain additional beneficial mutations in the cofactor binding site. Two primers, pBAD__230f (SEQ ID NO: 73) and pBAD__601__021308r (SEQ ID NO: 74), were used to amplify the mutants listed in Table 12. PCR reagents used were from Invitrogen (Cat#10572-014, Invitrogen, Carlsbad, Calif.).

The PR Reaction Mixture Contained:

| | |
|---|---|
| PCR SuperMix | 180 µl |
| pBAD__230.f (18 nM) | 5.0 µl |
| pBAD__601__021308r (10 nM) | 9.0 µl |
| Template mix (5.0 ng/µl) | 6.0 µl |

The PCR Reaction Program was:

| | |
|---|---|
| (1) 95° C. | 30 sec |
| (2) 95° C. | 20 sec |
| (3) 55° C. | 20 sec |
| (4) 72° C. | 60 sec |
| (5) Go to step (2) | repeat 35 times |
| (6) 72° C. | 4 min |
| (7) 4° C. | press enter |

After the PCR reaction, 1.0 µl Dpn I restriction enzyme (supplied with the kit above) was directly added into the PCR reaction mixture, which was then incubated at 37° C. for 1 h to remove the DNA templates. The Dpn I digested PCR product was cleaned up by the Zymo DNA clearance kit (Cat#D4003, Zymo Research, Orange, Calif.) as recommended by the manufacturer and 42 µl cleaned DNA product containing beneficial mutations in the cofactor binding sites obtained was designated as Megaprimer.

The Megaprimers thus obtained were then used to generate the domain swapping library using the QuickChange II XL site directed mutagenesis kit (Catalog #200524, Stratagene, La Jolla Calif.). The templates used in Example 4 were also used in this experiment. A 50 µl reaction mixture containing: 5.0 µl of 10× reaction buffer, 1.0 µl of 5.0 ng/µl template, 42 µl Megaprimer, 1.0 µl of 40 mM dNTP mix, 1.0 µl pfu-ultra DNA polymerase was prepared. Except for the Megaprimer and the templates, all reagents used here were supplied with the purchased kit. This reaction mixture was placed in a thin well 200 µl capacity PCR tube and the following reactions were used for the PCR. The starting temperature was 95° C. for 30 sec followed by 30 heating/cooling cycles. Each cycle consisted of 95° C. for 30 sec, 55° C. for 1 min, and 68° C. for 6 min. At the completion of the temperature cycling, the samples were kept at 68° C. for 8 min, and then stored at 4° C. for later processing. Dpn I restriction enzyme (1.0 µl) (supplied with the kit above) was directly added to the finished reaction mixture, enzyme digestion was performed at 37° C. for 1 h and the PCR product was cleaned up using a DNA cleaning kit (Zymo Research). The cleaned PCR product (10 µl) contained mutated genes for a gene library.

The mutated genes were transformed into an electro-competent strain of *E. coli* Bw25113 (ΔilvC) using a BioRad Gene Pulser II (Bio-Rad Laboratories Inc., Hercules, Calif.). The transformed clones were streaked on LB agar plates containing 100 µg/ml ampicillin (Cat#L1004, Teknova Inc. Hollister, Calif.) and incubated at 37° C. overnight. Dozens of clones were randomly chosen for DNA sequencing to confirm the quality of the library.

This library yielded many mutants with high NADH activity (low $K_M$ for NADH), which also had very low NADPH activity. (Table 12 and FIG. 12). Their cofactor consumption is also shown in Table 13 (The data was based on three parallel measurements).

TABLE 12

Mutants with improved $K_M$ (for NADH) obtained from the domain swapping library

| Mutant | Mutation Locations | NADH $K_M$ (µM) |
|---|---|---|
| JEA1 | Y24F/C33L/R47P/S50F/T52D/L61F/T80I/A156V | 9.1 |
| JEG2 | Y24F/C33L/R47F/S50A/T52D/V53A/L61F/T80I/A156V | 9.4 |
| JEG4 | Y24F/C33L/R47N/S50N/T52D/V53A/L61F/T80I/A156V | 9.6 |
| JEA7 | Y24F/C33L/R47P/S50N/T52D/V53A/L61F/T80I/A156V | 10.6 |
| JED1 | C33L/R47N/S50N/T52D/V53A/L61F/T80I/A156V | 11.0 |

TABLE 13

The cofactor consumption of some mutants after 5 min reaction (decrease in $OD_{340}$ nm)

| | 0.2 mM NADH | | 0.2 mM NADPH | |
|---|---|---|---|---|
| Mutants | average | stdev | average | stdev |
| JEA1 | −0.285 | 0.030 | −0.110 | 0.025 |
| JED1 | −0.287 | 0.032 | −0.074 | 0.014 |
| JEG2 | −0.261 | 0.009 | −0.078 | 0.009 |
| JEG4 | −0.227 | 0.016 | −0.050 | 0.016 |
| JEA7 | −0.205 | 0.079 | −0.038 | 0.009 |
| Z4B8 | −0.178 | 0.042 | −0.170 | 0.013 |

TABLE 13-continued

The cofactor consumption of some mutants after 5 min reaction (decrease in $OD_{340}$ nm)

| Mutants | 0.2 mM NADH average | 0.2 mM NADH stdev | 0.2 mM NADPH average | 0.2 mM NADPH stdev |
|---|---|---|---|---|
| PF5_WT | −0.078 | 0.014 | −0.320 | 0.024 |
| Negative | −0.061 | 0.029 | −0.015 | 0.014 |

Example 6

Thermostability of Pf5-Ilvc and its Mutants

The wildtype PF5-ILVC and various cells containing mutated pBad-ilvC were grown overnight at 37° C. in 25 ml of the LB medium containing 100 μg/ml ampicillin and 0.02% (w/v) arabinose inducer while shaking at 250 rpm. The cells were then harvested by centrifugation at 18,000×g for 1 min at room temperature and the cell pellets were re-suspended in 300 μl of BugBuster Master Mix (EMD Chemicals). The reaction mixture was first incubated at room temperature for 20 min and aliquots of this cell mixture (e.g. 50 μl) were incubated at different temperatures (from room temperature to 75° C.) for 10 min. The precipitate was removed by centrifugation at 18,000×g for 5 min at room temperature. The remaining activity of the supernatant was analyzed as described above. As shown in FIG. 7, pBad-ilvC was very stable with $T_{50}$ at 68° C. ($T_{50}$ is the temperature, at which 50% of protein lost its activity after 10 min incubation).

The thermostability of PF5-ilvC allowed destruction of most of the other non-KARI NADH oxidation activity within these cells, reducing the NADH background consumption and thus facilitating the KARI activity assays. This heat treatment protocol was used in all screening and re-screening assays. The mutants thus obtained were all thermostable which allowed easier selection of the desirable mutants.

Example 7

Stoichiometric Production of 2,3-Dihydroxyisovalerate By Kari During Consumption of NADH or NADPH as Cofactors Screening and routine assays of KARI activity rely on the 340 nm absorption decrease associated with oxidation of the pyridine nucleotides NADPH or NADH. To insure that this metric was coupled to the formation of the reaction product (i.e., 2,3-dihydroxyisovalerate), oxidation of both pyridine nucleotide and formation of 2,3-dihydroxyisovalerate were measured in the same samples.

The oxidation of NADH or NADPH was measured at 340 nm in a 1 cm path length cuvette on a Agilent model 8453 spectrophotometer (Agilent Technologies, Wilmington Del.). Crude cell extract (0.1 ml) prepared as described above containing either wild type PF5 KARI or the C3B11 mutant, was added to 0.9 ml of K-phosphate buffer (10 mM, pH 7.6), containing 10 mM $MgCl_2$, and 0.2 mM of either NADPH or NADH. The reaction was initiated by the addition of acetolactate to a final concentration of 0.4 mM. After 10-20% decrease in the absorption (about 5 min), 50 μl of the reaction mixture was rapidly withdrawn and added to a 1.5 ml Eppendorf tube containing 10 μl 0.5 mM EDTA to stop the reaction and the actual absorption decrease for each sample was accurately recorded. Production of 2,3-dihydroxyisovalerate was measured and quantitated by HPLC/MS as described above.

The coupling ratio is defined by the ratio between the amount of 2,3-dihydroxyisovalerate (DHIV) produced and the amount of either NADH or NADPH consumed during the experiment. The coupling ratio for the wild type enzyme (PF5-ilvC), using NADPH, was 0.98 DHIV/NADPH, while that for the mutant (C3B11), using NADH, was on average around 1.10 DHIVINADPH underlining the high activity of the mutant enzyme to consume NADH and produce DHIV.

HMMER2.0 [2.2g]
NAME Functionally Verified KARIs
LENG 354
ALPH Amino
MAP yes
COM hmmbuild-n Functionally Verified KARIs exp-KARI.hmm exp-KARI_mod.aln
COM hmmcalibrate exp-KARI.hmm
NSEQ 25
DATE Mon Dec 8 17:34:51 2008
XT −8455 −4 −1000 −1000 −8455 −4 −8455 −4
NULT −4 −8455
NULE 595 −1558 85 338 −294 453 −1158 197 249 902 −1085 −142 −21 −313 45 531 201 384 −1998 −644
EVD −333.712708 0.110102

File format version: a unique identifier for this save file format.
Name of me profile HMM
Model length: the number of match states in the model.
Symbol alphabet: This determines the symbol alphabet and the size of the symbol emission probabilty distributions.
IAmino, the alphabet size is set to 20 and the symbol alphabet to "ACDEFGHIKLMNPQRSTVWY" (alphabetic order).
Map annotation flag: If set to yes, each line of data for the match state/consensus column in the main section of the file is followed by an extra number. This number gives the Index of the alignment column that the match state was made from. This information provides a "map" of the match states (1..M) onto the columns of the alignment (1.alen). It is used for quickly aligning the model back to the original alignment e.g. when using hmmalign-mapali.
Command line for every HMMER command that modifies the save file: This one means that hmmbuild (default patrameters) was applied to generate the save file.
Command line for every HMMER command that modifies the save file: This one means that hmmcalibrate (default parameters) was applied to the save profile.
Sequence number: the number of sequences the HMM was trained on
Creation date: When was the save file was generated.
Eight "special" transitions for controlling parts of the algorithm-specific parts of the Plan7 model.
The null probabilty used to convert these back to model probabilities is 1.0. The order of the eight fields is N->B, N->N, E->C, E->J, C->T, C->C, J->B, J->J.
The transition probabilty distribution for the null model (single G state).
The extreme value distribution parameters μ and lambda respectively; both floating point values. These values are set when the model is calibrated with hmmcalibrate. They are used to determine E-values of bit scores.

| | A | C | D | E | F | G | H | I | K | | | | | | | | | | | | Position in |
|---|---|---|---|---|---|---|---|---|---|---|---|---|---|---|---|---|---|---|---|---|---|
| HMM | m->m | m->i | m->d | i->m | i->i | d->m | d->d | b->m | m->e | L | M | N | P | Q | R | S | T | V | W | Y | alignment |
| | −650 | * | −1463 | | | | | | | | | | | | | | | | | | |
| 1(Q) | −648 | −1356 | −136 | −44 | −1453 | −1166 | −219 | −1455 | 321 | −1477 | −911 | −227 | −1496 | 3263 | 122 | −643 | −684 | −1239 | −1542 | −1030 | 7100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −701 | −1378 | −650 | * | | | | | | | | | | | | |
| 2(M) | −4231 | −3929 | −5216 | −5402 | −3438 | −4370 | −4528 | −3232 | −5113 | −2613 | 5320 | −5052 | −4790 | −4977 | −4823 | −4692 | −4459 | −3629 | −4103 | −4017 | 7200% |
| — | −147 | −501 | 232 | 42 | −382 | 397 | 104 | −625 | 209 | −467 | −722 | 276 | 396 | 44 | 95 | 361 | 121 | −368 | 296 | −251 | |
| — | −3303 | −3318 | −325 | −3473 | −136 | −701 | −1378 | * | * | | | | | | | | | | | | |
| 3(F) | −1308 | −1104 | −2227 | −2120 | 3516 | −2093 | −244 | −196 | −1891 | 64 | 66 | −1626 | −2278 | −1503 | −1798 | −1617 | −1350 | −389 | 305 | 1355 | 8600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −943 | −1060 | * | * | | | | | | | | | | | | |
| 4(A) | 1616 | −1744 | 1125 | 33 | −2015 | −1540 | −262 | −1686 | 937 | −1765 | −911 | −252 | −1658 | 154 | −383 | −488 | 640 | −3 | −2038 | −1421 | 8700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −901 | −7402 | −1125 | −894 | −1115 | −2352 | −314 | * | * | | | | | | | | | | | | |
| 5(C) | −346 | 2578 | 1084 | −712 | 2092 | −1540 | −384 | −167 | −624 | −482 | 125 | −731 | −1705 | −451 | −883 | −631 | −338 | −50 | −774 | −133 | 8800% |
| — | −149 | −500 | 235 | 43 | −381 | 398 | 106 | −626 | 210 | −466 | −721 | 275 | 394 | 45 | 96 | 359 | 118 | −369 | −295 | −249 | |
| — | −1009 | −1006 | −7567 | −131 | −3597 | −1916 | −444 | * | * | | | | | | | | | | | | |
| 6(S) | 800 | −586 | −1937 | −1415 | −821 | −1740 | −954 | 1279 | −1204 | −584 | 19 | −1258 | −1964 | −1013 | −1358 | 1715 | −476 | 1117 | −1320 | −938 | 9000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −17 | −6953 | −7995 | −894 | −1115 | −146 | −3378 | * | * | | | | | | | | | | | | |
| 7(K) | −956 | −2411 | −803 | 501 | −2743 | −1919 | −558 | −2483 | 2435 | −2420 | −1520 | 57 | −2010 | 1146 | 458 | 829 | 224 | −2040 | −2577 | −1913 | 9100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 8(V) | −2472 | −2010 | −5089 | −4702 | −2534 | −4789 | −4391 | 2241 | −4574 | −151 | −1318 | −4442 | −4600 | −4417 | −4628 | −4080 | −82 | 3023 | −3952 | −3510 | 9200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 9(Y) | −4673 | −3685 | −5210 | −5505 | 2423 | −5069 | −1332 | −3424 | −5065 | −392 | −2838 | −3726 | −4920 | −3835 | −4458 | −4313 | −4533 | −3643 | −581 | 4349 | 9300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 10(Y) | −2170 | −2625 | −2489 | −2097 | −1555 | −2986 | −1481 | −2628 | 906 | −2674 | −2098 | −2051 | −3206 | −1513 | −1078 | −2258 | 1039 | −2435 | −2009 | 4185 | 9400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 11(D) | −2498 | −4412 | 3500 | 1042 | −4581 | −2437 | −1765 | −4500 | 733 | −4361 | −3682 | 515 | −2961 | −1429 | −2799 | −2158 | −2558 | −3974 | −4550 | −3541 | 9500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 12(K) | 11 | −2371 | 348 | 819 | −2692 | −535 | −527 | −2443 | 2294 | −2387 | −1461 | 590 | −1960 | −68 | 904 | −67 | −837 | −1993 | −2554 | −1871 | 9600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 13(D) | −2663 | −4633 | 3700 | 580 | −4789 | −2487 | −1872 | −4738 | 731 | −4578 | −3963 | −1073 | −3046 | −1551 | −2987 | −2292 | −2742 | −4201 | −4759 | −3709 | 9700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 14(C) | 2503 | 3193 | −4266 | −3818 | −2010 | −3276 | −2896 | 762 | −3517 | −1437 | −1051 | −3233 | −3509 | −3212 | −3411 | −2499 | −1792 | 1507 | −2796 | −2431 | 9800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 15(D) | −1363 | −2905 | 2748 | 542 | −3202 | −2072 | −920 | −2977 | 290 | −2912 | −2023 | 1270 | −2294 | −489 | −1189 | 53 | 1116 | −2518 | −3086 | −2349 | 9900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 16(L) | −1268 | −1113 | −3338 | −540 | −1057 | −2827 | −1716 | 569 | −2409 | 2299 | −236 | −2381 | −2862 | −2089 | −2316 | −232 | −1213 | 1306 | −1645 | −1304 | 10000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 17(S) | −1350 | −2877 | 588 | 1045 | −3189 | −496 | −920 | −2963 | −628 | −2901 | −2011 | 1860 | −2289 | −489 | −1184 | 2139 | 190 | −2503 | −3077 | −2343 | 10100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2336 | −8139 | −325 | −894 | −1115 | −701 | −1378 | * | * | | | | | | | | | | | | |
| 18(G) | −454 | −832 | −968 | −1110 | −2112 | 3143 | −1211 | −2091 | −1317 | −2264 | −1691 | −978 | −1499 | −1202 | −1421 | −646 | −774 | −1550 | −1916 | −1919 | 10200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6881 | −894 | −1115 | −3098 | −179 | * | * | | | | | | | | | | | | |
| 19(H) | −898 | −1313 | −545 | −482 | −320 | −1336 | 4297 | −1552 | −160 | −1493 | −1035 | −579 | −1675 | −363 | −322 | −934 | −951 | −1354 | −725 | 107 | 10300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −3098 | −179 | * | * | | | | | | | | | | | | |
| 20(D) | −872 | −1812 | 3234 | 432 | −2215 | −967 | −433 | −2172 | −569 | −2269 | −1704 | 99 | −1453 | −184 | −1141 | −728 | −973 | −1814 | −2146 | −1646 | 10400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −3098 | −179 | * | * | | | | | | | | | | | | |
| 21(E) | −766 | −1695 | 521 | 2831 | −2050 | −1029 | −293 | −1804 | −118 | −1919 | −1331 | 69 | −1441 | −4 | −257 | −653 | −814 | −1512 | −1968 | −1505 | 10500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −3098 | −179 | * | * | | | | | | | | | | | | |
| 22(Y) | −1337 | −1229 | −1681 | −1596 | 1268 | −1957 | 121 | −918 | −1294 | −769 | −585 | −1229 | −2163 | −1111 | −1301 | −1443 | −1359 | −932 | 592 | 3932 | 10600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −109 | −3775 | * | * | | | | | | | | | | | | |
| 23(I) | −2294 | −1931 | −4749 | −4227 | −1724 | −4227 | −3320 | 2306 | −3952 | 1990 | −684 | −3878 | 94 | −3538 | −3812 | −3411 | −2247 | 1576 | −2891 | −2629 | 10700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 24(I) | −2801 | −2299 | −5406 | −5003 | −2108 | −5164 | −4649 | 3051 | −4846 | 1593 | −869 | −4829 | −4788 | −4454 | −4829 | −4493 | −2764 | 1435 | −3781 | −3585 | 10800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 25(K) | −234 | −2632 | 306 | −500 | −3007 | −2141 | −719 | −2712 | 2540 | −2619 | −1730 | −778 | −2231 | 2257 | 968 | −1109 | −1152 | −2288 | −2738 | −2136 | 10900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26(G) | −2184 | −3900 | 796 | 392 | −4174 | 2903 | −1580 | −4030 | −1636 | −3937 | −3173 | −967 | −2810 | −1 | −2362 | 1069 | −2220 | −3530 | −4130 | −3229 | 11000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −155 | −3318 | −9181 | −3674 | −118 | −701 | −1378 | * | * | | | | | | | | | | | | |
| 27(K) | −3243 | −3775 | −4129 | −2558 | −4750 | −3647 | −1490 | −4021 | 3681 | −3617 | −2982 | −2368 | −3580 | −1076 | 1318 | −3119 | −2876 | −3817 | −3395 | −3374 | 12600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 28(K) | −1684 | −2925 | −1665 | −979 | −3407 | −2535 | −923 | −3021 | 2737 | −2865 | −2032 | 202 | −2582 | 1301 | 804 | −1564 | 1681 | −2645 | −2905 | −2448 | 12700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 29(V) | −2623 | −2122 | −5300 | −4990 | −2769 | −5101 | −5131 | 2388 | −4945 | −1532 | −1474 | −4790 | −4868 | −4890 | −5101 | −4482 | −2619 | 3219 | −4505 | −3990 | 12800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 30(A) | 3309 | −1828 | −4057 | −4294 | −4382 | 656 | −3657 | −4147 | −4169 | −4428 | −3497 | −2821 | −2904 | −3694 | −3937 | −1470 | 59 | −2957 | −4610 | −4522 | 12900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 31(V) | −2625 | −2122 | −5304 | −4993 | −2772 | −5111 | −5142 | 2881 | −4950 | −1532 | −1474 | −4796 | −4873 | −4896 | −5108 | −4492 | −2621 | 2896 | −4512 | −3997 | 13000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 32(I) | −2790 | −2287 | −5403 | −5009 | −2155 | −5170 | −4698 | 3324 | −4899 | 1175 | −912 | −4835 | −4802 | −4495 | −4860 | −4506 | −2757 | 1192 | −3838 | −3622 | 13100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 33(G) | −4435 | −4203 | −5092 | −5462 | −5893 | 3834 | −5028 | −6627 | −5765 | −6297 | −5970 | −5141 | −4804 | −5546 | −5385 | −4727 | −4815 | −5862 | −4924 | −5849 | 13200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 34(Y) | −4838 | −3766 | −5229 | −5579 | 1502 | −5108 | −1300 | −3726 | −5134 | −3040 | −3131 | −3723 | −4963 | −3861 | −4500 | −4356 | −4689 | −3881 | 2986 | 4507 | 13300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 35(G) | −4435 | −4203 | −5092 | −5462 | −5893 | 3834 | −5028 | −6627 | −5765 | −6297 | −5970 | 5141 | −4804 | −5546 | −5385 | −4727 | −4815 | −5862 | −4924 | −5849 | 13400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 36(S) | −1473 | −2007 | −3647 | −3780 | −3430 | −2363 | −3314 | 228 | −3616 | −3373 | −2876 | −2840 | −3093 | −3395 | −3541 | 3475 | −1885 | −2307 | −3927 | −3474 | 13500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 37(Q) | −4589 | −4392 | −3927 | −4146 | −5099 | −4221 | −4099 | −5973 | −3840 | −5564 | −5304 | −4230 | −4693 | 4575 | −3826 | −4704 | −4772 | −5612 | −4577 | −4751 | 13600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 38(G) | 677 | −2128 | −3838 | −4171 | −4647 | 3536 | −3816 | −4506 | −4340 | −4749 | −3857 | −3009 | −3149 | −3871 | −4137 | −1784 | −2005 | −3297 | −4725 | −4735 | 13700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 39(H) | −2667 | −3375 | −2682 | −2114 | −3744 | −3201 | −4738 | −3782 | −445 | −3553 | −2886 | −2112 | 866 | −1265 | 1506 | −2614 | −2557 | −3469 | −3282 | −2908 | 13800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 40(A) | 3631 | −2768 | −4492 | −4815 | −4888 | −2992 | −4271 | −4781 | −4818 | −5025 | −4365 | −3727 | −3728 | −4477 | −4545 | −2567 | −2762 | −3852 | −4724 | −4942 | 13900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 41(H) | −3103 | −3404 | −2950 | −2573 | −783 | −3679 | 4549 | −3407 | −1372 | −3071 | −2715 | −2454 | −3764 | 2546 | −1428 | −2990 | −2976 | −3308 | 2269 | −295 | 14000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 42(A) | 3357 | −1795 | −4134 | −4277 | −4057 | −2118 | −3548 | −3549 | −4035 | −4024 | −3192 | −2817 | −2900 | −3608 | −3823 | 217 | −1660 | −276 | −4363 | −4211 | 14100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43(Q) | −1061 | 1950 | −2044 | −1475 | −1236 | −2372 | −1154 | −789 | −1218 | −1062 | −1123 | −743 | −2446 | 2895 | −1441 | −1392 | −1005 | −693 | −1678 | −1278 | 14200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 44(N) | −4000 | −4117 | −3389 | −3749 | −5073 | −3911 | −4123 | −6022 | −4503 | −5797 | −5419 | 4397 | −4479 | −4255 | −4592 | −4115 | −4312 | −5371 | −4650 | −4731 | 14300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 45(L) | −4414 | −3800 | −5638 | −5628 | −2290 | −4980 | −4628 | −1886 | −5423 | 3316 | −1236 | −5514 | −4997 | −4750 | −5002 | −5379 | −4399 | −2629 | −3665 | −3690 | 14400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 46(R) | −1731 | −3051 | 275 | −931 | −3487 | −2518 | −973 | −3116 | 2321 | −2955 | −2123 | −224 | −2603 | 256 | 2808 | −1596 | −1613 | −2730 | −2995 | −2515 | 14500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 47(D) | −2896 | −4843 | 3855 | 944 | −5037 | −2600 | −2082 | −5082 | −2528 | −4903 | −4373 | −1209 | −3196 | −1786 | −3536 | −2501 | −3007 | −4517 | −5004 | −3956 | 14600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 48(S) | −1538 | −2212 | −2363 | −2679 | −4293 | −2279 | −3082 | −4365 | −3331 | −4524 | −3676 | 288 | −3026 | −2967 | −3497 | 3508 | −1962 | −3259 | −4477 | −4066 | 14700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −155 | −3318 | −9181 | −2405 | −302 | −701 | −1378 | * | * | | | | | | | | | | | | |
| 49(G) | −2521 | −3968 | 1232 | −911 | −4849 | 3373 | −2126 | −4854 | −2535 | −4752 | −4136 | −53 | −3115 | −1836 | −3440 | −2284 | −2716 | −4157 | −4880 | −3914 | 15400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 50(V) | −2767 | −2324 | −5232 | −4770 | 396 | −4827 | −3784 | −36 | −4546 | 848 | −611 | −4472 | −4518 | −3980 | −4367 | −4081 | −2716 | 3323 | −3037 | −2660 | 15500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −148 | −3381 | −9181 | −203 | −2928 | −701 | −1378 | * | * | | | | | | | | | | | | |
| 51(D) | −1684 | −3285 | 2735 | 2014 | −3554 | −2196 | −1177 | −3350 | 92 | −3279 | −2427 | 692 | −2505 | −770 | −1595 | −1483 | −1666 | 332 | −3460 | −2676 | 15700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 52(V) | −3122 | −2888 | −5092 | −5160 | −3522 | −4180 | −4687 | −905 | −5060 | −2626 | −2570 | −4662 | −4579 | −4940 | −4923 | −4013 | −3297 | 3796 | −4414 | −4190 | 15800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 53(V) | 369 | 366 | −3075 | −2462 | −883 | −2257 | −1420 | 1415 | 378 | −757 | −117 | −2098 | −2610 | −1809 | −2037 | −1630 | 1166 | 2145 | −1365 | −343 | 15900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 54(V) | −2624 | −2122 | −5302 | −4991 | −2772 | −5108 | −5139 | 2623 | −4948 | −1533 | −1475 | −4794 | −4871 | −4894 | −5106 | −4488 | −2620 | 3088 | −4511 | −3996 | 16000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 55(G) | 929 | −2107 | −3852 | −4182 | −4633 | 3492 | −3809 | −4486 | −4335 | −4732 | −3835 | −2997 | −3132 | −3863 | −4127 | −1761 | −1982 | −3275 | −4720 | −4725 | 16100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 56(L) | −3427 | −2938 | −5791 | −5325 | −1449 | −5374 | −4410 | −543 | −5063 | 3041 | −255 | −5207 | −4820 | −4126 | −4691 | −4757 | −3351 | 883 | −3184 | −3234 | 16200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 57(R) | −3040 | −3724 | −3266 | 82 | −4620 | −3470 | −1396 | −3905 | 804 | −3529 | −2874 | −2133 | −3439 | −978 | 3800 | −2894 | −2709 | −3682 | −3353 | −3267 | 16300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 58(K) | 31 | −2412 | −803 | 1532 | −2743 | −1920 | −559 | −2483 | 1772 | −2421 | −1503 | −556 | 1229 | 727 | 1079 | −566 | −893 | −2041 | −2579 | −1915 | 16400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 59(G) | −2671 | −4661 | 1614 | 587 | −4832 | 3103 | −1901 | −4803 | −2269 | −4648 | −4047 | 421 | −3049 | −1587 | −3230 | 2297 | −2766 | −4245 | −4850 | −3752 | 16500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 60(S) | −1499 | −2308 | −1932 | −1859 | −4006 | 1604 | −2121 | −3754 | 1362 | −3793 | −2945 | −1833 | −2827 | −1794 | −1902 | 2738 | −1771 | −2970 | −3910 | −3479 | 16600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −247 | −8139 | −2699 | −894 | −1115 | −701 | −1378 | * | * | | | | | | | | | | | | |
| 61(K) | 1362 | −2232 | −619 | −98 | −2567 | −427 | −435 | −2309 | 1599 | −2265 | −1349 | 1101 | −1861 | 886 | −512 | 833 | −740 | −1868 | −2441 | −1767 | 16700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7900 | −8943 | −894 | −1115 | −344 | −2238 | * | * | | | | | | | | | | | | |
| 62(S) | −1288 | −1904 | −3742 | −4011 | −4384 | −2155 | −3593 | −4209 | −3996 | −4479 | −3573 | −2789 | −2948 | −3606 | −3832 | 3517 | 228 | −3028 | −4600 | −4451 | 16800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 63(W) | 726 | −873 | −3261 | −2634 | 1926 | −2567 | −1425 | 660 | −2252 | −701 | −68 | −2174 | −2617 | −1898 | 18 | −1648 | −972 | 983 | 4091 | −958 | 16900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 64(E) | 1527 | −244 | 212 | 1636 | −2722 | −1878 | −556 | −2474 | 1241 | −2419 | −1497 | 350 | −1985 | −100 | −659 | 96 | 70 | −2025 | −2589 | −1903 | 17000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 65(K) | −8 | −2242 | −895 | 770 | −2502 | −1963 | −609 | −2192 | 2589 | 22 | −1353 | −631 | −2052 | 692 | −617 | −889 | −906 | −361 | −2455 | −1836 | 17100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 66(A) | 3631 | −2768 | −4492 | −4815 | −4888 | −2992 | −4271 | −4781 | −4818 | −5025 | −4365 | −3727 | −3728 | −4477 | −4545 | −2567 | −2762 | −3852 | −4724 | −4942 | 17200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 67(Q) | −1006 | −2441 | −869 | 1767 | −2780 | −1965 | −586 | −2510 | 1702 | −2445 | −1534 | −603 | −2052 | 1923 | 873 | −888 | 236 | −630 | −2596 | 1949 | 17300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 68(A) | 1489 | −2393 | 167 | 1234 | −2711 | −1873 | −547 | −2462 | 895 | −2408 | −1485 | 1161 | −1977 | −90 | −648 | 666 | 141 | −2014 | −2577 | −1892 | 17400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 69(D) | 2104 | −2898 | 2124 | 985 | −3163 | 2096 | 1397 | −2935 | −693 | −2897 | −2025 | −723 | −2329 | −543 | −1250 | −1245 | −1368 | −2501 | −3087 | −530 | 17500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 70(G) | −2294 | −2898 | −2521 | −2885 | −4852 | 3641 | −3456 | −5042 | −3796 | −5094 | −4356 | −365 | −3545 | −3376 | −4005 | −2451 | −2700 | −3996 | −4706 | −4575 | 17600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 71(F) | −2596 | −2266 | −4685 | −4188 | 3199 | −4136 | 1018 | 505 | −3812 | 1986 | −405 | −3595 | −3961 | −3157 | −3524 | −3277 | −2509 | −1337 | −1621 | −840 | 17700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 72(K) | 47 | −2348 | 338 | 950 | −2668 | −1854 | −512 | −507 | 1721 | −2364 | −1438 | −490 | −1947 | 672 | 436 | 806 | 687 | −1970 | −2533 | −1851 | 17800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −155 | −3318 | −9181 | −2159 | −366 | −701 | −1378 | * | * | | | | | | | | | | | | |
| 73(V) | −1810 | −1639 | −4149 | −3689 | −1869 | −3417 | −2822 | 29 | −3369 | 320 | −897 | −3230 | 112 | −3099 | −3291 | −2619 | −767 | 3269 | −2708 | −2354 | 18400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 74(K) | 847 | −1093 | −2131 | −1554 | 304 | 127 | −1127 | −637 | 1445 | 645 | 1186 | −1534 | −2401 | −1174 | −1547 | −764 | −172 | −528 | −1519 | 1413 | 18500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 75(T) | −1284 | −2794 | 1526 | 1290 | −3096 | −2041 | 1289 | −2863 | −548 | −2808 | −1914 | −668 | −2242 | −427 | −1095 | 1451 | 1827 | −2411 | −2986 | −2264 | 18600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 76(V) | −1089 | −957 | −3143 | −2535 | −943 | −2618 | −1496 | 1052 | −2198 | −792 | 1859 | −146 | 686 | −1884 | −2111 | −1695 | 945 | 2346 | −1458 | −1106 | 18700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77(W) | 1606 | −2321 | −752 | 612 | −2628 | −323 | −527 | −2366 | 1480 | −2331 | −1416 | −510 | −789 | −73 | 421 | 23 | −829 | −1936 | 2212 | −1843 | 18800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 78(E) | −1509 | −3540 | 1372 | 3127 | −3861 | −120 | −1391 | −3685 | −1319 | −3605 | −2787 | −900 | −2659 | −1005 | −1976 | −400 | −655 | −3194 | −3790 | −2957 | 18900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 79(A) | 3390 | −1868 | −4092 | −4341 | −4332 | −2153 | −3680 | −3942 | −4157 | −4333 | −3471 | −2869 | −2948 | −3730 | −3919 | −1525 | 931 | −2894 | −4580 | −4483 | 19000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 80(V) | 2003 | −1721 | −4449 | −3995 | −2160 | −3763 | −3240 | −1342 | −3745 | −1435 | −1124 | −3561 | −3855 | −3494 | −3700 | −2979 | −58 | 2574 | −3091 | −2698 | 19100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 81(K) | 1714 | −2501 | −959 | 446 | −2858 | −2043 | −654 | −2574 | 1964 | −2506 | −1609 | −689 | −2135 | −203 | 1088 | 423 | −1032 | −2148 | −2652 | −2027 | 19200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 82(W) | 265 | −2347 | 815 | 432 | −2663 | 634 | −519 | −210 | 619 | −2361 | −1438 | −495 | −1952 | 1955 | −609 | −382 | 147 | −1966 | 2858 | −1853 | 19300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 83(A) | 3391 | −1860 | −3998 | −4279 | −4411 | −2128 | −3684 | −4207 | −4197 | −4490 | −3585 | −2837 | −2929 | −3729 | −3959 | 706 | −1718 | −3007 | −4636 | −4534 | 19400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 84(D) | −2747 | −4795 | 3813 | 396 | −4912 | −2496 | −1935 | −4905 | −2324 | −4735 | −4166 | −1079 | −3082 | 603 | −3296 | −2353 | −2844 | −4347 | −4929 | −3809 | 19500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 85(V) | −2717 | −2220 | −5338 | −4951 | −2254 | −5099 | −4670 | 1963 | −4844 | 1553 | −1011 | −4759 | −4771 | −4509 | −4836 | −4427 | −2688 | 2741 | −3899 | −3628 | 19600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 86(V) | −2635 | −2129 | −5306 | −4970 | −2652 | −5125 | −5011 | 2554 | −4915 | −354 | −1368 | −4781 | −4852 | −4798 | −5038 | −4487 | −2622 | 3019 | −4355 | −3902 | 19700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 87(M) | −1340 | −1208 | −3317 | −2708 | −968 | −2860 | −1708 | 577 | −2346 | 932 | 4131 | −2382 | −2878 | 250 | −2265 | −228 | −1278 | −506 | −1629 | −1313 | 19800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 88(I) | −2566 | −2177 | −5017 | −4470 | 669 | −4496 | −3487 | 2791 | −4191 | 1116 | 1394 | −4156 | −4228 | −3615 | −3972 | −3687 | −2499 | 1692 | −2860 | −2711 | 19900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 89(L) | −4414 | −3800 | −5638 | −5628 | −2290 | −4980 | −4628 | −1886 | −5423 | 3316 | −1236 | −5514 | −4997 | −4750 | −5002 | −5379 | −4399 | −2629 | −3665 | −3690 | 20000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 90(I) | 1212 | −1286 | −3846 | −3262 | −1360 | −3195 | −2166 | 1616 | −2918 | 1031 | −493 | −2824 | −3211 | −2583 | −2782 | −2308 | 1598 | 1299 | −2020 | −1668 | 20100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 91(P) | −1614 | −2214 | −3396 | −3710 | −4516 | −2407 | −2618 | −4516 | −3976 | −4705 | −3849 | −2890 | 3993 | −3625 | −3900 | 666 | −2068 | −3354 | −4610 | −4474 | 20200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 92(D) | −4580 | −4701 | 4174 | −3014 | −5700 | −3967 | −3905 | −6376 | −4478 | −6024 | −5744 | −3355 | −4501 | −3870 | −4926 | −4440 | −4750 | −5894 | −4922 | −5231 | 20300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 93(E) | −1123 | −2199 | −983 | 2715 | −2589 | −2046 | −942 | −2250 | −625 | −2356 | 1979 | −870 | −2250 | −554 | −1093 | 463 | 932 | −1902 | −2660 | −2064 | 20400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 94(H) | 399 | −1137 | −2012 | −14 | 1582 | −2306 | 1600 | 246 | −1252 | 190 | −325 | −1456 | −2374 | 1474 | −1479 | −94 | −905 | 896 | −1557 | −1158 | 20500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 95(Q) | −2742 | −3142 | −2766 | −2681 | −2790 | −3344 | −2460 | −160 | −1802 | −2456 | −2353 | −2682 | −3710 | 4317 | −1866 | −2894 | −2844 | −2559 | −3295 | −2711 | 20600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 96(A) | 1981 | −2315 | −809 | −268 | −2645 | −531 | −579 | −2374 | 232 | −2350 | −1445 | −567 | 1217 | 711 | 445 | 447 | −874 | −1951 | −2540 | −1883 | 20700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 97(D) | 491 | −2351 | 1394 | 1381 | −2671 | −1854 | 1062 | −2421 | 1010 | −2367 | −1440 | −489 | −1947 | 1017 | 362 | −760 | 250 | −623 | −2535 | −1852 | 20800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 98(V) | −2039 | −1706 | −4456 | −3939 | −1846 | −3939 | −3049 | 1986 | −3656 | 1460 | −826 | 804 | −3870 | −3351 | −3565 | −3105 | −2000 | 2330 | −2796 | −2442 | 20900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 99(Y) | −4840 | −3766 | −5230 | −5581 | 1898 | −5109 | −1300 | −3727 | −5135 | −3041 | −3132 | −3723 | −4964 | −3861 | −4501 | −4357 | −4690 | −3883 | 3325 | 4377 | 21000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 100(E) | −163 | −2353 | −734 | 1681 | −2674 | −1859 | 888 | −2422 | 1668 | −792 | −1443 | 777 | −1952 | 890 | 286 | −766 | 238 | −1975 | −2536 | −1856 | 21100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −257 | −8139 | −2649 | −894 | −1115 | −701 | −1378 | * | * | | | | | | | | | | | | |
| 101(E) | 1017 | −2763 | 862 | 2042 | −3060 | −1913 | −775 | −2836 | −495 | −2773 | −1886 | 1956 | −2143 | −136 | −1056 | 265 | −1185 | −2377 | −2948 | −2207 | 21200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7891 | −8933 | −894 | −1115 | −338 | −2261 | * | * | | | | | | | | | | | | |
| 102(E) | −944 | −2422 | 863 | 2138 | −2740 | −436 | −567 | −2493 | 894 | −2437 | −1515 | −518 | −1994 | 1767 | −673 | 109 | −885 | −1023 | −2605 | −1917 | 21300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 103(I) | −2660 | −2156 | −5316 | −4965 | −2520 | −5119 | −4900 | 3165 | −4894 | 297 | −1251 | −4775 | −4828 | −4705 | −4975 | −4470 | −2642 | 2240 | −4202 | −3814 | 21400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 104(E) | 1068 | −2341 | −760 | 2003 | 628 | −1887 | 876 | −2380 | 1240 | −2347 | −1436 | −529 | −1983 | 881 | −618 | −804 | −855 | −1954 | −2530 | −1862 | 21500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 105(P) | −343 | −3144 | 1561 | 442 | −3538 | −489 | −1216 | −3329 | −1038 | −3274 | −2420 | −848 | 2974 | −812 | −1635 | 469 | −1644 | −2849 | −3462 | −2693 | 21600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 106(N) | −1173 | −2375 | −814 | 827 | −2376 | −2071 | 1767 | −2279 | −479 | −2338 | −1509 | 3151 | −2218 | −415 | −957 | −1093 | −1120 | −198 | −2486 | 647 | 21700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 107(M) | −3415 | −2890 | −5826 | −5252 | −1352 | −5488 | −4282 | 1361 | −5022 | 2621 | 2728 | −5181 | −4778 | −4005 | −4613 | −4776 | −3292 | 69 | −3071 | −3194 | 21800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 108(K) | −1941 | −3098 | −1997 | −1232 | −3650 | −2740 | −1025 | −3210 | 3059 | −3010 | −2208 | 499 | −2766 | 1457 | 1261 | −1817 | −90 | −2858 | −3002 | −2622 | 21900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 109(P) | 1129 | −2426 | −740 | 964 | −2747 | −1913 | −589 | −2491 | 1139 | −2440 | −1525 | −552 | 1941 | 1446 | −655 | −480 | −913 | −2050 | −2610 | −1935 | 22000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 110(G) | −2276 | −2907 | −2347 | −2709 | −4832 | 3554 | −3349 | −5005 | −3678 | −5053 | −4315 | 1193 | −3507 | −3243 | −3937 | −2418 | −2674 | −3974 | −4703 | −4521 | 22100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 111(A) | 1730 | −2349 | 958 | −198 | −2661 | −1868 | −535 | −2405 | 927 | −2362 | −1444 | 414 | −1966 | 788 | −630 | 790 | −840 | −303 | −2540 | −1863 | 22200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 112(T) | 1350 | −1149 | −14 | −1461 | −1155 | −2314 | −1111 | 758 | −1275 | −1024 | 1167 | −1475 | −2388 | −1111 | −1501 | 334 | 1843 | 354 | −1581 | −1182 | 22300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 113(L) | −333 | −2796 | −5806 | −5293 | −1506 | −5535 | −4502 | 1096 | −5103 | 2935 | −282 | −5232 | −4857 | −4172 | −4762 | −4864 | −3236 | 506 | −3264 | −3351 | 22400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 114(A) | 1769 | −1525 | 158 | −857 | −1603 | 148 | −891 | −1181 | −752 | 187 | −712 | −1040 | −2228 | 660 | −1135 | −1111 | −913 | 1305 | −1913 | −1442 | 22500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 115(F) | −4110 | −3437 | −5436 | −5431 | 4216 | −5143 | −2159 | −1742 | −5074 | 563 | −1124 | −4290 | −4871 | −3987 | −4561 | −4547 | −4016 | −2374 | −1356 | −292 | 22600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 116(A) | 3091 | −1829 | −3998 | −4219 | −4413 | 119 | −3637 | −4216 | −4134 | −4469 | −3523 | −2798 | −2896 | −3656 | −3927 | 1514 | −1679 | −2983 | −4632 | −4539 | 22700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 117(H) | −5197 | −4539 | −4720 | −5009 | −4036 | −4506 | 5435 | −6314 | −4911 | −5786 | −5667 | −4954 | −4960 | −5011 | −4732 | −5391 | −5395 | −6022 | −4063 | −3641 | 22800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 118(G) | −4435 | −4203 | −5092 | −5462 | −5893 | 3834 | −5028 | −6627 | −5765 | −6297 | −5970 | −5141 | −4804 | −5546 | −5385 | −4727 | −4815 | −5862 | −4924 | −5849 | 22900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 119(F) | −4044 | −3387 | −5534 | −5444 | 4093 | −5246 | −2370 | −1514 | −5107 | 1089 | −868 | −4443 | −4880 | −3998 | −4592 | −4639 | −3934 | −2200 | −1536 | −523 | 23000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 120(N) | 885 | −1899 | −2020 | −1781 | −2956 | −2135 | −1925 | −2602 | −1809 | 3 | −2052 | 3468 | −2633 | −1676 | −2141 | 413 | −1437 | −2139 | −3194 | −2737 | 23100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 121(I) | −2673 | −2169 | −5324 | −4969 | −2477 | −5123 | −4876 | 3293 | −4893 | 358 | −1211 | −4780 | −4824 | −4681 | −4961 | −4427 | −2653 | 1969 | −4158 | −3791 | 23200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 122(H) | −3381 | −3705 | −3197 | −3491 | −4166 | 638 | 5216 | −5496 | −3798 | −5304 | −4811 | −3481 | −4185 | −3770 | −3879 | −3508 | −3702 | −4793 | −4170 | −3759 | 23300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 123(Y) | −4816 | −3757 | −5210 | −5549 | 3410 | −5097 | 2153 | −3719 | −5105 | −3041 | −3127 | −3715 | −4955 | −3851 | −4483 | −4344 | −4669 | −3870 | −547 | 3677 | 23400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 124(G) | −1065 | −2519 | 948 | −272 | −2820 | 1844 | 998 | −2566 | 972 | −284 | −1622 | 1553 | −2090 | −229 | −802 | −938 | −1011 | −2133 | 2708 | −2021 | 23500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 125(Q) | −412 | −2285 | −2466 | −2186 | −2068 | −2877 | −2019 | −1589 | −1588 | 1526 | −1121 | −2187 | −3153 | 3585 | −1718 | −2137 | −1964 | −1719 | −2789 | −2414 | 23600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 126(I) | −2254 | −1916 | −4813 | −4439 | −2466 | −4221 | −3932 | 3248 | −4248 | −1515 | −1324 | −4044 | −4259 | −4063 | −4255 | 230 | −2280 | 2003 | −3673 | −3237 | 23700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 127(K) | −888 | −2234 | 334 | 1172 | −2504 | −1881 | −546 | −93 | 1370 | −300 | −1337 | 465 | −1974 | 655 | −646 | −794 | −827 | 1255 | −2448 | −1798 | 23800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 128(P) | 715 | −1925 | −3618 | −3897 | −4464 | 653 | −3594 | −4274 | −4053 | −4520 | −3596 | −2770 | 3775 | −3593 | −3911 | −1550 | −1770 | −3067 | −4647 | −4548 | 23900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 129(P) | 479 | −2398 | −1173 | −637 | −2915 | −2106 | −848 | −2610 | −289 | −2586 | −1713 | −884 | 2238 | 1247 | 2195 | 51 | −1147 | −2184 | −2757 | −2174 | 24000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 130(A) | 1787 | −2663 | 1377 | 529 | −2976 | −1992 | −762 | −2736 | 1785 | −2680 | −1776 | −623 | −2161 | −319 | −936 | 297 | −1120 | −2285 | −2853 | −2146 | 24100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2336 | −8139 | −325 | −894 | −1115 | −701 | −1378 | * | * | | | | | | | | | | | | |
| 131(F) | −1308 | −1104 | −2227 | −2120 | 3516 | −2093 | −244 | −196 | −1891 | 64 | 66 | −1626 | −2278 | −1503 | −1798 | −1617 | −1350 | −389 | 305 | 1335 | 24200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −3098 | −179 | * | * | | | | | | | | | | | | |
| 132(P) | −603 | −937 | −997 | −1058 | −1832 | −1041 | −1092 | −1737 | −1074 | −1874 | −1416 | −992 | 3539 | −1065 | −1192 | −789 | −866 | −1383 | −1765 | −1661 | 24300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −3098 | −179 | * | * | | | | | | | | | | | | |
| 133(K) | −804 | −1483 | −564 | −230 | −1920 | −1335 | −101 | −1605 | 2889 | −1630 | −1021 | −349 | −1569 | 232 | 698 | −786 | −759 | −1358 | −1637 | −1317 | 24400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −109 | −3775 | * | * | | | | | | | | | | | | |
| 134(D) | −2405 | −4159 | 3349 | −651 | −4260 | −261 | −1744 | −4307 | −1947 | −4207 | −3514 | 2151 | −2936 | −1416 | −2754 | −2102 | −2471 | −3802 | −4324 | 637 | 24500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 135(I) | −2047 | −1713 | −4504 | −3983 | −1821 | −3943 | −3061 | 2461 | −3697 | 1581 | −797 | −3593 | −3873 | −3371 | −3587 | −342 | −2009 | 1904 | −2784 | −2441 | 24600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 136(D) | −2024 | −3444 | 3495 | −680 | −3868 | −2331 | −1596 | −44 | −1632 | −3675 | −2915 | 685 | −2782 | −1248 | −2305 | 478 | −2088 | −3196 | −3911 | −3096 | 24700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 137(V) | −3122 | −2888 | −5092 | −5160 | −3522 | −4180 | −4687 | −905 | −5060 | −2626 | −2570 | −4662 | −4579 | −4940 | −4923 | −4013 | −3297 | 3796 | −4414 | −4190 | 24800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 138(I) | −53 | −875 | −3230 | −2609 | 1867 | −393 | −1422 | 2613 | −2236 | −723 | −81 | −2157 | −2608 | −1885 | −2086 | 1633 | 276 | −271 | −1325 | 844 | 24900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 139(M) | 315 | −2345 | −4754 | −4279 | −1396 | −4001 | −3301 | −697 | −3877 | 816 | 4676 | −3879 | −3994 | −3361 | −3676 | −3242 | −2531 | −1114 | −2746 | −2629 | 25000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 140(V) | −2623 | −2122 | −5301 | −4990 | −2770 | −5102 | −5132 | 2415 | −4945 | −1532 | −1474 | −4791 | −4869 | −4890 | −5102 | −4483 | −2619 | 3206 | −4506 | −3991 | 25100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 141(A) | 3405 | 2528 | −4529 | −4796 | −4340 | −2257 | −3851 | −3901 | −4447 | −4351 | −3532 | −3057 | −3052 | −3976 | −4112 | −1643 | −1844 | −2929 | −4572 | −4519 | 25200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 142(P) | −4853 | −4392 | −5213 | −5573 | −5853 | −4408 | −5077 | −6679 | −5780 | −6281 | −6067 | −5357 | 4310 | −5648 | −5396 | −5166 | −5194 | −6092 | −4900 | −5786 | 25300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 143(K) | −4484 | −4357 | −4380 | −3992 | −5413 | −4236 | −3307 | −5555 | 3994 | −5171 | −4707 | −3921 | −4535 | −3079 | −2169 | −4529 | −4408 | −5264 | −4403 | −4729 | 25400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 144(G) | 2167 | −1833 | −3963 | −4199 | −4430 | 2715 | −3642 | −4236 | −4146 | −4489 | −3540 | −2795 | −2898 | −3661 | −3939 | 910 | −1682 | −2994 | −4647 | −4556 | 25500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 145(P) | −2604 | −2948 | −4094 | −4235 | −3544 | −3269 | −3767 | −3353 | −3912 | −3066 | 2095 | −3659 | 4036 | −3912 | −3822 | −2883 | −2963 | −3249 | −4027 | −3787 | 25600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 146(G) | −4435 | −4203 | −5092 | −5462 | −5893 | 3834 | −5028 | −6627 | −5765 | −6297 | −5970 | −5141 | −4804 | −5546 | −5385 | −4727 | −4815 | −5862 | −4924 | −5849 | 25700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 147(H) | −2569 | −3440 | −1867 | −1702 | −3820 | −2996 | 4731 | −3830 | 634 | −3639 | −2963 | −1838 | 1551 | −1305 | −748 | −2470 | −2510 | −3482 | −3434 | −2990 | 25800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 148(T) | 194 | −1498 | −3255 | −2899 | −2240 | −2226 | −2291 | −1754 | −2652 | 1634 | −1430 | −2330 | −2747 | −2399 | −2684 | 567 | 2687 | −1484 | −2682 | −2351 | 25900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 149(V) | −3122 | −2888 | −5092 | −5160 | −3522 | −4180 | −4687 | −905 | −5060 | −2626 | −2570 | −4662 | −4579 | −4940 | −4923 | −4013 | −3297 | 3796 | −4414 | −4190 | 26000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 150(R) | −4845 | −4446 | −5107 | −4682 | −5507 | −4412 | −3791 | −5946 | −2789 | −5502 | −5118 | −4521 | −4754 | −3672 | 4219 | −4989 | −4832 | −5644 | −4538 | −4993 | 26100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 151(R) | −962 | −2395 | −777 | 1012 | −2721 | 76 | 1031 | −2459 | −142 | −2413 | −1501 | −560 | −2018 | −128 | 2038 | 1224 | −66 | −2023 | −2585 | −1919 | 26200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 152(E) | −902 | −2032 | −899 | 2078 | −2228 | −1934 | −611 | −1897 | −259 | −221 | −1156 | 520 | −2024 | 816 | −736 | −858 | 1303 | −287 | −2295 | 537 | 26300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 153(Y) | −4823 | −3765 | −5219 | −5565 | 3303 | −5093 | −1317 | −3703 | −5127 | −3017 | −3111 | −3732 | −4959 | −3868 | −4500 | −4356 | −4679 | −3867 | −565 | 4052 | 26400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 154(V) | 129 | −1901 | −989 | 821 | −2060 | −1969 | −654 | −1704 | 498 | −52 | −1037 | −703 | −2057 | 695 | −796 | 443 | −344 | 1871 | −2192 | −1626 | 26500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 155(Q) | 576 | −2355 | 344 | 1156 | −2675 | −1856 | −515 | −508 | 1502 | −2370 | −1444 | 571 | −1949 | 1878 | 419 | −764 | −822 | −1976 | −2538 | −1856 | 26600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 156(G) | −3239 | −3889 | 516 | −2361 | −5355 | 3646 | −3337 | −5629 | −3818 | −5498 | −4951 | −2619 | −3905 | −3187 | −4377 | −3211 | −3532 | −4837 | −4895 | −4826 | 26700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −155 | −3318 | −9181 | −2159 | −367 | −701 | −1378 | * | * | | | | | | | | | | | | |
| 157(G) | 753 | −2516 | −789 | 488 | −2848 | 2300 | −672 | −2582 | 596 | −2529 | −1627 | 481 | −2112 | −224 | 471 | −962 | −1024 | −2149 | −2694 | −2033 | 27300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 158(G) | −52 | −2212 | −3792 | −4133 | −4698 | 3627 | −2843 | −4580 | −4356 | −4812 | −3937 | −3058 | −3216 | −3901 | −4170 | −1874 | −2095 | −3384 | −4734 | −4766 | 27400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 159(V) | −2485 | −2030 | −5123 | −4769 | −2667 | −4797 | −4593 | 2349 | −4661 | −1545 | −1424 | −4502 | −4648 | −4554 | −4752 | −4115 | 825 | 2986 | −4159 | −3678 | 27500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 160(P) | −2541 | −3139 | −2413 | −2753 | −4726 | −2991 | −3342 | −5055 | −3527 | −5058 | −4393 | 1199 | 4031 | −3244 | −3757 | −2665 | −2911 | −4148 | −4583 | −4362 | 27600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 161(C) | 1577 | 3078 | 1357 | −656 | −2664 | −219 | 891 | −2359 | −617 | −2434 | −1576 | −891 | −2199 | −545 | −1093 | 872 | −1043 | −1946 | −2701 | −2102 | 27700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 162(L) | −2140 | −2404 | −3995 | −3997 | −2053 | −3121 | −3283 | −1687 | −3689 | 3041 | −1200 | −3360 | −3626 | −3433 | −3567 | 480 | −2414 | −1973 | −3145 | −2755 | 27800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 163(I) | −2527 | −2092 | −5072 | −4613 | 2047 | −4674 | −3911 | 2668 | −4413 | 117 | −841 | −4323 | −4439 | −4023 | −4320 | −3916 | −2488 | 2176 | −3342 | −3040 | 27900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 164(A) | 3631 | −2766 | −4492 | −4815 | −4888 | −2992 | −4271 | −4781 | −4818 | −5025 | −4365 | −3727 | −3728 | −4477 | −4545 | −2567 | −2762 | −3852 | −4724 | −4942 | 28000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 165(V) | −2623 | −2122 | −5301 | −4990 | −2770 | −5102 | −5132 | 2426 | −4946 | −1532 | −1474 | −4791 | −4869 | −4891 | −5102 | −4483 | −2619 | 3200 | −4506 | −3991 | 28100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 166(H) | −495 | −2631 | 903 | −2051 | 722 | −3242 | 3753 | −2386 | −2056 | −2342 | −1863 | −2074 | −3330 | −1815 | −2362 | −2318 | −2233 | −2272 | −981 | 3315 | 28200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 167(Q) | −4589 | −4392 | −3927 | −4148 | −5090 | −4221 | −4099 | −5973 | −3840 | −5564 | −5304 | −4230 | −4693 | 4575 | −3826 | −4704 | −4772 | −5612 | −4577 | −4751 | 28300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 168(D) | −2873 | −4605 | 3943 | −902 | −4948 | −2633 | −2157 | −5087 | −2604 | −4922 | −4387 | 428 | −3235 | −1872 | −3575 | −2522 | −3009 | −4491 | −4932 | −3946 | 28400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 169(A) | 1776 | −1612 | −1274 | 138 | −1698 | −2092 | −816 | −1295 | 150 | −1526 | −780 | −943 | 1212 | −538 | −1013 | −1056 | −894 | 1275 | −1968 | 635 | 28500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 170(S) | −1545 | −2420 | 1001 | −1518 | −4049 | −2206 | −2206 | −3839 | −2264 | −3938 | −3103 | −1627 | −2814 | −1909 | −2758 | 2666 | 2312 | −3045 | −4143 | −3560 | 28600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 171(G) | −2999 | −3461 | −2978 | −3207 | −5161 | 3669 | −3454 | −5283 | 15 | −5188 | −4565 | −3174 | −3946 | −3312 | −3140 | −3128 | −3317 | −4492 | −4622 | −4749 | 28700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 172(N) | −887 | −2349 | −736 | 911 | −2668 | −1860 | −518 | −2415 | 711 | −2362 | −1440 | 1880 | −1954 | 436 | 799 | 671 | 1230 | −539 | −2534 | −1855 | 28800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 173(A) | 3631 | −2768 | −4492 | −4815 | −4888 | −2992 | −4271 | −4781 | −4818 | −5025 | −4365 | −3727 | −3728 | −4477 | −4545 | −2567 | −2762 | −3852 | −4724 | −4942 | 28900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 174(K) | −1368 | −2597 | −1358 | −720 | −2953 | −2298 | 1933 | −2603 | 1975 | 851 | −1706 | −958 | −2360 | 859 | 1012 | −1273 | 1094 | −2245 | −2690 | −2165 | 29000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 175(D) | −27 | −2613 | 2320 | 1049 | −2923 | −1962 | 1973 | −2684 | 544 | −2624 | −1712 | 1408 | −2115 | 345 | −869 | −969 | −1058 | −2231 | −2793 | −2087 | 29100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 176(V) | −1096 | −938 | −3279 | −2658 | −899 | −2643 | −1513 | 1265 | 1006 | 1388 | −124 | −2232 | −2688 | −1950 | −2151 | −1725 | −311 | 1669 | −1425 | 827 | 29200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 177(A) | 3342 | −1826 | −4064 | −4295 | −4368 | 111 | −3651 | −4129 | −4159 | −4412 | −3484 | −2820 | −2903 | −3689 | −3929 | −1469 | 409 | −2949 | −4599 | −4508 | 29300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 178(L) | −4414 | −3800 | −5638 | −5628 | −2290 | −4980 | −4628 | −1886 | −5423 | 3316 | −1236 | −5514 | −4997 | −4750 | −5002 | −5379 | −4399 | −2629 | −3665 | −3690 | 29400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 179(S) | 2216 | −1831 | −3961 | −4157 | −4409 | 656 | −3608 | −4213 | −4076 | −4462 | −3514 | −2782 | −2892 | −3613 | −3895 | 2686 | −1675 | −2982 | −4623 | −4523 | 29500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 180(Y) | −3634 | −3050 | −4918 | −4872 | 36 | −4597 | −1405 | 223 | −4437 | −250 | −1998 | −3545 | −4494 | −3522 | −4004 | −3782 | −3536 | −2621 | 2928 | 4349 | 29600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 181(A) | 3391 | −1860 | −3998 | −4279 | −4411 | −2128 | −3684 | −4207 | −4197 | −4490 | −3585 | −2837 | −2929 | −3729 | −3959 | 706 | −1718 | −3001 | −4636 | −4534 | 29700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 182(K) | 370 | 307 | 113 | −351 | −2280 | −1925 | −615 | 324 | 1888 | −2040 | −1194 | −632 | −2022 | −205 | −736 | 1541 | 14 | −1628 | −2330 | −1726 | 29800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 183(G) | 2572 | −2028 | −3934 | −4246 | −4575 | 2752 | −3783 | −4406 | −4316 | −4661 | −3751 | −2958 | −3070 | −3837 | −4092 | −1679 | −1898 | −3191 | −4701 | −4686 | 29900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 184(I) | −2178 | −1808 | −4630 | −4153 | −2094 | −4190 | −3417 | 3121 | −3909 | 311 | −1023 | 698 | −4099 | −3656 | −3864 | −3388 | −2148 | 1742 | −3147 | −2761 | 30000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 185(G) | −4435 | −4203 | −5092 | −5462 | −5893 | 3834 | −5028 | −6627 | −5765 | −6297 | −5970 | −5141 | −4804 | −5546 | −5385 | −4727 | −4815 | −5862 | −4924 | −5849 | 30100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 186(G) | 1392 | 2751 | −4353 | −4536 | −4308 | 2864 | −3681 | −4084 | −4233 | −4354 | −3425 | −2859 | −2890 | −3744 | −3957 | 712 | −1656 | −2914 | −4553 | −4470 | 30200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 187(G) | 855 | −1822 | −3738 | −3769 | −4188 | 2507 | −3358 | −3950 | −3667 | −4196 | −3283 | −2667 | 986 | −3302 | −3621 | −1441 | 2334 | −2867 | −4408 | −4236 | 30300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 188(R) | −3706 | −3692 | −4490 | −3846 | 1391 | −4057 | −2273 | −3795 | −1906 | −3355 | −3181 | −3458 | −4263 | −2675 | 3948 | −3768 | −3671 | −3813 | −2293 | −1328 | 30400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 189(A) | 2844 | −1670 | −3814 | −3873 | −4048 | −1958 | −3316 | −3787 | −3686 | −4061 | −3156 | −2598 | −2734 | −3301 | −3572 | 1088 | 1907 | −2713 | −4286 | −4136 | 30500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 190(G) | −4176 | −3995 | −4855 | −5222 | −5686 | 3828 | −4823 | −6386 | −5533 | −6087 | −5741 | −4896 | −4606 | −5312 | −5178 | −4461 | −4560 | −5613 | −4754 | −5635 | 30600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 191 (V) | −2496 | −2036 | −5139 | −4788 | −2680 | −4825 | −4637 | 2522 | −4686 | −1579 | −1431 | −4527 | −4668 | −4584 | −4783 | −4148 | 629 | 2919 | −4191 | −3706 | 30700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 192(I) | −2760 | −2307 | −5270 | −4785 | 1172 | −4884 | −3992 | 3346 | −4576 | 662 | −572 | −4539 | −4535 | −4008 | −4400 | −4134 | −2703 | 757 | −3223 | −3041 | 30800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 193(E) | 454 | −3086 | −801 | 3279 | −4125 | −2346 | −1868 | −3919 | −1868 | −3932 | −3156 | −1291 | 1208 | −1533 | −2450 | −1842 | −2097 | −3305 | −4121 | −3395 | 30900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 194(T) | −2738 | −3109 | −4509 | −4810 | −4918 | −3305 | −4346 | −4865 | −4769 | −5072 | −4551 | −3987 | −3998 | −4580 | −4545 | −2999 | 4033 | −4113 | −4684 | −4915 | 31000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 195(T) | −1323 | −1975 | −2766 | −2978 | −4207 | −2152 | −3105 | −4004 | −3295 | −4229 | −3354 | 134 | −2901 | −2988 | −3387 | −113 | 3742 | −2969 | −4405 | −4119 | 31100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 196(F) | −4110 | −3437 | −5436 | −5431 | 4126 | −5143 | −2159 | −1742 | −5074 | 563 | −1124 | −4290 | −4871 | −3987 | −4561 | −4547 | −4016 | −2374 | −1356 | −292 | 31200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 197(K) | −111 | −2844 | −1470 | 1220 | −3294 | −2415 | −860 | −2939 | 2448 | −2798 | −1945 | −1056 | −2475 | 767 | 2054 | −1421 | −1432 | −2544 | −2858 | −2356 | 31300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 198(E) | 545 | −3735 | 1715 | 2880 | −2308 | −3981 | −1442 | −3818 | −1408 | −3725 | 2924 | −909 | −2713 | 1281 | −2087 | −1777 | −2041 | −3331 | −3909 | −3046 | 31400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 199(E) | −4574 | −4665 | −2714 | 3919 | −5655 | −3995 | −3886 | −6219 | −4238 | −5898 | −5604 | −3415 | −4513 | −3838 | −4570 | −4456 | −4726 | −5786 | −4878 | −5197 | 31500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 200(T) | −1211 | 1331 | −3446 | −2962 | −1399 | −2495 | −1930 | −869 | −2610 | −1374 | −769 | −2403 | −2815 | −2309 | −2526 | −1685 | −3305 | 195 | −1933 | 1430 | 31600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 201(E) | −1941 | −3222 | −921 | 3293 | −3618 | −2473 | −1316 | −3186 | −916 | −3225 | −2465 | −1147 | −2749 | −923 | −1064 | −1790 | −1902 | −171 | −3398 | −2802 | 31700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 202(T) | −1286 | −1898 | −3764 | −4016 | −4329 | −2157 | −3572 | −4120 | −3959 | −4408 | −3517 | −2789 | −2947 | −3588 | −3797 | 697 | 3756 | −2989 | −4554 | −4399 | 31800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 203(D) | −4580 | −4701 | 4174 | −3014 | −5700 | −3967 | −3905 | −6376 | −4478 | −6024 | −5744 | −3355 | −4501 | −3870 | −4926 | −4440 | −4750 | −5894 | −4922 | −5231 | 31900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 204(L) | −3705 | −3122 | −6060 | −5527 | −1359 | −5814 | −4569 | 1065 | −5292 | 3069 | −146 | −5564 | −4963 | −4163 | −4828 | −5215 | −3571 | −1279 | −3159 | −3298 | 32000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 205(F) | −3777 | −3220 | −5271 | −5259 | 4268 | −4892 | −2120 | 417 | −4916 | −1143 | −1314 | −4142 | −4753 | −3956 | −4473 | −4270 | −3740 | −1899 | −1349 | −269 | 32100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 206(G) | −4435 | −4203 | −5092 | −5462 | −5893 | 3834 | −5028 | −6627 | −5765 | −6297 | −5970 | −5141 | −4804 | −5546 | −5385 | −4727 | −4815 | −5862 | −4924 | −5849 | 32200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 207(E) | −4574 | −4665 | −2714 | 3919 | −5655 | −3995 | −3886 | −6219 | −4238 | −5898 | −5604 | −3415 | −4513 | −3838 | −4570 | −4456 | −4726 | −5786 | −4878 | −5197 | 32300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 208(Q) | −3157 | −3746 | −3170 | −2450 | −4497 | −3515 | −1763 | −4161 | −443 | −3809 | −3189 | −2392 | −3620 | 4200 | 1284 | −3063 | −2944 | −3900 | −3556 | −3420 | 32400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 209(A) | 2672 | −1334 | −3318 | −2853 | −1740 | 371 | −2072 | 483 | −2577 | −1549 | −928 | −2359 | −2798 | −2295 | −2567 | −1629 | 191 | 932 | −2245 | −1899 | 32500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 210(V) | −2620 | −2125 | −5293 | −4983 | −2756 | −5076 | −5100 | 1877 | −4932 | −1522 | −1466 | −4777 | −4855 | −4870 | −5082 | −4456 | −2619 | 3416 | −4480 | −3969 | 32600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 211(L) | −4414 | −3800 | −5638 | −5628 | −2290 | −4980 | −4628 | −1886 | −5423 | 3316 | −1236 | −5514 | −4997 | −4750 | −5002 | −5379 | −4399 | −2629 | −3665 | −3690 | 32700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 212(C) | −2243 | 5044 | −4840 | −4445 | −1998 | −3905 | −3598 | −31 | −4138 | 449 | −930 | −3902 | −4040 | −3778 | −4010 | −3184 | −2306 | 1347 | −3209 | −2883 | 32800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 213(G) | −4435 | −4203 | −5092 | −5462 | −5893 | 3834 | −5028 | −6627 | −5765 | −6297 | −5970 | −5141 | −4804 | −5546 | −5385 | −4727 | −4815 | −5862 | −4924 | −5849 | 32900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 214(G) | 677 | −2128 | −3838 | −4171 | −4647 | 3536 | −3816 | −4506 | −4340 | −4749 | −3857 | −3009 | −3149 | −3871 | −4137 | −1784 | −2005 | −3297 | −4725 | −4735 | 33000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 215(V) | 378 | 724 | −3707 | −3104 | −1180 | −2986 | −1919 | 1210 | −2734 | 1302 | −359 | −2627 | −3014 | −2382 | −2566 | −2089 | 1123 | 1949 | −1773 | −1423 | 33100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 216(M) | −948 | −1407 | −1515 | 156 | −1452 | −2164 | 1677 | −1030 | −821 | −1302 | 1976 | −1113 | −2245 | −718 | −1173 | 773 | 1715 | 1332 | −1794 | −1343 | 33200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 217(E) | −1397 | −2528 | −725 | 2286 | −2392 | 240 | −791 | −2681 | 328 | −2645 | −1744 | −674 | −2162 | −351 | −939 | 545 | −1095 | −2227 | −2828 | −2143 | 33300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 218(L) | −3705 | −3122 | −6060 | −5527 | −1359 | −5814 | −4589 | 1065 | −5292 | 3069 | −146 | −5564 | −4963 | −4163 | −4828 | −5212 | −3571 | −1279 | −3159 | −3298 | 33400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 219(V) | −2600 | −2108 | −5251 | −4894 | −2568 | −5025 | −4783 | 2479 | −4810 | −1354 | 1358 | −4683 | −4772 | −4654 | −4895 | −4362 | −2584 | 3018 | −4181 | −3758 | 33500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 220(K) | −1633 | −2905 | −1573 | 706 | −3375 | −2487 | −900 | −3003 | 2925 | −2849 | −2008 | −1128 | −2541 | 1714 | 784 | −1509 | −105 | −2617 | −2894 | −2418 | 33600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 221(A) | 2352 | 2066 | −2593 | −2000 | −947 | −2434 | −1271 | −486 | −32 | −832 | 714 | −1817 | −2498 | −1493 | −1792 | −1483 | 274 | 453 | −1419 | 501 | 33700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 222(G) | 224 | −1905 | −3562 | −3696 | −3684 | 3361 | −3297 | −3220 | −3625 | 81 | −2886 | −2733 | −2977 | −3326 | −3545 | −1606 | −1763 | −2574 | −4068 | −3810 | 33800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 223(F) | −4781 | −3756 | −5207 | −5542 | 4341 | −5070 | −1342 | −3653 | −5111 | −2971 | −3065 | −3743 | −4949 | −3874 | −4496 | −4351 | −4650 | −3829 | −591 | 1725 | 33900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 224(E) | −2413 | −4114 | 221 | 3465 | −4392 | −2485 | −1689 | −4248 | −1608 | −4112 | −3396 | −1094 | −2951 | −1336 | 871 | −2119 | −2441 | −3763 | −4239 | −3395 | 34000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 225(T) | −1461 | −1864 | −3139 | −2645 | −2659 | −2483 | −2136 | −1734 | −1646 | −2359 | −1761 | −2298 | −2936 | −1995 | 920 | −1748 | 3354 | 967 | −2989 | −2654 | 34100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 226(L) | −3831 | −3266 | −5314 | −5148 | −673 | −5068 | −2476 | −1443 | −4706 | 3059 | −789 | −4359 | −4756 | −3864 | −4314 | −4462 | −3729 | −2115 | −1672 | 1736 | 34200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 227(V) | −1819 | −1960 | −4426 | −4359 | −2977 | −3037 | −3800 | −439 | −4098 | −2145 | −1909 | −3451 | −3600 | −3879 | −4011 | −2397 | 2510 | 2999 | −3974 | −3608 | 34300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 228(E) | −2863 | −4790 | 1397 | 3563 | −4990 | −2594 | −2061 | −5021 | −2476 | −4848 | 4298 | −1204 | −3182 | −1761 | −3454 | −2476 | −2968 | −4462 | −4951 | −3920 | 34400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 229(A) | 2686 | −1916 | −1440 | 275 | −2529 | −292 | −1240 | −2176 | −998 | −2345 | 1183 | −1184 | −2355 | −905 | −1425 | 512 | −1158 | −1817 | −2697 | −2174 | 34500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 230(G) | −4435 | −4203 | −5092 | −5462 | −5893 | −3834 | −5028 | −6627 | −5765 | −6297 | −5970 | −5141 | −4804 | −5546 | −5385 | −4727 | −4815 | −5862 | −4924 | −5849 | 34600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 231(Y) | −4099 | −3483 | −4921 | −5048 | −109 | −4705 | −1565 | −2914 | −4494 | −2334 | 2010 | −3723 | −4707 | −3735 | −4111 | −4065 | −4068 | −3172 | −847 | 4618 | 34700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 232(Q) | 1711 | −2410 | −772 | 934 | −2739 | −1925 | −604 | −2477 | −171 | −2433 | −1524 | −574 | −2035 | 2086 | 345 | 902 | −923 | −2042 | −2608 | −1941 | 34800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 233(P) | −3403 | −4071 | −1922 | 817 | −5220 | −3359 | −3173 | −5423 | −3337 | −5281 | −4771 | −2564 | 4045 | −2989 | −3760 | −3320 | −3624 | −4817 | −4763 | −4636 | 34900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 234(E) | −2870 | −4786 | 1265 | 3587 | −4993 | −2600 | −2068 | −5026 | −2483 | −4852 | −4303 | −1212 | −3188 | −1768 | −3458 | −2484 | −2974 | −4467 | −4950 | −3925 | 35000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 235(M) | −3089 | −2618 | −5523 | −4976 | −1443 | −5128 | −4045 | 653 | −4735 | 1429 | 4269 | −4803 | −4610 | −2915 | −4423 | −4378 | −2995 | 1140 | −3054 | −3074 | 35100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 236(A) | 3631 | −2768 | −4492 | −4815 | −4888 | −2992 | −4271 | −4781 | −4818 | −5025 | −4365 | −3727 | −3728 | −4477 | −4545 | −2567 | −2762 | −3852 | −4724 | −4942 | 35200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 237(Y) | −4797 | −3764 | −5203 | −5543 | 1114 | −5069 | −1339 | −3694 | −5111 | −3013 | −3107 | −3741 | −4351 | −3876 | −4497 | −4354 | −4666 | −3859 | −588 | 4723 | 35300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 238(F) | −3828 | −3605 | −4146 | −4086 | 4292 | −4207 | −2060 | −3492 | 774 | −3071 | −3005 | −3556 | −4434 | −3287 | −2952 | −3868 | −3858 | −3571 | −1593 | −494 | 35400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 239(E) | −2775 | −4471 | −511 | 3582 | −4815 | −2610 | −2057 | −4863 | −2317 | −4711 | −4124 | 1234 | −3182 | −1755 | −3103 | −2442 | −2884 | −4306 | −4753 | −3820 | 35500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 240(C) | −1407 | 5023 | −4397 | −4323 | −3016 | −2468 | −3398 | −1251 | −3952 | −2540 | −2082 | −3044 | −3133 | −3588 | −3744 | −1803 | 1473 | 1125 | −3677 | −3390 | 35600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 241(L) | −3370 | −2847 | −5795 | −5233 | −1386 | −5465 | −4298 | 708 | −5010 | 2859 | 1349 | −5155 | −4777 | −4026 | −4622 | −4755 | −3254 | 814 | −3103 | −3213 | 35700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 242(H) | −2519 | −4224 | −445 | −46 | −4287 | −2505 | 4583 | −4377 | −1764 | −4237 | −3571 | 2007 | −3009 | −1439 | −2361 | −2209 | −2569 | −3893 | −4267 | −3353 | 35800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 243(E) | −3177 | 2571 | −2701 | 3711 | −4581 | −3438 | −3479 | −4765 | −3558 | −4932 | −4406 | −3081 | −4005 | −3370 | −3802 | −3269 | −3451 | −4260 | −4554 | −4524 | 35900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 244(L) | −85 | −1333 | −3893 | −3280 | −1111 | −3185 | −2083 | 1066 | −2910 | 2310 | 1961 | −2823 | −3170 | −2501 | −2721 | −2289 | −113 | 436 | −1859 | −1558 | 36000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 245(K) | −2513 | −3173 | −2941 | −2370 | −4402 | −3094 | −1824 | −3895 | 3666 | −3734 | −3068 | −2271 | −3377 | −1447 | −616 | −2537 | 751 | −3485 | −3625 | −3471 | 36100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −155 | −3318 | −9181 | −196 | −2974 | −701 | −1378 | * | * | | | | | | | | | | | | |
| 246(L) | −3571 | −3023 | −5954 | −5375 | −1321 | −5646 | −4390 | −632 | −5138 | 2962 | 1671 | −5358 | −4852 | −4044 | −4689 | −4963 | −3436 | 742 | −3082 | −3239 | 36300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 247(I) | −2980 | −2484 | −5473 | −5109 | −1958 | −5196 | −4587 | 3728 | −4915 | 267 | −781 | −4933 | −4833 | −4427 | −4799 | −4598 | −2949 | −64 | −3627 | −3397 | 36400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 248(V) | −1685 | −1668 | −4095 | −3732 | −2081 | −3082 | −2893 | −277 | −3402 | −1488 | 1383 | −3123 | −3419 | −3145 | −3320 | 367 | −1807 | 3332 | −2874 | −2504 | 36500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 249(D) | −2963 | −4569 | 3864 | −1039 | −4953 | −2751 | −2187 | −4998 | 767 | −4822 | −4260 | −1424 | −3314 | −1891 | −3072 | −2624 | −3060 | −4467 | −4770 | −3962 | 36600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 250(L) | −2768 | −2715 | −4842 | −4633 | −1675 | −3998 | −3790 | −1038 | −4207 | 3056 | −562 | −4150 | −4179 | −3740 | −3989 | −3399 | 699 | −1545 | −3154 | −3367 | 36700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 251(M) | −2822 | −2356 | −5342 | −4861 | −1759 | −4985 | −4151 | 2587 | −4663 | 173 | 4005 | −4649 | −4601 | −4076 | −4487 | −4251 | −2764 | 766 | −3321 | −3210 | 36800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 252(Y) | −4562 | −3630 | −5142 | −5401 | 1516 | −4992 | −1300 | −3544 | −4968 | −2963 | −2986 | −3671 | −4868 | −3786 | −4393 | 381 | −4432 | −3662 | 2413 | 4375 | 36900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 253(E) | −1959 | −3457 | −568 | 3135 | −3841 | −2347 | −1410 | −3622 | −1165 | −3547 | −2751 | −1000 | −2716 | 1879 | −1666 | −1757 | 692 | −3162 | −3709 | −2960 | 37000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 254(G) | −347 | −2818 | −1215 | 201 | −3253 | 2635 | −921 | −2921 | 1474 | −2822 | −1972 | −1002 | −2459 | −486 | 658 | −1397 | −1435 | −2521 | −2923 | −2378 | 37100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 255(G) | −4435 | −4203 | −5092 | −5462 | −5893 | 3834 | −5028 | −6627 | −5765 | −6297 | −5970 | −5141 | −4804 | −5546 | −5385 | −4727 | −4815 | −5862 | −4924 | −5849 | 37200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 256(I) | −2042 | −1769 | −4321 | −3740 | −1316 | −3753 | −2668 | 3134 | −3389 | 1017 | 1999 | 194 | −3653 | −2958 | −3221 | −2884 | −1980 | −344 | −2325 | −2073 | 37300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 257(A) | 1914 | −1640 | −1237 | 128 | −1748 | −661 | −793 | −1355 | −577 | −49 | −817 | −905 | −2155 | −498 | −993 | 1037 | 162 | −1149 | −2002 | 624 | 37400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 258(N) | 365 | −3809 | 1001 | 557 | −4083 | 1196 | −1518 | −3930 | −1535 | −3838 | −3055 | 3219 | −2763 | −1148 | −2243 | −1845 | −2131 | −3433 | −4027 | −3144 | 37500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 259(M) | −3656 | −3159 | −5816 | −5350 | −1349 | −5421 | −4248 | −822 | −4928 | 948 | 4920 | −5248 | −4838 | −4039 | −4539 | −4860 | −3558 | −1557 | −3044 | −3030 | 37600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 260(R) | −1614 | −1949 | −2260 | −1663 | −886 | −2765 | −1089 | −1596 | −1089 | 360 | −1133 | 2239 | −2814 | −1215 | 2408 | −1789 | −1535 | −1468 | 1995 | 1546 | 37700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 261(Y) | −1548 | −2973 | 568 | −509 | −2846 | −2207 | 1172 | −2986 | 441 | −2941 | −2110 | 1645 | −2446 | −659 | −1264 | −1389 | −1509 | −2582 | −2924 | 3695 | 37800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 262(S) | 279 | −1844 | −3877 | −4131 | −4448 | 136 | −3634 | −4260 | −4132 | −4511 | −3561 | −2782 | −2903 | −3648 | −3936 | 3391 | −1692 | −3009 | −4661 | −4566 | 37900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 263(I) | −2653 | −2419 | −5311 | −4961 | −2538 | −5114 | −4905 | 2957 | −4891 | 332 | −1267 | −4770 | −4827 | −4713 | −4978 | −4466 | −2636 | 2521 | −4218 | −3821 | 38000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 264(S) | −2212 | −2711 | −4019 | −4348 | −4697 | −2899 | −4045 | −4988 | −4527 | −5102 | −4364 | −3492 | −3638 | −4203 | −4355 | 3681 | −2664 | −3902 | −4616 | −4605 | 38100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 265(N) | −2725 | −4778 | 2906 | 990 | −4896 | −2486 | −1922 | −4885 | −2320 | −4718 | −4140 | 3045 | −3069 | −1612 | −3311 | −2334 | −2821 | −4325 | −4919 | −3794 | 38200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 266(T) | −2061 | −3396 | −596 | 903 | −4071 | −2367 | −1713 | −3874 | −1685 | −3859 | −3103 | 2125 | −2850 | −1369 | −2277 | −1897 | 3157 | −3351 | −4055 | −3271 | 38300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 267(A) | 3410 | −2035 | −3979 | −4290 | −4573 | 659 | −3798 | −4400 | −4332 | −4660 | −3754 | −2978 | −3080 | −3858 | −4099 | −1690 | −1908 | −3194 | −4697 | −4687 | 38400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 268(E) | −2118 | −3486 | −1036 | 2964 | −3935 | −2588 | −1284 | −3596 | 1878 | −3417 | −2636 | −1209 | −2827 | 1323 | −773 | −1923 | −2032 | −3199 | −3455 | −2917 | 38500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 269(Y) | −4524 | −3618 | −5100 | −5310 | 1910 | −4972 | −1299 | −3522 | 634 | −2951 | −2965 | −3649 | −4847 | −3741 | −4299 | −4199 | −4391 | −3637 | 2997 | 4211 | 38600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −155 | −8139 | −3345 | −894 | −1115 | −701 | −1378 | * | * | | | | | | | | | | | | |
| 270(G) | −4176 | −3995 | −4855 | −5222 | −5686 | 3828 | −4823 | −6386 | −5533 | −6087 | −5741 | −4896 | −4606 | −5312 | −5178 | −4461 | −4560 | −5613 | −4754 | −5635 | 38700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −7992 | −9034 | −894 | −1115 | −422 | −1980 | * | * | | | | | | | | | | | | |
| 271(D) | −2710 | −4705 | 3025 | 1828 | −4880 | 1758 | −1932 | −4863 | −2320 | −4703 | −4115 | −1084 | −3073 | −1621 | −3297 | −2330 | −2809 | −4301 | −4894 | −3793 | 38800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 272(Y) | −2497 | −2175 | −4651 | −4137 | 2447 | −4046 | −2215 | 255 | −3766 | 892 | 1558 | −3537 | −3886 | −3109 | −3468 | −3181 | −2410 | −1282 | −1615 | 3508 | 38900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 273(V) | −1425 | −1250 | −3480 | −2894 | −1283 | −3035 | −1955 | 691 | −2570 | −1 | −429 | −2568 | −3060 | 942 | −2514 | −2129 | 1701 | 2578 | −1907 | −1553 | 39000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 274(T) | 516 | −1643 | −1918 | −1401 | −2170 | −2112 | −1387 | −1759 | −1234 | −2016 | −1265 | −1442 | −2421 | −1149 | 877 | 1341 | 2345 | 822 | −2454 | −2006 | 39100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 275(G) | 677 | −2128 | −3838 | −4171 | −4647 | 3536 | −3816 | −4506 | −4340 | −4749 | −3857 | −3009 | −3149 | −3871 | −4137 | −1784 | −2005 | −3297 | −4725 | −4735 | 39200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 276(P) | −992 | −2210 | 343 | −359 | −2447 | −1960 | −675 | −2143 | 533 | −2204 | −1351 | −651 | 2813 | −260 | −802 | 465 | −939 | −873 | −2467 | 1093 | 39300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 277(R) | −1214 | −2448 | −1097 | 1072 | 175 | −2145 | −716 | −2587 | 848 | −2528 | −1653 | −795 | −2228 | −273 | 2862 | 417 | −1133 | −2191 | −2671 | −2084 | 39400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 278(V) | 289 | −2035 | −5133 | −4789 | −2692 | −4777 | −4639 | 2142 | −4689 | −1561 | −1443 | −4511 | −4649 | −4585 | −4784 | −4102 | −2487 | 3125 | −4202 | −3717 | 39500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 279(I) | −2286 | −1919 | −4828 | −4452 | −2473 | −4254 | −3954 | 3155 | −4265 | −1516 | −1326 | −4066 | −4279 | −4082 | −4274 | 226 | −2288 | −2182 | −3686 | −3250 | 39600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 280(D) | −1731 | −3162 | 2329 | −550 | −3318 | −2239 | −1273 | −3221 | −1145 | −3214 | −2406 | 2295 | −2573 | −899 | −1742 | −1561 | 1851 | −2804 | −3366 | 1327 | 39700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 281(E) | 1097 | −2699 | 1227 | −2368 | −2994 | −2011 | −796 | −2753 | 291 | −2704 | −1808 | −640 | −2190 | −358 | −992 | −1065 | −1162 | −2310 | −2885 | 1152 | 39800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 282(E) | −166 | −2372 | 859 | 1835 | −2692 | −1861 | 1182 | −2444 | 490 | −2388 | −1462 | 590 | 478 | 1356 | −620 | 116 | −837 | −1994 | −2555 | −1871 | 39900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 283(T) | 228 | −1688 | −3655 | −3444 | −3179 | −2145 | −2891 | −2611 | −3215 | −3076 | −2328 | −2557 | −2821 | −2916 | −3214 | 2251 | 2366 | 1397 | −3549 | −3270 | 40000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 284(K) | −2991 | −3623 | −3848 | −2331 | −4472 | −3512 | −1356 | −3763 | 2942 | −3413 | 1860 | −2188 | −3430 | −937 | 2705 | −2874 | −2650 | −3556 | −3267 | −3189 | 40100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 285(E) | 443 | −2370 | 732 | 1690 | −2691 | −1863 | −526 | −2442 | 1639 | −2385 | −1460 | −498 | −1960 | 1120 | 437 | 106 | −836 | −1992 | −2552 | −1869 | 40200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 286(A) | 1871 | −2286 | −843 | 814 | −2570 | −1928 | −578 | 269 | 1096 | −2279 | −1391 | −586 | −2019 | −136 | 1056 | −62 | −881 | −1889 | −2488 | −1849 | 40300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 287(M) | −3656 | −3159 | −5816 | −5350 | −1349 | −5421 | −4248 | −822 | −4928 | 948 | 4920 | −5248 | −4838 | −4039 | −4539 | −4860 | −3558 | −1557 | −3044 | −3030 | 40400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 288(K) | −1646 | −2891 | −1591 | 287 | −3346 | −526 | −912 | −2971 | 2831 | −2832 | −1997 | −1146 | −2554 | −472 | 1762 | −1527 | −1524 | −2597 | −2885 | 1245 | 40500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 289(E) | −172 | −2394 | 367 | 2205 | −2713 | −487 | −545 | −2465 | −134 | −2409 | −1485 | 1305 | −1957 | 663 | 831 | −795 | 72 | −2015 | 2577 | −1891 | 40600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 290(C) | 1574 | 3024 | −4584 | −4122 | −2155 | −3932 | −3330 | 1746 | −3870 | −1406 | −1109 | −3691 | −3957 | −3613 | −3805 | −3144 | −2046 | 2342 | −3118 | −2720 | 40700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 291(L) | −187 | −2175 | −4307 | −3889 | −898 | −3779 | −2344 | −944 | −3485 | 2855 | −478 | −3390 | −3782 | −3025 | −3298 | −2972 | −2345 | −1269 | −1846 | 1565 | 40800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 292(K) | 862 | −2347 | 143 | 1211 | −2665 | −1855 | 873 | −2414 | 1692 | −2392 | 917 | −492 | −1949 | 889 | −603 | −763 | 783 | −1968 | −2532 | −1851 | 40900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 293(D) | −2148 | −3878 | 2790 | 1765 | −4119 | −2356 | −1511 | −3962 | −1467 | −3852 | −3075 | 24 | −2782 | −1139 | 2142 | −189 | −2163 | −3473 | −4024 | −3155 | 41000% |
| | −149 | −500 | 233 | 43 | −381 | 399 | 106 | −626 | 210 | −466 | −720 | 275 | 394 | 45 | 96 | 359 | 117 | −369 | −294 | −249 | |
| | −8 | −8139 | −9181 | −894 | −1115 | −701 | −1378 | * | * | | | | | | | | | | | | |
| 294(I) | −2630 | −2131 | −5302 | −4991 | −2737 | −5092 | −5106 | 3464 | −4941 | −1495 | −1447 | −4789 | −4862 | −4869 | −5086 | −4473 | −2627 | 2071 | −4467 | −3968 | 41100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 295(Q) | 346 | −3134 | −1818 | −1401 | −3862 | −2760 | −1314 | −3433 | 1329 | −3271 | −2513 | −1545 | −2936 | 3817 | −430 | −2018 | −2031 | −3060 | −3278 | −2908 | 41200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 296(S) | −1354 | −2895 | 1712 | 354 | −3192 | −2068 | −914 | −2967 | −621 | −2903 | −2012 | −1817 | −2288 | 724 | −1177 | 1978 | −96 | −2508 | −3076 | −2340 | 41300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 297(G) | −4435 | −4203 | −5092 | −5462 | −5893 | 3834 | −5028 | −6627 | −5765 | −6297 | −5970 | −5141 | −4804 | −5546 | −5385 | −4727 | −4815 | −5862 | −4924 | −5849 | 41400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 298(E) | −437 | −2374 | −769 | 2013 | −2697 | −1895 | −552 | −2438 | 623 | −2389 | −1472 | −536 | −1991 | −97 | 777 | 829 | 1488 | −1999 | −2559 | −1890 | 41500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 299(F) | −4347 | −3577 | −4619 | 543 | 3858 | −4820 | −1320 | −3438 | −4609 | −2900 | −2894 | −3532 | −4750 | −3628 | −4209 | −4078 | −4237 | −3546 | −601 | 2917 | 41600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 300(A) | 2827 | −1603 | −4068 | −3628 | −2047 | −3165 | −2823 | 1205 | −3349 | −1486 | −1089 | −3103 | −3432 | −3073 | −3298 | −2387 | 197 | 1100 | −2812 | −2447 | 41700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 301(K) | −2364 | −3363 | −2464 | 163 | −4038 | −3041 | −1188 | −3501 | 2928 | −3234 | −2787 | −1693 | −3047 | −758 | 2488 | −458 | −2152 | −3194 | −3159 | −2895 | 41800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 302(M) | −893 | −2361 | 740 | 1780 | −2680 | −537 | −524 | −2429 | 930 | −2376 | 1895 | −498 | −1958 | −66 | 722 | 775 | −833 | −1982 | −2545 | −1864 | 41900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 303(W) | −2965 | 2533 | −4795 | −4482 | 3045 | −4315 | −1779 | −1426 | −4093 | 92 | −987 | −3564 | −4179 | −3330 | −3743 | −3475 | −2878 | 664 | 4754 | −84 | 42000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 304(I) | −2621 | −2136 | −5246 | −4859 | −2364 | −4987 | −4577 | 3052 | −4747 | −250 | 1043 | −4641 | −4713 | −4488 | −4769 | −4301 | −2597 | 2384 | −3934 | −3596 | 41200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 305(L) | 684 | −1319 | −1741 | 761 | −1375 | −2223 | −1037 | −927 | −1042 | 1693 | −533 | −1287 | −2325 | −915 | −1349 | 767 | −152 | 84 | −1756 | −1329 | 42200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 306(E) | 364 | −4165 | 621 | 3314 | −4393 | −2398 | −1686 | −4292 | −1836 | −4169 | −3446 | 728 | −2893 | −1339 | −2626 | −2045 | −2402 | −3767 | −4362 | −3401 | 42300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 307(N) | −939 | 979 | −1235 | −681 | −1738 | 1352 | 935 | −1357 | −549 | −1572 | −816 | 2186 | −2155 | −482 | 165 | −1022 | −880 | 30 | −1990 | 1446 | 42400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 308(Q) | 667 | −2393 | −773 | 511 | −2721 | −316 | −544 | −2465 | 1211 | −2405 | −1484 | 584 | −1989 | 2135 | 1528 | −812 | −868 | −2019 | −2566 | −1895 | 42500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 309(A) | 2050 | −1857 | −1081 | −526 | −2013 | −2012 | 188 | −1645 | −385 | −1213 | −1011 | 486 | −2103 | −346 | 1657 | −953 | 306 | −261 | −2189 | −1624 | 42600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 310(G) | −1848 | −2469 | −2089 | −2292 | 1262 | 2944 | −2358 | −3563 | −2904 | −3628 | −3017 | 2347 | −3167 | −2550 | −3185 | −1986 | −2162 | −3006 | −2814 | −1874 | 42700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 311(Y) | 475 | 1019 | −1606 | −1042 | 225 | −2192 | −935 | −946 | −891 | −1226 | 1222 | 357 | −2267 | 1002 | −1577 | −1172 | −888 | −800 | −1730 | 2446 | 42800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 312(P) | −87 | −2372 | −1362 | 756 | −3738 | −2205 | −2007 | −3445 | −1924 | −3575 | −2761 | −1555 | 3598 | −1697 | −2362 | −1566 | 286 | −2803 | −3832 | −3277 | 42900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2336 | −8139 | −325 | −894 | −1115 | −701 | −1378 | * | * | | | | | | | | | | | | |
| 313(K) | −804 | −1483 | −564 | −230 | −1920 | −1335 | −101 | −1605 | 2889 | −1630 | −1021 | −349 | −1569 | 232 | 698 | −786 | −759 | −1358 | −1637 | −1317 | 43000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −3098 | −179 | * | * | | | | | | | | | | | | |
| 314(E) | −766 | −1695 | 521 | 2831 | −2050 | −1029 | −293 | −1804 | −118 | −1919 | −1331 | 69 | −1441 | −4 | −527 | −653 | −814 | −1512 | −1988 | −1505 | 43100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −109 | −3375 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 315(T) | −942 | −2382 | −739 | 1086 | −2714 | 151 | −581 | −2459 | −171 | −2415 | −1499 | 414 | −2004 | −128 | 839 | 1365 | 1730 | −2017 | −2592 | −1915 | 43200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 316(M) | −2196 | −1920 | −4499 | −3891 | 1726 | −3822 | −2504 | −645 | −3523 | 1973 | 3030 | −3442 | −3673 | −2938 | −3257 | −2944 | −2114 | 326 | −2014 | 1662 | 43300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 317(H) | −883 | −2314 | −747 | 517 | −2618 | −1863 | 1714 | −647 | 1272 | −2322 | −1408 | 1011 | 472 | −69 | 433 | −772 | 1411 | −299 | −2507 | −1836 | 43400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 318(A) | 2474 | −2397 | −816 | −367 | −2797 | −273 | −722 | −2529 | 555 | −2507 | −1610 | 592 | −2110 | 837 | −805 | −138 | −1006 | −2092 | −2699 | −2039 | 43500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 319(M) | −154 | −986 | −2485 | −337 | 1024 | −375 | −1232 | 325 | −444 | 867 | 1235 | −1752 | −2474 | −1419 | 1020 | −1455 | 670 | −411 | 831 | 535 | 43600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 320(R) | −1311 | −2432 | −1349 | −724 | −2724 | −2272 | −799 | −2361 | 613 | −644 | 1079 | 976 | 597 | −382 | 2908 | −1246 | −1219 | −2044 | −2579 | −2061 | 43700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 321(R) | 897 | −2364 | −833 | 905 | −2678 | −1930 | −568 | −2405 | 1293 | −2366 | 1485 | −575 | −2020 | −117 | 2045 | 95 | −893 | −1984 | −2543 | −1892 | 43800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 322(N) | 505 | −2300 | −750 | 523 | −2596 | 121 | −525 | −594 | 485 | 95 | −1395 | 1720 | −1957 | 348 | 224 | 551 | −821 | −1910 | −2497 | −1828 | 43900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 323(E) | 444 | −2266 | −766 | 1488 | −2551 | −1871 | −533 | −2275 | 889 | −2266 | 1474 | 1478 | −1963 | 682 | −629 | −781 | 12 | −279 | −2472 | 476 | 44000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 324(N) | 1511 | −1170 | −728 | −204 | −2244 | −1781 | −426 | 282 | 601 | −2121 | −1133 | 1769 | −1827 | −1398 | 447 | −748 | −766 | −1713 | −1779 | −1595 | 44100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 325(N) | 1053 | −3109 | 1756 | 1735 | −3404 | −2143 | −1074 | −3191 | −846 | −3124 | −2254 | 2158 | −2417 | −657 | −1430 | −1361 | 197 | −2727 | −3303 | −2540 | 44200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 326(H) | −2064 | −3071 | −1245 | −1267 | −3262 | −2570 | 4711 | −3611 | −1060 | −3525 | −2812 | −1479 | −2961 | 1288 | −1287 | 670 | −2133 | −3161 | −3310 | −2601 | 44300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 327(Q) | −891 | −2294 | 332 | 948 | −2585 | −739 | −537 | −2316 | −131 | −138 | −1391 | −518 | 1404 | 2021 | −634 | −785 | 619 | −561 | −2495 | −1830 | 44400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 328(I) | −1632 | −1661 | −2846 | −86 | −1626 | −2983 | −1663 | 3240 | −1327 | −191 | −722 | −2160 | −3016 | −1615 | 822 | −2097 | −1556 | −560 | −2157 | −1805 | 44500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 329(E) | −2734 | −3605 | −1382 | 3593 | −3624 | −2986 | −2317 | −3317 | −2175 | −3167 | 1983 | −1898 | −3440 | −2054 | −2556 | −2649 | −2820 | −3234 | −3920 | −3370 | 44600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2336 | −8139 | −325 | −894 | −1115 | −701 | −1378 | * | * | | | | | | | | | | | | |
| 330(W) | −1530 | −1265 | −2068 | −1964 | 479 | −1810 | −483 | −1181 | −1470 | −968 | −802 | −1648 | −2104 | −1454 | −1405 | −1757 | −1583 | −1218 | 5462 | 838 | 44700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −38 | −5840 | −6882 | −894 | −1115 | −109 | −3775 | * | * | | | | | | | | | | | | |
| 331(K) | 8 | −2067 | −905 | 437 | −2275 | −1941 | −611 | −307 | 2031 | −2031 | −1189 | −636 | −2030 | 1425 | −709 | −864 | −350 | 1337 | −2323 | −1722 | 44800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 332(V) | −2445 | −2012 | −5067 | −4708 | −2628 | −4682 | −4459 | 1586 | −4580 | −1533 | −1402 | −4414 | −4575 | −4456 | −4653 | −3990 | 1117 | 3227 | −4065 | −3597 | 44900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 333(G) | −4435 | −4203 | −5092 | −5462 | −5893 | 3834 | −5028 | −6627 | −5765 | −6297 | −5970 | −5141 | −4804 | −5546 | −5385 | −4727 | −4815 | −5862 | −4924 | −5849 | 45000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 334(E) | 1477 | −2744 | −762 | 2410 | −3114 | −2113 | −884 | −2850 | −445 | −2792 | −1912 | 619 | −2297 | −451 | 1346 | −1191 | −1280 | −2412 | −2952 | −2288 | 45100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 335(K) | −1204 | −2643 | 366 | −1309 | −3998 | −2086 | −724 | −2722 | 2626 | −2637 | −1741 | −718 | −2200 | 1198 | 862 | −1073 | −1133 | −2287 | −2770 | −2133 | 45200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 336(L) | −3571 | −3023 | −5954 | −5375 | −1321 | −5646 | −4390 | −632 | −5138 | 2962 | 1671 | −5358 | −4852 | −4044 | −4689 | −4963 | −3436 | 742 | −3082 | −3239 | 45300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 337(R) | −4845 | −4446 | −5107 | −4682 | −5507 | −4412 | −3791 | −5676 | −2789 | −5502 | −5118 | −4521 | −4754 | −3672 | 4219 | −4989 | −4832 | −5644 | −4538 | −4993 | 45400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 338(E) | 943 | −2422 | 1002 | 1200 | −2741 | 377 | −572 | −2493 | 982 | −2439 | −1517 | −522 | −1998 | −117 | −681 | 1129 | −534 | −2044 | −2609 | −1921 | 45500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 339(M) | −3391 | −2886 | −5774 | −5202 | −1338 | −5407 | −4210 | −576 | −4943 | 1721 | 4369 | −5109 | −4742 | −3639 | −4548 | −4689 | −3273 | 771 | −3038 | −3137 | 45600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 340(M) | −1812 | −1601 | −3997 | −3375 | 696 | −3401 | −2222 | −516 | −2983 | 441 | 4360 | −2991 | −3334 | −2559 | 641 | −2503 | −1740 | 404 | −1934 | −1661 | 45700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8139 | −9181 | −894 | −1115 | −701 | −1378 | * | * | | | | | | | | | | | | |
| 341(P) | 102 | −1789 | −1729 | −1313 | 428 | −2112 | −1410 | −2021 | −1236 | −2235 | −1470 | −1394 | 3205 | 695 | −1607 | 703 | −1207 | −1700 | −2613 | −2121 | 45800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −259 | −8139 | −2637 | −894 | −1115 | −701 | −1378 | * | * | | | | | | | | | | | | |
| 342(W) | −3486 | −3022 | −4312 | −4121 | 1891 | −4228 | −1173 | −2749 | 310 | −2389 | −2250 | −3147 | −4206 | −2971 | −3005 | −3484 | −3396 | −2818 | 5644 | 611 | 45900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −239 | −7889 | −2749 | −894 | −1115 | −1590 | −583 | * | * | | | | | | | | | | | | |
| 343(I) | −2220 | −1737 | −4860 | −4531 | −2271 | −4617 | −4497 | 3348 | −4448 | −1059 | −1008 | −4311 | −4707 | −4340 | −4559 | −3974 | −2216 | 2150 | −3915 | −3445 | 46000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −114 | −7660 | −3820 | −894 | −1115 | −1149 | −865 | * | * | | | | | | | | | | | | |
| 344(A) | 1699 | −2218 | 532 | −33 | −2555 | −553 | −413 | −2304 | 1212 | −2260 | −1348 | 582 | −1822 | 37 | −536 | 966 | −724 | −1859 | −2439 | 1755 | 46100% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7753 | −8795 | −894 | −1115 | −897 | −1111 | * | * | | | | | | | | | | | | |
| 345(A) | 1523 | −2068 | −769 | −231 | −2383 | 1040 | −522 | −2084 | 928 | −2120 | −1245 | −517 | −1922 | 1335 | −611 | 251 | −768 | −123 | −2361 | −1732 | 46200% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7949 | −8991 | −894 | −1115 | −1432 | −668 | * | * | | | | | | | | | | | | |
| 346(N) | −1650 | −3264 | 1760 | −348 | −3555 | −230 | −1131 | −3362 | 324 | −3285 | −2448 | 2847 | 1624 | −733 | −1607 | −1438 | −1645 | −2887 | −3466 | −2662 | 46300% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −193 | −7842 | −3049 | −894 | −1115 | −1432 | −668 | * | * | | | | | | | | | | | | |
| 347(K) | 150 | −2932 | −2433 | −1483 | −3710 | −2747 | −907 | −3141 | 3369 | −2897 | −2178 | −1487 | −2774 | −488 | 1175 | −1994 | −1888 | −2848 | −2822 | −2610 | 46400% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7660 | −8702 | −894 | −1115 | −1824 | −479 | * | * | | | | | | | | | | | | |
| 348(L) | −740 | −922 | −1768 | 154 | −921 | −2070 | −829 | −1384 | 247 | 1472 | −100 | −1202 | −2134 | −805 | 485 | −1085 | −677 | 471 | −1340 | −944 | 46500% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7660 | −8702 | −894 | −1115 | −943 | −1059 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 349(V) | 138 | −1046 | −3186 | −2599 | −1089 | −2803 | −1711 | 589 | 645 | 945 | −236 | −2305 | −2803 | −2012 | −2236 | −1892 | −1154 | −253 | −1701 | −1344 | 46600% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7842 | −8885 | −894 | −1115 | −380 | −2109 | * | * | | | | | | | | | | | | |
| 350(D) | −2086 | −3722 | 2888 | 1158 | −4001 | 1601 | −1510 | −3811 | −1573 | −3773 | −3018 | −904 | −2733 | −1154 | −2294 | −1833 | −2125 | 575 | −3993 | −3117 | 46700% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8046 | −9088 | −894 | −1115 | −701 | −1378 | * | * | | | | | | | | | | | | |
| 351(K) | −78 | −2308 | 398 | −137 | −2626 | −483 | 542 | −2374 | 2441 | −2323 | −1400 | −447 | 531 | 720 | −562 | −724 | 290 | −1929 | −2493 | −1812 | 46800% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8046 | −9088 | −894 | −1115 | −701 | −1378 | * | * | | | | | | | | | | | | |
| 352(D) | 898 | −1911 | 1604 | −335 | −2089 | −1892 | −573 | −1746 | 489 | −144 | 811 | −609 | 34 | −182 | −708 | 541 | −74 | −281 | −2188 | −1605 | 46900% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7745 | −8787 | −894 | −1115 | −701 | −1378 | * | * | | | | | | | | | | | | |
| 353(K) | −1676 | −2544 | −1956 | −1135 | −2823 | −2531 | −800 | −2469 | 2955 | −2426 | −1683 | −1204 | −2548 | −407 | 1469 | −1628 | −1517 | −119 | −2497 | 1619 | 47000% |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −11 | −7649 | −8691 | −894 | −1115 | −701 | −1378 | * | * | | | | | | | | | | | | |
| 354(N) | −1074 | −1925 | −1092 | −1190 | −3523 | −1781 | −1760 | −3345 | −1701 | −3432 | −2589 | 3429 | 1327 | −1460 | −2119 | 1182 | −1362 | −2558 | −3601 | 3046 | 47100% |
| — | * | * | * | * | * | * | * | * | * | * | * | * | * | * | * | * | * | * | * | * | |
| — | * | * | * | * | * | * | * | * | 0 | | | | | | | | | | | | |

What is claimed is:

1. A recombinant host cell comprising a mutant ketol-acid reductoisomerase enzyme, wherein said enzyme has a ketol-acid reductoisomerase HMM search profile E value of $<10^{-3}$ using the hmmsearch program and comprises at least one mutation within the phosphate binding loop of said enzyme wherein said at least one mutation comprises a substitution at the residue corresponding to T52 of SEQ ID NO:17 wherein the substitution at residue T52 is a substitution to a polar, negatively charged amino acid.

2. The recombinant host cell of claim 1, wherein the recombinant host cell is a member of a genera selected from *Clostridium, Zymomonas, Escherichia, Salmonella, Rhodococcus, Pseudomonas, Bacillus, Vibrio, Lactobacillus, Enterococcus, Alcaligenes, Klebsiella, Paenibacillus, Arthobacter, Corynebacterium, Brevibacterium, Pichia, Candida, Hansenula*, and *Saccharomyces*.

3. The recombinant host cell of claim 2, wherein the host cell is a *Saccharomyces*.

4. The recombinant host cell of claim 1, wherein the mutant ketol-acid reductoisomerase enzyme comprises a GxGxx(G/A) cofactor binding motif.

5. The recombinant host cell of claim 1, wherein the host cell further comprises an acetolactate synthase enzyme.

6. The recombinant host cell of claim 5, wherein the acetolactate synthase enzyme is a *Bacillus subtilis* acetolactate synthase enzyme.

7. A method of converting acetolactate to 2,3-dihydroxyisovalerate, the method comprising:

(a) providing a recombinant host cell comprising a mutant ketol-acid reductoisomerase enzyme, wherein said enzyme has a ketol-acid reductoisomerase HMM search profile E value of $<10^{-3}$ using the hmmsearch program and comprises at least one mutation within the phosphate binding loop of said enzyme wherein said at least one mutation comprises a substitution at the residue corresponding to T52 of SEQ ID NO:17 wherein the substitution at residue T52 is a substitution to a polar, negatively charged amino acid; and (b) contacting the recombinant host cell with acetolactate, wherein the recombinant host cell converts acetolactate to 2,3-dihydroxyisovalerate.

8. The method of claim 7, wherein the recombinant host cell is a member of a genera selected from *Clostridium, Zymomonas, Escherichia, Salmonella, Rhodococcus, Pseudomonas, Bacillus, Vibrio, Lactobacillus, Enterococcus, Alcaligenes, Klebsiella, Paenibacillus, Arthobacter, Corynebacterium, Brevibacterium, Pichia, Candida, Hansenula*, and *Saccharomyces*.

9. The method of claim 8, wherein the recombinant host cell is a *Saccharomyces*.

10. The method of claim 7, wherein the mutant ketol-acid reductoisomerase enzyme comprises a GxGxx(G/A) cofactor binding motif.

11. A method of producing isobutanol, the method comprising:

(a) providing a recombinant host cell comprising an isobutanol biosynthetic pathway, wherein the isobutanol biosynthetic pathway comprises a mutant ketol-acid reductoisomerase enzyme, wherein the enzyme has a ketol-acid reductoisomerase HMM search profile E value of $<10^{-3}$ using the hmmsearch program and comprises at least one mutation within the phosphate binding loop of said enzyme wherein said at least one mutation comprises a substitution at the residue corresponding to T52 of SEQ ID NO:17 wherein the substitution at residue T52 is a substitution to a polar, negatively charged amino acid; and (b) contacting the recombinant host cell with a fermentable carbon substrate, wherein the recombinant host cell produces isobutanol.

12. The method of claim 11, wherein the recombinant host cell is a member of a genera selected from *Clostridium, Zymomonas, Escherichia, Salmonella, Rhodococcus, Pseudomonas, Bacillus, Vibrio, Lactobacillus, Enterococcus, Alcaligenes, Klebsiella, Paenibacillus, Arthobacter, Corynebacterium, Brevibacterium, Pichia, Candida, Hansenula*, and *Saccharomyces*.

13. The method of claim 12, wherein the recombinant host cell is a *Saccharomyces*.

14. The method of claim 11, wherein the mutant ketol-acid reductoisomerase enzyme comprises a GxGxx(G/A) cofactor binding motif.

15. The method of claim 11, wherein the recombinant host cell further comprises an acetolactate synthase enzyme.

16. The method of claim 15, wherein the acetolactate synthase enzyme is a *Bacillus subtilus* acetolactate synthase enzyme.

* * * * *

SEQUENCE LISTING

<160> NUMBER OF SEQ ID NOS: 98

<210> SEQ ID NO 1
<211> LENGTH: 30
<212> TYPE: DNA
<213> ORGANISM: artificial sequence
<220> FEATURE:
<223> OTHER INFORMATION: primer

<400> SEQUENCE: 1
tgatgaacat cttcgcgtat tcgccgtcct 30

<210> SEQ ID NO 2
<211> LENGTH: 68
<212> TYPE: DNA
<213> ORGANISM: artificial sequence
<220> FEATURE:
<223> OTHER INFORMATION: forward primer for library C
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 2
gcgtagacgt gactgttggc ctgnntaaag gcnnggctnn ctgggccaag gctgaagccc 60
acggcttg 68

<210> SEQ ID NO 3
<211> LENGTH: 68
<212> TYPE: DNA
<213> ORGANISM: artificial sequence
<220> FEATURE:
<223> OTHER INFORMATION: forward primer for library E
<220> FEATURE:
<221> NAME/KEY: misc_feature
<222> LOCATION: (24)..(25)
<223> OTHER INFORMATION: n is a, c, g, or t

<400> SEQUENCE: 3
gcgtagacgt gactgttggc ctgnntaaag gctcggctac cgttgccaag gctgaagccc 60
acggcttg 68

<210> SEQ ID NO 4
<211> LENGTH: 68
<212> TYPE: DNA
<213> ORGANISM: artificial sequence
<220> FEATURE:
<223> OTHER INFORMATION: forward primer for library F
<220> FEATURE:
<221> NAME/KEY: misc_feature
<222> LOCATION: (33)..(34)
<223> OTHER INFORMATION: n is a, c, g, or t

<400> SEQUENCE: 4
gcgtagacgt gactgttggc ctgcgtaaag gcnntgctac cgttgccaag gctgaagccc 60
acggcttg 68

<210> SEQ ID NO 5
<211> LENGTH: 68

<212> TYPE: DNA
<213> ORGANISM: artificial sequence
<220> FEATURE:
<223> OTHER INFORMATION: forward primer for library G
<220> FEATURE:
<221> NAME/KEY: misc_feature
<222> LOCATION: (39)..(40)
<223> OTHER INFORMATION: n is a, c, g, or t

<400> SEQUENCE: 5
gcgtagacgt gactgttggc ctgcgtaaag gctcggctnn tgttgccaag gctgaagccc 60
acggcttg 68

<210> SEQ ID NO 6
<211> LENGTH: 68
<212> TYPE: DNA
<213> ORGANISM: artificial sequence
<220> FEATURE:
<223> OTHER INFORMATION: forward primer for library H
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 6
gcgtagacgt gactgttggc ctgnntaaag gcnntgctnn tgttgccaag gctgaagccc 60
acggcttg 68

<210> SEQ ID NO 7
<211> LENGTH: 20
<212> TYPE: DNA
<213> ORGANISM: artificial sequence
<220> FEATURE:
<223> OTHER INFORMATION: sequencing primer (forward)

<400> SEQUENCE: 7
aagattagcg gatcctacct 20

<210> SEQ ID NO 8
<211> LENGTH: 20
<212> TYPE: DNA
<213> ORGANISM: artificial sequence
<220> FEATURE:
<223> OTHER INFORMATION: sequencing primer (reverse)

<400> SEQUENCE: 8
aacagccaag cttttagttc 20

<210> SEQ ID NO 9
<211> LENGTH: 330
<212> TYPE: PRT
<213> ORGANISM: Methanococcus maripaludis

<400> SEQUENCE: 9

Met Lys Val Phe Tyr Asp Ser Asp Phe Lys Leu Asp Ala Leu Lys Glu
1 5 10 15

Lys Thr Ile Ala Val Ile Gly Tyr Gly Ser Gln Gly Arg Ala Gln Ser
20 25 30

```
Leu Asn Met Lys Asp Ser Gly Leu Asn Val Val Val Gly Leu Arg Lys
        35                  40                  45

Asn Gly Ala Ser Trp Glu Asn Ala Lys Ala Asp Gly His Asn Val Met
    50                  55                  60

Thr Ile Glu Glu Ala Ala Glu Lys Ala Asp Ile Ile His Ile Leu Ile
65                  70                  75                  80

Pro Asp Glu Leu Gln Ala Glu Val Tyr Glu Ser Gln Ile Lys Pro Tyr
                85                  90                  95

Leu Lys Glu Gly Lys Thr Leu Ser Phe Ser His Gly Phe Asn Ile His
            100                 105                 110

Tyr Gly Phe Ile Val Pro Pro Lys Gly Val Asn Val Val Leu Val Ala
        115                 120                 125

Pro Lys Ser Pro Gly Lys Met Val Arg Arg Thr Tyr Glu Glu Gly Phe
    130                 135                 140

Gly Val Pro Gly Leu Ile Cys Ile Glu Ile Asp Ala Thr Asn Asn Ala
145                 150                 155                 160

Phe Asp Ile Val Ser Ala Met Ala Lys Gly Ile Gly Leu Ser Arg Ala
                165                 170                 175

Gly Val Ile Gln Thr Thr Phe Lys Glu Glu Thr Glu Thr Asp Leu Phe
            180                 185                 190

Gly Glu Gln Ala Val Leu Cys Gly Gly Val Thr Glu Leu Ile Lys Ala
        195                 200                 205

Gly Phe Glu Thr Leu Val Glu Ala Gly Tyr Ala Pro Glu Met Ala Tyr
    210                 215                 220

Phe Glu Thr Cys His Glu Leu Lys Leu Ile Val Asp Leu Ile Tyr Gln
225                 230                 235                 240

Lys Gly Phe Lys Asn Met Trp Asn Asp Val Ser Asn Thr Ala Glu Tyr
                245                 250                 255

Gly Gly Leu Thr Arg Arg Ser Arg Ile Val Thr Ala Asp Ser Lys Ala
            260                 265                 270

Ala Met Lys Glu Ile Leu Lys Glu Ile Gln Asp Gly Arg Phe Thr Lys
        275                 280                 285

Glu Phe Val Leu Glu Lys Gln Val Asn His Ala His Leu Lys Ala Met
    290                 295                 300

Arg Arg Ile Glu Gly Asp Leu Gln Ile Glu Glu Val Gly Ala Lys Leu
305                 310                 315                 320

Arg Lys Met Cys Gly Leu Glu Lys Glu Glu
                325                 330


<210> SEQ ID NO 10
<211> LENGTH: 330
<212> TYPE: PRT
<213> ORGANISM: Methanococcus maripaludis

<400> SEQUENCE: 10

Met Lys Val Phe Tyr Asp Ser Asp Phe Lys Leu Asp Ala Leu Lys Glu
1               5                   10                  15

Lys Thr Ile Ala Val Ile Gly Tyr Gly Ser Gln Gly Arg Ala Gln Ser
            20                  25                  30

Leu Asn Met Lys Asp Ser Gly Leu Asn Val Val Val Gly Leu Arg Lys
        35                  40                  45

Asn Gly Ala Ser Trp Asn Asn Ala Lys Ala Asp Gly His Asn Val Met
    50                  55                  60

Thr Ile Glu Glu Ala Ala Glu Lys Ala Asp Ile Ile His Ile Leu Ile
65                  70                  75                  80
```

```
Pro Asp Glu Leu Gln Ala Glu Val Tyr Glu Ser Gln Ile Lys Pro Tyr
                85                  90                  95

Leu Lys Glu Gly Lys Thr Leu Ser Phe Ser His Gly Phe Asn Ile His
            100                 105                 110

Tyr Gly Phe Ile Val Pro Pro Lys Gly Val Asn Val Val Leu Val Ala
        115                 120                 125

Pro Lys Ser Pro Gly Lys Met Val Arg Arg Thr Tyr Glu Glu Gly Phe
    130                 135                 140

Gly Val Pro Gly Leu Ile Cys Ile Glu Ile Asp Ala Thr Asn Asn Ala
145                 150                 155                 160

Phe Asp Ile Val Ser Ala Met Ala Lys Gly Ile Gly Leu Ser Arg Ala
                165                 170                 175

Gly Val Ile Gln Thr Thr Phe Lys Glu Glu Thr Glu Thr Asp Leu Phe
            180                 185                 190

Gly Glu Gln Ala Val Leu Cys Gly Gly Val Thr Glu Leu Ile Lys Ala
        195                 200                 205

Gly Phe Glu Thr Leu Val Glu Ala Gly Tyr Ala Pro Glu Met Ala Tyr
    210                 215                 220

Phe Glu Thr Cys His Glu Leu Lys Leu Ile Val Asp Leu Ile Tyr Gln
225                 230                 235                 240

Lys Gly Phe Lys Asn Met Trp Asn Asp Val Ser Asn Thr Ala Glu Tyr
                245                 250                 255

Gly Gly Leu Thr Arg Arg Ser Arg Ile Val Thr Ala Asp Ser Lys Ala
            260                 265                 270

Ala Met Lys Glu Ile Leu Arg Glu Ile Gln Asp Gly Arg Phe Thr Lys
        275                 280                 285

Glu Phe Leu Leu Glu Lys Gln Val Ser Tyr Ala His Leu Lys Ser Met
    290                 295                 300

Arg Arg Leu Glu Gly Asp Leu Gln Ile Glu Glu Val Gly Ala Lys Leu
305                 310                 315                 320

Arg Lys Met Cys Gly Leu Glu Lys Glu Glu
                325                 330


<210> SEQ ID NO 11
<211> LENGTH: 330
<212> TYPE: PRT
<213> ORGANISM: Methanococcus vannielii

<400> SEQUENCE: 11

Met Lys Val Phe Tyr Asp Ala Asp Ile Lys Leu Asp Ala Leu Lys Ser
1               5                   10                  15

Lys Thr Ile Ala Val Ile Gly Tyr Gly Ser Gln Gly Arg Ala Gln Ser
            20                  25                  30

Leu Asn Met Lys Asp Ser Gly Leu Asn Val Val Val Gly Leu Arg Lys
        35                  40                  45

Asn Gly Ala Ser Trp Glu Asn Ala Lys Asn Asp Gly His Glu Val Leu
    50                  55                  60

Thr Ile Glu Glu Ala Ser Lys Lys Ala Asp Ile Ile His Ile Leu Ile
65                  70                  75                  80

Pro Asp Glu Leu Gln Ala Glu Val Tyr Glu Ser Gln Ile Lys Pro Tyr
                85                  90                  95

Leu Thr Glu Gly Lys Thr Leu Ser Phe Ser His Gly Phe Asn Ile His
            100                 105                 110

Tyr Gly Phe Ile Ile Pro Pro Lys Gly Val Asn Val Val Leu Val Ala
```

```
        115                 120                 125

Pro Lys Ser Pro Gly Lys Met Val Arg Lys Thr Tyr Glu Glu Gly Phe
    130                 135                 140

Gly Val Pro Gly Leu Ile Cys Ile Glu Val Asp Ala Thr Asn Thr Ala
145                 150                 155                 160

Phe Glu Thr Val Ser Ala Met Ala Lys Gly Ile Gly Leu Ser Arg Ala
                165                 170                 175

Gly Val Ile Gln Thr Thr Phe Arg Glu Glu Thr Glu Thr Asp Leu Phe
            180                 185                 190

Gly Glu Gln Ala Val Leu Cys Gly Gly Val Thr Glu Leu Ile Lys Ala
        195                 200                 205

Gly Phe Glu Thr Leu Val Glu Ala Gly Tyr Ser Pro Glu Met Ala Tyr
    210                 215                 220

Phe Glu Thr Cys His Glu Leu Lys Leu Ile Val Asp Leu Ile Tyr Gln
225                 230                 235                 240

Lys Gly Phe Lys Asn Met Trp His Asp Val Ser Asn Thr Ala Glu Tyr
                245                 250                 255

Gly Gly Leu Thr Arg Arg Ser Arg Ile Val Thr Ala Asp Ser Lys Ala
            260                 265                 270

Ala Met Lys Glu Ile Leu Lys Glu Ile Gln Asp Gly Arg Phe Thr Lys
        275                 280                 285

Glu Phe Val Leu Glu Asn Gln Ala Lys Met Ala His Leu Lys Ala Met
    290                 295                 300

Arg Arg Leu Glu Gly Glu Leu Gln Ile Glu Glu Val Gly Ser Lys Leu
305                 310                 315                 320

Arg Lys Met Cys Gly Leu Glu Lys Asp Glu
                325                 330


<210> SEQ ID NO 12
<211> LENGTH: 349
<212> TYPE: PRT
<213> ORGANISM: Saccharomyces cerevisiae

<400> SEQUENCE: 12

Met Leu Lys Gln Ile Asn Phe Gly Gly Thr Val Glu Thr Val Tyr Glu
1               5                   10                  15

Arg Ala Asp Trp Pro Arg Glu Lys Leu Leu Asp Tyr Phe Lys Asn Asp
            20                  25                  30

Thr Phe Ala Leu Ile Gly Tyr Gly Ser Gln Gly Tyr Gly Gln Gly Leu
        35                  40                  45

Asn Leu Arg Asp Asn Gly Leu Asn Val Ile Ile Gly Val Arg Lys Asp
    50                  55                  60

Gly Ala Ser Trp Lys Ala Ala Ile Glu Asp Gly Trp Val Pro Gly Lys
65                  70                  75                  80

Asn Leu Phe Thr Val Glu Asp Ala Ile Lys Arg Gly Ser Tyr Val Met
                85                  90                  95

Asn Leu Leu Ser Asp Ala Ala Gln Ser Glu Thr Trp Pro Ala Ile Lys
            100                 105                 110

Pro Leu Leu Thr Lys Gly Lys Thr Leu Tyr Phe Ser His Gly Phe Ser
        115                 120                 125

Pro Val Phe Lys Asp Leu Thr His Val Glu Pro Pro Lys Asp Leu Asp
    130                 135                 140

Val Ile Leu Val Ala Pro Lys Gly Ser Gly Arg Thr Val Arg Ser Leu
145                 150                 155                 160
```

```
Phe Lys Glu Gly Arg Gly Ile Asn Ser Ser Tyr Ala Val Trp Asn Asp
                165                 170                 175

Val Thr Gly Lys Ala His Glu Lys Ala Gln Ala Leu Ala Val Ala Ile
            180                 185                 190

Gly Ser Gly Tyr Val Tyr Gln Thr Thr Phe Glu Arg Glu Val Asn Ser
        195                 200                 205

Asp Leu Tyr Gly Glu Arg Gly Cys Leu Met Gly Gly Ile His Gly Met
    210                 215                 220

Phe Leu Ala Gln Tyr Asp Val Leu Arg Glu Asn Gly His Ser Pro Ser
225                 230                 235                 240

Glu Ala Phe Asn Glu Thr Val Glu Glu Ala Thr Gln Ser Leu Tyr Pro
                245                 250                 255

Leu Ile Gly Lys Tyr Gly Met Asp Tyr Met Tyr Asp Ala Cys Ser Thr
            260                 265                 270

Thr Ala Arg Arg Gly Ala Leu Asp Trp Tyr Pro Ile Phe Lys Asn Ala
        275                 280                 285

Leu Lys Pro Val Phe Gln Asp Leu Tyr Glu Ser Thr Lys Asn Gly Thr
    290                 295                 300

Glu Thr Lys Arg Ser Leu Glu Phe Asn Ser Gln Pro Asp Tyr Arg Glu
305                 310                 315                 320

Lys Leu Glu Lys Glu Leu Asp Thr Ile Arg Asn Met Glu Ile Trp Lys
                325                 330                 335

Val Gly Lys Glu Val Arg Lys Leu Arg Pro Glu Asn Gln
            340                 345


<210> SEQ ID NO 13
<211> LENGTH: 335
<212> TYPE: PRT
<213> ORGANISM: Sulfolobus solfataricus

<400> SEQUENCE: 13

Met Lys Cys Thr Ser Lys Ile Tyr Thr Asp Asn Asp Ala Asn Leu Asp
1               5                   10                  15

Leu Ile Lys Gly Lys Arg Ile Ala Val Leu Gly Tyr Gly Ser Gln Gly
            20                  25                  30

Arg Ala Trp Ala Gln Asn Leu Arg Asp Ser Gly Leu Asn Val Val Val
        35                  40                  45

Gly Leu Glu Arg Glu Gly Lys Ser Trp Glu Leu Ala Lys Ser Asp Gly
    50                  55                  60

Ile Thr Pro Leu His Thr Lys Asp Ala Val Lys Asp Ala Asp Ile Ile
65                  70                  75                  80

Ile Phe Leu Val Pro Asp Met Val Gln Arg Thr Leu Trp Leu Glu Ser
                85                  90                  95

Val Gln Pro Tyr Met Lys Lys Gly Ala Asp Leu Val Phe Ala His Gly
            100                 105                 110

Phe Asn Ile His Tyr Lys Leu Ile Asp Pro Pro Lys Asp Ser Asp Val
        115                 120                 125

Tyr Met Ile Ala Pro Lys Gly Pro Gly Pro Thr Val Arg Glu Tyr Tyr
    130                 135                 140

Lys Ala Gly Gly Gly Val Pro Ala Leu Val Ala Val His Gln Asp Val
145                 150                 155                 160

Ser Gly Thr Ala Leu His Lys Ala Leu Ala Ile Ala Lys Gly Ile Gly
                165                 170                 175

Ala Thr Arg Ala Gly Val Ile Pro Thr Thr Phe Lys Glu Glu Thr Glu
            180                 185                 190
```

```
Thr Asp Leu Phe Gly Glu Gln Val Ile Leu Val Gly Gly Ile Met Glu
        195                 200                 205

Leu Met Arg Ala Ala Phe Glu Thr Leu Val Glu Glu Gly Tyr Gln Pro
    210                 215                 220

Glu Val Ala Tyr Phe Glu Thr Ile Asn Glu Leu Lys Met Leu Val Asp
225                 230                 235                 240

Leu Val Tyr Glu Lys Gly Ile Ser Gly Met Leu Lys Ala Val Ser Asp
                245                 250                 255

Thr Ala Lys Tyr Gly Gly Met Thr Val Gly Lys Phe Val Ile Asp Glu
            260                 265                 270

Ser Val Arg Lys Arg Met Lys Glu Ala Leu Gln Arg Ile Lys Ser Gly
        275                 280                 285

Lys Phe Ala Glu Glu Trp Val Glu Glu Tyr Gly Arg Gly Met Pro Thr
    290                 295                 300

Val Val Asn Gly Leu Ser Asn Val Gln Asn Ser Leu Glu Glu Lys Ile
305                 310                 315                 320

Gly Asn Gln Leu Arg Asp Leu Val Gln Lys Gly Lys Pro Lys Ser
                325                 330                 335


<210> SEQ ID NO 14
<211> LENGTH: 328
<212> TYPE: PRT
<213> ORGANISM: Pyrobaculum aerophilum

<400> SEQUENCE: 14

Met Ala Lys Ile Tyr Thr Asp Arg Glu Ala Ser Leu Glu Pro Leu Lys
1               5                   10                  15

Gly Lys Thr Ile Ala Val Ile Gly Tyr Gly Ile Gln Gly Arg Ala Gln
            20                  25                  30

Ala Leu Asn Leu Arg Asp Ser Gly Leu Glu Val Ile Ile Gly Leu Arg
        35                  40                  45

Arg Gly Gly Lys Ser Trp Glu Leu Ala Thr Ser Glu Gly Phe Arg Val
    50                  55                  60

Tyr Glu Ile Gly Glu Ala Val Arg Lys Ala Asp Val Ile Leu Val Leu
65                  70                  75                  80

Ile Pro Asp Met Glu Gln Pro Lys Val Trp Gln Glu Gln Ile Ala Pro
                85                  90                  95

Asn Leu Lys Glu Gly Val Val Val Asp Phe Ala His Gly Phe Asn Val
            100                 105                 110

His Phe Gly Leu Ile Lys Pro Pro Lys Asn Ile Asp Val Ile Met Val
        115                 120                 125

Ala Pro Lys Ala Pro Gly Lys Ala Val Arg Glu Glu Tyr Leu Ala Gly
    130                 135                 140

Arg Gly Val Pro Ala Leu Val Ala Val Tyr Gln Asp Tyr Ser Gly Ser
145                 150                 155                 160

Ala Leu Lys Tyr Ala Leu Ala Leu Ala Lys Gly Ile Gly Ala Thr Arg
                165                 170                 175

Ala Gly Val Ile Glu Thr Thr Phe Ala Glu Glu Thr Glu Thr Asp Leu
            180                 185                 190

Ile Gly Glu Gln Ile Val Leu Val Gly Gly Leu Met Glu Leu Ile Lys
        195                 200                 205

Lys Gly Phe Glu Val Leu Val Glu Met Gly Tyr Gln Pro Glu Val Ala
    210                 215                 220

Tyr Phe Glu Val Leu Asn Glu Ala Lys Leu Ile Met Asp Leu Ile Trp
```

```
225                 230                 235                 240

Gln Arg Gly Ile Tyr Gly Met Leu Asn Gly Val Ser Asp Thr Ala Lys
                245                 250                 255

Tyr Gly Gly Leu Thr Val Gly Pro Arg Val Ile Asp Glu Asn Val Lys
            260                 265                 270

Arg Lys Met Lys Glu Ala Ala Met Arg Val Lys Ser Gly Glu Phe Ala
        275                 280                 285

Lys Glu Trp Val Glu Glu Tyr Asn Arg Gly Ala Pro Thr Leu Arg Lys
    290                 295                 300

Leu Met Glu Glu Ala Arg Thr His Pro Ile Glu Lys Val Gly Glu Glu
305                 310                 315                 320

Met Arg Lys Leu Leu Phe Gly Pro
                325


<210> SEQ ID NO 15
<211> LENGTH: 338
<212> TYPE: PRT
<213> ORGANISM: Ralstonia solanacearum

<400> SEQUENCE: 15

Met Lys Val Phe Tyr Asp Lys Asp Ala Asp Leu Ser Leu Ile Lys Gly
1               5                   10                  15

Lys Asn Val Thr Ile Ile Gly Tyr Gly Ser Gln Gly His Ala His Ala
            20                  25                  30

Leu Asn Leu Asn Asp Ser Gly Val Lys Val Thr Val Gly Leu Arg Lys
        35                  40                  45

Asn Gly Ala Ser Trp Asn Lys Ala Val Asn Ala Gly Leu Gln Val Lys
    50                  55                  60

Glu Val Ala Glu Ala Val Lys Asp Ala Asp Val Val Met Ile Leu Leu
65                  70                  75                  80

Pro Asp Glu Gln Ile Ala Asp Val Tyr Lys Asn Glu Val His Gly Asn
                85                  90                  95

Ile Lys Gln Gly Ala Ala Leu Ala Phe Ala His Gly Phe Asn Val His
            100                 105                 110

Tyr Gly Ala Val Ile Pro Arg Ala Asp Leu Asp Val Ile Met Val Ala
        115                 120                 125

Pro Lys Ala Pro Gly His Thr Val Arg Gly Thr Tyr Ala Gln Gly Gly
    130                 135                 140

Gly Val Pro His Leu Ile Ala Val His Gln Asp Lys Ser Gly Ser Ala
145                 150                 155                 160

Arg Asp Ile Ala Leu Ser Tyr Ala Thr Ala Asn Gly Gly Gly Arg Ala
                165                 170                 175

Gly Ile Ile Glu Thr Asn Phe Arg Glu Glu Thr Glu Thr Asp Leu Phe
            180                 185                 190

Gly Glu Gln Ala Val Leu Cys Gly Gly Thr Val Glu Leu Ile Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Ile Tyr Glu
225                 230                 235                 240

Gly Gly Ile Gly Asn Met Asn Tyr Ser Ile Ser Asn Asn Ala Glu Tyr
                245                 250                 255

Gly Glu Tyr Val Thr Gly Pro Arg Val Val Thr Ala Glu Thr Lys Gln
            260                 265                 270
```

```
Ala Met Lys Gln Cys Leu His Asp Ile Gln Thr Gly Glu Tyr Ala Lys
        275                 280                 285

Ser Phe Leu Leu Glu Asn Lys Ala Gly Ala Pro Thr Leu Ile Ser Arg
    290                 295                 300

Arg Arg Leu Thr Ala Asp His Gln Ile Glu Gln Val Gly Ala Lys Leu
305                 310                 315                 320

Arg Ala Met Met Pro Trp Ile Ala Lys Asn Lys Leu Val Asp Gln Ser
                325                 330                 335

Lys Asn


<210> SEQ ID NO 16
<211> LENGTH: 338
<212> TYPE: PRT
<213> ORGANISM: Pseudomonas aeruginosa

<400> SEQUENCE: 16

Met Arg Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala His Ala
            20                  25                  30

Cys Asn Leu Lys Asp Ser Gly Val Asp Val Thr Val Gly Leu Arg Ser
        35                  40                  45

Gly Ser Ala Thr Val Ala Lys Ala Glu Ala His Gly Leu Lys Val Ala
    50                  55                  60

Asp Val Lys Thr Ala Val Ala Ala Ala Asp Val Val Met Ile Leu Thr
65                  70                  75                  80

Pro Asp Glu Phe Gln Gly Arg Leu Tyr Lys Glu Glu Ile Glu Pro Asn
                85                  90                  95

Leu Lys Lys Gly Ala Thr Leu Ala Phe Ala His Gly Phe Ser Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Cys Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Cys Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Ala
            260                 265                 270

Ala Met Arg Asn Ala Leu Lys Arg Ile Gln Asp Gly Glu Tyr Ala Lys
        275                 280                 285

Met Phe Ile Thr Glu Gly Ala Ala Asn Tyr Pro Ser Met Thr Ala Tyr
    290                 295                 300
```

```
Arg Arg Asn Asn Ala Ala His Pro Ile Glu Gln Ile Gly Glu Lys Leu
305                 310                 315                 320

Arg Ala Met Met Pro Trp Ile Ala Ala Asn Lys Ile Val Asp Lys Ser
                325                 330                 335

Lys Asn


<210> SEQ ID NO 17
<211> LENGTH: 338
<212> TYPE: PRT
<213> ORGANISM: Pseudomonas fluorescens

<400> SEQUENCE: 17

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Arg Lys
        35                  40                  45

Gly Ser Ala Thr Val Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335
```

Lys Asn

<210> SEQ ID NO 18
<211> LENGTH: 338
<212> TYPE: PRT
<213> ORGANISM: Spinacia oleracea

<400> SEQUENCE: 18

```
Met Arg Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala His Ala
            20                  25                  30

Cys Asn Leu Lys Asp Ser Gly Val Asp Val Thr Val Gly Leu Arg Ser
        35                  40                  45

Gly Ser Ala Thr Val Ala Lys Ala Glu Ala His Gly Leu Lys Val Ala
    50                  55                  60

Asp Val Lys Thr Ala Val Ala Ala Ala Asp Val Val Met Ile Leu Thr
65                  70                  75                  80

Pro Asp Glu Phe Gln Gly Arg Leu Tyr Lys Glu Glu Ile Glu Pro Asn
                85                  90                  95

Leu Lys Lys Gly Ala Thr Leu Ala Phe Ala His Gly Phe Ser Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Cys Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Cys Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Ala
            260                 265                 270

Ala Met Arg Asn Ala Leu Lys Arg Ile Gln Asp Gly Glu Tyr Ala Lys
        275                 280                 285

Met Phe Ile Thr Glu Gly Ala Ala Asn Tyr Pro Ser Met Thr Ala Tyr
    290                 295                 300

Arg Arg Asn Asn Ala Ala His Pro Ile Glu Gln Ile Gly Glu Lys Leu
305                 310                 315                 320

Arg Ala Met Met Pro Trp Ile Ala Ala Asn Lys Ile Val Asp Lys Ser
                325                 330                 335

Lys Asn
```

<210> SEQ ID NO 19
<211> LENGTH: 338
<212> TYPE: PRT

```
<213> ORGANISM: Pseudomonas fluorescens

<400> SEQUENCE: 19

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Cys Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Ala Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 20
<211> LENGTH: 24
<212> TYPE: DNA
<213> ORGANISM: artificial sequence
<220> FEATURE:
<223> OTHER INFORMATION: primer pBAD 266

<400> SEQUENCE: 20
```

ctctctactg tttctccata cccg 24

<210> SEQ ID NO 21
<211> LENGTH: 27
<212> TYPE: DNA
<213> ORGANISM: artificial sequence
<220> FEATURE:
<223> OTHER INFORMATION: primer PF5- 53Mt
<220> FEATURE:
<221> NAME/KEY: misc_feature
<222> LOCATION: (26)..(27)
<223> OTHER INFORMATION: n is a, c, g, or t

<400> SEQUENCE: 21
caagccgtgg gcttcagcct tggcknn 27

<210> SEQ ID NO 22
<211> LENGTH: 23
<212> TYPE: DNA
<213> ORGANISM: artificial sequence
<220> FEATURE:
<223> OTHER INFORMATION: primer pBAD 866

<400> SEQUENCE: 22
cggtttcagt ctcgtccttg aag 23

<210> SEQ ID NO 23
<211> LENGTH: 0
<212> TYPE: PRT
<213> ORGANISM: artificial sequence
<220> FEATURE:
<223> OTHER INFORMATION: Blank sequence

<400> SEQUENCE: 23

000

<210> SEQ ID NO 24
<211> LENGTH: 338
<212> TYPE: PRT
<213> ORGANISM: artificial sequence
<220> FEATURE:
<223> OTHER INFORMATION: synthetic construct mutant ilcV

<400> SEQUENCE: 24

```
Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Cys Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140
```

```
Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 25
<211> LENGTH: 338
<212> TYPE: PRT
<213> ORGANISM: artificial sequence
<220> FEATURE:
<223> OTHER INFORMATION: synthetic construct mutant ilcV

<400> SEQUENCE: 25

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
```

```
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 26
<211> LENGTH: 338
<212> TYPE: PRT
<213> ORGANISM: artificial sequence
<220> FEATURE:
<223> OTHER INFORMATION: synthetic construct mutant ilcV

<400> SEQUENCE: 26

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190
```

```
Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 27
<211> LENGTH: 338
<212> TYPE: PRT
<213> ORGANISM: Artificial sequence
<220> FEATURE:
<223> OTHER INFORMATION: synthetic construct mutant ilcV

<400> SEQUENCE: 27

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Ala Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205
```

```
Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 28
<211> LENGTH: 338
<212> TYPE: PRT
<213> ORGANISM: Artificial sequence
<220> FEATURE:
<223> OTHER INFORMATION: synthetic construct mutant ilcV

<400> SEQUENCE: 28

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Ala Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
```

```
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 29
<211> LENGTH: 338
<212> TYPE: PRT
<213> ORGANISM: Artificial sequence
<220> FEATURE:
<223> OTHER INFORMATION: synthetic construct
<220> FEATURE:
<221> NAME/KEY: MISC_FEATURE
<222> LOCATION: (24)..(24)
<223> OTHER INFORMATION: Xaa = Tyr or Phe
<220> FEATURE:
<221> NAME/KEY: MISC_FEATURE
<222> LOCATION: (33)..(33)
<223> OTHER INFORMATION: Xaa = Cys or Leu
<220> FEATURE:
<221> NAME/KEY: MISC_FEATURE
<222> LOCATION: (47)..(47)
<223> OTHER INFORMATION: Xaa = Arg or Tyr
<220> FEATURE:
<221> NAME/KEY: MISC_FEATURE
<222> LOCATION: (50)..(50)
<223> OTHER INFORMATION: Xaa = Ser or Ala
<220> FEATURE:
<221> NAME/KEY: MISC_FEATURE
<222> LOCATION: (52)..(52)
<223> OTHER INFORMATION: Xaa = Thr or Asp
<220> FEATURE:
<221> NAME/KEY: MISC_FEATURE
<222> LOCATION: (53)..(53)
<223> OTHER INFORMATION: Xaa = Val or Ala
<220> FEATURE:
<221> NAME/KEY: MISC_FEATURE
<222> LOCATION: (61)..(61)
<223> OTHER INFORMATION: Xaa = Leu or Phe
<220> FEATURE:
<221> NAME/KEY: MISC_FEATURE
<222> LOCATION: (80)..(80)
<223> OTHER INFORMATION: Xaa = Thr or Iso
<220> FEATURE:
<221> NAME/KEY: MISC_FEATURE
<222> LOCATION: (156)..(156)
<223> OTHER INFORMATION: Xaa = Ala or Val
<220> FEATURE:
<221> NAME/KEY: MISC_FEATURE
<222> LOCATION: (170)..(170)
<223> OTHER INFORMATION: Xaa = Gly or Ala

<400> SEQUENCE: 29

Met Lys Val Phe Tyr Asp Lys Asp Cys Asp Leu Ser Ile Ile Gln Gly
1               5                   10                  15

Lys Lys Val Ala Ile Ile Gly Xaa Gly Ser Gln Gly His Ala Gln Ala
            20                  25                  30

Xaa Asn Leu Lys Asp Ser Gly Val Asp Val Thr Val Gly Leu Xaa Lys
```

```
        35                  40                  45

Gly Xaa Ala Xaa Xaa Ala Lys Ala Glu Ala His Gly Xaa Lys Val Thr
    50                  55                  60

Asp Val Ala Ala Ala Val Ala Gly Ala Asp Leu Val Met Ile Leu Xaa
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Xaa Ser Gly Asn Ala
145                 150                 155                 160

Lys Asn Val Ala Leu Ser Tyr Ala Ala Xaa Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 30
<211> LENGTH: 331
<212> TYPE: PRT
<213> ORGANISM: Natronomonas pharaanis

<400> SEQUENCE: 30

Met Thr Asp Ala Thr Ile Tyr Tyr Asp Asp Asp Ala Glu Ser Thr Val
1               5                   10                  15

Leu Asp Asp Lys Thr Val Ala Val Leu Gly Tyr Gly Ser Gln Gly His
            20                  25                  30

Ala His Ala Gln Asn Leu Asp Asp Ser Gly Val Asp Val Val Val Gly
        35                  40                  45

Leu Arg Glu Asp Ser Ser Ser Arg Ser Ala Ala Glu Ala Asp Gly Leu
    50                  55                  60

Asp Val Ala Thr Pro Arg Gly Ala Ala Glu Gln Ala Asp Leu Val Ser
```

```
65                  70                  75                  80

Val Leu Val Pro Asp Thr Val Gln Pro Ala Val Tyr Glu Gln Ile Glu
                85                  90                  95

Asp Val Leu Gln Pro Gly Asp Thr Leu Gln Phe Ala His Gly Phe Asn
            100                 105                 110

Ile His Tyr Gly Gln Ile Glu Pro Ser Glu Asp Val Asn Val Thr Met
        115                 120                 125

Val Ala Pro Lys Ser Pro Gly His Leu Val Arg Arg Asn Tyr Glu Asn
    130                 135                 140

Asp Glu Gly Thr Pro Gly Leu Leu Ala Val Tyr Gln Asp Pro Ser Gly
145                 150                 155                 160

Glu Ala His Asp Leu Gly Leu Ala Tyr Ala Lys Ala Ile Gly Cys Thr
                165                 170                 175

Arg Ala Gly Val Val Glu Thr Thr Phe Arg Glu Glu Thr Glu Thr Asp
            180                 185                 190

Leu Phe Gly Glu Gln Ala Val Leu Cys Gly Gly Val Thr Ser Leu Val
        195                 200                 205

Lys Thr Gly Tyr Glu Thr Leu Val Asp Ala Gly Tyr Ser Pro Glu Met
    210                 215                 220

Ala Tyr Phe Glu Cys Leu Asn Glu Leu Lys Leu Ile Val Asp Leu Met
225                 230                 235                 240

Tyr Glu Gly Gly Asn Ser Glu Met Trp Asp Ser Val Ser Asp Thr Ala
                245                 250                 255

Glu Tyr Gly Gly Leu Thr Arg Gly Asp Arg Ile Val Asp Asp His Ala
            260                 265                 270

Arg Glu Lys Met Glu Glu Val Leu Glu Glu Val Gln Asn Gly Thr Phe
        275                 280                 285

Ala Arg Glu Trp Ile Ser Glu Asn Gln Ala Gly Arg Pro Ser Tyr Lys
    290                 295                 300

Gln Leu Arg Ala Ala Glu Lys Asn His Asp Ile Glu Ala Val Gly Glu
305                 310                 315                 320

Asp Leu Arg Ala Leu Phe Ala Trp Gly Asp Asp
                325                 330


<210> SEQ ID NO 31
<211> LENGTH: 342
<212> TYPE: PRT
<213> ORGANISM: Bacillus subtilis

<400> SEQUENCE: 31

Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
            20                  25                  30

Ala Leu Asn Leu Lys Glu Ser Gly Val Asp Val Ile Val Gly Val Arg
        35                  40                  45

Gln Gly Lys Ser Phe Thr Gln Ala Gln Glu Asp Gly His Lys Val Phe
    50                  55                  60

Ser Val Lys Glu Ala Ala Ala Gln Ala Glu Ile Ile Met Val Leu Leu
65                  70                  75                  80

Pro Asp Glu Gln Gln Gln Lys Val Tyr Glu Ala Glu Ile Lys Asp Glu
                85                  90                  95

Leu Thr Ala Gly Lys Ser Leu Val Phe Ala His Gly Phe Asn Val His
            100                 105                 110
```

```
Phe His Gln Ile Val Pro Pro Ala Asp Val Asp Val Phe Leu Val Ala
        115                 120                 125

Pro Lys Gly Pro Gly His Leu Val Arg Arg Thr Tyr Glu Gln Gly Ala
    130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
                165                 170                 175

Gly Val Leu Glu Thr Thr Phe Lys Glu Glu Thr Glu Thr Asp Leu Phe
            180                 185                 190

Gly Glu Gln Ala Val Leu Cys Gly Gly Leu Ser Ala Leu Val Lys Ala
        195                 200                 205

Gly Phe Glu Thr Leu Thr Glu Ala Gly Tyr Gln Pro Glu Leu Ala Tyr
    210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
        275                 280                 285

Glu Trp Ile Val Glu Asn Gln Val Asn Arg Pro Arg Phe Asn Ala Ile
    290                 295                 300

Asn Ala Ser Glu Asn Glu His Gln Ile Glu Val Val Gly Arg Lys Leu
305                 310                 315                 320

Arg Glu Met Met Pro Phe Val Lys Gln Gly Lys Lys Lys Glu Ala Val
                325                 330                 335

Val Ser Val Ala Gln Asn
            340


<210> SEQ ID NO 32
<211> LENGTH: 338
<212> TYPE: PRT
<213> ORGANISM: Corynebacterium glutamicun

<400> SEQUENCE: 32

Met Ala Ile Glu Leu Leu Tyr Asp Ala Asp Ala Asp Leu Ser Leu Ile
1               5                   10                  15

Gln Gly Arg Lys Val Ala Ile Val Gly Tyr Gly Ser Gln Gly His Ala
            20                  25                  30

His Ser Gln Asn Leu Arg Asp Ser Gly Val Glu Val Val Ile Gly Leu
        35                  40                  45

Arg Glu Gly Ser Lys Ser Ala Glu Lys Ala Lys Glu Ala Gly Phe Glu
    50                  55                  60

Val Lys Thr Thr Ala Glu Ala Ala Ala Trp Ala Asp Val Ile Met Leu
65                  70                  75                  80

Leu Ala Pro Asp Thr Ser Gln Ala Glu Ile Phe Thr Asn Asp Ile Glu
                85                  90                  95

Pro Asn Leu Asn Ala Gly Asp Ala Leu Leu Phe Gly His Gly Leu Asn
            100                 105                 110

Ile His Phe Asp Leu Ile Lys Pro Ala Asp Asp Ile Ile Val Gly Met
        115                 120                 125

Val Ala Pro Lys Gly Pro Gly His Leu Val Arg Arg Gln Phe Val Asp
    130                 135                 140
```

Gly Lys Gly Val Pro Cys Leu Ile Ala Val Asp Gln Asp Pro Thr Gly
145 150 155 160

Thr Ala Gln Ala Leu Thr Leu Ser Tyr Ala Ala Ala Ile Gly Gly Ala
165 170 175

Arg Ala Gly Val Ile Pro Thr Thr Phe Glu Ala Glu Thr Val Thr Asp
180 185 190

Leu Phe Gly Glu Gln Ala Val Leu Cys Gly Gly Thr Glu Glu Leu Val
195 200 205

Lys Val Gly Phe Glu Val Leu Thr Glu Ala Gly Tyr Glu Pro Glu Met
210 215 220

Ala Tyr Phe Glu Val Leu His Glu Leu Lys Leu Ile Val Asp Leu Met
225 230 235 240

Phe Glu Gly Gly Ile Ser Asn Met Asn Tyr Ser Val Ser Asp Thr Ala
245 250 255

Glu Phe Gly Gly Tyr Leu Ser Gly Pro Arg Val Ile Asp Ala Asp Thr
260 265 270

Lys Ser Arg Met Lys Asp Ile Leu Thr Asp Ile Gln Asp Gly Thr Phe
275 280 285

Thr Lys Arg Leu Ile Ala Asn Val Glu Asn Gly Asn Thr Glu Leu Glu
290 295 300

Gly Leu Arg Ala Ser Tyr Asn Asn His Pro Ile Glu Glu Thr Gly Ala
305 310 315 320

Lys Leu Arg Asp Leu Met Ser Trp Val Lys Val Asp Ala Arg Ala Glu
325 330 335

Thr Ala

<210> SEQ ID NO 33
<211> LENGTH: 339
<212> TYPE: PRT
<213> ORGANISM: Phaeospririlum molischianum
<220> FEATURE:
<221> NAME/KEY: misc_feature
<222> LOCATION: (310)..(310)
<223> OTHER INFORMATION: Xaa can be any naturally occurring amino acid

<400> SEQUENCE: 33

Met Arg Val Tyr Tyr Asp Arg Asp Ala Asp Val Asn Leu Ile Lys Ser
1 5 10 15

Lys Lys Val Ala Val Ile Gly Tyr Gly Ser Gln Gly His Ala His Val
20 25 30

Leu Asn Leu Arg Asp Ser Gly Val Lys Asp Val Ala Val Ala Leu Arg
35 40 45

Pro Gly Ser Ala Ser Ile Lys Lys Ala Glu Ala Glu Gly Leu Lys Val
50 55 60

Leu Thr Pro Ala Glu Ala Ala Ala Trp Ala Asp Val Val Met Ile Leu
65 70 75 80

Thr Pro Asp Glu Leu Gln Ala Asp Leu Tyr Lys Ser Glu Leu Ala Ala
85 90 95

Asn Leu Lys Pro Gly Ala Ala Leu Val Phe Ala His Gly Leu Ala Ile
100 105 110

His Phe Lys Leu Ile Glu Ala Arg Ala Asp Leu Asp Val Phe Met Val
115 120 125

Ala Pro Lys Gly Pro Gly His Thr Val Arg Gly Glu Tyr Leu Lys Gly
130 135 140

Gly Gly Val Pro Cys Leu Val Ala Val Ala Gln Asn Pro Thr Gly Asn

```
145                 150                 155                 160

Ala Leu Glu Leu Ala Leu Ser Tyr Ala Ser Ala Ile Gly Gly Gly Arg
                165                 170                 175

Ser Gly Ile Ile Glu Thr Thr Phe Arg Glu Glu Cys Glu Thr Asp Leu
            180                 185                 190

Phe Gly Glu Gln Val Val Leu Cys Gly Gly Leu Ser Lys Leu Ile Gln
        195                 200                 205

Tyr Gly Phe Glu Thr Leu Val Glu Ala Gly Tyr Ala Pro Glu Met Ala
    210                 215                 220

Tyr Phe Glu Cys Leu His Glu Val Lys Leu Ile Val Asp Leu Ile Tyr
225                 230                 235                 240

Glu Gly Gly Ile Ala Asn Met Arg Tyr Ser Ile Ser Asn Thr Ala Glu
                245                 250                 255

Tyr Gly Asp Tyr Val Thr Gly Ser Arg Ile Ile Thr Glu Ala Thr Lys
            260                 265                 270

Ala Glu Met Lys Arg Val Leu Ala Asp Ile Gln Ser Gly Arg Phe Val
        275                 280                 285

Arg Asp Trp Met Leu Glu Cys Lys Ala Gly Gln Pro Ser Phe Lys Ala
    290                 295                 300

Thr Arg Arg Ile Gln Xaa Glu His Val Ile Glu Val Val Gly Glu Lys
305                 310                 315                 320

Leu Arg Gly Met Met Pro Trp Ile Ser Lys Asn Lys Leu Val Asp Lys
                325                 330                 335

Ala Arg Asn


<210> SEQ ID NO 34
<211> LENGTH: 339
<212> TYPE: PRT
<213> ORGANISM: Zymomonas mobilis

<400> SEQUENCE: 34

Met Lys Val Tyr Tyr Asp Ser Asp Ala Asp Leu Gly Leu Ile Lys Ser
1               5                   10                  15

Lys Lys Ile Ala Ile Leu Gly Tyr Gly Ser Gln Gly His Ala His Ala
            20                  25                  30

Gln Asn Leu Arg Asp Ser Gly Val Ala Glu Val Ala Ile Ala Leu Arg
        35                  40                  45

Pro Asp Ser Ala Ser Val Lys Lys Ala Gln Asp Ala Gly Phe Lys Val
    50                  55                  60

Leu Thr Asn Ala Glu Ala Ala Lys Trp Ala Asp Ile Leu Met Ile Leu
65                  70                  75                  80

Ala Pro Asp Glu His Gln Ala Ala Ile Tyr Ala Glu Asp Leu Lys Asp
                85                  90                  95

Asn Leu Arg Pro Gly Ser Ala Ile Ala Phe Ala His Gly Leu Asn Ile
            100                 105                 110

His Phe Gly Leu Ile Glu Pro Arg Lys Asp Ile Asp Val Phe Met Ile
        115                 120                 125

Ala Pro Lys Gly Pro Gly His Thr Val Arg Ser Glu Tyr Val Arg Gly
    130                 135                 140

Gly Gly Val Pro Cys Leu Val Ala Val Asp Gln Asp Ala Ser Gly Asn
145                 150                 155                 160

Ala His Asp Ile Ala Leu Ala Tyr Ala Ser Gly Ile Gly Gly Gly Arg
                165                 170                 175

Ser Gly Val Ile Glu Thr Thr Phe Arg Glu Glu Val Glu Thr Asp Leu
```

```
            180                 185                 190

Phe Gly Glu Gln Ala Val Leu Cys Gly Gly Leu Thr Ala Leu Ile Thr
        195                 200                 205

Ala Gly Phe Glu Thr Leu Thr Glu Ala Gly Tyr Ala Pro Glu Met Ala
    210                 215                 220

Phe Phe Glu Cys Met His Glu Met Lys Leu Ile Val Asp Leu Ile Tyr
225                 230                 235                 240

Glu Ala Gly Ile Ala Asn Met Arg Tyr Ser Ile Ser Asn Thr Ala Glu
                245                 250                 255

Tyr Gly Asp Ile Val Ser Gly Pro Arg Val Ile Asn Glu Glu Ser Lys
            260                 265                 270

Lys Ala Met Lys Ala Ile Leu Asp Asp Ile Gln Ser Gly Arg Phe Val
        275                 280                 285

Ser Lys Phe Val Leu Asp Asn Arg Ala Gly Gln Pro Glu Leu Lys Ala
    290                 295                 300

Ala Arg Lys Arg Met Ala Ala His Pro Ile Glu Gln Val Gly Ala Arg
305                 310                 315                 320

Leu Arg Lys Met Met Pro Trp Ile Ala Ser Asn Lys Leu Val Asp Lys
                325                 330                 335

Ala Arg Asn


<210> SEQ ID NO 35
<211> LENGTH: 338
<212> TYPE: PRT
<213> ORGANISM: Alkalilimnicola ehrlichei

<400> SEQUENCE: 35

Met Gln Val Tyr Tyr Asp Lys Asp Ala Asp Leu Ser Ile Ile Gln Gly
1               5                   10                  15

Lys Lys Val Ala Val Ile Gly Tyr Gly Ser Gln Gly His Ala His Ala
            20                  25                  30

Asn Asn Leu Lys Glu Ser Gly Val Asp Val Val Val Gly Leu Arg Glu
        35                  40                  45

Gly Ser Ser Ser Ala Ala Lys Ala Gln Lys Ala Gly Leu Ala Val Ala
    50                  55                  60

Ser Ile Glu Asp Ala Ala Ala Gln Ala Asp Val Val Met Ile Leu Ala
65                  70                  75                  80

Pro Asp Glu His Gln Ala Val Ile Tyr His Asn Gln Ile Ala Pro Asn
                85                  90                  95

Val Lys Pro Gly Ala Ala Ile Ala Phe Ala His Gly Phe Asn Ile His
            100                 105                 110

Phe Gly Gln Ile Gln Pro Ala Ala Asp Leu Asp Val Ile Met Val Ala
        115                 120                 125

Pro Lys Gly Pro Gly His Leu Val Arg Ser Thr Tyr Val Glu Gly Gly
    130                 135                 140

Gly Val Pro Ser Leu Ile Ala Ile His Gln Asp Ala Thr Gly Lys Ala
145                 150                 155                 160

Lys Asp Ile Ala Leu Ser Tyr Ala Ser Ala Asn Gly Gly Gly Arg Ala
                165                 170                 175

Gly Val Ile Glu Thr Ser Phe Arg Glu Glu Thr Glu Thr Asp Leu Phe
            180                 185                 190

Gly Glu Gln Ala Val Leu Cys Gly Gly Ile Thr Ser Leu Ile Gln Ala
        195                 200                 205

Gly Phe Glu Thr Leu Val Glu Ala Gly Tyr Ala Pro Glu Met Ala Tyr
```

```
    210                 215                 220

Phe Glu Cys Leu His Glu Thr Lys Leu Ile Val Asp Leu Leu Tyr Gln
225                 230                 235                 240

Gly Gly Ile Ala Asn Met Arg Tyr Ser Ile Ser Asn Thr Ala Glu Tyr
                245                 250                 255

Gly Asp Phe Thr Arg Gly Pro Arg Val Ile Asn Glu Glu Ser Arg Glu
            260                 265                 270

Ala Met Arg Glu Ile Leu Ala Glu Ile Gln Glu Gly Glu Phe Ala Arg
        275                 280                 285

Glu Phe Val Leu Glu Asn Gln Ala Gly Cys Pro Thr Leu Thr Ala Arg
    290                 295                 300

Arg Arg Leu Ala Ala Glu His Glu Ile Glu Val Val Gly Glu Arg Leu
305                 310                 315                 320

Arg Gly Met Met Pro Trp Ile Asn Ala Asn Lys Leu Val Asp Lys Asp
                325                 330                 335

Lys Asn


<210> SEQ ID NO 36
<211> LENGTH: 340
<212> TYPE: PRT
<213> ORGANISM: Campylobacter lari

<400> SEQUENCE: 36

Met Ala Val Ser Ile Tyr Tyr Asp Lys Asp Cys Asp Ile Asn Leu Ile
1               5                   10                  15

Lys Ser Lys Lys Val Ala Ile Ile Gly Phe Gly Ser Gln Gly His Ala
            20                  25                  30

His Ala Met Asn Leu Arg Asp Ser Gly Val Glu Val Ile Ile Gly Leu
        35                  40                  45

Lys Glu Gly Gly Gln Ser Trp Ala Lys Ala Gln Lys Ala Asn Phe Ile
    50                  55                  60

Val Lys Ser Val Lys Glu Ala Thr Lys Glu Ala Asp Leu Ile Met Ile
65                  70                  75                  80

Leu Ala Pro Asp Glu Ile Gln Ser Glu Ile Phe Asn Glu Glu Ile Lys
                85                  90                  95

Pro Glu Leu Lys Ala Gly Lys Thr Leu Ala Phe Ala His Gly Phe Asn
            100                 105                 110

Ile His Tyr Gly Gln Ile Val Ala Pro Lys Gly Ile Asp Val Ile Met
        115                 120                 125

Ile Ala Pro Lys Ala Pro Gly His Thr Val Arg His Glu Phe Ser Ile
    130                 135                 140

Gly Gly Gly Thr Pro Cys Leu Ile Ala Ile His Gln Asp Glu Ser Lys
145                 150                 155                 160

Asn Ala Lys Asn Leu Ala Leu Ser Tyr Ala Ser Ala Ile Gly Gly Gly
                165                 170                 175

Arg Thr Gly Ile Ile Glu Thr Thr Phe Lys Ala Glu Thr Glu Thr Asp
            180                 185                 190

Leu Phe Gly Glu Gln Ala Val Leu Cys Gly Gly Leu Ser Ala Leu Ile
        195                 200                 205

Gln Ala Gly Phe Glu Thr Leu Val Glu Ala Gly Tyr Glu Pro Glu Met
    210                 215                 220

Ala Tyr Phe Glu Cys Leu His Glu Met Lys Leu Ile Val Asp Leu Ile
225                 230                 235                 240

Tyr Gln Gly Gly Ile Ala Asp Met Arg Tyr Ser Val Ser Asn Thr Ala
```

```
            245                 250                 255

Glu Tyr Gly Asp Tyr Ile Thr Gly Pro Lys Ile Ile Thr Lys Glu Thr
            260                 265                 270

Lys Glu Ala Met Lys Gly Val Leu Lys Asp Ile Gln Asn Gly Ser Phe
        275                 280                 285

Ala Lys Asp Phe Ile Leu Glu Arg Arg Ala Asn Phe Ala Arg Met His
    290                 295                 300

Ala Glu Arg Lys Leu Met Asn Asp Ser Leu Ile Glu Lys Thr Gly Arg
305                 310                 315                 320

Glu Leu Arg Ala Met Met Pro Trp Ile Ser Ala Lys Lys Leu Val Asp
                325                 330                 335

Lys Asp Lys Asn
            340


<210> SEQ ID NO 37
<211> LENGTH: 338
<212> TYPE: PRT
<213> ORGANISM: Marinobacter aquaeolei

<400> SEQUENCE: 37

Met Gln Val Tyr Tyr Asp Lys Asp Cys Asp Leu Ser Ile Ile Gln Gly
1               5                   10                  15

Lys Lys Val Ala Ile Leu Gly Phe Gly Ser Gln Gly His Ala His Ala
            20                  25                  30

Cys Asn Leu Lys Asp Ser Gly Val Asp Val Val Val Gly Leu Arg Ala
        35                  40                  45

Gly Ser Ser Ser Ile Ala Lys Ala Glu Ala Tyr Gly Leu Lys Thr Ser
    50                  55                  60

Asp Val Ala Ser Ala Val Ala Ser Ala Asp Val Val Met Val Leu Thr
65                  70                  75                  80

Pro Asp Glu Phe Gln Ala Gln Leu Tyr Arg Glu Glu Ile Glu Pro Asn
                85                  90                  95

Leu Lys Gln Gly Ala Thr Leu Ala Phe Ala His Gly Phe Ala Ile His
            100                 105                 110

Tyr Asn Gln Ile Val Pro Arg Lys Asp Leu Asp Val Ile Met Val Ala
        115                 120                 125

Pro Lys Ala Pro Gly His Thr Val Arg Thr Glu Phe Thr Lys Gly Gly
    130                 135                 140

Gly Ile Pro Asp Leu Ile Ala Ile Phe Gln Asp Ala Ser Gly Asn Ala
145                 150                 155                 160

Lys Asn Val Ala Leu Ser Tyr Ala Ser Gly Ile Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Ala Val Glu Leu Val Lys Ala
        195                 200                 205

Gly Phe Glu Thr Leu Thr Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Glu Gln Ser Arg Glu
            260                 265                 270
```

```
Ala Met Arg Asn Ala Leu Lys Arg Ile Gln Ser Gly Glu Tyr Ala Lys
        275                 280                 285

Met Phe Ile Ser Glu Gly Ala Leu Asn Tyr Pro Ser Met Thr Ala Arg
    290                 295                 300

Arg Arg Gln Asn Ala Ala His Glu Ile Glu Thr Val Gly Glu Lys Leu
305                 310                 315                 320

Arg Ser Met Met Pro Trp Ile Ser Ala Asn Lys Ile Val Asp Lys Asp
                325                 330                 335

Lys Asn


<210> SEQ ID NO 38
<211> LENGTH: 338
<212> TYPE: PRT
<213> ORGANISM: Psychrobacter arcticus

<400> SEQUENCE: 38

Met Asn Val Tyr Tyr Asp Lys Asp Cys Asp Leu Ser Ile Val Gln Gly
1               5                   10                  15

Lys Lys Val Ala Ile Ile Gly Tyr Gly Ser Gln Gly His Ala His Ala
            20                  25                  30

Leu Asn Leu Gln Asp Ser Asn Val Asp Val Thr Val Gly Leu Arg Ala
        35                  40                  45

Asp Ser Gly Ser Trp Lys Lys Ala Glu Asn Ala Gly Leu Lys Val Ala
    50                  55                  60

Glu Val Glu Glu Ala Val Lys Ala Ala Asp Ile Ile Met Ile Leu Thr
65                  70                  75                  80

Pro Asp Glu Phe Gln Lys Glu Leu Tyr Asn Asp Val Ile Glu Pro Asn
                85                  90                  95

Ile Lys Gln Gly Ala Thr Leu Ala Phe Ala His Gly Phe Ala Ile His
            100                 105                 110

Tyr Asn Gln Val Ile Pro Arg Ser Asp Leu Asp Val Ile Met Val Ala
        115                 120                 125

Pro Lys Ala Pro Gly His Thr Val Arg Ser Glu Phe Ala Lys Gly Gly
    130                 135                 140

Gly Ile Pro Asp Leu Ile Ala Ile Tyr Gln Asp Ala Ser Gly Gln Ala
145                 150                 155                 160

Lys Gln Leu Ala Leu Ser Tyr Ala Ala Gly Val Gly Gly Gly Arg Ser
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Ala Val Glu Leu Val Lys Met
        195                 200                 205

Gly Phe Glu Thr Leu Thr Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asp Met Asn Tyr Ser Ile Ser Asn Asn Ala Glu Tyr
                245                 250                 255

Gly Glu Tyr Val Thr Gly Pro Glu Val Ile Asn Glu Gln Ser Arg Glu
            260                 265                 270

Ala Met Arg Asn Ala Leu Lys Arg Ile Gln Ser Gly Glu Tyr Ala Lys
        275                 280                 285

Met Phe Ile Ser Glu Gly Ala Thr Asn Tyr Pro Ser Met Thr Ala Arg
    290                 295                 300
```

```
Arg Arg Asn Asn Ala Glu His Gln Ile Glu Ile Thr Gly Ala Lys Leu
305                 310                 315                 320

Arg Gly Met Met Pro Trp Ile Gly Gly Asn Lys Ile Ile Asp Lys Asp
                325                 330                 335

Lys Asn


<210> SEQ ID NO 39
<211> LENGTH: 338
<212> TYPE: PRT
<213> ORGANISM: Hahella chejuensis

<400> SEQUENCE: 39

Met Gln Val Tyr Tyr Asp Lys Asp Cys Asp Leu Ser Ile Ile Gln Gly
1               5                   10                  15

Lys Lys Val Ala Ile Ile Gly Tyr Gly Ser Gln Gly His Ala His Ala
            20                  25                  30

Asn Asn Leu Lys Asp Ser Gly Val Asp Val Cys Val Gly Leu Arg Lys
        35                  40                  45

Gly Ser Gly Ser Trp Ala Lys Ala Glu Asn Ala Gly Leu Ala Val Lys
    50                  55                  60

Glu Val Ala Glu Ala Val Ala Gly Ala Asp Val Val Met Ile Leu Thr
65                  70                  75                  80

Pro Asp Glu Phe Gln Ala Gln Leu Tyr Lys Ser Glu Ile Glu Pro Asn
                85                  90                  95

Leu Lys Ser Gly Ala Thr Leu Ala Phe Ala His Gly Phe Ser Ile His
            100                 105                 110

Tyr Asn Gln Ile Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Phe Gln Asp Ala Ser Gly Ser Ala
145                 150                 155                 160

Lys Asp Leu Ala Leu Ser Tyr Ala Ser Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Ala Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Asp Gln Ser Arg Ala
            260                 265                 270

Ala Met Arg Asn Ala Leu Lys Arg Ile Gln Asp Gly Glu Tyr Ala Lys
        275                 280                 285

Met Phe Ile Ala Glu Gly Ala His Asn Tyr Pro Ser Met Thr Ala Tyr
    290                 295                 300

Arg Arg Asn Asn Ala Ala His Pro Ile Glu Gln Val Gly Glu Lys Leu
305                 310                 315                 320

Arg Ser Met Met Pro Trp Ile Ala Ser Asn Lys Ile Val Asp Lys Ser
                325                 330                 335
```

Lys Asn

<210> SEQ ID NO 40
<211> LENGTH: 338
<212> TYPE: PRT
<213> ORGANISM: Thiobacillus denitrificans

<400> SEQUENCE: 40

```
Met Lys Val Tyr Tyr Asp Lys Asp Ala Asp Leu Ser Leu Ile Lys Gln
1               5                   10                  15

Arg Lys Val Ala Ile Val Gly Tyr Gly Ser Gln Gly His Ala His Ala
            20                  25                  30

Asn Asn Leu Lys Asp Ser Gly Val Asp Val Thr Val Ala Leu Arg Pro
        35                  40                  45

Gly Ser Ala Ser Ala Lys Lys Ala Glu Asn Ala Gly Leu Thr Val Lys
    50                  55                  60

Ser Val Pro Glu Ala Val Ala Gly Ala Asp Leu Val Met Ile Leu Thr
65                  70                  75                  80

Pro Asp Glu Phe Gln Ser Arg Leu Tyr Arg Asp Glu Ile Glu Pro Asn
                85                  90                  95

Ile Lys Gln Gly Ala Thr Leu Ala Phe Ala His Gly Phe Ser Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Lys Ala
145                 150                 155                 160

Lys Glu Thr Ala Leu Ser Tyr Ala Ser Ala Ile Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Ala Val Glu Leu Val Lys Ala
        195                 200                 205

Gly Phe Asp Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Val Lys Val Ile Asn Glu Gln Ser Arg Ala
            260                 265                 270

Ala Met Lys Glu Cys Leu Ala Asn Ile Gln Asn Gly Ala Tyr Ala Lys
        275                 280                 285

Arg Phe Ile Leu Glu Gly Gln Ala Asn Tyr Pro Glu Met Thr Ala Trp
    290                 295                 300

Arg Arg Asn Asn Ala Ala His Gln Ile Glu Val Val Gly Ala Lys Leu
305                 310                 315                 320

Arg Ser Met Met Pro Trp Ile Ala Ala Asn Lys Leu Val Asp His Ser
                325                 330                 335

Lys Asn
```

<210> SEQ ID NO 41
<211> LENGTH: 338
<212> TYPE: PRT

<213> ORGANISM: Azotobacter vinelandii

<400> SEQUENCE: 41

Met Lys Val Tyr Tyr Asp Lys Asp Cys Asp Leu Ser Ile Ile Gln Ser
1 5 10 15

Lys Lys Val Ala Ile Ile Gly Tyr Gly Ser Gln Gly His Ala His Ala
20 25 30

Cys Asn Leu Lys Asp Ser Gly Val Asp Val Tyr Val Gly Leu Arg Ala
35 40 45

Gly Ser Ala Ser Val Ala Lys Ala Glu Ala His Gly Leu Thr Val Lys
50 55 60

Ser Val Lys Asp Ala Val Ala Ala Ala Asp Val Val Met Ile Leu Thr
65 70 75 80

Pro Asp Glu Phe Gln Gly Arg Leu Tyr Lys Asp Glu Ile Glu Pro Asn
85 90 95

Leu Lys Lys Gly Ala Thr Leu Ala Phe Ala His Gly Phe Ser Ile His
100 105 110

Tyr Asn Gln Val Val Pro Arg Ala Asp Leu Asp Val Ile Met Ile Ala
115 120 125

Pro Lys Ala Pro Gly His Thr Val Arg Ser Glu Phe Val Arg Gly Gly
130 135 140

Gly Ile Pro Asp Leu Ile Ala Val Tyr Gln Asp Ala Ser Gly Asn Ala
145 150 155 160

Lys Asn Leu Ala Leu Ser Tyr Ala Cys Gly Val Gly Gly Gly Arg Thr
165 170 175

Gly Ile Ile Glu Thr Thr Phe Lys Asp Glu Thr Glu Thr Asp Leu Phe
180 185 190

Gly Glu Gln Ala Val Leu Cys Gly Gly Cys Val Glu Leu Val Lys Ala
195 200 205

Gly Phe Glu Thr Leu Val Glu Ala Gly Tyr Ala Pro Glu Met Ala Tyr
210 215 220

Phe Glu Cys Leu His Glu Leu Lys Leu Ile Val Asp Leu Met Phe Glu
225 230 235 240

Gly Gly Ile Ala Asn Met Asn Tyr Ser Ile Ser Asn Asn Ala Glu Tyr
245 250 255

Gly Glu Tyr Val Thr Gly Pro Glu Val Ile Asn Glu Gln Ser Arg Gln
260 265 270

Ala Met Arg Asn Ala Leu Lys Arg Ile Gln Asp Gly Glu Tyr Ala Lys
275 280 285

Met Phe Ile Thr Glu Gly Ala Ala Asn Tyr Pro Ser Met Thr Ala Tyr
290 295 300

Arg Arg Asn Asn Ala Ala His Gln Ile Glu Val Val Gly Glu Lys Leu
305 310 315 320

Arg Thr Met Met Pro Trp Ile Ala Ala Asn Lys Ile Val Asp Lys Thr
325 330 335

Lys Asn

<210> SEQ ID NO 42
<211> LENGTH: 338
<212> TYPE: PRT
<213> ORGANISM: Pseudomonas syringae

<400> SEQUENCE: 42

Met Lys Val Phe Tyr Asp Lys Asp Cys Asp Leu Ser Ile Ile Gln Gly
1 5 10 15

```
Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Arg Lys
        35                  40                  45

Gly Ser Ala Thr Val Ala Lys Ala Glu Ala His Gly Leu Lys Val Thr
    50                  55                  60

Asp Val Ala Ser Ala Val Ala Ala Ala Asp Leu Val Met Ile Leu Thr
65                  70                  75                  80

Pro Asp Glu Phe Gln Ser Gln Leu Tyr Lys Asn Glu Val Glu Pro Asn
                85                  90                  95

Leu Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Thr Glu Phe Val Lys Gly Gly
    130                 135                 140

Gly Ile Pro Asp Leu Ile Ala Val Tyr Gln Asp Ala Ser Gly Asn Ala
145                 150                 155                 160

Lys Asn Val Ala Leu Ser Tyr Ala Ser Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Lys Leu
305                 310                 315                 320

Arg Ser Met Met Pro Trp Ile Ala Ala Asn Lys Ile Val Asp Lys Asp
                325                 330                 335

Lys Asn


<210> SEQ ID NO 43
<211> LENGTH: 338
<212> TYPE: PRT
<213> ORGANISM: Pseudomonas syringae

<400> SEQUENCE: 43

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Arg Lys
        35                  40                  45
```

```
Gly Ser Ala Thr Val Ala Lys Ala Glu Ala His Gly Leu Lys Val Thr
    50                  55                  60

Asp Val Ala Ser Ala Val Ala Ala Ala Asp Leu Val Met Ile Leu Thr
65                  70                  75                  80

Pro Asp Glu Phe Gln Ser Gln Leu Tyr Lys Asn Glu Val Glu Pro Asn
                85                  90                  95

Leu Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Thr Glu Phe Val Lys Gly Gly
    130                 135                 140

Gly Ile Pro Asp Leu Ile Ala Val Tyr Gln Asp Ala Ser Gly Asn Ala
145                 150                 155                 160

Lys Asn Val Ala Leu Ser Tyr Ala Ser Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Thr Glu Gly Ala Thr Gly Tyr Pro Ser Met Thr Ala Lys
    290                 295                 300

Arg Arg Asn Asn Ala Glu His Gly Ile Glu Val Ile Gly Glu Lys Leu
305                 310                 315                 320

Arg Ser Met Met Pro Trp Ile Ala Ala Asn Lys Ile Val Asp Lys Asp
                325                 330                 335

Lys Asn


<210> SEQ ID NO 44
<211> LENGTH: 338
<212> TYPE: PRT
<213> ORGANISM: Pseudomonas putida

<400> SEQUENCE: 44

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Arg Lys
        35                  40                  45

Gly Ser Ala Thr Val Ala Lys Ala Glu Ala His Gly Leu Lys Val Ala
    50                  55                  60

Asp Val Ala Thr Ala Val Ala Ala Ala Asp Leu Val Met Ile Leu Thr
65                  70                  75                  80
```

```
Pro Asp Glu Phe Gln Gly Ala Leu Tyr Lys Asn Glu Ile Glu Pro Asn
                85                  90                  95

Ile Lys Lys Gly Ala Thr Leu Ala Phe Ser His Gly Phe Ser Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ser Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Glu Glu Ser Arg Lys
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Asn Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Ser Ala Asn Lys Ile Val Asp Lys Thr
                325                 330                 335

Lys Asn


<210> SEQ ID NO 45
<211> LENGTH: 338
<212> TYPE: PRT
<213> ORGANISM: Pseudomonas entomophila

<400> SEQUENCE: 45

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Ile Gly Leu Arg Lys
        35                  40                  45

Gly Ser Ala Thr Val Ala Lys Ala Glu Ala His Gly Leu Lys Val Thr
    50                  55                  60

Asp Val Ala Thr Ala Val Ala Ala Ala Asp Leu Val Met Ile Leu Thr
65                  70                  75                  80

Pro Asp Glu Phe Gln Gly Gln Leu Tyr Lys Gln Glu Ile Glu Pro Asn
                85                  90                  95

Ile Lys Lys Gly Ala Thr Leu Ala Phe Ser His Gly Phe Ala Ile His
            100                 105                 110
```

```
Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ser Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Glu Glu Ser Arg Lys
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Asn Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Ser Ala Asn Lys Ile Val Asp Lys Thr
                325                 330                 335

Lys Asn


<210> SEQ ID NO 46
<211> LENGTH: 338
<212> TYPE: PRT
<213> ORGANISM: Pseudomonas mendocina

<400> SEQUENCE: 46

Met Lys Val Tyr Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Ile Gly Leu Arg Lys
        35                  40                  45

Gly Ser Ala Thr Val Ala Lys Ala Glu Ala His Gly Leu Lys Val Thr
    50                  55                  60

Asp Val Ala Ser Ala Val Ala Ala Ala Asp Leu Val Met Ile Leu Thr
65                  70                  75                  80

Pro Asp Glu Phe Gln Gly Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Thr Glu Phe Val Lys Gly Gly
    130                 135                 140
```

Gly Ile Pro Asp Leu Ile Ala Val Tyr Gln Asp Ala Ser Gly Asn Ala
145 150 155 160

Lys Asn Val Ala Leu Ser Tyr Ala Ser Gly Val Gly Gly Gly Arg Thr
165 170 175

Gly Ile Ile Glu Thr Thr Phe Lys Asp Glu Thr Glu Thr Asp Leu Phe
180 185 190

Gly Glu Gln Ala Val Leu Cys Gly Gly Thr Val Glu Leu Val Lys Ala
195 200 205

Gly Phe Glu Thr Leu Val Glu Ala Gly Tyr Ala Pro Glu Met Ala Tyr
210 215 220

Phe Glu Cys Leu His Glu Leu Lys Leu Ile Val Asp Leu Met Tyr Glu
225 230 235 240

Gly Gly Ile Ala Asn Met Asn Tyr Ser Ile Ser Asn Asn Ala Glu Tyr
245 250 255

Gly Glu Tyr Val Thr Gly Pro Glu Val Ile Asn Ala Glu Ser Arg Gln
260 265 270

Ala Met Arg Asn Ala Leu Lys Arg Ile Gln Asp Gly Glu Tyr Ala Lys
275 280 285

Met Phe Ile Ser Glu Gly Ala Thr Gly Tyr Pro Ser Met Thr Ala Lys
290 295 300

Arg Arg Asn Asn Ala Ala His Gly Ile Glu Val Ile Gly Glu Gln Leu
305 310 315 320

Arg Ala Met Met Pro Trp Ile Ala Ala Asn Lys Ile Val Asp Lys Thr
325 330 335

Lys Asn

<210> SEQ ID NO 47
<211> LENGTH: 336
<212> TYPE: PRT
<213> ORGANISM: Bacillus cereus

<400> SEQUENCE: 47

Met Ala Lys Val Tyr Tyr Glu Lys Asp Val Thr Val Asn Val Leu Lys
1 5 10 15

Glu Lys Lys Val Ala Ile Ile Gly Tyr Gly Ser Gln Gly His Ala His
20 25 30

Ala Gln Asn Leu Arg Asp Asn Gly Phe Asp Val Val Val Gly Leu Arg
35 40 45

Lys Gly Lys Ser Trp Asp Lys Ala Lys Glu Asp Gly Phe Ser Val Tyr
50 55 60

Thr Val Ala Glu Ala Ala Lys Gln Ala Asp Val Val Met Ile Leu Leu
65 70 75 80

Pro Asp Glu Leu Gln Pro Glu Val Tyr Glu Ala Glu Ile Ala Pro Asn
85 90 95

Leu Gln Ala Gly Asn Ser Leu Val Phe Ala His Gly Phe Asn Val His
100 105 110

Phe Asp Gln Val Lys Pro Pro Ala Asn Val Asp Val Phe Leu Val Ala
115 120 125

Pro Lys Gly Pro Gly His Leu Val Arg Arg Thr Phe Ser Glu Gly Gly
130 135 140

Ala Val Pro Ala Leu Phe Ala Val Tyr Gln Asp Ala Thr Gly Val Ala
145 150 155 160

Thr Glu Lys Ala Leu Ser Tyr Ala Asp Gly Ile Gly Ala Thr Arg Ala
165 170 175

```
Gly Val Leu Glu Thr Thr Phe Lys Glu Glu Thr Glu Thr Asp Leu Phe
            180                 185                 190

Gly Glu Gln Ala Val Leu Cys Gly Gly Val Thr Ala Leu Val Lys Ala
        195                 200                 205

Gly Phe Glu Thr Leu Val Asp Ala Gly Tyr Gln Pro Glu Leu Ala Tyr
    210                 215                 220

Phe Glu Cys Leu His Glu Leu Lys Leu Ile Val Asp Leu Met Tyr Glu
225                 230                 235                 240

Gly Gly Leu Glu Asn Met Arg Tyr Ser Val Ser Asp Thr Ala Gln Trp
                245                 250                 255

Gly Asp Phe Val Ser Gly Pro Arg Val Val Thr Glu Asp Thr Lys Lys
            260                 265                 270

Ala Met Gly Thr Val Leu Ala Glu Ile Gln Asp Gly Thr Phe Ala Arg
        275                 280                 285

Gly Trp Ile Ala Glu His Lys Ala Gly Arg Pro Asn Phe His Ala Thr
    290                 295                 300

Asn Glu Lys Glu Asn Glu His Glu Ile Glu Val Val Gly Arg Lys Leu
305                 310                 315                 320

Arg Glu Met Met Pro Phe Val Gln Pro Arg Val Lys Val Gly Met Lys
                325                 330                 335
```

<210> SEQ ID NO 48
<211> LENGTH: 335
<212> TYPE: PRT
<213> ORGANISM: Bacillus cereus

<400> SEQUENCE: 48

```
Met Lys Thr Tyr Tyr Glu Lys Asp Ala Asn Val Glu Leu Leu Lys Gly
1               5                   10                  15

Lys Thr Val Ala Val Ile Gly Tyr Gly Ser Gln Gly His Ala Gln Ala
            20                  25                  30

Gln Asn Leu Arg Asp Ser Gly Val Glu Val Val Val Gly Val Arg Pro
        35                  40                  45

Gly Lys Ser Phe Glu Val Ala Lys Thr Asp Gly Phe Glu Val Met Ser
    50                  55                  60

Val Ser Glu Ala Val Arg Thr Ala Gln Val Val Gln Met Leu Leu Pro
65                  70                  75                  80

Asp Glu Gln Gln Ala His Val Tyr Lys Ala Gly Val Glu Glu Asn Leu
                85                  90                  95

Arg Glu Gly Gln Met Leu Leu Phe Ser His Gly Phe Asn Ile His Phe
            100                 105                 110

Gly Gln Ile Asn Pro Pro Ser Tyr Val Asp Val Ala Met Val Ala Pro
        115                 120                 125

Lys Ser Pro Gly His Leu Val Arg Arg Val Phe Gln Glu Gly Asn Gly
    130                 135                 140

Val Pro Ala Leu Val Ala Val His Gln Asp Ala Thr Gly Thr Ala Leu
145                 150                 155                 160

His Val Ala Leu Ala Tyr Ala Lys Gly Val Gly Cys Thr Arg Ala Gly
                165                 170                 175

Val Ile Glu Thr Thr Phe Gln Glu Glu Thr Glu Thr Asp Leu Phe Gly
            180                 185                 190

Glu Gln Thr Val Leu Cys Gly Gly Val Thr Ala Leu Val Lys Ala Gly
        195                 200                 205

Phe Glu Thr Leu Thr Glu Gly Gly Tyr Arg Pro Glu Ile Ala Tyr Phe
```

```
    210                 215                 220

Glu Cys Leu His Glu Leu Lys Leu Ile Val Asp Leu Met Tyr Glu Gly
225                 230                 235                 240

Gly Leu Thr Asn Met Arg His Ser Ile Ser Asp Thr Ala Glu Phe Gly
                245                 250                 255

Asp Tyr Val Thr Gly Ser Arg Ile Val Thr Asp Glu Thr Lys Lys Glu
            260                 265                 270

Met Lys Arg Val Leu Thr Glu Ile Gln Gln Gly Glu Phe Ala Lys Lys
        275                 280                 285

Trp Ile Leu Glu Asn Gln Ala Gly Arg Pro Thr Tyr Asn Ala Met Lys
    290                 295                 300

Lys Ala Glu Gln Asn His Gln Leu Glu Lys Val Gly Ala Glu Leu Arg
305                 310                 315                 320

Glu Met Met Ser Trp Ile Asp Ala Pro Lys Glu Leu Val Lys Lys
                325                 330                 335


<210> SEQ ID NO 49
<211> LENGTH: 22
<212> TYPE: DNA
<213> ORGANISM: artificial sequence
<220> FEATURE:
<223> OTHER INFORMATION: primer pBAD-405
<220> FEATURE:
<221> NAME/KEY: misc_feature
<222> LOCATION: (10)..(11)
<223> OTHER INFORMATION: n is a, c, g, or t

<400> SEQUENCE: 49

gctcaagcan nkaacctgaa gg                                            22


<210> SEQ ID NO 50
<211> LENGTH: 22
<212> TYPE: DNA
<213> ORGANISM: artificial sequence
<220> FEATURE:
<223> OTHER INFORMATION: primer pBAD 427
<220> FEATURE:
<221> NAME/KEY: misc_feature
<222> LOCATION: (12)..(13)
<223> OTHER INFORMATION: n is a, c, g, or t

<400> SEQUENCE: 50

ccttcaggtt knntgcttga gc                                            22


<210> SEQ ID NO 51
<211> LENGTH: 21
<212> TYPE: DNA
<213> ORGANISM: artificial sequence
<220> FEATURE:
<223> OTHER INFORMATION: primer pBAD435
<220> FEATURE:
<221> NAME/KEY: misc_feature
<222> LOCATION: (10)..(11)
<223> OTHER INFORMATION: n is a, c, g, or t

<400> SEQUENCE: 51

gtagacgtgn nkgttggcct g                                             21


<210> SEQ ID NO 52
<211> LENGTH: 21
<212> TYPE: DNA
<213> ORGANISM: artificial sequence
<220> FEATURE:
<223> OTHER INFORMATION: primer pBAD456
<220> FEATURE:
```

```
<221> NAME/KEY: misc_feature
<222> LOCATION: (11)..(12)
<223> OTHER INFORMATION: n is a, c, g, or t

<400> SEQUENCE: 52

caggccaack nncacgtcta c                                              21


<210> SEQ ID NO 53
<211> LENGTH: 25
<212> TYPE: DNA
<213> ORGANISM: artificial sequence
<220> FEATURE:
<223> OTHER INFORMATION: primer pBAD484
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t

<400> SEQUENCE: 53

ctgaagccnn kggcnnkaaa gtgac                                          25


<210> SEQ ID NO 54
<211> LENGTH: 25
<212> TYPE: DNA
<213> ORGANISM: artificial sequence
<220> FEATURE:
<223> OTHER INFORMATION: primer pBAD509
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t

<400> SEQUENCE: 54

gtcactttkn ngccknnggc ttcag                                          25


<210> SEQ ID NO 55
<211> LENGTH: 22
<212> TYPE: DNA
<213> ORGANISM: artificial sequence
<220> FEATURE:
<223> OTHER INFORMATION: Primer pBAD519
<220> FEATURE:
<221> NAME/KEY: misc_feature
<222> LOCATION: (10)..(11)
<223> OTHER INFORMATION: n is a, c, g, or t

<400> SEQUENCE: 55

gcagccgttn nkggtgccga ct                                             22


<210> SEQ ID NO 56
<211> LENGTH: 22
<212> TYPE: DNA
<213> ORGANISM: artificial sequence
<220> FEATURE:
<223> OTHER INFORMATION: Primer pBAD541
<220> FEATURE:
<221> NAME/KEY: misc_feature
<222> LOCATION: (12)..(13)
<223> OTHER INFORMATION: n is a, c, g, or t

<400> SEQUENCE: 56

agtcggcacc knnaacggct gc                                             22
```

<210> SEQ ID NO 57
<211> LENGTH: 22
<212> TYPE: DNA
<213> ORGANISM: artificial sequence
<220> FEATURE:
<223> OTHER INFORMATION: Primer pBAD545
<220> FEATURE:
<221> NAME/KEY: misc_feature
<222> LOCATION: (11)..(12)
<223> OTHER INFORMATION: n is a, c, g, or t

<400> SEQUENCE: 57
catgatcctg nnkccggacg ag 22

<210> SEQ ID NO 58
<211> LENGTH: 22
<212> TYPE: DNA
<213> ORGANISM: artificial sequence
<220> FEATURE:
<223> OTHER INFORMATION: Primer pBAD567
<220> FEATURE:
<221> NAME/KEY: misc_feature
<222> LOCATION: (11)..(12)
<223> OTHER INFORMATION: n is a, c, g, or t

<400> SEQUENCE: 58
ctcgtccggk nncaggatca tg 22

<210> SEQ ID NO 59
<211> LENGTH: 23
<212> TYPE: DNA
<213> ORGANISM: artificial sequence
<220> FEATURE:
<223> OTHER INFORMATION: Primer pBAD608
<220> FEATURE:
<221> NAME/KEY: misc_feature
<222> LOCATION: (11)..(12)
<223> OTHER INFORMATION: n is a, c, g, or t

<400> SEQUENCE: 59
caagaagggc nnkactctgg cct 23

<210> SEQ ID NO 60
<211> LENGTH: 23
<212> TYPE: DNA
<213> ORGANISM: artificial sequence
<220> FEATURE:
<223> OTHER INFORMATION: Primer 60 pBAD631
<220> FEATURE:
<221> NAME/KEY: misc_feature
<222> LOCATION: (12)..(13)
<223> OTHER INFORMATION: n is a, c, g, or t

<400> SEQUENCE: 60
aggccagagt knngcccttc ttg 23

<210> SEQ ID NO 61
<211> LENGTH: 22
<212> TYPE: DNA
<213> ORGANISM: artificial sequence
<220> FEATURE:
<223> OTHER INFORMATION: primer pBAD663
<220> FEATURE:
<221> NAME/KEY: misc_feature
<222> LOCATION: (10)..(11)
<223> OTHER INFORMATION: n is a, c, g, or t

<400> SEQUENCE: 61
gttgtgcctn nkgccgacct cg 22

<210> SEQ ID NO 62
<211> LENGTH: 22
<212> TYPE: DNA
<213> ORGANISM: artificial sequence
<220> FEATURE:
<223> OTHER INFORMATION: Primer pBAD685
<220> FEATURE:
<221> NAME/KEY: misc_feature
<222> LOCATION: (12)..(13)
<223> OTHER INFORMATION: n is a, c, g, or t

<400> SEQUENCE: 62
cgaggtcggc knnaggcaca ac 22

<210> SEQ ID NO 63
<211> LENGTH: 491
<212> TYPE: PRT
<213> ORGANISM: Escherichia coli

<400> SEQUENCE: 63

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285
```

```
Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490


<210> SEQ ID NO 64
<211> LENGTH: 493
<212> TYPE: PRT
<213> ORGANISM: gamma proteobacterium N4-7

<400> SEQUENCE: 64

Met Ala Asn Tyr Phe Asn Thr Leu Ser Leu Arg Asp Lys Leu Thr Gln
1               5                   10                  15

Leu Gly Lys Cys Arg Phe Met Asp Arg Ser Glu Phe Thr Asp Gly Cys
            20                  25                  30

Asp Phe Ile Lys Asp Trp Asn Ile Val Ile Ile Gly Cys Gly Ala Gln
        35                  40                  45

Gly Leu Asn Gln Gly Leu Asn Met Arg Asp Ser Gly Leu Asn Ile Ser
    50                  55                  60

Tyr Ala Leu Arg Ala Gln Ala Ile Ala Glu Lys Arg Gln Ser Phe Val
65                  70                  75                  80

Trp Ala Ser Glu Asn Gly Phe Thr Val Gly Thr Ala Glu Glu Leu Val
                85                  90                  95

Pro Ala Ala Asp Leu Val Leu Asn Leu Thr Pro Asp Lys Gln His Thr
            100                 105                 110

Ala Ala Val Thr Ala Val Met Pro Leu Met Lys Gln Gly Ala Thr Leu
        115                 120                 125

Ala Tyr Ser His Gly Phe Asn Ile Val Glu Glu Gly Met Gln Ile Arg
    130                 135                 140

Pro Asp Leu Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
```

```
                165                 170                 175

Val His Pro Glu Asn Asp Pro Gln Gly Asn Gly His Ala Ile Ala Lys
            180                 185                 190

Ala Tyr Ala Ser Ala Thr Gly Gly Asp Arg Ala Gly Val Leu Glu Ser
        195                 200                 205

Ser Phe Ile Ala Glu Val Lys Ser Asp Leu Met Gly Glu Gln Thr Ile
    210                 215                 220

Leu Cys Gly Met Leu Gln Thr Gly Ala Val Leu Gly His Gln Gln Leu
225                 230                 235                 240

Ile Asn Leu Gly Val Asp Ala Ala Tyr Ala Arg Lys Leu Ile Gln Tyr
                245                 250                 255

Gly Trp Glu Thr Val Thr Glu Gly Leu Lys His Gly Gly Ile Thr Asn
            260                 265                 270

Met Met Asp Arg Leu Ser Asn Pro Ala Lys Ile Lys Ala Phe Asp Met
        275                 280                 285

Ser Glu Glu Leu Lys Val Thr Leu Arg Pro Leu Phe Glu Lys His Met
    290                 295                 300

Asp Asp Ile Ile Glu Gly Glu Phe Ser His Thr Met Met Ile Asp Trp
305                 310                 315                 320

Ala Asn Asp Asp Ala Asn Leu Leu Lys Trp Arg Ala Glu Thr Ala Asp
                325                 330                 335

Ser Ser Phe Glu Gln Ala Ala Asp Cys Asp Ile Glu Ile Thr Glu Gln
            340                 345                 350

Glu Phe Tyr Asp Lys Gly Ile Tyr Leu Val Ala Met Ile Lys Ala Gly
        355                 360                 365

Val Glu Leu Ala Phe Glu Thr Met Val Ala Ser Gly Ile Ile Glu Glu
    370                 375                 380

Ser Ala Tyr Tyr Glu Ser Leu His Glu Thr Pro Leu Ile Ala Asn Cys
385                 390                 395                 400

Ile Ala Arg Asn Lys Leu Tyr Glu Met Asn Val Val Ile Ser Asp Thr
                405                 410                 415

Ala Glu Tyr Gly Asn Tyr Leu Phe Thr His Ala Ala Val Pro Leu Leu
            420                 425                 430

Gln Ala His Ala Ser Ser Leu Thr Leu Glu Glu Leu Gly Gly Gly Leu
        435                 440                 445

Ala Asp Ser Ser Asn Ala Val Asp Asn Leu Arg Leu Ile Glu Val Asn
    450                 455                 460

Asp Ala Ile Arg Asp His Asp Val Glu Ile Ile Gly His Glu Leu Arg
465                 470                 475                 480

Gly Tyr Met Thr Asp Met Lys Arg Ile Val Glu Ala Gly
                485                 490


<210> SEQ ID NO 65
<211> LENGTH: 490
<212> TYPE: PRT
<213> ORGANISM: Desulfuromonas acetoxidans

<400> SEQUENCE: 65

Met Gly Gln Asn Tyr Phe Asn Thr Leu Ser Met Arg Glu Lys Leu Asp
1               5                   10                  15

Glu Leu Gly Thr Cys Arg Phe Met Asp Ala Ser Glu Phe Ala Gly Gly
            20                  25                  30

Cys Glu Tyr Ala Lys Gly Lys Lys Ile Val Ile Val Gly Cys Gly Ala
        35                  40                  45
```

```
Gln Gly Leu Asn Gln Gly Leu Asn Met Arg Asp Ser Gly Leu Asp Val
    50                  55                  60

Ser Tyr Thr Leu Arg Lys Glu Ala Ile Ala Glu Lys Arg Gln Ser Tyr
65                  70                  75                  80

Ile Asn Ala Thr Glu Asn Gly Phe Thr Val Gly Ser Tyr Glu Glu Leu
                85                  90                  95

Leu Pro Thr Ala Asp Ile Val Met Asn Leu Ala Pro Asp Lys Gln His
            100                 105                 110

Thr Asp Val Val Asn Thr Val Val Pro Leu Met Lys Gln Gly Ala Thr
        115                 120                 125

Phe Ser Tyr Ala His Gly Phe Asn Ile Val Glu Glu Gly Thr Ile Ile
    130                 135                 140

Arg Lys Asp Leu Thr Val Ile Met Val Ala Pro Lys Cys Pro Gly Ser
145                 150                 155                 160

Glu Val Arg Ala Glu Tyr Gln Arg Gly Phe Gly Val Pro Thr Leu Ile
                165                 170                 175

Ala Val His Lys Glu Asn Asp Pro Asn Gly Asp Gly Leu Glu Leu Ala
            180                 185                 190

Lys Ala Leu Cys Ser Ala Gln Gly Gly Asp Arg Ala Gly Val Leu Glu
        195                 200                 205

Ser Ser Phe Val Ala Glu Val Lys Ser Asp Leu Met Gly Glu Gln Thr
    210                 215                 220

Ile Leu Cys Gly Met Leu Gln Ala Gly Ala Leu Leu Cys Phe Asp Lys
225                 230                 235                 240

Met Val Glu Asn Gly Ile Glu Ala Pro Tyr Ala Val Lys Leu Ile Gln
                245                 250                 255

Tyr Gly Trp Glu Thr Ile Thr Glu Ala Leu Lys His Gly Gly Ile Thr
            260                 265                 270

Asn Met Met Asp Arg Leu Ser Asn Pro Ala Lys Leu Glu Ala Tyr Glu
        275                 280                 285

Leu Ala Glu Glu Leu Lys Glu Ile Met Arg Pro Leu Phe Arg Lys His
    290                 295                 300

Met Asp Asp Ile Ile Thr Gly Val Phe Ser Ser Thr Met Met Glu Asp
305                 310                 315                 320

Trp Ala Asn Asp Asp Ile Asn Leu Leu Thr Trp Arg Glu Gln Thr Gly
                325                 330                 335

Gln Thr Ala Phe Glu Lys Thr Glu Ala Ala Gly Glu Ile Ser Glu Gln
            340                 345                 350

Glu Tyr Phe Asp Lys Ala Ile Leu Met Val Ala Met Val Lys Ala Gly
        355                 360                 365

Val Glu Leu Ala Phe Glu Ser Met Val Glu Val Gly Ile Glu Pro Glu
    370                 375                 380

Ser Ala Tyr Tyr Glu Ser Leu His Glu Thr Pro Leu Ile Ala Asn Thr
385                 390                 395                 400

Ile Ala Arg Lys Lys Leu Tyr Glu Met Asn Arg Val Ile Ser Asp Thr
                405                 410                 415

Ala Glu Tyr Gly Cys Tyr Leu Phe Ala His Ala Cys Val Pro Leu Leu
            420                 425                 430

Lys Asp Phe Met Ala Ser Val Thr Thr Glu Val Ile Gly Lys Gly Leu
        435                 440                 445

Asp Asn Val Asp Thr Ser Val Asp Asn Ser Thr Leu Val Arg Val Asn
    450                 455                 460

Ala Asp Ile Arg Ser His Tyr Ile Glu Glu Ile Gly Glu Glu Leu Arg
```

```
465                 470                 475                 480

Asp Ala Met Gln Gly Met Lys Ala Ile Val
                485                 490


<210> SEQ ID NO 66
<211> LENGTH: 581
<212> TYPE: PRT
<213> ORGANISM: Pisum sativum

<400> SEQUENCE: 66

Met Ala Ala Val Thr Ser Ser Cys Ser Thr Ala Ile Ser Ala Ser Ser
1               5                   10                  15

Lys Thr Leu Ala Lys Pro Val Ala Ala Ser Phe Ala Pro Thr Asn Leu
            20                  25                  30

Ser Phe Ser Lys Leu Ser Pro Gln Ser Ile Arg Ala Arg Arg Ser Ile
        35                  40                  45

Thr Val Gly Ser Ala Leu Gly Ala Thr Lys Val Ser Ala Pro Pro Ala
    50                  55                  60

Thr His Pro Val Ser Leu Asp Phe Glu Thr Ser Val Phe Lys Lys Glu
65                  70                  75                  80

Arg Val Asn Leu Ala Gly His Glu Glu Tyr Ile Val Arg Gly Gly Arg
                85                  90                  95

Asp Leu Phe His Leu Leu Pro Asp Ala Phe Lys Gly Ile Lys Gln Ile
            100                 105                 110

Gly Val Ile Gly Trp Gly Ser Gln Gly Pro Ala Gln Ala Gln Asn Leu
        115                 120                 125

Arg Asp Ser Leu Val Glu Ala Lys Ser Asp Ile Val Val Lys Val Gly
    130                 135                 140

Leu Arg Lys Gly Ser Ser Ser Phe Asn Glu Ala Arg Glu Ala Gly Phe
145                 150                 155                 160

Ser Glu Glu Lys Gly Thr Leu Gly Asp Ile Trp Glu Thr Ile Ser Gly
                165                 170                 175

Ser Asp Leu Val Leu Leu Leu Ile Ser Asp Ser Ala Gln Ala Asp Asn
            180                 185                 190

Tyr Glu Lys Ile Phe Ser His Leu Lys Pro Asn Ser Ile Leu Gly Leu
        195                 200                 205

Ser His Gly Phe Leu Leu Gly His Leu Gln Ser Ile Gly Leu Asp Phe
    210                 215                 220

Pro Lys Asn Phe Ser Val Ile Ala Val Cys Pro Lys Gly Met Gly Pro
225                 230                 235                 240

Ser Val Arg Arg Leu Tyr Val Gln Gly Lys Glu Ile Asn Gly Ala Gly
                245                 250                 255

Ile Asn Ser Ser Phe Gly Val His Gln Asp Val Asp Gly Arg Ala Thr
            260                 265                 270

Asn Val Ala Leu Gly Trp Ser Val Ala Leu Gly Ser Pro Phe Thr Phe
        275                 280                 285

Ala Thr Thr Leu Glu Gln Glu Tyr Lys Ser Asp Ile Phe Gly Glu Arg
    290                 295                 300

Gly Ile Leu Leu Gly Ala Val His Gly Ile Val Glu Ser Leu Phe Arg
305                 310                 315                 320

Arg Tyr Thr Glu Asn Gly Met Ser Glu Asp Leu Ala Tyr Lys Asn Thr
                325                 330                 335

Val Glu Ser Ile Thr Gly Val Ile Ser Lys Thr Ile Ser Thr Gln Gly
            340                 345                 350
```

```
Met Leu Ala Val Tyr Asn Ala Leu Ser Glu Asp Gly Lys Lys Glu Phe
        355                 360                 365

Glu Lys Ala Tyr Ser Ala Ser Phe Tyr Pro Cys Met Glu Ile Leu Tyr
    370                 375                 380

Glu Cys Tyr Glu Asp Val Ala Ser Gly Ser Glu Ile Arg Ser Val Val
385                 390                 395                 400

Leu Ala Gly Arg Arg Phe Tyr Glu Lys Glu Gly Leu Pro Ala Phe Pro
                405                 410                 415

Met Gly Lys Ile Asp Gln Thr Arg Met Trp Lys Val Gly Glu Arg Val
            420                 425                 430

Arg Ser Thr Arg Pro Ala Gly Asp Leu Gly Pro Leu Tyr Pro Phe Thr
        435                 440                 445

Ala Gly Val Phe Val Ala Met Met Met Ala Gln Ile Glu Val Leu Arg
    450                 455                 460

Lys Lys Gly His Ser Tyr Ser Glu Ile Ile Asn Glu Ser Val Ile Glu
465                 470                 475                 480

Ser Val Asp Ser Leu Asn Pro Phe Met His Ala Arg Gly Val Ser Phe
                485                 490                 495

Met Val Asp Asn Cys Ser Thr Thr Ala Arg Leu Gly Ser Arg Lys Trp
            500                 505                 510

Ala Pro Arg Phe Asp Tyr Ile Leu Thr Gln Gln Ala Leu Val Ala Val
        515                 520                 525

Asp Ser Gly Ala Pro Ile Asn Gln Asp Leu Ile Ser Asn Phe Val Ser
    530                 535                 540

Asp Pro Val His Gly Ala Ile Gln Val Cys Ala Glu Leu Arg Pro Thr
545                 550                 555                 560

Leu Asp Ile Ser Val Pro Ala Ala Ala Asp Phe Val Arg Pro Glu Leu
                565                 570                 575

Arg Gln Cys Ser Asn
            580


<210> SEQ ID NO 67
<211> LENGTH: 338
<212> TYPE: PRT
<213> ORGANISM: artificial sequence
<220> FEATURE:
<223> OTHER INFORMATION: mutant KARI 3361G8

<400> SEQUENCE: 67

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125
```

```
Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 68
<211> LENGTH: 338
<212> TYPE: PRT
<213> ORGANISM: artificial sequence
<220> FEATURE:
<223> OTHER INFORMATION: KARI mutant 2H10

<400> SEQUENCE: 68

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ile Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
```

```
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 69
<211> LENGTH: 338
<212> TYPE: PRT
<213> ORGANISM: artificial sequence
<220> FEATURE:
<223> OTHER INFORMATION: KARI mutant 1D2

<400> SEQUENCE: 69

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Cys Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175
```

```
Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 70
<211> LENGTH: 338
<212> TYPE: PRT
<213> ORGANISM: artificial sequence
<220> FEATURE:
<223> OTHER INFORMATION: KARI mutant 3F12

<400> SEQUENCE: 70

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190
```

```
Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 71
<211> LENGTH: 62
<212> TYPE: DNA
<213> ORGANISM: artificial sequence
<220> FEATURE:
<223> OTHER INFORMATION: primer pf5-4mtF
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 71

gtagacgtga ctgttggcct gnnkaaaggc nnkgctnnkn nkgccaaggc tgaagcccac      60

gg                                                                     62


<210> SEQ ID NO 72
<211> LENGTH: 62
<212> TYPE: DNA
<213> ORGANISM: artificial sequence
<220> FEATURE:
<223> OTHER INFORMATION: primer pf5-4mtR
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
```

<221> NAME/KEY: misc_feature
<222> LOCATION: (40)..(41)
<223> OTHER INFORMATION: n is a, c, g, or t

<400> SEQUENCE: 72
ccgtgggctt cagccttggc knnknnagck nngcctttkn ncaggccaac agtcacgtct 60
ac 62

<210> SEQ ID NO 73
<211> LENGTH: 20
<212> TYPE: DNA
<213> ORGANISM: artificial sequence
<220> FEATURE:
<223> OTHER INFORMATION: primer pbad-230

<400> SEQUENCE: 73
aagattagcg gatcctacct 20

<210> SEQ ID NO 74
<211> LENGTH: 24
<212> TYPE: DNA
<213> ORGANISM: artificial sequence
<220> FEATURE:
<223> OTHER INFORMATION: primer pbad-601

<400> SEQUENCE: 74
gagtggcgcc cttcttgatg ttcg 24

<210> SEQ ID NO 75
<211> LENGTH: 338
<212> TYPE: PRT
<213> ORGANISM: artificial sequence
<220> FEATURE:
<223> OTHER INFORMATION: mutant JB1C6

<400> SEQUENCE: 75

Met Lys Val Phe Tyr Asp Lys Asp Cys Asp Leu Ser Ile Ile Gln Gly
1 5 10 15

Lys Lys Val Ala Ile Ile Gly Phe Gly Ser Gln Gly His Ala Gln Ala
20 25 30

Leu Asn Leu Lys Asp Ser Gly Val Asp Val Thr Val Gly Leu His Lys
35 40 45

Gly Asp Ala Tyr Tyr Ala Lys Ala Glu Ala His Gly Phe Lys Val Thr
50 55 60

Asp Val Ala Ala Ala Val Ala Gly Ala Asp Leu Val Met Ile Leu Ile
65 70 75 80

Pro Asp Glu Phe Gln Ser Gln Leu Tyr Lys Asn Glu Ile Glu Pro Asn
85 90 95

Ile Lys Lys Gly Ala Thr Leu Ala Phe Ser His Gly Phe Ala Ile His
100 105 110

Tyr Asn Gln Val Val Pro Arg Ala Asp Leu Asp Val Ile Met Ile Ala
115 120 125

Pro Lys Ala Pro Gly His Thr Val Arg Ser Glu Phe Val Lys Gly Gly
130 135 140

Gly Ile Pro Asp Leu Ile Ala Ile Tyr Gln Asp Val Ser Gly Asn Ala
145 150 155 160

Lys Asn Val Ala Leu Ser Tyr Ala Ala Gly Val Gly Gly Gly Arg Thr
165 170 175

Gly Ile Ile Glu Thr Thr Phe Lys Asp Glu Thr Glu Thr Asp Leu Phe
180 185 190

```
Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 76
<211> LENGTH: 338
<212> TYPE: PRT
<213> ORGANISM: artificial sequence
<220> FEATURE:
<223> OTHER INFORMATION: mutant 16445E4

<400> SEQUENCE: 76

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Leu Asn Leu Lys Asp Ser Gly Val Asp Val Thr Val Gly Leu Pro Lys
        35                  40                  45

Gly Val Ala Asp Gly Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205
```

```
Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 77
<211> LENGTH: 338
<212> TYPE: PRT
<213> ORGANISM: artificial sequence
<220> FEATURE:
<223> OTHER INFORMATION: mutant 16468D7

<400> SEQUENCE: 77

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Thr Lys
        35                  40                  45

Gly Ile Ala Asp Arg Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
```

225 230 235 240

Gly Gly Ile Ala Asn Met Asn Tyr Ser Ile Ser Asn Asn Ala Glu Tyr
245 250 255

Gly Glu Tyr Val Thr Gly Pro Glu Val Ile Asn Ala Glu Ser Arg Gln
260 265 270

Ala Met Arg Asn Ala Leu Lys Arg Ile Gln Asp Gly Glu Tyr Ala Lys
275 280 285

Met Phe Ile Ser Glu Gly Ala Thr Gly Tyr Pro Ser Met Thr Ala Lys
290 295 300

Arg Arg Asn Asn Ala Ala His Gly Ile Glu Ile Ile Gly Glu Gln Leu
305 310 315 320

Arg Ser Met Met Pro Trp Ile Gly Ala Asn Lys Ile Val Asp Lys Ala
325 330 335

Lys Asn

<210> SEQ ID NO 78
<211> LENGTH: 338
<212> TYPE: PRT
<213> ORGANISM: artificial sequence
<220> FEATURE:
<223> OTHER INFORMATION: mutant 16469F3

<400> SEQUENCE: 78

Met Lys Val Phe Tyr Asp Lys Asp Cys Asp Leu Ser Ile Ile Gln Gly
1 5 10 15

Lys Lys Val Ala Ile Ile Gly Tyr Gly Ser Gln Gly His Ala Gln Ala
20 25 30

Leu Asn Leu Lys Asp Ser Gly Val Asp Val Thr Val Gly Leu Glu Lys
35 40 45

Gly Ala Ala Asp Ala Ala Lys Ala Glu Ala His Gly Phe Lys Val Thr
50 55 60

Asp Val Ala Ala Ala Val Ala Gly Ala Asp Leu Val Met Ile Leu Ile
65 70 75 80

Pro Asp Glu Phe Gln Ser Gln Leu Tyr Lys Asn Glu Ile Glu Pro Asn
85 90 95

Ile Lys Lys Gly Ala Thr Leu Ala Phe Ser His Gly Phe Ala Ile His
100 105 110

Tyr Asn Gln Val Val Pro Arg Ala Asp Leu Asp Val Ile Met Ile Ala
115 120 125

Pro Lys Ala Pro Gly His Thr Val Arg Ser Glu Phe Val Lys Gly Gly
130 135 140

Gly Ile Pro Asp Leu Ile Ala Ile Tyr Gln Asp Ala Ser Gly Asn Ala
145 150 155 160

Lys Asn Val Ala Leu Ser Tyr Ala Ala Gly Val Gly Gly Gly Arg Thr
165 170 175

Gly Ile Ile Glu Thr Thr Phe Lys Asp Glu Thr Glu Thr Asp Leu Phe
180 185 190

Gly Glu Gln Ala Val Leu Cys Gly Gly Thr Val Glu Leu Val Lys Ala
195 200 205

Gly Phe Glu Thr Leu Val Glu Ala Gly Tyr Ala Pro Glu Met Ala Tyr
210 215 220

Phe Glu Cys Leu His Glu Leu Lys Leu Ile Val Asp Leu Met Tyr Glu
225 230 235 240

Gly Gly Ile Ala Asn Met Asn Tyr Ser Ile Ser Asn Asn Ala Glu Tyr
245 250 255

```
Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 79
<211> LENGTH: 338
<212> TYPE: PRT
<213> ORGANISM: artificial sequence
<220> FEATURE:
<223> OTHER INFORMATION: mutant JEA1

<400> SEQUENCE: 79

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Pro Lys
        35                  40                  45

Gly Phe Ala Asp Val Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270
```

```
Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 80
<211> LENGTH: 338
<212> TYPE: PRT
<213> ORGANISM: artificial sequence
<220> FEATURE:
<223> OTHER INFORMATION: mutant JEG2

<400> SEQUENCE: 80

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Phe Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
```

```
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 81
<211> LENGTH: 338
<212> TYPE: PRT
<213> ORGANISM: artificial sequence
<220> FEATURE:
<223> OTHER INFORMATION: mutant JEG4

<400> SEQUENCE: 81

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Asn Lys
        35                  40                  45

Gly Asn Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320
```

```
Arg Ser Met Met Pro Trp Ile Gly Ala Asn Lys Ile Val Asp Lys Ala
                325                 330                 335

Lys Asn


<210> SEQ ID NO 82
<211> LENGTH: 338
<212> TYPE: PRT
<213> ORGANISM: artificial sequence
<220> FEATURE:
<223> OTHER INFORMATION: mutant JEA7

<400> SEQUENCE: 82

Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Pro Lys
        35                  40                  45

Gly Asn Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335
```

```
Lys Asn


<210> SEQ ID NO 83
<211> LENGTH: 338
<212> TYPE: PRT
<213> ORGANISM: artificial sequence
<220> FEATURE:
<223> OTHER INFORMATION: mutant JED1

<400> SEQUENCE: 83

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Leu Asn Leu Lys Asp Ser Gly Val Asp Val Thr Val Gly Leu Asn Lys
        35                  40                  45

Gly Asn Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 84
```

<211> LENGTH: 338
<212> TYPE: PRT
<213> ORGANISM: artificial sequence
<220> FEATURE:
<223> OTHER INFORMATION: mutant 3361E1

<400> SEQUENCE: 84

```
Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Cys Asn Leu Lys Asp Ser Gly Val Asp Val Thr Val Gly Leu Tyr Lys
        35                  40                  45

Gly Ala Ala Asp Ala Ala Lys Ala Glu Ala His Gly Phe Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn
```

<210> SEQ ID NO 85
<211> LENGTH: 338
<212> TYPE: PRT
<213> ORGANISM: artificial sequence
<220> FEATURE:

<223> OTHER INFORMATION: mutant C2F6

<400> SEQUENCE: 85

```
Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Pro Lys
        35                  40                  45

Gly Val Ala Asp Trp Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn
```

<210> SEQ ID NO 86
<211> LENGTH: 338
<212> TYPE: PRT
<213> ORGANISM: artificial sequence
<220> FEATURE:
<223> OTHER INFORMATION: mutant C3B11

<400> SEQUENCE: 86

```
Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Phe Lys
        35                  40                  45

Gly Ala Ala Asp Trp Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 87
<211> LENGTH: 338
<212> TYPE: PRT
<213> ORGANISM: artificial sequence
<220> FEATURE:
<223> OTHER INFORMATION: mutant C4D12

<400> SEQUENCE: 87

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
```

```
            20                  25                  30

Cys Asn Leu Lys Asp Ser Gly Val Asp Val Thr Val Gly Leu Cys Lys
        35                  40                  45

Gly Trp Ala Gly Trp Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 88
<211> LENGTH: 338
<212> TYPE: PRT
<213> ORGANISM: artificial sequence
<220> FEATURE:
<223> OTHER INFORMATION: mutant SE

<400> SEQUENCE: 88

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Ala Lys
        35                  40                  45
```

```
Gly Trp Ala Gly Trp Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 89
<211> LENGTH: 338
<212> TYPE: PRT
<213> ORGANISM: artificial sequence
<220> FEATURE:
<223> OTHER INFORMATION: mutant SE2

<400> SEQUENCE: 89

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Pro Lys
        35                  40                  45

Gly Glu Ala Ala Trp Ala Lys Ala Glu Ala His Gly Leu Lys Val Thr
    50                  55                  60
```

```
Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 90
<211> LENGTH: 338
<212> TYPE: PRT
<213> ORGANISM: artificial sequence
<220> FEATURE:
<223> OTHER INFORMATION: mutant SB3

<400> SEQUENCE: 90

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Gly Lys
        35                  40                  45

Gly Trp Ala Gly Trp Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
```

```
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 91
<211> LENGTH: 338
<212> TYPE: PRT
<213> ORGANISM: artificial sequence
<220> FEATURE:
<223> OTHER INFORMATION: mutant SD3

<400> SEQUENCE: 91

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Leu Lys
        35                  40                  45

Gly Trp Ala Gly Trp Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110
```

```
Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 92
<211> LENGTH: 338
<212> TYPE: PRT
<213> ORGANISM: artificial sequence
<220> FEATURE:
<223> OTHER INFORMATION: mutant 9650E5

<400> SEQUENCE: 92

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Asn Lys
        35                  40                  45

Gly Trp Ala Gly His Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125
```

```
Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 93
<211> LENGTH: 338
<212> TYPE: PRT
<213> ORGANISM: artificial sequence
<220> FEATURE:
<223> OTHER INFORMATION: mutant 9667A11

<400> SEQUENCE: 93

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Asn Lys
        35                  40                  45

Gly Asn Ala Gly His Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
```

```
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 94
<211> LENGTH: 338
<212> TYPE: PRT
<213> ORGANISM: artificial sequence
<220> FEATURE:
<223> OTHER INFORMATION: mutant 9862B9

<400> SEQUENCE: 94

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Asp Lys
        35                  40                  45

Gly Trp Ala Gly Trp Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175
```

```
Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 95
<211> LENGTH: 338
<212> TYPE: PRT
<213> ORGANISM: artificial sequence
<220> FEATURE:
<223> OTHER INFORMATION: mutant 9875B9

<400> SEQUENCE: 95

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Asn Lys
        35                  40                  45

Gly Asn Ala Asp Trp Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190
```

```
Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 96
<211> LENGTH: 338
<212> TYPE: PRT
<213> ORGANISM: artificial sequence
<220> FEATURE:
<223> OTHER INFORMATION: mutant 11461D8

<400> SEQUENCE: 96

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Phe Lys
        35                  40                  45

Gly Ala Ala Asp Ala Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
```

```
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 97
<211> LENGTH: 338
<212> TYPE: PRT
<213> ORGANISM: artificial sequence
<220> FEATURE:
<223> OTHER INFORMATION: mutant 11463

<400> SEQUENCE: 97

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Pro Lys
        35                  40                  45

Gly Phe Ala Asp Val Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240
```

```
Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn


<210> SEQ ID NO 98
<211> LENGTH: 338
<212> TYPE: PRT
<213> ORGANISM: artificial sequence
<220> FEATURE:
<223> OTHER INFORMATION: mutant 1151B4

<400> SEQUENCE: 98

Met Lys Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala Gln Ala
            20                  25                  30

Cys Asn Leu Lys Asp Ser Gly Val Asp Val Thr Val Gly Leu Asn Lys
        35                  40                  45

Gly Asn Ala Asp Ala Ala Lys Ala Glu Ala His Gly Leu Lys Val Thr
    50                  55                  60

Asp Val Ala Ala Ala Val Ala Gly Ala Asp Leu Val Met Ile Leu Thr
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255
```

-continued

```
Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
        275                 280                 285

Met Phe Ile Ser Glu Gly Ala Thr Gly Tyr Pro Ser Met Thr Ala Lys
    290                 295                 300

Arg Arg Asn Asn Ala Ala His Gly Ile Glu Ile Ile Gly Glu Gln Leu
305                 310                 315                 320

Arg Ser Met Met Pro Trp Ile Gly Ala Asn Lys Ile Val Asp Lys Ala
                325                 330                 335

Lys Asn
```